US008030298B2

(12) United States Patent
Messinger et al.

(10) Patent No.: US 8,030,298 B2
(45) Date of Patent: Oct. 4, 2011

(54) 17β-HSD1 AND STS INHIBITORS

(75) Inventors: Josef Messinger, Sehnde (DE);
Heinrich-Hubert Thole, Hannover (DE); Bettina Husen, Hannover (DE);
Michael Weske, Burgdorf (DE); Pasi Koskimies, Turku (FI); Lila Pirkkala, Kaarina (FI)

(73) Assignee: Abbott Products GmbH, Hannover (DE)

( * ) Notice: Subject to any disclaimer, the term of this patent is extended or adjusted under 35 U.S.C. 154(b) by 1192 days.

(21) Appl. No.: 11/441,200

(22) Filed: May 26, 2006

(65) Prior Publication Data

US 2006/0281710 A1    Dec. 14, 2006

Related U.S. Application Data

(60) Provisional application No. 60/684,540, filed on May 26, 2005.

(51) Int. Cl.
*A61K 31/565* (2006.01)
*A61K 31/58* (2006.01)
*C07J 1/00* (2006.01)
*C07J 53/00* (2006.01)
*C07J 71/00* (2006.01)

(52) U.S. Cl. .......... 514/182; 514/176; 540/54; 552/500; 552/539; 552/627

(58) Field of Classification Search .................. 552/500, 552/539, 627; 540/54; 514/176, 182
See application file for complete search history.

(56) References Cited

U.S. PATENT DOCUMENTS

| 3,275,623 | A | 9/1966 | Knox |
| 3,347,878 | A | 10/1967 | Boswell |
| 3,413,321 | A | 11/1968 | Boswell |
| 5,204,337 | A | 4/1993 | Labrie et al. |
| 6,043,236 | A | 3/2000 | Brattsand et al. |
| 2003/0170292 | A1 | 9/2003 | Young et al. |
| 2005/0192263 | A1* | 9/2005 | Messinger et al. |
| 2006/0009434 | A1 | 1/2006 | Hillisch et al. |
| 2006/0052461 | A1 | 3/2006 | Hillisch et al. |

FOREIGN PATENT DOCUMENTS

| EP | 0 367 576 A2 | 5/1990 |
| WO | WO 93/05063 A1 | 3/1993 |
| WO | WO 93/05064 A1 | 3/1993 |
| WO | WO 96/15257 A2 | 5/1996 |
| WO | WO 96/28462 A1 | 9/1996 |
| WO | WO 99/50453 A1 | 10/1999 |
| WO | WO 00/07996 A2 | 2/2000 |
| WO | WO 02/32409 A2 | 4/2002 |
| WO | WO 03/017973 A1 | 3/2003 |
| WO | WO 2004/080271 A2 | 9/2004 |
| WO | WO 2004/085345 A2 | 10/2004 |
| WO | WO 2004/085457 A2 | 10/2004 |
| WO | WO 2004/085459 A1 | 10/2004 |
| WO | WO 2005/047303 A2 | 5/2005 |
| WO | WO 2006/003012 A1 | 1/2006 |
| WO | WO 2006/003013 A2 | 1/2006 |
| WO | WO 2006/027347 A1 | 3/2006 |

OTHER PUBLICATIONS

Akanni et al., "Preparation of 16-formylestradiol and the 16-(α-methylenebutanolide) derivative", Steroids, May 1993, vol. 58, pp. 234-238.
Cushman et al., "Synthesis, Antitubulin and Antimitotic Activity, and Cytotoxicity of Analogs of 2-Methoxyestradiol, an Endogenous Mammalian Metabolite of Estradiol That Inhibits Tubulin Polymerization by Binding to the Colchicine Binding Site", Journal of Medicinal Chemistry, 1995, vol. 38, No. 12, pp. 2041-2049.
Cushman et al., "The Effect of Exchanging Various Substituents at the 2-Position of 2-Methoxyestradiol on Cytotoxicity in Human Cancer Cell Cultures and Inhibition of Tubulin Polymerization", Journal of Medicinal Chemistry, 2002, vol. 45, No. 21, pp. 4748-4754.
Day et al., "The effects of 2-substituted oestrogen sulphamates on the growth of prostate and ovarian cancer cells", Journal of Steroid Biochemistry & Molecular Biology, 2003, vol. 84, pp. 317-325.
Edwards et al., "Difluoromethyldiphenylphosphine Oxide. A New Reagent for Conversion of Carbonyl Compounds to 1,1-Difluoroolefins", Tetrahedron Letters, 1990, vol. 31, No. 39, pp. 5571-5574.
González et al., "Synthesis and Pharmacological Evaluation of 8α-Estradiol Derivatives", Steroids, Aug. 1982, vol. 40, No. 2, pp. 171-187.
Koffman et al., "Evidence for Involvement of Tyrosine in Estradiol Binding by Rat Uterus Estrogen Receptor", Journal of Steroid Biochemistry & Molecular Biology, 1991, vol. 38, No. 2, pp. 135-139.
Labaree et al., "Synthesis and Evaluation of B-, C-, and D-Ring-Substituted Estradiol Carboxylic Acid Esters as Locally Active Estrogens", Journal of Medicinal Chemistry, 2003, vol. 46, No. 10, pp. 1886-1904.
Labrie et al., "The key role of 17β-hydroxysteroid dehydrogenases in sex steroid biology", Steroids, Jan. 1997, vol. 62, pp. 148-158.
Lawrence et al., "Novel and Potent 17β-Hydroysteroid Dehydrogenase Type 1 Inhibitors", Journal of Medicinal Chemistry, 2005, vol. 48, No. 8, pp. 2759-2762.
Ley et al., "Tetrapropylammonium Perruthenate, $Pr_4N+RuO_4-$, TPAP: A Catalytic Oxidant for Organic Synthesis", Synthesis, Jul. 1994, pp. 639-666.
Liu et al., "Synthesis of High Affinity Fluorine-Substituted Ligands for the Androgen Receptor. Potential Agents for Imaging Prostatic Cancer by Positron Emission Tomography", Journal of Medicinal Chemistry, 1992, vol. 35, No. 11, pp. 2113-2129.

(Continued)

*Primary Examiner* — Barbara P Badio
(74) *Attorney, Agent, or Firm* — Crowell & Moring LLP

(57) ABSTRACT

The present invention relates to novel substituted steroid derivatives which represent selective inhibitors of the 17β-hydroxysteroid dehydrogenase type I (17β-HSD1) and, in addition, which may represent inhibitors of the steroid sulphatase, as well as to their salts, to pharmaceutical preparations containing these compounds and to processes for the preparation of these compounds. Furthermore, the invention concerns the therapeutic use of said novel substituted steroid derivatives, particularly their use in the treatment, inhibition, prophylaxis or prevention of steroid hormone dependent diseases or disorders, such as steroid hormone dependent diseases or disorders requiring the inhibition of 17β-hydroxysteroid dehydrogenase type I and/or steroid sulphatase enzymes and/or requiring the lowering of the endogenous 17β-estradiol concentration.

23 Claims, No Drawings

OTHER PUBLICATIONS

Lunn et al., "The Adamantyl Carbonium Ion as a Dehydrogenating Agent, Its Reactions with Estrone", Tetrahedron, 1968, vol. 24, pp. 6773-6776.

Mindnich et al., "The role of 17 beta-hydroxysteroid dehydrogenases", Molecular and Cellular Endocrinology, 2004, vol. 218, pp. 7-20.

Mohanakrishnan et al., "Pd(0)-Mediated Cross Coupling of 2-Iodoestradiol with Organozinc Bromides: A General Route to the Synthesis of 2-Alkynyl, 2-Alkenyl and 2-Alkylestradiol Analogs", Synlett, 1999, No. 07, pp. 1097-1099.

Nambara et al., "Syntheses of Estetrol Monoglucuronides[1]", Steroids, Jan. 1976, vol. 27, No. 1, pp. 111-122.

Nussbaumer et al., "Steroid sulfatase inhibitors", Expert Opin. Ther. Patents, 2003, vol. 13, No. 5, pp. 605-625.

Nussbaumer et al., "Steroid Sulfatase Inhibitors", Medicinal Research Reviews, 2004, vol. 24, No. 4, pp. 529-576.

Oda et al., "The Hydrogenation of α-Hydroxymethylene-ketone Derivatives to α-Hydroxymethylene-ketone Derivatives with a Cell-Free System of *Streptomyces cinereocrocatus*", Chem. Pharm. Bull., 1989, vol. 37, No. 2, pp. 502-505.

Page et al., "Efficient Regioselective A-Ring Functionalization of Oestrogens", Tetrahedron, 1990, vol. 46, No. 6, pp. 2059-2068.

Pelletier et al., "Synthesis and Evaluation of Estradiol Derivatives With 16α-(Bromoalkylamide), 16α-(Bromoalkyl) or 16α-(Bromoalkynyl) Side Chain as Inhibitors of 17β-Hydroxysteroid Dehydrogenase Type 1 Without Estrogenic Activity", Bioorganic & Medicinal Chemistry, 1996, vol. 4, No. 10, pp. 1617-1628.

Poirier, "Inhibitors of 17β-Hydroxysteroid Dehydrogenases", Current Medicinal Chemistry, 2003, vol. 10, No. 6, pp. 453-477.

Poirier et al., "Synthesis of 17β-Estradiol Derivatives with N-Butyl, N-Methyl Alkylamide Side Chain at Position 15", Tetrahedron, 1991, vol. 47, No. 37, pp. 7751-7766.

Poirier et al., "D-Ring Alkylamide Derivatives of Estradiol: Effect on ER-Binding Affinity and Antiestrogenic Activity", Bioorganic & Medicinal Chemistry Letters, 1996, vol. 6, No. 21, pp. 2537-2542.

Poirer et al., "A 6β-(Thiaheptanamide) derivative of Estradiol as Inhibitor of 17β-Hydroxysteroid Dehydrogenase Type 1", J. Steroid Biochem. Molec. Biol., 1998, vol. 64, pp. 83-90.

Puranen et al., "Site-directed mutagenesis of the putative active site of human 17β-hydroxysteroid dehydrogenase type 1", Biochem. J., 1994, vol. 304, pp. 289-293.

Roa et al., "A new, pratical synthesis of 2-methoxyestradiols", Steroids, 2002, vol. 67, pp. 1065-1070.

Reed et al., "Steroid Sulfatase: Molecular Biology, Regulation, and Inhibition", Endocrine Reviews, 2005, vol. 26, No. 2, pp. 171-202.

Sam et al., "C16 and C17 Derivatives of Estradiol as Inhibitors of 17β-Hydroxysteroid Dehydrogenase Type 1: Chemical Synthesis and Structure-Activity Relationships", Drug Design and Discovery, 1998, vol. 15, pp. 157-180.

Schneider et al., "A Convenient Method for the Formation of 16-Methylene-17-ketosteroids", Synthesis, Aug. 1983, pp. 665-669.

Schwarz et al., "Studies on modified estrogens: Towards the synthesis of novel 14,15-cyclopropa[a]estra-1,3,5(10),8-tetraenes", Pharmazie, 2001, vol. 56, No. 11, pp. 843-849.

Tamaya et al., "Comparison of Cellular Levels of Steroid Receptors in Uterine Leiomyoma and Myometrium", Acta Obstet Gynecol Scand, 1985, vol. 64, pp. 307-309.

Tremblay et al., "Overview of a Rational Approach to Design Type I 17β-Hydroxysteroid Dehydrogenase Inhibitors Without Estrogenic Activity: Chemical Synthesis and Biological Evaluation", J. Steroid Biochem. Molec. Biol., 1998, vol. 66, No. 4, pp. 179-191.

Verdier-Pinard et al., "A Steroid Derivative with Paclitaxel-Like Effects on Tubulin Polymerization", Molecular Pharmacology, 2000, vol. 57, pp. 568-575.

Wang et al., "Trifluoromethylation of steroidal ketones", Journal of Fluorine Chemistry, 1994, vol. 69, pp. 1-3.

Woelfling et al., "Synthesis and receptor-binding examinations of the normal and 13-*epi*-D-homoestrones and their 3-methyl ethers", Steroids, 2003, vol. 68, pp. 277-288.

Xenos et al., "Synthesis of 16,17-Pyrazolo-fused Derivatives of A-Homo-steroidal Ring A Lactams", Synthesis, Mar. 1985, pp. 307.

Yoshikawa et al., "Diastereo- and Enantioselective Direct Catalytic Aldol Reaction of 2-Hydroxyacetophenones with Aldehydes Promoted by a Heteropolymetallic Complex: Catalytic Asymmetric Synthesis of *anti*-1,2-Diols", J. Org. Chem., 2002, vol. 67, No. 8, pp. 2556-2565.

\* cited by examiner

17β-HSD1 AND STS INHIBITORS

CROSS-REFERENCE TO RELATED APPLICATIONS

This application claims the benefit under 35 U.S.C. §119(e) to U.S. provisional patent application Ser. No. 60/684,540 filed May 26, 2005, the entire disclosure of which is incorporated hereby in its entirety.

FIELD OF INVENTION

The present invention relates to novel substituted steroid derivatives which represent selective inhibitory compounds of the 17β-hydroxysteroid dehydrogenase type I (17β-HSD1) enzyme, and, in addition, which may represent inhibitors of the steroid sulphatase, as well as to the salts of these compounds, to pharmaceutical preparations containing these compounds and to processes for the preparation of these compounds. Furthermore, the invention concerns the therapeutic use of said novel substituted steroid derivatives, particularly their use in the treatment, inhibition, prophylaxis or prevention of steroid hormone dependent diseases or disorders, such as steroid hormone dependent diseases or disorders requiring the inhibition of the 17β-HSD1 enzyme and/or steroid sulphatase enzymes and/or requiring the lowering of the endogenous 17β-estradiol concentration.

BACKGROUND

The publications and other materials used herein to illuminate the background of the invention, and in particular, cases to provide additional details respecting the practice, are incorporated by reference.

Mammalian 17β-hydroxysteroid dehydrogenases (17β-HSDs) are NAD(H) or NADP(H) dependent enzymes which convert inactive 17-keto-steroids into their active 17β-hydroxy-forms or catalyse the oxidation of the 17β-hydroxy-forms into the 17-keto-steroids. Because both estrogens and androgens have the highest affinity for their receptors in the 17β-hydroxy form, 17β-HSD enzymes play an essential role in the tissue-selective regulation of the activity of sex steroid hormones. At present, 10 human members of the 17β-HSD enzyme family have been described (types 1-5,7,8,10-12), whereby each type of 17β-HSD has a selective substrate affinity, directional (reductive or oxidative) activity in intact cells, and a particular tissue distribution.

Due to their essential role in the tissue-selective regulation of the activity of sex steroid hormones, 17β-HSDs can be involved in the occurrence and development of estrogen-sensitive pathologies (f. ex. breast, ovarian, and endometrium cancers etc.) and androgen-sensitive pathologies (f. ex. prostate cancer, benign prostatic hyperplasia, acne, hirsutism, etc). Furthermore, many types of 17β-HSD have been shown to be involved in the pathogenesis of particular human disorders such as pseudohermaphroditism (17β-HSD3), polycystic kidney disease (17β-HSD8) and bifunctional enzyme deficiency (17β-HSD4) [reviewed by: Mindnich et al (2004)]. Therefore treatment of sex steroid-sensitive diseases by administration of specific inhibitors of the 17β-HSDs enzymes have been suggested, optionally in combination with potent and specific anti-estrogens and anti-androgens [Labrie et al. (1997)].

The best characterized member of the 17β-HSD family is the 17β-HSD1 [EC 1.1.1.62]. The 17β-HSD1 enzyme catalyzes in vitro the reduction and the oxidation between estrone (E1) and estradiol (E2). However, under physiological in vivo conditions the enzyme only catalyses the reductive reaction from the estrone (E1) to the estradiol (E2). The 17β-HSD1 was found to be expressed in a variety of hormone-dependent tissues, e.g. placenta, mammary gland tissue or uterus and endometrium tissue, respectively.

Estradiol itself is, especially in comparison to the significantly less active estrone, a very potent hormone, which regulates the expression of a variety of genes by binding to the nuclear estrogen receptor and plays an essential role in the proliferation and differentiation of the target cell. Physiological as well as pathological cell proliferations can be estradiol dependent. Especially many breast cancer cells are stimulated by a locally raised estradiol concentration. Furthermore, the occurrence or course of benign pathologies such as endometriosis, uterine leiomyomas (fibroids or myomas), adenomyosis, menorrhagia, metrorrhagia and dysmenorrhoea is dependent from the existence of significantly high estradiol levels.

Endometriosis is a well-known gynaecological disorder that affects 10 to 15% of women in the reproductive age. It is a benign disease defined as the presence of viable endometrial gland and stroma cells outside the uterine cavity. It is most frequently found in the pelvic area. In women developing endometriosis, the endometrial cells entering the peritoneal cavity by retrograde menstruation (the most likely mechanism) have the capacity to adhere to and invade the peritoneal lining, and are then able to implant and grow. The implants respond to steroid hormones of the menstrual cycle in a similar way as the endometrium in the uterus. The infiltrating lesions and the blood from these lesions which are unable to leave the body cause inflammation of the surrounding tissue. The most common symptoms of endometriosis are dysmenorrhoea, dyspareunia and (chronic) abdominal pain. The occurrence of these symptoms is not related to the extent of the lesions. Some women with severe endometriosis are asymptomatic, while women with mild endometriosis may have severe pain. Up to now, no reliable non-invasive test is available to diagnose endometriosis. Laparoscopy has to be performed to diagnose the disease. Endometriosis is classified according to the 4 stages set up by the American Fertility Society (AFS). Stage I corresponds to minimal disease while stage IV is severe, depending on the location and the extent of the endometriosis. Endometriosis is found in up to 50% of the women with infertility. However, currently no causal relation has been proven between mild endometriosis and infertility. Moderate to severe endometriosis can cause tubal damage and adhesions leading to infertility. The aims of treatment of endometriosis are pain relief, resolution of the endometriotic tissue and restoration of fertility (if desired). The two common treatments are surgery or anti-inflammatory and/or hormonal therapy or a combination thereof.

Uterine leiomyomas (fibroids or myomas), benign clonal tumours, arise from smooth muscle cells of the human uterus. They are clinically apparent in up to 25% of women and are the single, most common indication for hysterectomy. They cause significant morbidity, including prolonged and heavy menstrual bleeding, pelvic pressure and pain, urinary problems, and, in rare cases, reproductive dysfunction. Myomas are found submucosally (beneath the endometrium), intramurally (within the myometrium) and subserosally (projecting out of the serosal compartment of the uterus), but mostly are mixed forms of these 3 different types. The presence of estrogen receptors in leiomyoma cells has been studied by Tamaya et al. [Tamaya et al. (1985)]. They have shown that the ratios of estrogen receptor compared to progesterone and androgen receptor levels were higher in leiomyomas than in the corresponding normal myometrium. Surgery has long been the main treatment for myomas. Furthermore, medical therapies that have been proposed to treat myomas include administration of a variety of steroids such as the androgenic steroids danazol or gestrinone and progestogens, or of compounds modulating the steroid hormone plasma levels like e.g. GnRH agonists and GnRH antagonists, whereby the administration is often associated a variety of serious side-effects.

Everything that has been said above in relation to the treatment of uterine leiomyomas and endometriosis equally applies to other benign gynaecological disorders, notably adenomyosis, functional menorrhagia and metrorrhagia. These benign gynaecological disorders are all estrogen sensitive and are treated in a comparable way as described herein before in relation to uterine leiomyomas and endometriosis. The available pharmaceutical treatments, however, suffer from the same major drawbacks, i.e. they have to be discontinued once the side-effects become more serious than the symptoms to be treated and symptoms reappear after discontinuation of the therapy.

Since the aforementioned malignant and benign pathologies are all 17β-estradiol dependent, a reduction of the endogenous 17β-estradiol concentration in the respective tissue will result in an impaired or reduced proliferation of 17β-estradiol responsive cells in said tissues. Therefore, selective inhibitors of the 17β-HSD1 enzyme are well suited for their use to impair endogenous productions of estrogens, in particular of 17β-estradiol, in myomas, endometriotic, adenomyotic and endometrial tissue. The application of a compound acting as selective inhibitor on the 17β-HSD1 which preferentially catalyses the reductive reaction will result in a lowered intracellular estradiolconcentration, since the reductive conversion of the estrone into the active estradiol is reduced or suppressed. Therefore, reversible or even irreversible inhibitors of the 17β-HSD1 may play a significant role in the prophylaxis and/or treatment of steroid-hormone, in particular 17β-estradiol, dependent disorders or diseases. Furthermore, the reversible or even irreversible inhibitors of the 17β-HSD1 should have no or only pure antagonistic binding activities to the estradiol receptor, in particular to the estrogen receptor α subtype, since agonistic binding of the estrogen receptor would lead to activation and subsequently to the proliferation and differentiation of the target cell. In contrast, antagonists of the estrogen receptor, so called anti-estrogens, bind competitively to the specific receptor protein thus preventing access of endogenous estrogens to their specific binding site.

At present it is described in the literature that several malignant disease as breast cancer, prostate carcinoma, ovarian cancer, uterine cancer, endometrial cancer and endometrial hyperplasia may be treated by the administration of a selective 17β-HSD1 inhibitor. Furthermore, a selective 17β-HSD1 inhibitor may be useful for the prevention of the aforementioned hormone-dependent cancers, especially breast cancer (e.g. WO 2004/080271). Furthermore, international patent application WO 03/017973 describes the use of a selective estrogen enzyme modulator (SEEM) in the manufacture of a drug delivery vehicle for intravaginal administration to treat or prevent a benign gynaecological disorder such as endometriosis in a mammalian female.

Another known target for estrogen deprivation is the steroid sulphatase enzyme (STS) (E.C. 3.1.6.2), which regulates the local production of estrogens and androgens from systemic precursors in several tissues [reviewed by Reed et al (2005)]. The enzyme catalyzes the hydrolysis of the sulphate esters of 3-hydroxy steroids, which are inactive transport or precursor forms of the active 3-hydroxy steroids. In particular, STS hydrolyzes in-active estron-sulphate into estrone, which is then further converted into the active estradiol by action of the above described 17β-HSD1 enzyme. Therefore, STS has a pivotal role in regulating the formation of biologically active steroids. The enzyme is widely distributed throughout the body and its action is implicated in physiological processes and pathological conditions, such as hormone-dependent tumors. STS expression is increased in breast tumors and has prognostic significance. The role of STS in supporting tumor growth of the breast and prostate prompted the development of potent STS inhibitors, since STS inhibitors are expected to block the local production and, consequently, to reduce the local levels of the hormones. Therefore, they are considered as potential therapeutic agents for the treatment of estrogen- and androgen-dependent disorders in general. Indications may range from cancers of the breast, endometrium and prostate to disorders of the pilosebaceous unit, e.g. acne, androgenetic alopecia, and hirsutism. Furthermore, STS inhibitors may be useful as immunosuppressive agents, and have been shown to enhance memory when delivered to the brain.

Acne is a polyetiological disease caused by the interplay of numerous factors, such as inheritance, sebum, hormones, and bacteria. The most important causative factor in acne is sebum production; in almost all acne patients sebaceous glands are larger and more sebum is produced than in persons with healthy skin. The development of the sebaceous gland and the extent of sebum production is controlled hormonally by androgens; therefore, androgens play a crucial role in the pathogenesis of acne. In man, there are two major sources supplying androgens to target tissues: (i) the gonades which secrete testosterone, (ii) the adrenals producing dehydroepiandrosterone (DHEA) which is secreted as the sulfate conjugate (DHEAS). Testosterone and DHEAS are both converted to the most active androgen, dihydrotestosterone (DHT), in the target tissue, e.g. in the skin. There is evidence that these pathways of local synthesis of DHT in the skin are more important than direct supply with active androgens from the circulation. Therefore, reduction of endogeneous levels of androgens in the target tissue by specific inhibitors should be of therapeutic benefit in acne and seborrhoea. Furthermore, it opens the perspective to treat these disorders through modulation of local androgen levels by topical treatment, rather than influencing circulating hormone levels by systemic therapies.

Androgenetic male alopecia is very common in the white races, accounting for about 95% of all types of alopecia. Male-pattern baldness is caused by an increased number of hair follicles in the scalp entering the telogen phase and by the telogen phase lasting longer. It is a genetically determined hair loss affected through androgens. Elevated serum DHEA but normal testosterone levels have been reported in balding men compared with non-balding controls, implying that target tissue androgen production is important in androgenetic alopecia.

Hirsutism is the pathological thickening and strengthening of the hair which is characterized by a masculine pattern of hair growth in children and women. Hirsutism is androgen induced, either by increased formation of androgens or by increased sensitivity of the hair follicle to androgens.

The presence of the STS enzyme in keratinocytes and in skin-derived fibroblasts has been described, and the potential use of STS inhibitors for the reduction of endogenous levels of steroid hormones in the skin was confirmed using known steroid sulfatase inhibitors, such as EMATE. Additionally, it has been described that inhibitors of placenta steroid sulfatase also inhibit steroid sulfatase in human keratinocyte or human skin-derived fibroblast cell lines. Therefore, STS inhibitors may be used to reduce androgen and estrogen levels in the skin, e.g. for the local treatment of androgen-dependent disorders of the pilosebaceous unit (such as acne, seborrhoea, androgenetic alopecia, hirsutism). STS inhibitors are also useful for the treatment of cancer, especially for the treatment of estrogen- and androgen-dependent cancers, such as cancer of the breast and endometrium, squamous cell carcinoma, and cancer of the prostata.

In addition, STS inhibitors may be useful for the prevention and treatment of further estrogen- or androgen-dependent diseases or disorders and/or diseases or disorders requiring the lowering of the endogeneous estrogen or androgen concentration in a generalized or tissue-specific manner, such as inflammatory and autoimmune diseases, e.g. rheumatoid arthritis, type I and II diabetes, systemic lupus erythematosus, multiple sclerosis, myastenia gravis, thyroiditis, vasculitis, ulcerative colitis, and Crohn's disease, psoriasis, contact dermatitis, graft versus host disease, eczema, asthma and organ rejection following transplantation. STS inhibitors are also useful for the enhancement of cognitive function, especially in the treatment of senile dementia, including Alzheimer's disease, by increasing the DHEAS levels in the central nervous system.

Several reversible or irreversible inhibitors of the 17β-HSD1 enzyme or of the steroid sulphatase of steroidal and even non-steroidal origin are already known from the literature. The characteristics of the inhibitory molecules of the 17β-HSD1 enzyme, which mainly have a substrate or cofactor-like core structure, have been reported in the literature [reviewed in: Poirier D. (2003)]. The characteristics and structure-activity relationship of known irreversible as well as reversible STS inhibitors have been reviewed in the literature [reviewed by Nussbaumer & Billich (2004) and (2003)]. Even dual inhibitors of the 17β-HSD1 enzyme and of the steroid sulphatase have been described in international patent application WO 02/32409.

The following compounds or compound classes have already been described as 17β-HSD1 inhibitors: For example, Tremblay and Poirier describe an estradiol derivative, 16-[carbamoyl-(bromo-methyl)-alkyl]estradiol, and tested the same in respect of its inhibition of the estradiol formation catalysed by the enzyme 17β-HSD1 [Tremblay & Poirier (1998)]. Poirier and colleagues describe a 6β-thiaheptan-butyl-methyl-amide derivative of estradiol as a potent and selective inhibitor of the 17HSD1 enzyme [Poirier et al. (1998)]. Furthermore, Poirier and colleagues describe new derivatives of 17β-estradiol with long N-butyl, N-methyl alkylamide side chains of three different lengths (n=8, or 12) at position 15, which might be potential inhibitors of the 17β-HSD1 enzyme [Poirier et al. (1991)]. Similar compounds were also disclosed within European patent application EP0367576. However, the biological activity of these compounds was only tested with regard to estrogen receptor binding affinity, estrogenic and anti-estrogenic activity [Poirier et al. (1996)], but not with regard to their ability to inhibit the 17β-HSD1 enzyme. In addition, Pelletier and Poirier describe novel 17β-estradiol derivatives with different bromo-alkyl side chains, which might be potential inhibitors of the 17β-HSD1 enzyme [Pelletier & Poirier (1996)]. Sam and colleagues describe several estradiol derivatives with a halogenated alkyl side chain in 16α or 17α position of the steroidal D-ring which possess 17β-HSD1 inhibiting properties [Sam et al. (1998)]. Furthermore, the finding that some anti-estrogens, such as tamoxifen, possess weak 17β-HSD1 inhibiting properties suggested that it may be possible to develop a potent 17β-HSD1 inhibitor that is also anti-estrogenic [reviewed in: Poirier D. (2003)]. Several of the aforementioned already known compounds also display anti-estrogenic properties (e.g. the 6β-thiaheptan-butyl-methyl-amide derivative of estradiol described by Poirier and colleagues [Poirier et al. (1998)]). None of the aforementioned compounds has been clinically used so far.

Furthermore, the international patent application WO 2004/085457 discloses a variety of estron derivatives with different substituents in C2, C3, C6, C16 and/or C17 position as potent 17β-HSD1 inhibitors. For some of the compounds it was shown that the substitution of steroid based 17β-HSD1 inhibitors at the C2 position with small hydrophobic groups renders the compounds less estrogenic and are favourable for 17β-HSD1 over 17β-HSD2 discrimination [Lawrence et al (2005)].

The international application WO 2005/047303, published on the filing date of the priority application of the present invention, discloses new 3, 15 substituted 17β-estradiol derivatives with different kind of side chains at position 15, which are potent and selective 17β-HSD1 inhibitors.

Additional compounds representing potential 17β-HSD1 inhibitors were disclosed within international applications WO 2006/003012 and WO 2006/003013 in the form of novel 2-substituted D-homo-estra-1,3,5(10)-trienes and novel 2-substituted estra-1,3,5(10)-trien-17-ones.

The synthesis of different B-, C- and D-ring substituted estradiol carboxylic esters was described by Labaree et al. [Labaree et al. (2003)]. However, these esters were only analysed with regard to their estrogenic potential. The related international patent application WO 2004/085345 discloses 15α substituted estradiol compounds bearing a —$(CH_2)_m$—CO—O—R side chain, wherein R is H, a $C_1$-$C_5$ alkyl group, optionally substituted with at least one halogen group, such as $CH_2CH_2F$, or other group (e.g. $CH_2CHF_2$, $CH_2CF_3$ or $CF_3$ group); and m is from 0-5. These 15α estradiol esters are described as locally active estrogens without significant systemic action.

Furthermore, international application WO 2006/027347 discloses 15β substituted estradiol derivatives having selective estrogen receptor activity towards the estrogen receptor α-subtype.

Several compounds and compound classes have already been identified as STS inhibitors. They all share the common structural feature of an aromatic ring bearing a substituent that mimics the phenolic A-ring of the enzyme substrate, estrone-sulphate. On the development of steroidal inhibitors, a wide variety of chemical groups have been introduced at C3, of which the 3-O-sulfamate was found to be the most potent for the estrone molecule. The resulting compound, estrone-3-O-sulfamate ("EMATE") led to the identification of the aryl-O-sulphamate structure as an active pharmacophore required for potent inhibition of STS (as disclosed in international patent application WO 93/05064). EMATE was shown to inhibit steroid sulphate activity in a time- and concentration-dependent manner and was active in vivo on oral administration. It was however revealed to be highly estrogenic which raised the need to design STS inhibitors devoid of agonist activity on the human estrogen receptor. For example, the recently published international patent application WO 2004/085459 discloses a variety of estron derivatives with different subsituents in C2, C3, C4 and/or C17 position as potent STS inhibitors.

Accordingly, there is still a need for the development of compounds which are suited for the treatment and/or prevention of steroid hormone dependent diseases or disorders such as breast cancer, endometriosis and uterine leiomyomas by selectively inhibiting the 17β-HSD1 enzyme and preferably additionally inhibiting the STS enzyme, while desirably failing to substantially inhibit other members of the 17β-HSD protein family or other catalysts of sex steroid degradation or activation. In particular, it is an aim of the present invention to develop selective inhibitors of the 17β-HSD1 enzyme, whereby in addition the compounds have no or only pure antagonistic binding affinities to the estrogen receptor (both subtypes α and β) and have favourably no residual activity on the 17β-HSD2 enyme. Furthermore, an increased metabolic stability of the compounds, in particular of the C17 keto position of the steroidal core, would be desirable, in order to prevent conversion of the estron to the respective estradiol derivative, which shows less inhibitory potential on the 17β-HSD1 enzyme.

SUMMARY OF THE INVENTION

Therefore, one object of the present invention is to provide novel inhibitors of the enzyme 17β-HSD1 and preferably also of the enzyme STS, which have valuable pharmacological properties and which are suited for the treatment of estrogen dependent diseases and disorders.

It has now been found that novel 3, 15 substituted estrone derivatives bearing a side chain of the amide, ester, carbonyl, hydrazone, alcohol, ether, urea, carbamate, "retro"-amide, sulfonyl urea, sulfamide, sulfamate, "retro"-sulfonamide, "retro"-carbamate, "retro"-ester or sulfonylcarbamate type in position C15 and being additionally modified by substitution in position C2, C3, C16 and/or C17 position of the estron core, would be valuable in therapy, especially in the treatment or prevention of steroid hormone dependent diseases or disorders requiring the lowering of the endogeneous estradiol concentration, in humans and other mammals. In particular, compounds of formula (I) represent potent inhibitors of the 17β-HSD1 enzyme and optionally of the STS enzyme, and possess valuable pharmacological properties for the treatment and/or prophylaxis of malignant steroid dependent diseases or disorders such as breast cancer, prostate carcinoma, ovarian cancer, uterine cancer, endometrial cancer and endometrial hyperplasia, but also for the treatment and/or prophylaxis of benign steroid dependent diseases or disorders such as endometriosis, uterine fibroids, uterine leiomyoma, adenomyosis, dysmenorrhoea, menorrhagia, metrorrhagia, prostadynia, benign prostatic hyperplasia, urinary dysfunction or lower urinary tract syndrome. Further estrogen-dependent diseases which may be treated and/or prevented with an effective amount of a compound of the invention are multiple sclerosis, rheumatoid arthritis, colon cancer, tissue wounds, skin wrinkles and cataracts. The compounds of the present invention have been developed as improved inhibitors of the enzyme 17β-HSD1, in addition showing no or only pure antagonistic binding affinities to the estrogen receptor (both subtypes α and β) and having favourably no residual activity on the 17β-HSD2 enyme, and/or showing an increased metabolic stability of the C17 keto function of the steroidal core.

Accordingly, the present invention relates to a compound having the structural formula I (I)

wherein
X represents:
(a) a bond,
(b) —NH—, or
(c) —O—;
A represents:
(a) —CO—, or
(b) under the proviso that X represents —NH—, A represents —SO$_2$—;
Y represents:
(a) —NR$^4$—,
(b) —O—, under the proviso that X represents a bond or —NH—,
(c) a bond,
(d) —NH—SO$_2$—, under the proviso that X represents —NH— and A represents —CO—,
(e) —NH—SO$_2$—NR$^4$—, under the proviso that X represents —O—, or
(f) —NH—NR$^4$—, under the proviso that X represents a bond; or
—X-A-Y— together represent —O—;
and wherein
R$^1$ is selected from:
(a) —H,
(b) —(C$_1$-C$_6$)alkyl, which is optionally substituted with halogen, nitril, —OR$^6$, —SR$^6$, or —COOR$^6$; the number of said substituents being up to three for halogen, and up to two for any combination of said halogen, nitril, —OR$^6$, —SR$^6$, or —COOR$^6$ moieties,
(c) -phenyl, which is optionally substituted with halogen, nitril, —OR$^6$, —SR$^6$, —R$^6$, or —COOR$^6$, the number of said substituents being up to perhalo for halogen, and up to two for any combination of said halogen, nitril, —OR$^6$, —SR$^6$, —R$^6$ or —COOR$^6$ moieties,
(d) —(C$_1$-C$_4$)alkyl-phenyl, in which the alkyl portion is optionally substituted with up to three halogens; and the phenyl portion is optionally substituted with halogen, nitril, —OR$^6$, —SR$^6$, —R$^6$ or —COOR$^6$, the number of substituents on said phenyl portion being up to perhalo for halogen, and up to two for any combination of said halogen, nitril, —OR$^6$, —SR$^6$, —R$^6$ or —COOR$^6$ moieties,
(e) —SO$_2$—NR$^3$R$^{3'}$,
(f) —CO—NR$^3$R$^{3'}$,
(g) —PO(OR$^{16}$)—R$^3$,
(h) —PS(OR$^{16}$)—R$^3$,
(i) —PO(OR$^{16}$)—O—R$^3$
(j) —SO$_2$—R$^3$, and
(k) —SO$_2$—O—R$^3$;
wherein
R$^6$ represents H, —(C$_1$-C$_4$)alkyl or halogenated —(C$_1$-C$_4$)alkyl;
R$^3$ and R$^{3'}$ are independently selected from H, alkyl, aryl and arylalkyl, or R$^3$ and R$^{3'}$ form together with the nitrogen atom, to which R$^3$ and R$^{3'}$ are attached, a heterocyclic 4-, 5-, 6-, 7- or 8-membered ring, which is optionally saturated, partly unsaturated, or aromatic; which optionally contains up to three additional heteroatoms selected from N, O or S, the number of additional N atoms being 0, 1, 2 or 3 and the number of O and S atoms each being 0, 1 or 2; and
R$^{16}$ represents —H, alkyl, or arylalkyl;
R$^2$ and R$^4$ are independently selected from:
(a) —H, wherein if X represents a bond, A represents —CO— and Y represents —O— or a bond, then R$^2$ is different from —H;
(b) optionally substituted alkyl, (c) optionally substituted acyl, under the proviso that Y represents —NH—NR$^4$—,
(d) optionally substituted aryl,
(e) optionally substituted heteroaryl, and
(f) optionally substituted cycloheteroalkyl, or, under the proviso that Y represents —NR$^4$—, —NH—NR$^4$— or —NH—SO$_2$—NR$^4$—, R$^2$ and R$^4$ form together with the nitrogen atom, to which R$^2$ and R$^4$ are attached, a heterocyclic 4-, 5-, 6-, 7- or 8-membered ring, which is optionally saturated, partly unsaturated, or aromatic; which optionally contains up to three additional heteroatoms selected from N, O or S, the number of additional N atoms being 0, 1, 2 or 3 and the number of O and S atoms each being 0, 1 or 2; and which ring is optionally part of a multiple condensed ring-system, wherein the ring or the ring-system is optionally substituted;

the substituents R$^{10}$, R$^{11}$, R$^{12}$ and R$^{13}$ together with the carbon atoms, to which they are attached, form a structure —CR$^{13}$R$^{12}$—CR$^{11}$R$^{10}$—, wherein
(a) R$^{10}$ and R$^{11}$ both represent —H and R$^{12}$ and R$^{13}$ together represent a group selected from =O, =CF$_2$, =N—O-alkyl, and =N—OH, or
(b) R$^{10}$ and R$^{11}$ both represent —H, and R$^{12}$ and R$^{13}$ both individually represent —F, or
(c) R$^{10}$, R$^{11}$ and R$^{13}$ all represent —H, and R$^{12}$ is selected from —OH, —CN, —F, —CF$_3$, and —CF$_2$H, or
(d) R$^{10}$ represents —H, R$^{11}$ together with R$^{13}$ forms a bond, and R$^{12}$ is selected from —CN, —F, —CF$_3$, and —CF$_2$H; or
(e) R$^{10}$ represents —H, R$^{11}$ represents —CHO, and R$^{12}$ and R$^{13}$ together represent =O;

or, the substituents R$^{10}$, R$^{12}$ and R$^{13}$ together with the carbon atoms, to which R$^{10}$, R$^{11}$, R$^{12}$ and R$^{13}$ are attached, form a heterocyclic 5- or 6-membered ring, which is partly unsaturated or aromatic, which contains one, two or three heteroatoms independently selected from N, O or S, the number of N atoms being 0, 1, 2 or 3 and the number of O and S atoms each being 0, 1 or 2, wherein one heteroatom is directly attached to the C17 C-atom of the steroidal core; and which ring is optionally substituted with an alkyl group;

R$^{14}$ represents an alkyl, alkoxy, or alkoxy-alkyl group, or under the proviso that at least
(i) R$^1$ represents —SO$_2$—NR$^3$R$^{3'}$, —CO—NR$^3$R$^{3'}$, —PO(OR$^{16}$)—R$^3$, —PS(OR$^{16}$)—R$^3$, —PO(OR$^{16}$)—OR$^3$, —SO$_2$—R$^3$, or —SO$_2$—OR$^3$; or
(ii) R$^{10}$ or R$^{11}$ is different from —H, or
(iii) R$^{10}$, R$^{11}$ and R$^{13}$ all represent —H, and R$^{12}$ does not represent —OH, or
(iv) R$^{12}$ and R$^{13}$ together do not represent =O,
then R$^{14}$ may represent —H; and n represents 0, 1, 2, 3, 4, 5 or 6, wherein, if X represents —NH— or —O—, then n is different from 0,
and all stereoisomers, pharmacologically acceptable salts and prodrugs thereof.

Accordingly, the present inventions relates to a compound of the general formula I, wherein —X-A-Y— together represent a group selected from
(a) —CO—NR$^4$—,
(b) —CO—O—,
(c) —CO—,
(d) —CO—NH—NR$^4$—,
(e) —NH—CO—NR$^4$—, preferably —NH—CO—NH—,
(f) —NH—CO—O—,
(g) —NH—CO—,
(h) —NH—CO—NH—SO$_2$—,
(i) —NH—SO$_2$—NR$^4$—, preferably —NH—SO$_2$—NH—,
(j) —NH—SO$_2$—O—,
(k) —NH—SO$_2$—
(l) —O—CO—NR$^4$—, preferably —O—CO—NH—,
(m) —O—CO—,
(n) —O—CO—NH—SO$_2$—NR$^4$—, and
(O) —O—;

n represents 1, 2, 3, 4, 5 or 6, or, if —X-A-Y— represents —CO—NR$^4$—, —CO—O—, —CO—, or —CO—NH—NR$^4$—, then n may also represent 0;

R$^1$ is selected from:
(a) —H,
(b) —(C$_1$-C$_6$)alkyl, which is optionally substituted with halogen, nitril, —OR$^6$, —SR$^6$, or —COOR$^6$; the number of said substituents being up to three for halogen, and up to two for any combination of said halogen, nitril, —OR$^6$, —SR$^6$, or —COOR$^6$ moieties,
(c) -phenyl, which is optionally substituted with halogen, nitril, —OR$^6$, —SR$^6$, —R$^6$, or —COOR$^6$, the number of said substituents being up to perhalo for halogen, and up to two for any combination of said halogen, nitril, —OR$^6$, —SR$^6$, —R$^6$ or —COOR$^6$ moieties,
(d) —(C$_1$-C$_4$)alkyl-phenyl, in which the alkyl portion is optionally substituted with up to three halogens; and the phenyl portion is optionally substituted with halogen, nitril, —OR$^6$, —SR$^6$, —R$^6$ or —COOR$^6$, the number of substituents on said phenyl portion being up to perhalo for halogen, and up to two for any combination of said halogen, nitril, —OR$^6$, —SR$^6$, —R$^6$ or —COOR$^6$ moieties,
(e) —SO$_2$—NR$^3$R$^{3'}$,
(f) —CO—NR$^3$R$^{3'}$,
(g) —PO(OR$^{16}$)—R$^3$,
(h) —PS(OR$^{16}$)—R$^3$,
(i) —PO(OR$^{16}$)—O—R$^3$,
(j) —SO$_2$—R$^3$, and
(k) —SO$_2$—O—R$^3$;

wherein
R$^6$ represents H, —(C$_1$-C$_4$)alkyl or halogenated —(C$_1$-C$_4$) alkyl;
R$^3$ and R$^{3'}$ are independently selected from H, alkyl, aryl and arylalkyl, or R$^3$ and R$^{3'}$ form together with the nitrogen atom, to which R$^3$ and R$^{3'}$ are attached, a heterocyclic 4-, 5-, 6-, 7- or 8-membered ring, which is optionally saturated, partly unsaturated, or aromatic; which optionally contains up to three additional heteroatoms selected from N, O and S, the number of additional N atoms being 0, 1, 2 or 3 and the number of O and S atoms each being 0, 1 or 2; and
R$^{16}$ represents —H, alkyl, or arylalkyl;
R$^2$ and R$^4$ are independently selected from:
(a) —H,
(b) optionally substituted alkyl,
(c) optionally substituted acyl, under the proviso that —X-A-Y— represent —CO—NH—NR$^4$—,
(d) optionally substituted aryl or arylalkyl,
(e) optionally substituted heteroaryl or heteroarylalkyl, and
(f) optionally substituted cycloheteroalkyl or cycloheteroalkyl-alkyl, or R$^2$ and R$^4$ form together with the nitrogen atom, to which R$^2$ and R$^4$ are attached, a heterocyclic 4-, 5-, 6-, 7- or 8-membered ring, which is optionally saturated, partly unsaturated, or aromatic; which optionally contains up to three additional heteroatoms selected from N, O and S, the number of additional N atoms being 0, 1, 2 or 3 and the number of O and S atoms each being 0, 1 or 2; and which ring is optionally part of a multiple condensed ring-system, wherein the ring or the ring-system is optionally substituted; the substituents $R^{10}$, $R^{11}$, $R^{12}$ and $R^{13}$ together with the carbon atoms, to which they are attached, form a structure

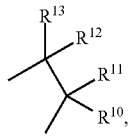

which is selected from the group of

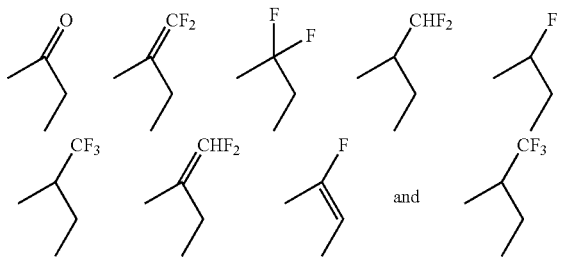

or, the substituents $R^{10}$, $R^{11}$, $R^{12}$ and $R^{13}$ together with the carbon atoms, to which they are attached, form a heterocyclic 5- or 6-membered ring, which is partly unsaturated or aromatic, which contains one, two or three heteroatoms independently selected from N, O and S, the number of N atoms being 0, 1, 2 or 3 and the number of O and S atoms each being 0, 1 or 2, wherein one heteroatom is directly attached to the C17 C-atom of the steroidal core; and which ring is optionally substituted with an alkyl group;

$R^{14}$ represents an alkyl, alkoxy, or alkoxy-alkyl group, or $R^{14}$ may also represent —H, under the proviso that at least (i) $R^1$ represents —SO$_2$—NR$^3$R$^{3'}$, —CO—NR$^3$R$^{3'}$, —PO(OR$^{16}$)—R$^3$, —PS(OR$^{16}$)—R$^3$, —PO(OR$^{16}$)—OR$^3$, —SO$_2$—R$^3$, or —SO$_2$—OR$^3$; or (ii)

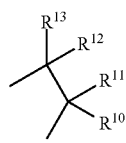

is different from

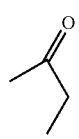

and all pharmacologically acceptable salts thereof.

In one embodiment, the present invention relates to a compound of the general formula I, which is an optically pure 15α enantiomer having the formula (II)

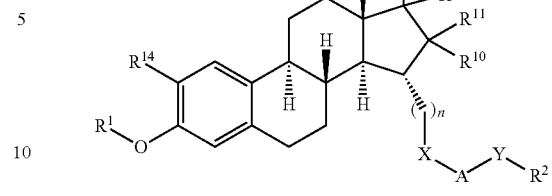

or a physiologically acceptable salt thereof. In a further embodiment, the present invention relates to the 15α enantiomer having formula (II), wherein n represents 1, 2, 3 or 4.

In another embodiment, the present invention relates to a compound of the general formula I, which is an optically pure 15β enantiomer having the formula (III)

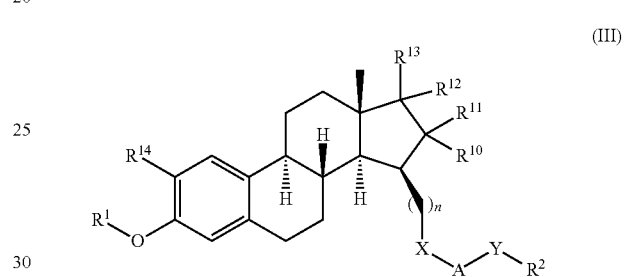

or a physiologically acceptable salt thereof. In a further embodiment, the present invention relates to the 15β enantiomer having formula (III), wherein n represents 2, 3, 4, or 5.

One embodiment of the present invention relates to compounds of formula I, wherein $R^1$ is selected from:
(a) —SO$_2$—NR$^3$R$^{3'}$,
(b) —CO—NR$^3$R$^{3'}$,
(c) —PO(OR$^{16}$)—R$^3$,
(d) —PS(OR$^{16}$)—R$^3$,
(e) —PO(OR$^{16}$)—O—R$^3$,
(f) —SO$_2$—R$^3$; and
(g) —SO$_2$—O—R$^3$;

wherein $R^3$ and $R^{3'}$ are independently selected from H, alkyl, aryl and arylalkyl, or $R^3$ and $R^{3'}$ form together with the nitrogen atom, to which $R^3$ and $R^{3'}$ are attached, a heterocyclic 4-, 5-, 6-, 7- or 8-membered ring, which is optionally saturated, partly unsaturated, or aromatic; which optionally contains up to three additional heteroatoms selected from N, O or S, the number of additional N atoms being 0, 1, 2 or 3 and the number of O and S atoms each being 0, 1 or 2; and $R^{16}$ represents —H, alkyl, or arylalkyl.

In a preferred subgroup of this embodiment, $R^{10}$ and $R^{11}$ both represent —H and $R^{12}$ and $R^{13}$ together represent =O; and/or $R^{14}$ represents —H, —(C$_1$-C$_8$)alkyl, —O—(C$_1$-C$_8$)alkyl, or —(C$_1$-C$_8$)alkyl-O—(C$_1$-C$_8$)alkyl.

In this embodiment, $R^3$ and $R^{3'}$ are preferably independently selected from —H, —(C$_1$-C$_8$)alkyl, phenyl and —(C$_1$-C$_4$)alkyl-phenyl, or $R^3$ and $R^{3'}$ together with the nitrogen atom, to which $R^3$ and $R^{3'}$ are attached, form a heterocyclic 4-, 5-, 6-, 7- or 8-membered ring, which is selected from the group consisting of

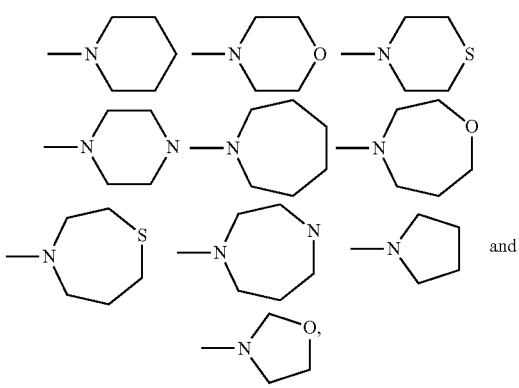

and
R$^{16}$ represents —H, —(C$_1$-C$_4$)alkyl, or —(C$_1$-C$_4$)alkyl-phenyl, preferably —H.

Particularly preferred compounds are those, wherein R$^1$ is selected from —SO$_2$—NR$^3$R$^{3'}$, —CO—NR$^3$R$^{3'}$, —PO(OR$^{16}$)—R$^3$, and —SO$_2$—R$^3$; preferably —SO$_2$—NR$^3$R$^{3'}$, wherein R$^3$ and R$^{3'}$ together with the nitrogen atom, to which R$^3$ and R$^{3'}$ are attached, form a heterocyclic ring selected from morpholine, thiomorpholine and piperazyl, and even more preferred —SO$_2$—NH$_2$. Preferably, those compounds carry a substituent R$^{14}$ representing —H.

One embodiment of the present invention relates to compounds of formula I, wherein R$^{14}$ represents an alkyl, alkoxy, or alkoxy-alkyl group.

In a further embodiment, the invention relates compounds of the general formula I, wherein
R$^1$ represents —H, (C$_1$-C$_4$)alkyl, or —(C$_1$-C$_4$)alkyl-phenyl;
R$^{10}$ and R$^{11}$ both represent —H and R$^{12}$ and R$^{13}$ together represent =O; and
R$^{14}$ represents —(C$_1$-C$_8$)alkyl, —O—(C$_1$-C$_8$)alkyl, or —(C$_1$-C$_8$)alkyl-O—(C$_1$-C$_8$)alkyl.

In this context, mostly preferred are compounds of the general formula I, wherein R$^{14}$ represents —(C$_1$-C$_4$)alkyl, —O—(C$_1$-C$_4$)alkyl, or —(C$_1$-C$_4$)alkyl-O—(C$_1$-C$_4$)alkyl, preferably ethyl, propyl, methoxyethyl, methoxy, ethoxy or methoxyethoxy, and R$^1$ is independently selected from —H, (C$_1$-C$_4$)alkyl, preferably methyl, and phenyl(C$_1$-C$_4$)alkyl, preferably benzyl, most preferred —H.

A further preferred embodiment of the present invention relates to compounds of the general formula I, wherein the substituents R$^{10}$, R$^{11}$, R$^{12}$ and R$^{13}$ together with the carbon atoms, to which they are attached, form a structure

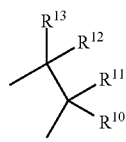

which is selected from the group of

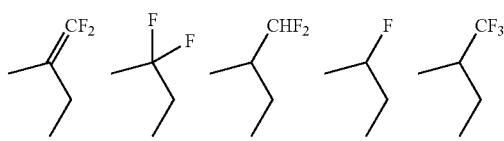

-continued

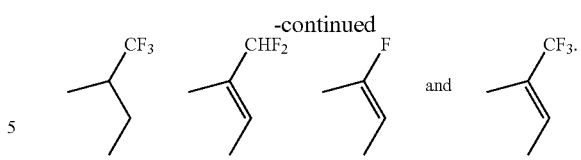

In a subgroup of this embodiment, additionally R$^{14}$ represents —H, —(C$_1$-C$_8$)alkyl, —O—(C$_1$-C$_8$)alkyl, or —(C$_1$-C$_8$)alkyl-O—(C$_1$-C$_8$)alkyl, and R$^1$ represents —H, (C$_1$-C$_4$)alkyl, or —(C$_1$-C$_4$)alkyl-phenyl;

In this context preferred compounds are those, wherein the substituents R$^{10}$, R$^{11}$, R$^{12}$ and R$^{13}$ together with the carbon atoms, to which they are attached, form a structure

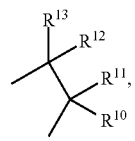

which is selected from the group of

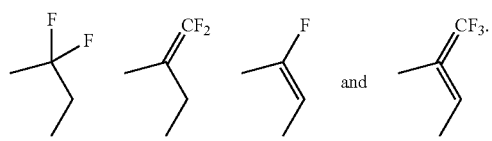

Preferably, those compounds carry substituents R$^1$ and R$^{14}$ which are each individually —H.

In an additional embodiment of the present invention, compounds of the general formula I are disclosed, wherein
the substituents R$^{10}$, R$^{11}$, R$^{12}$ and R$^{13}$ together with the carbon atoms, to which R$^{10}$, R$^{11}$, R$^{12}$ and R$^{13}$ are attached, form a heterocyclic 5- or 6-membered ring, which is partly unsaturated or aromatic, which contains one, two or three heteroatoms independently selected from N, O or S, the number of N atoms being 0, 1, 2 or 3 and the number of O and S atoms each being 0, 1 or 2, wherein one heteroatom is directly attached to the C17 C-atom of the steroidal core; and which ring is optionally substituted with an alkyl group; and In a subgroup of this embodiment, additionally R$^1$ represents —H, (C$_1$-C$_4$)alkyl, or —(C$_1$-C$_4$)alkyl-phenyl, and R$^{14}$ represents —H, —(C$_1$-C$_8$)alkyl, —O—(C$_1$-C$_8$)alkyl, or —(C$_1$-C$_8$)alkyl-O—(C$_1$-C$_8$)alkyl.

In this context, the present invention preferably relates to compounds, wherein the substituents R$^{10}$, R$^{11}$, R$^{12}$ and R$^{13}$ together with the carbon atoms, to which R$^{10}$, R$^{11}$, R$^{12}$ and R$^{13}$ are attached, form a heterocyclic 5- or 6-membered ring to provide a compound of one of the following formulas

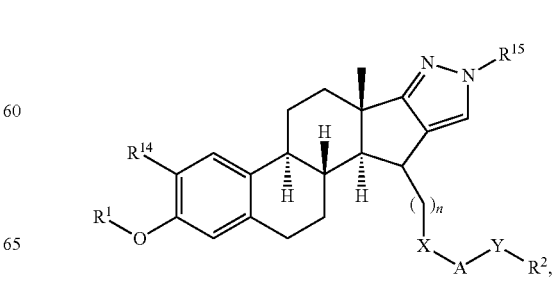

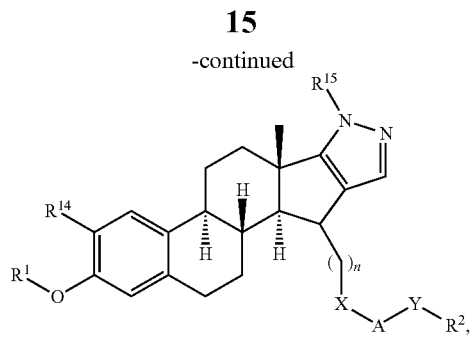

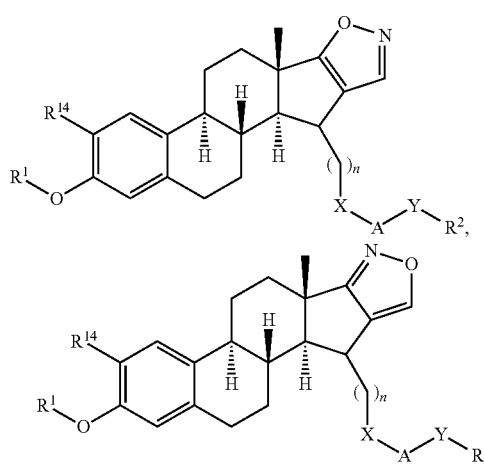

wherein R[15] represents —H or —(C[1]-C[4])alkyl. Preferably, those compounds carry substituents R[1] and R[14] each individually representing —H.

One embodiment of the present invention relates to compounds of formula I, wherein
R[1] is selected from:
(a) —H,
(b) —(C[1]-C[6])alkyl,
(c) -phenyl,
(d) —(C[1]-C[4])alkyl-phenyl,
(e) —SO[2]—NR[3]R[3'],
(f) —CO—NR[3]R[3'],
(g) —PO(OH)—R[3],
(h) —PS(OH)—R[3],
(i) —PO(OH)—O—R[3]
(j) —SO[2]—R[3], and
(k) —SO[2]—O—R[3];
wherein
R[6] represents H, —(C[1]-C[4])alkyl or halogenated —(C[1]-C[4])alkyl;
R[3] and R[3'] are independently selected from —H, —(C[1]-C[8])alkyl, phenyl and —(C[1]-C[4])alkyl-phenyl, or R[3] and R[3'] together with the nitrogen atom, to which R[3] and R[3'] are attached, form a heterocyclic 4-, 5-, 6-, 7- or 8-membered ring, which is selected from the group consisting of

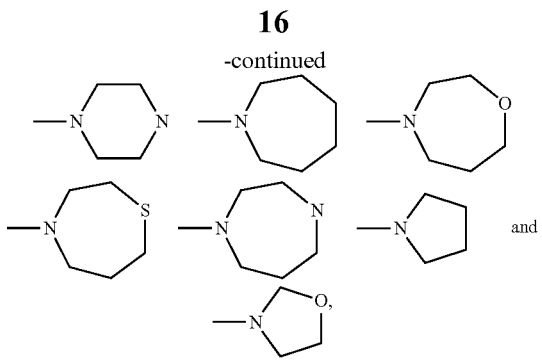

even more preferred selected from morpholine, thiomorpholine and piperazyl,
the substituents R[10], R[11], R[12] and R[13] together with the carbon atoms, to which they are attached, form a structure

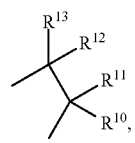

which is selected from the group of

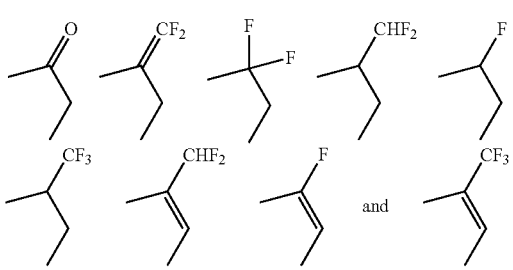

or, the substituents R[10], R[11], R[12] and R[13] together with the carbon atoms, to which R[10], R[11], R[12] and R[13] are attached, form a heterocyclic 5- or 6-membered ring to provide a compound of one of the following formulas

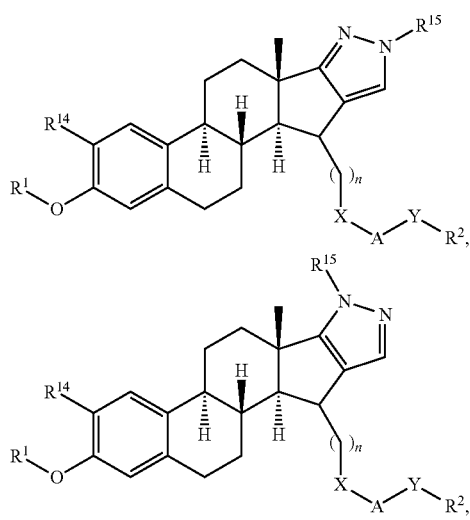

-continued

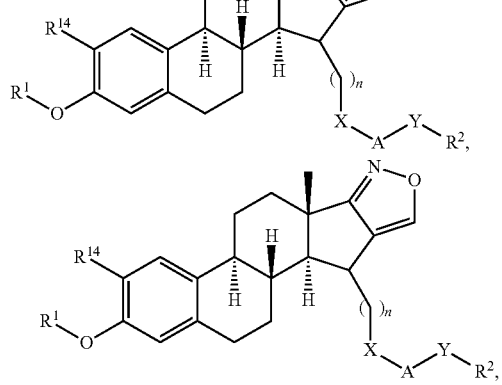

wherein $R^{15}$ represents —H or —($C_1$-$C_4$)alkyl; and $R^{14}$ represents —($C_1$-$C_4$)alkyl, —O—($C_1$-$C_4$)alkyl, or —($C_1$-$C_4$)alkyl-O—($C_1$-$C_4$)alkyl, or $R^{11}$ may also represent —H, under the proviso that at least
(i) $R^1$ represents —$SO_2$—$NR^3R^{3'}$, —CO—$NR^3R^{3'}$, —PO(OH)—$R^3$, —PS(OH)—$R^3$, —PO(OH)—$OR^3$, —$SO_2$—$R^3$, or —$SO_2$—$OR^3$; or

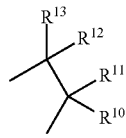

is different from

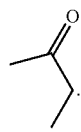

A further embodiment of the present invention relates to compounds of the formula (I), wherein
$R^1$ represents —H or —$SO_2$—$NH_2$,
the substituents $R^{10}$, $R^{11}$, $R^{12}$ and $R^{13}$ together with the carbon atoms, to which they are attached, form a structure

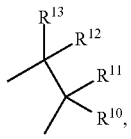

which is selected from the group of

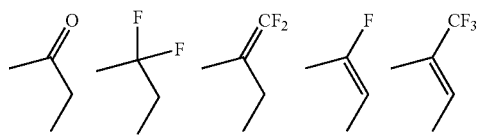

-continued

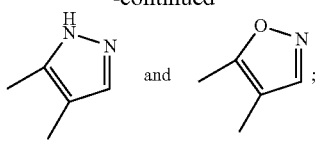

and
$R^{14}$ represents —H, —($C_1$-$C_4$)alkyl, —O—($C_1$-$C_4$)alkyl, or —($C_1$-$C_4$)alkyl-O—($C_1$-$C_4$)alkyl.
$R^{11}$ in particular may represent —H, when at least
(i) $R^1$ represents —$SO_2$—$NH_2$, or
(ii)

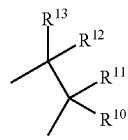

is different from

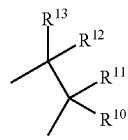

A preferred embodiment of the present invention relates to compounds of formula I, wherein
$R^2$ and $R^4$ are independently selected from:
(a) —H, wherein if —X-A-Y— together represents —CO—O— or —CO—, then $R^2$ is different from —H,
(b) —($C_1$-$C_{12}$)alkyl, optionally substituted with up to five substituents independently selected from the group consisting of halogen, hydroxyl, thiol, nitrile, alkoxy, aryloxy, arylalkyloxy, amino, amido, alkylthio, arylthio, arylalkylthio, sulfamoyl, sulfonamide, acyl, carboxyl, acylamino,
aryl, which aryl is optionally substituted with up to three substituents independently selected from the group consisting of halogen, hydroxyl, ($C_1$-$C_6$)alkoxy, ($C_1$-$C_6$)alkyl, halogenated ($C_1$-$C_6$)alkyl, halogenated ($C_1$-$C_6$)alkoxy, carboxyl-($C_1$-$C_6$)alkyl, thiol, nitrile, sulfamoyl, sulfonamide, carboxyl, aryloxy, arylalkyloxy, ($C_1$-$C_6$)alkylthio, arylthio, arylalkylthio, amino, amido, acyl, acylamino and heteroaryl; or which aryl is optionally substituted by two groups which are attached to adjacent carbon atoms and are combined into a saturated or partly unsaturated cyclic 5, 6, 7, or 8-membered ring system, optionally containing up to three heteroatoms selected from N, O and S, the number of N atoms being 0, 1, 2 or 3 and the number of O and S atoms each being being 0, 1 or 2;
heteroaryl, which heteroaryl is optionally substituted with up to three substituents independently selected from the group consisting of halogen, hydroxyl, ($C_1$-$C_6$)alkoxy, ($C_1$-$C_6$)alkyl, halogenated ($C_1$-$C_6$)alkyl, halogenated ($C_1$-$C_6$)alkoxy, carboxyl-($C_1$-$C_6$)alkyl, thiol, nitrile, sulfamoyl, sulfonamide, carboxyl, aryloxy, arylalkyloxy, ($C_1$-$C_6$)alkylthio, arylthio, arylalkylthio, amino, amido, acyl, acylamino, aryl-($C_1$-$C_4$)-alkyl and aryl;

whereby each aryl group is optionally substituted with up to three substituents independently selected from the group consisting of hydroxyl, halogen, $(C_1-C_6)$alkoxy, $(C_1-C_6)$alkyl, halogenated $(C_1-C_6)$alkyl and halogenated $(C_1-C_6)$ alkoxy; and cycloheteroalkyl, which cycloheteroalkyl group is optionally substituted with up to three substituents independently selected from the group consisting of oxo, $(C_1-C_8)$-alkyl, aryl, aryl-$(C_1-C_4)$-alkyl, hydroxyl, $(C_1-C_6)$alkoxy, carboxyl-$(C_1-C_6)$alkyl, thiol, nitrile, sulfamoyl, sulfonamide, carboxyl, aryloxy, arylalkyloxy, $(C_1-C_6)$alkylthio, arylthio, arylalkylthio, amino, amido, acyl, and acylamino, whereby each aryl group is optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, and halogenated $(C_1-C_4)$-alkoxy);

(c) acyl —(C=O)—R', wherein R' represents hydrogen, $(C_1-C_4)$alkyl, aryl, or aryl-$(C_1-C_4)$alkyl, or heteroaryl-$(C_1-C_4)$alkyl;

which aryl or aryl-$(C_1-C_4)$alkyl is optionally substituted in the aryl, preferably phenyl, moiety with up to three substituents independently selected from the group consisting of hydroxyl, halogen, $(C_1-C_4)$alkoxy, $(C_1-C_4)$-alkyl or halogenated $(C_1-C_4)$alkyl;

(d) aryl, which aryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, carboxyl-$(C_1-C_6)$alkyl, thiol, nitrile, nitro, sulfamoyl, sulfonamide, carboxyl, aryloxy, arylalkyloxy, $(C_1-C_6)$alkylsulfonyl, arylsulfonyl, $(C_1-C_6)$alkylthio, arylthio, arylalkylthio, amino, amido, acyl, acylamino and heteroaryl; or which aryl is optionally substituted by two groups which are attached to adjacent carbon atoms and are combined into a saturated or partly unsaturated cyclic 5, 6, 7, or 8-membered ring system, optionally containing up to three heteroatoms selected from N, O and S, the number of N atoms being 0, 1, 2 or 3 and the number of O and S atoms each being 0, 1 or 2;

(e) heteroaryl, which heteroaryl is optionally substituted with up to three substituents independently selected from the group consisting of halogen, hydroxyl, $(C_1-C_6)$ alkoxy, $(C_1-C_6)$alkyl, halogenated $(C_1-C_6)$alkyl, halogenated $(C_1-C_6)$alkoxy, carboxyl-$(C_1-C_6)$alkyl, thiol, nitrile, sulfamoyl, sulfonamide, arylsulfoxy, carboxyl, aryloxy, arylalkyloxy, $(C_1-C_6)$alkylsulfonyl, arylsulfonyl, $(C_1-C_6)$alkylthio, arylthio, arylalkylthio, amino, amido, acyl, acylamino, aryl-$(C_1-C_4)$-alkyl and aryl, whereby each aryl group is optionally substituted with up to three substituents independently selected from the group consisting of hydroxyl, halogen, $(C_1-C_6)$alkoxy, $(C_1-C_6)$alkyl, halogenated $(C_1-C_6)$alkyl and halogenated $(C_1-C_6)$ alkoxy; or (f) cycloheteroalkyl, which cycloheteroalkyl is optionally substituted with up to three substituents independently selected from the group consisting of oxo, $(C_1-C_{14})$-alkyl, aryl, aryl-$(C_1-C_4)$-alkyl, hydroxyl, $(C_1-C_6)$alkoxy, carboxyl-$(C_1-C_6)$alkyl, thiol, nitrile, sulfamoyl, sulfonamide, carboxyl, aryloxy, arylalkyloxy, $(C_1-C_6)$alkylthio, arylthio, arylalkylthio, amino, amido, acyl, and acylamino, whereby each aryl group is optionally further substituted with up to three substituents independently selected from the group consisting of hydroxyl, halogen, $(C_1-C_4)$-alkyl, $(C_1-C_4)$-alkoxy, halogenated $(C_1-C_4)$-alkyl, and halogenated $(C_1-C_4)$-alkoxy;

or wherein, $R^2$ and $R^4$ form together with the nitrogen atom, to which $R^2$ and $R^4$ are attached, a heterocyclic 4-, 5-, 6-, 7- or 8-membered ring, which is optionally saturated or partly unsaturated; which optionally contains up to three additional heteroatoms selected from N, O and S, the number of additional N atoms being 0, 1, 2 or 3 and the number of O and S atoms each being 0, 1 or 2; and which ring is optionally part of a multiple condensed ring-system, wherein the ring or the ring-system is optionally substituted (i) with up to three substituents independently selected from the group consisting of $(C_1-C_8)$-alkyl, halogen, hydroxyl, carboxyl, thiol, nitrile, $(C_1-C_6)$-alkoxy, carboxyl-$(C_1-C_6)$alkyl, aryloxy, arylalkyloxy, amino, amido, alkylthio, arylthio, arylalkylthio, sulfamoyl, sulfonamide, aryl, aryl-$(C_1-C_4)$-alkyl, heteroaryl, and cycloheteroalkyl, wherein the $(C_1-C_8)$-alkyl group is optionally substituted with up to three substituents independently selected among hydroxyl, halogen, $(C_1-C_4)$-alkoxy, or halogenated $(C_1-C_4)$-alkoxy, whereby the alkyl-chain of the $(C_1-C_4)$-alkoxy moiety is optionally substituted with hydroxyl;

wherein the aryl group or aryl moiety is optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, halogenated $(C_1-C_4)$-alkoxy and carboxyl-$(C_1-C_6)$alkyl, or wherein the aryl moiety is optionally substituted by two groups which are attached to adjacent carbon atoms and are combined into a saturated or partly unsaturated cyclic 5, 6, 7, or 8 membered ring system, optionally containing up to three heteroatoms selected from N, O and S, the number of N atoms being 0, 1, 2 or 3 and the number of O and S atoms each being 0, 1 or 2;

wherein the heteroaryl group is optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, halogenated $(C_1-C_4)$-alkoxy) and carboxyl-$(C_1-C_6)$alkyl;

wherein the cycloheteroalkyl is optionally substituted with up to three substituents independently selected from the group consisting of oxo, $(C_1-C_8)$-alkyl, aryl, aryl-$(C_1-C_4)$-alkyl, hydroxyl, $(C_1-C_6)$alkoxy, carboxyl-$(C_1-C_6)$alkyl, and carboxyl, whereby each aryl group is optionally further substituted with up to three substituents independently selected from the group consisting of hydroxyl, halogen, $(C_1-C_4)$-alkyl, $(C_1-C_4)$-alkoxy, halogenated $(C_1-C_4)$-alkyl, and halogenated $(C_1-C_4)$-alkoxy); or (ii) by two groups which are attached to the same carbon atom and are combined into a saturated or partly unsaturated cyclic 4, 5, 6, 7, or 8-membered ring system, optionally containing up to three heteroatoms selected from N, O and S, the number of N atoms being 0, 1, 2 or 3 and the number of O and S atoms each being 0, 1 or 2, whereby the cyclic ring system is optionally substituted by up to two substituents independently selected from oxo, $(C_1-C_6)$-alkyl, aryl and aryl-$(C_1-C_4)$-alkyl;
and wherein n represents
(a) 1, 2, 3, 4, 5 or 6, if —X-A-Y— together represent —NH—CO—NH—, —NH—CO—O—, —NH—CO—, —NH—CO—NH—SO$_2$—, —NH—SO$_2$—NH—, —NH—SO$_2$—O—, —NH—SO$_2$—, —O—CO—NH—, —O—CO—, —O—CO—NH—SO$_2$—NR$^4$—, or —O—, or
(b) 0, 1, 2, 3, 4, or 5, if —X-A-Y— together represent —CO—NR$^4$—, —CO—O—, —CO—, or —CO—NH—NR$^4$—.

In one preferred embodiment of the present invention, the residues R$^2$ and R$^4$ in the compounds of the general formula I may independently represent —H, wherein, if —X-A-Y— together represents —CO—O— or —CO—, then R$^2$ is different from —H.

In a further embodiment of the present invention relates to compounds of formula I, wherein
R$^2$ and R$^4$ are independently selected from:
(a) —$(C_1-C_{12})$alkyl, optionally substituted with up to five substituents independently selected from the group consisting of halogen, hydroxyl, nitrile, —O—R$^7$; —O—Ar$^1$, —O—$(C_1-C_4)$alkyl-Ar$^1$, alkylamino, alkylamido, —S—R$^7$, —S—Ar$^1$, —S—$(C_1-C_4)$alkyl-Ar$^1$, —(C═O)—OR$^8$, aryl, heteroaryl, and cycloheteroalkyl,
wherein the aryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, —$(C_1-C_6)$alkyl-(C═O)—OR$^8$, nitrile, sulfamoyl, —(C═O)—OR$^8$, —O—Ar$^1$, —O—$(C_1-C_4)$alkyl-Ar$^1$, $(C_1-C_6)$alkylthio, —S—Ar$^1$, —S—$(C_1-C_4)$alkyl-Ar$^1$, alkylamino, and alkylamido; or
wherein the aryl is optionally substituted by two groups which are attached to adjacent carbon atoms and are combined into a saturated cyclic 5 or 6 membered ring system, optionally containing up to three heteroatoms selected from N or O, the number of N atoms being 0, 1, 2 or 3 and the number of O atoms each being 0, 1, or 2;
wherein the heteroaryl is optionally substituted with up to three substituents independently selected from the group consisting of halogen, hydroxyl, $(C_1-C_6)$alkoxy, $(C_1-C_6)$-alkyl, halogenated $(C1-C_6)$alkyl, halogenated $(C_1-C_6)$alkoxy, —$(C_1-C_6)$alkyl-(C═O)—OR$^8$, nitrile, sulfamoyl, —(C═O)—OR$^8$, —O—Ar$^1$, —O—$(C_1-C_4)$alkyl-Ar$^1$, $(C_1-C_6)$-alkylthio, —S—Ar$^1$, —S—$(C_1-C_4)$alkyl-Ar$^1$, alkylamino, alkylamido, —$(C_1-C_4)$alkyl-Ar$^1$ and Ar$^1$; and
wherein the cycloheteroalkyl group is optionally substituted with up to three substituents independently selected from the group consisting of oxo, $(C_1-C_8)$-alkyl, Ar$^1$, —$(C_1-C_4)$-alkyl-Ar$^1$, hydroxyl, $(C_1-C_6)$ alkoxy, —$(C_1-C_6)$alkyl-(C═O)—OR$^8$, nitrile, —(C═O)—OR$^8$, —O—Ar$^1$, —O—$(C_1-C_4)$alkyl-Ar$^1$, $(C_1-C_6)$alkylthio, —S—Ar$^1$, —S—$(C_1-C_4)$alkyl-Ar$^1$, alkylamino and alkylamido;
(b) aryl,
which aryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, —$(C_1-C_6)$alkyl-(C═O)—OR$^8$, nitro, nitrile, sulfamoyl, —(C═O)—OR$^8$, —(C═O)—R$^8$, —O—Ar$^1$, —O—$(C_1-C_4)$alkyl-Ar$^1$, $(C_1-C_6)$— alkylthio, —S—Ar$^1$, —S—$(C_1-C_4)$alkyl-Ar$^1$, $(C_1-C_6)$ alkylsulfonyl, —SO$_2$—Ar$^1$, alkylamino, alkylamide, —NH—CO—R$^8$, Ar$^1$ and heteroaryl; or
which aryl is optionally substituted by two groups which are attached to adjacent carbon atoms and are combined into a saturated cyclic 5 or 6 membered ring system, optionally containing up to three heteroatoms selected from N and O, the number of N atoms being 0, 1, 2 or 3 and the number of O atoms being 0, 1 or 2;
(c) heteroaryl,
which heteroaryl is optionally substituted with up to three substituents independently selected from the group consisting of halogen, hydroxyl, $(C_1-C_6)$ alkoxy, $(C_1-C_6)$alkyl, halogenated $(C_1-C_6)$ alkyl, halogenated $(C_1-C_6)$alkoxy, —$(C_1-C_6)$alkyl-(C═O)—OR$^8$, nitrile, sulfamoyl, —(C═O)—OR$^8$, —O—Ar$^1$, —O—$(C_1-C_4)$alkyl-Ar$^1$, $(C_1-C_6)$alkylthio, —S—Ar$^1$, —S—$(C_1-C_4)$alkyl-Ar$^1$, $(C_1-C_6)$ alkylsulfonyl, —SO$_2$—Ar$^1$, alkylamino, alkylamido, —$(C_1-C_4)$alkyl-Ar$^1$ and Ar$^1$; or
(d) cycloheteroalkyl,
which cycloheteroalkyl group is optionally substituted with up to three substituents independently selected from the group consisting of oxo, $(C_1-C_E)$-alkyl, Ar$^1$, —$(C_1-C_4)$alkyl-Ar$^1$, hydroxyl, $(C_1-C_6)$alkoxy, —$(C_1-C_6)$alkyl-(C═O)—OR$^8$, nitrile, —(C═O)—OR$^8$, —O—Ar$^1$, —O—$(C_1-C_4)$alkyl-Ar$^1$, $(C_1-C_6)$ alkylthio, —S—Ar$^1$, —S—$(C_1-C_4)$alkyl-Ar$^1$, alkylamino and alkylamido;
wherein
R$^7$ represents $(C_1-C_6)$alkyl, optionally substituted with up to three hydroxy groups in the alkyl chain or halogenated $(C_1-C_6)$alkyl,
R$^8$ represents hydrogen, $(C_1-C_4)$alkyl, phenyl, or $(C_1-C_4)$ alkyl-phenyl,
wherein the phenyl-moiety is optionally substituted with up to three substituents independently selected from the group consisting of hydroxyl, halogen, $(C_1-C_4)$alkoxy, $(C_1-C_4)$-alkyl, halogenated $(C_1-C_4)$alkyl and halogenated $(C_1-C_4)$ alkoxy; and
Ar$^1$ represents phenyl or naphthyl, which are optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, or halogenated $(C_1-C_4)$-alkoxy;
or wherein the ring or ringsystem formed by R$^2$ and R$^4$ together with the nitrogen atom, to which R$^2$ and R$^4$ are attached, is selected from the group consisting of

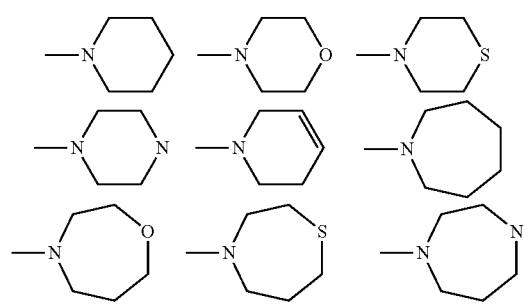

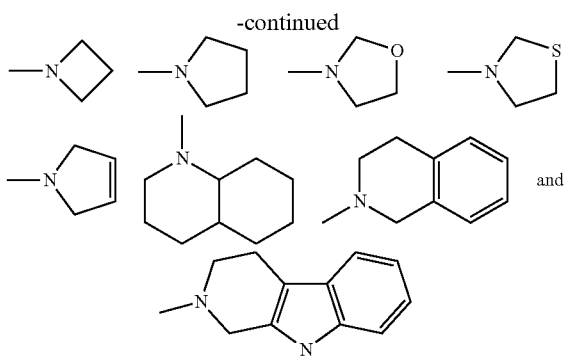

wherein the ring or the ring-system is optionally substituted (i) with up to three substituents independently selected from the group consisting of $(C_1-C_8)$-alkyl, oxo, hydroxyl, $(C_1-C_6)$alkoxy, $-(C_1-C_6)$alkyl-$(C=O)-$OR$^{8'}$, nitrile, $-(C=O)-OR^{8'}$, $-O-Ar^2$, $-O-(C_1-C_4)$alkyl-Ar$^2$, $(C_1-C_6)$alkylthio, alkylamino, alkylamido, aryl, aryl-$(C_1-C_4)$alkyl, heteroaryl, and cycloheteroalkyl, wherein the aryl and aryl-$(C_1-C_4)$alkyl group are optionally substituted in the aryl moiety with up to three substituents independently selected from the group consisting of hydroxyl, halogen, $(C_1-C_4)$-alkyl, $(C_1-C_4)$-alkoxy, halogenated $(C_1-C_4)$-alkyl, halogenated $(C_1-C_4)$-alkoxy and carboxyl-$(C_1-C_4)$alkyl, or wherein the aryl moiety is optionally substituted by two groups which are attached to adjacent carbon atoms and are combined into a saturated or partly unsaturated cyclic 5, 6, 7, or 8 membered ring system, optionally containing up to three heteroatoms selected from N, O and S, the number of N atoms being 0, 1, 2 or 3 and the number of O and S atoms each being 0, 1 or 2; and wherein the $(C_1-C_8)$-alkyl group is optionally substituted with up to three substituents independently selected among hydroxyl, halogen, halogenated $(C_1-C_4)$-alkoxy or $(C_1-C_4)$-alkoxy, whereby the alkyl-chain of the $(C_1-C_4)$-alkoxy moiety is optionally substituted with up to three hydroxyl;

wherein the heteroaryl is optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, halogenated $(C_1-C_4)$-alkoxy) and carboxyl-$(C_1-C_6)$alkyl; and wherein the cycloheteroalkyl is optionally substituted with up to three substituents independently selected from the group consisting of oxo, $(C_1-C_8)$-alkyl, hydroxyl, $(C_1-C_6)$alkoxy, $-(C=O)-OR^9$, and $-(C_1-C_6)$alkyl-$(C=O)-OR^9$; or (ii) by two groups which are attached to the same carbon atom and are combined into a saturated or partly unsaturated cyclic 4, 5, 6, 7, or 8-membered ring system, optionally containing up to three heteroatoms selected from N, O and S, the number of N atoms being 0, 1, 2 or-3 and the number of O and S atoms each being 0, 1 or 2, whereby the cyclic ring system is optionally substituted by up to three substitutents independently selected from oxo, $(C_1-C_6)$-alkyl, aryl and aryl-$(C_1-C_4)$-alkyl.

wherein

Ar$^2$ represents phenyl or naphthyl, which are optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, or halogenated $(C_1-C_4)$-alkoxy R$^9$ represents hydrogen, $(C_1-C_4)$alkyl, phenyl, or $(C_1-C_4)$alkyl-phenyl; whereby the phenyl is optionally substituted with up to three substituents independently selected from the group consisting of hydroxyl, halogen, $(C_1-C_4)$alkoxy, $(C_1-C_4)$-alkyl, halogenated $(C_1-C_4)$alkyl and halogenated $(C_1-C_4)$alkoxy.

In a further embodiment of the present invention relates to compounds of formula I, wherein R$^2$ and R$^4$ are independently selected from:

(a) an alkyl group selected from (i) $-(C_1-C_8)$alkyl, optionally substituted with substituents independently selected from the group consisting of hydroxyl, nitrile, $-O-R^{7'}$; $-O$-phenyl, $-O-(C_1-C_4)$alkyl-phenyl, alkylamino, alkylamido, preferably carbamoyl, $-S-R^{7'}$, and $-(C=O)-OR^{8'}$, the number of substituents on said alkyl portion being up to five for hydroxyl and one, two or three for any combination of said other substituents;

(ii) $-(C_1-C_4)$alkyl, optionally substituted with one or two substituents independently selected from the group consisting of aryl, heteroaryl, and cycloheteroalkyl, wherein the aryl is preferably selected among phenyl, naphthyl, indanyl, indenyl, and 1,2,3,4-tetrahydronaphthalen-1-yl, more preferably the aryl is phenyl or naphthyl, and which aryl is optionally substituted with halogen, hydroxyl, $(C_1-C_6)$alkoxy, $(C_1-C_6)$alkyl, halogenated $(C_1-C_4)$alkyl, halogenated $(C_1-C_4)$alkoxy, sulfamoyl, or alkylamide, preferably carbamoyl, the number of substituents on said aryl portion being up to three for halogen and one or two for any combination of said other substituents; or which aryl is optionally substituted by two groups which are attached to adjacent carbon atoms and are combined into a saturated cyclic 5 or 6 membered ring system, optionally containing up to three heteroatoms selected from N and O, the number of N atoms being 0, 1, 2 or 3 and the number of 0 atoms being 0, 1 or 2, preferably a [1,3]-dioxol group;

wherein the heteroaryl is preferably selected among pyrrolyl, thienyl, furyl, imidazolyl, thiazolyl, isothiazolyl, oxazolyl, isoxazolyl, pyrazolyl, pyridinyl, pyrimidinyl, pyrazinyl, pyridazinyl, benzothiazolyl, indolyl, quinolinyl, isoquinolinyl, benzoimidazolyl, benzofuran and benzo[b]thiophene, more preferably the heteroaryl is thienyl, furyl, imidazolyl, pyridinyl, indolyl, or benzoimidazolyl, and which heteroaryl is optionally substituted with one or two, preferably one substituent independently selected from the group consisting of $(C_1-C_4)$alkoxy, preferably methoxy, $(C_1-C_4)$alkyl, preferably methyl, and halogenated $(C_1-C_4)$-alkyl;

wherein the cycloheteroalkyl group is preferably selected from the group consisting of pyrrolidinyl, tetrahydrofuranyl, dihydro-1H-pyrrolyl, tetrahydrothiophenyl, tetrahydropyridinyl, azetidinyl, thiazolidinyl, oxazolidinyl, piperidinyl, morpholinyl, thiomorpholinyl, piperazinyl, 1,3-dihydrobenzoimidazolyl, azepanyl, diazepanyl, oxazepanyl and thiazepanyl, preferably the cycloheteroalkyl group is piperidinyl or morpholinyl; and which cycloheteroalkyl is optionally substituted with up to three substituents independently selected from the group consisting of oxo, hydroxyl, $(C_1-C_4)$-alkyl, phenyl, —$(C_1-C_4)$alkylphenyl, preferably benzyl, —(C=O)—O—$(C_1-C_4)$alkyl, and alkylamino, preferably the cycloheteroalkyl moiety is not substituted;

(iii) -cyclo$(C_3-C_8)$alkyl, optionally substituted with hydroxyl;

(iv) —$(C_1-C_4)$alkyl-cyclo$(C_3-C_8)$alkyl, optionally substituted with hydroxyl;

(v) a bicyclic ring system of 6 to 10 carbon atoms selected from the group consisting of Bicyclo[2.1.1]hexyl, Bicyclo[2.2.1]heptyl, Bicyclo[3.2.1]octyl, Bicyclo[2.2.2]octyl, Bicyclo[3.2.2]nonanyl, Bicydo [3.3.1]nonanyl, and Bicyclo [3.3.2]decanyl; and (vi) a fused ring system of up to 10 carbon atoms, preferably adamantyl;

(b) aryl, wherein the aryl is preferably selected among phenyl, naphthyl, indanyl, indenyl, and 1,2,3,4-tetrahydronaphthalen-1-yl, and which aryl is optionally substituted with substituents independently selected from the group consisting of hydroxyl; halogen, preferably fluorine or chlorine; $(C_1-C_6)$alkoxy, preferably $(C_1-C_2)$alkoxy; $(C_1-C_6)$alkyl, preferably $(C_1-C_4)$alkyl; halogenated $(C_1-C_6)$alkyl, preferably halogenated $(C_1-C_4)$alkyl, more preferably trifluoromethyl; halogenated $(C_1-C_6)$alkoxy, preferably halogenated $(C_1-C_4)$alkoxy, more preferably trifluoromethoxy; —$(C_1-C_4)$alkyl-(C=O)—$OR^{8'}$; nitrile, nitro, sulfamoyl, —(C=O)—$R^{8'}$, —(C=O)—$OR^{8'}$, —NH—(C=O)—$R^{8'}$, —S—$R^{8'}$, —$SO_2$—$R^{8'}$, alkylamino, alkylamido, preferably carbamoyl, phenyl, and a further heteroaryl group, optionally substituted with $(C_1-C_4)$alkyl, preferably 6-methyl-benzothiazolyl; the number of substituents on said aryl portion being up to three for halogen, and one or two for any combination of said other moieties; or which aryl is optionally substituted by two groups which are attached to adjacent carbon atoms and are combined into a saturated cyclic 5 or 6-membered ring system, optionally containing up to three heteroatoms selected from N and O, the number of N atoms being 0, 1, 2 or 3 and the number of O atoms being 0, 1 or 2, preferably a [1,3]-dioxol group;

(c) heteroaryl, wherein the heteroaryl is preferably selected among pyrrolyl, thienyl, furyl, imidazolyl, thiazolyl, isothiazolyl, oxazolyl, isoxazolyl, pyrazolyl, pyridinyl, pyrimidinyl, pyrazinyl, pyridazinyl, benzothiazolyl, indolyl, quinolinyl, isoquinolinyl, benzoimidazolyl, benzofuran and benzo[b]thiophene; more preferably heteroaryl is furyl, thiazolyl, pyrazolyl, pyridinyl, quinolinyl, or benzo[b]thiophene, and which heteroaryl is optionally substituted with up to three, preferably up to two substituents independently selected from the group consisting of halogen, $(C_1-C_4)$-alkyl, hydroxyl, halogenated $(C_1-C_4)$alkyl, —$(C_1-C_4)$alkoxy, —$(C_1-C_4)$alkyl-(C=O)—$OR^{8'}$, —O—$Ar^{1'}$, —$SO_2$—$Ar^{1'}$, phenyl, —$(C_1-C_4)$alkyl-phenyl, nitrile, alkylamino, and alkylamido, preferably carbamoyl; preferably selected from the group consisting of halogen, $(C_1-C_4)$alkyl, halogenated $(C_1-C_4)$alkyl, —$(C_1-C_4)$alkyl-(C=O)—$OR^{8'}$, —O—$Ar^{1'}$, —$SO_2$—$Ar^{1'}$ and phenyl; or (d) cycloheteroalkyl, wherein the cycloheteroalkyl is preferably selected among pyrrolidinyl, tetrahydrofuranyl, dihydro-1H-pyrrolyl, tetrahydrothiophenyl, tetrahydropyridinyl, azetidinyl, thiazolidinyl, oxazolidinyl, piperidinyl, morpholinyl, thiomorpholinyl, piperazinyl, 1,3-dihydro-benzoimidazolyl, azepanyl, diazepanyl, oxazepanyl and thiazepanyl; more preferably cycloheteroalkyl is pyrrolidinyl, morpholinyl, tetrahydrofuranyl, piperidinyl or azepanyl, and which cycloheteroalkyl is optionally substituted with up to three, preferably one or two substituents independently selected from the group consisting of oxo, $(C_1-C_4)$alkyl, phenyl, —$(C_1-C_4)$alkyl-phenyl, hydroxyl, $(C_1-C_4)$alkoxy, and —$(C_1-C_4)$alkyl-(C=O)—$OR^{8'}$; preferably selected from the group consisting of oxo, $(C_1-C_4)$alkyl, preferably methyl, and $(C_1-C_4)$alkyl-phenyl, preferably benzyl;

wherein $R^{7'}$ represents $(C_1-C_4)$alkyl, preferably $(C_1-C_2)$alkyl, optionally substituted with one or two hydroxyl groups, $R^{8'}$ represents hydrogen, $(C_1-C_4)$alkyl, preferably methyl, or $(C_1-C_2)$alkyl-phenyl, preferably benzyl; and $Ar^{1'}$ represents phenyl optionally substituted with up to three halogen atoms;

or wherein the ring or ringsystem formed by $R^2$ and $R^4$ together with the nitrogen atom, to which $R^2$ and $R^4$ are attached, is selected from the group consisting of

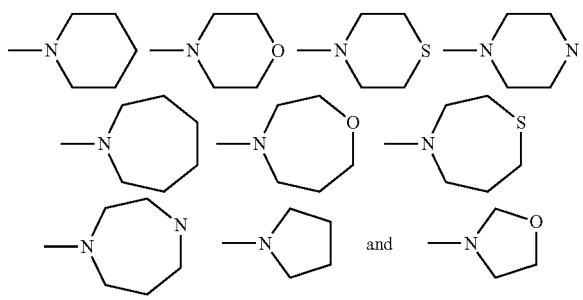

wherein the ring or the ring-system is optionally substituted
(i) with up to three substituents independently selected from the group consisting of
(a) hydroxyl,
(b) oxo,
(c) $(C_1-C_4)$-alkyl, optionally substituted with up to two hydroxyl and/or $(C_1-C_4)$-alkoxy groups, whereby the alkyl-chain of the $(C_1-C_4)$-alkoxy moiety may optionally be further substituted with one or two, preferably one hydroxyl group;
(d) cyclo$(C_3-C_8)$alkyl;
(e) —(C=O)—O—$(C_1-C_4)$-alkyl;
(f) phenyl, optionally substituted with halogen, $(C_1-C_4)$-alkyl, preferably methyl, $(C_1-C_4)$-alkoxy, or halogenated $(C_1-C_4)$-alkyl, preferably halogenated methyl, the number of said substituents on the phenyl moiety being up to three for halogen, and one or two for any combination of said other substituents;
(g) phenyl-$(C_1-C_4)$alkyl, preferably benzyl, optionally substituted in the phenyl group by up three halogen, or optionally substituted in the phenyl group by two groups which are attached to adjacent carbon atoms and are combined into a saturated or partly unsaturated cyclic 5 or 6-membered ring system, optionally containing up to two O atoms;
(h) alkylamide, preferably carbamoyl;
(i) heteroaryl, wherein the heteroaryl is preferably selected from the group consisting of pyridinyl, furyl, thienyl, thiazolyl, imidazolyl, pyrazolyl, indolyl, quinolinyl, benzoimidazolyl or benzo[b]thiophene, more preferably the heteroaryl is pyridinyl; and
(j) cycloheteroalkyl, wherein the cycloheteroalkyl is preferably selected from the group consisting of pyrrolidinyl, 1,3-dihydro-benzoimidazolyl, morpholinyl, tetrahydrofuranyl, piperidinyl and azepanyl; more preferably the cycloheteroalkyl group is pyrrolidinyl or 1,3-dihydro-benzoimidazolyl, which cycloheteroalkyl group is optionally substituted with oxo; or
(ii) by two groups which are attached to the same carbon atom and are combined into a saturated or partly unsaturated cyclic 5, 6, or 7-membered ring system, optionally containing up to three heteroatoms selected from N and O, the number of N atoms being 0, 1, 2 or 3 and the number of O atoms being 0, 1 or 2,
whereby the cyclic ring system may optionally be further substituted with up to two substituents independently selected from oxo and phenyl.

In one embodiment, the invention relates to a compound of the following formula XLII

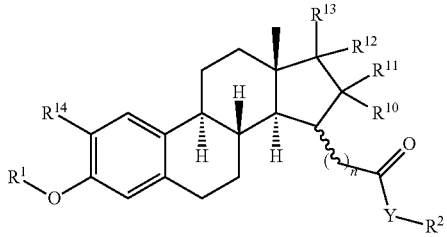

(XLII)

wherein
Y represents —NR$^4$—, —O—, a bond or —NH—NR$^4$—, i.e. compounds of formula I, wherein —X-A-Y— together represent a group selected from
(a) —CO—NR$^4$—,
(b) —CO—NR$^4$—,
(c) —CO—, and
(d) —CO—NH—NR$^4$—,
the preferred meanings of R$^1$, R$^{10}$, R$^{11}$, R$^{12}$, R$^{13}$ and R$^{14}$ are as indicated above, and
n represents 0, 1, 2, 3, 4, or 5.

In one embodiment, the invention relates to a compound of the following formula VI

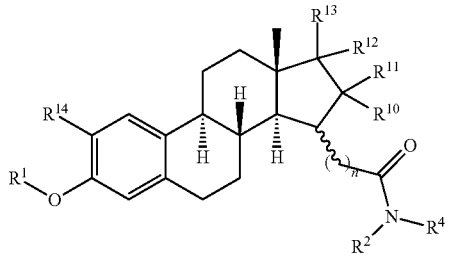

(VI)

i.e. a compound of formula I, wherein —X-A-Y— together represent —CO—NR$^4$—, and wherein the preferred meanings of R$^1$, R$^{10}$, R$^{11}$, R$^{12}$, R$^{13}$ and R$^{14}$ are as indicated above, and
n represents 0, 1, 2, 3, 4, or 5, preferably n represents 2, 3 or 4.

In this embodiment, R$^2$ preferably represents
(i) —(C$_1$-C$_4$)alkyl, which is optionally substituted with one or two substituents independently selected from the group consisting of hydroxyl, halogen, and (C$_1$-C$_4$) alkoxy;
(ii) —(C$_3$-C$_8$)cycloalkyl;
(iii) aryl or —(C$_1$-C$_4$)alkyl-aryl, wherein the aryl is phenyl or naphthyl,
which phenyl is optionally substituted with one or two substituents independently selected from the group consisting of hydroxyl, halogen, cyano, (C$_1$-C$_4$) alkoxy and halogenated (C$_1$-C$_4$)alkoxy; or
which phenyl is optionally substituted by two groups which are attached to adjacent carbon atoms and are combined into a saturated cyclic 5 or 6-membered ring system, containing 1 or 2 O atoms; or
(iv) heteroaryl or —(C$_1$-C$_4$)alkyl-heteroaryl, wherein the heteroaryl is furyl, thienyl, thiazolyl, imidazolyl, pyridinyl, indolyl, indazolyl, or benzoimidazolyl;
which heteroaryl is optionally substituted with one or two substituents independently selected from the group consisting of —(C$_1$-C$_4$)alkyl and —(C$_1$-C$_4$) alkyl-(C=O)—O—(C$_1$-C$_4$)alkyl;
and R$^4$ is independently selected from H or —(C$_1$-C$_4$)-alkyl or —(C$_1$-C$_4$)-alkyl-phenyl, wherein the phenyl group is optionally substituted with one or two (C$_1$-C$_4$)alkoxy groups; or
R$^2$ and R$^4$ form together with the nitrogen atom, to which R$^2$ and R$^4$ are attached, a ring, which is selected from the group consisting of morpholine, piperidine, thiomorpholine and piperazine,
wherein the ring is optionally substituted with a —(C$_1$-C$_4$) alkyl group.

In this embodiment, R$^2$ more preferably represents
(i) —(C$_1$-C$_4$)alkyl, which is optionally substituted with one or two (C$_1$-C$_4$)alkoxy groups;
(ii) —(C$_3$-C$_8$)cycloalkyl;
(iii) phenyl or —(C$_1$-C$_4$)alkyl-phenyl,
which phenyl is optionally substituted with one or two substituents independently selected from hydroxyl, halogen, cyano and (C$_1$-C$_4$)alkoxy; or
which phenyl is optionally substituted by two groups which are attached to adjacent carbon atoms and are combined into a saturated cyclic 5 or 6-membered ring system, containing 1 or 2 O-atoms; or
(iv) heteroaryl or —(C$_1$-C$_4$)alkyl-heteroaryl, wherein the heteroaryl is thiazolyl, pyridinyl, indolyl, or indazolyl;
which heteroaryl is optionally substituted with one or two —(C$_1$-C$_4$)alkyl groups;
and R$^4$ is independently selected from —H, —(C$_1$-C$_4$)-alkyl or —(C$_1$-C$_4$)-alkyl-phenyl, wherein the phenyl group is optionally substituted with one or two (C$_1$-C$_4$) alkoxy groups; or
R$^2$ and R$^4$ form together with the nitrogen atom, to which R$^2$ and R$^4$ are attached, a ring, which is selected from the group consisting of morpholine, piperidine, and piperazine,
wherein the ring is optionally substituted with a —(C$_1$-C$_4$)alkyl group.

Mostly preferred are compounds according to general formula VI, wherein $R^2$ represents a —$(C_1-C_4)$alkylphenyl, preferably a benzyl group, or a thiazolyl group, optionally substituted with —$(C_1-C_4)$-alkyl, preferably methyl, and $R^4$ represents —H; or $R^2$ and $R^4$ form together with the nitrogen atom, to which $R^2$ and $R^4$ are attached, a morpholine group, and n represents 2 or 3.

In a further embodiment the invention relates to a compound of the following formula XL

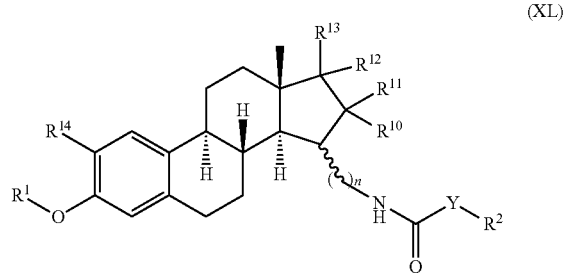
(XL)

wherein Y represents —NH—, a bond, or —O—; i.e compounds of formula I, wherein —X-A-Y— together represent —NH—CO—NH—, —NH—CO—O—, or —NH—CO—; the preferred meanings of $R^1$, $R^{10}$, $R^{11}$, $R^{12}$, $R^{13}$ and $R^{14}$ are as indicated above; and n represents 1, 2, 3, 4, 5 or 6, preferably 1, 2, 3 or 4.

A further embodiment of the invention relates to a compound of the following formula XVII,

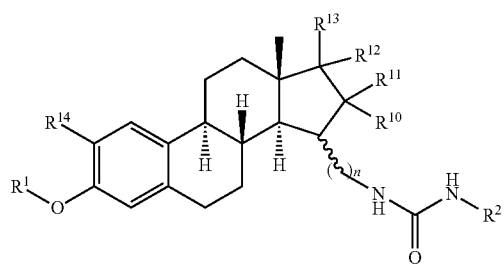
(XVII)

wherein the preferred meanings of $R^1$, $R^{10}$, $R^{11}$, $R^{12}$, $R^{13}$ and $R^{14}$ are as indicated above; and n preferably represents 1, 2, 3, or 4, even more preferably 3 or 4.

In this embodiment, $R^2$ preferably represents
(i) —$(C_1-C_4)$alkyl,
(ii) —$(C_3-C_8)$cycloalkyl,
(iii) —$(C_1-C_4)$alkyl-$(C_3-C_8)$cycloalkyl,
(iv) aryl, wherein the aryl is phenyl or naphthyl,
which phenyl is optionally substituted with one or two substituents independently selected from the group consisting of hydroxyl, halogen, —CO—O$(C_1-C_4)$alkyl and $(C_1-C_4)$alkoxy; or
which phenyl is optionally substituted by two groups which are attached to adjacent carbon atoms and are combined into a saturated cyclic 5 or 6-membered ring system, containing 1 or 2 O atoms, or
(v) —$(C_1-C_4)$alkyl-phenyl.

A further embodiment of the invention relates to a compound of the following formula XXIII,

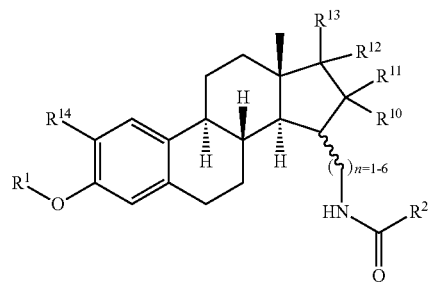
(XXIII)

wherein the preferred meanings of $R^1$, $R^{10}$, $R^{11}$, $R^{12}$, $R^{13}$ and $R^{14}$ are as indicated above; and n preferably represents 1, 2, 3, or 4.

In this embodiment, $R^2$ preferably represents
(i) —$(C_1-C_4)$alkyl,
(ii) —$(C_3-C_8)$cycloalkyl,
(iii) —$(C_1-C_4)$alkyl-$(C_3-C_8)$cycloalkyl,
(iv) —$(C_1-C_4)$alkyl, substituted with one or two substituents independently selected from the group consisting of —O—$(C_1-C_4)$alkyl and —O—$(C_1-C_4)$alkyl-phenyl,
(v) phenyl,
which phenyl is optionally substituted with one, two or three substituents independently selected from the group consisting of halogen and $(C_1-C_4)$alkoxy;
(vi) —$(C_1-C_4)$alkyl-phenyl; or
(vii) adamantly.

In another embodiment, the present invention relates to compounds of formula (I), wherein —X-A-Y— together represent a group selected from —NH—$SO_2$—NH—, —NH—$SO_2$—O—, and —NH—$SO_2$—, and n represents 1, 2, 3, or 4.

A further embodiment of the invention relates to a compound of the following formula XXIV,

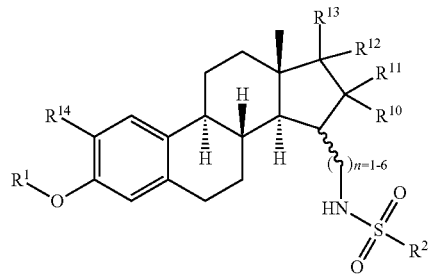
(XXIV)

wherein the preferred meanings of $R^1$, $R^{10}$, $R^{11}$, $R^{12}$, $R^{13}$ and $R^{14}$ are as indicated above; and n preferably represents 1, 2, 3, or 4.

In this embodiment, $R^2$ preferably represents
(i) aryl, wherein the aryl is selected among phenyl and naphthyl,
which aryl is optionally substituted with one or two substituents independently selected from the group consisting of halogen, nitro, $(C_1-C_4)$alkoxy, and —$(C_1-C_4)$alkyl; or
(ii) heteroaryl, wherein the heteroaryl is furyl, thienyl, or thiazolyl, or indolyl,
which heteroaryl is optionally substituted with one or two substituents independently selected from the group consisting of —$SO_2$-phenyl and $(C_1-C_4)$alkyl.

In another embodiment, the present invention relates to compounds of formula (I), wherein —X-A-Y— together represent a group selected from —O—CO—NH—, —O—CO—, and —O—CO—NH—SO$_2$—NR$^4$—, and n represents 1, 2, 3, 4, 5 or 6.

A further embodiment of the invention relates to a compound of the following formula XXVI,

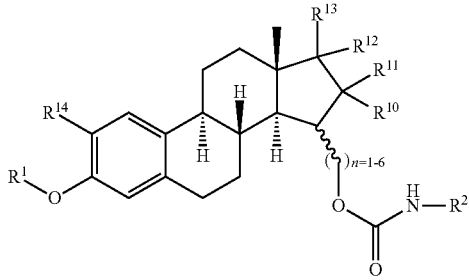

(XXVI)

wherein the preferred meanings of R$^1$, R$^{10}$, R$^{11}$, R$^{12}$, R$^{13}$ and R$^{14}$ are as indicated above; and n preferably represents 3, 4, 5 or 6.

In this embodiment, R$^2$ preferably represents phenyl or naphthyl,
which phenyl is optionally substituted with one or two substituents independently selected from the group consisting of hydroxyl, halogen, nitro, —CO—O(C$_1$-C$_4$)alkyl and (C$_1$-C$_4$)alkoxy and halogenated (C$_1$-C$_4$)alkyl; or
which phenyl is optionally substituted by two groups which are attached to adjacent carbon atoms and are combined into a saturated cyclic 5 or 6-membered ring system, containing 1 or 2 O atoms.

A further embodiment of the invention relates to a compound of the following formula XXVIII,

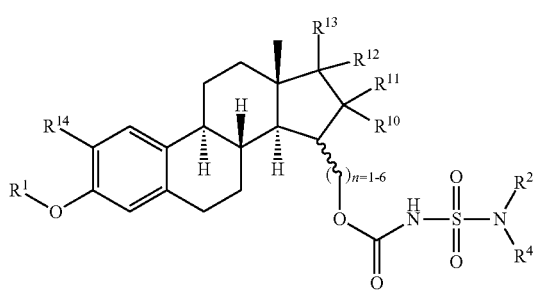

(XXVIII)

wherein the preferred meanings of R$^1$, R$^{10}$, R$^{11}$, R$^{12}$, R$^{13}$ and R$^{14}$ are as indicated above; and n preferably represents 3, 4, 5 or 6.

In this embodiment, R$^2$ preferably represents
(i) —(C$_1$-C$_4$)alkyl,
(ii) —(C$_3$-C$_8$)cycloalkyl,
(iii) —(C$_1$-C$_4$)alkyl-phenyl,
(iv) phenyl, or
(v) heteroaryl or —(C$_1$-C$_4$)alkyl-heteroaryl, wherein the heteroaryl is furyl, thienyl, thiazolyl, pyridinyl, indolyl, or benzoimidazolyl;
and preferably R$^4$ is independently selected from H, —(C$_1$-C$_4$)-alkyl and —(C$_1$-C$_4$)alkyl-phenyl; or
R$^2$ and R$^4$ may form together with the nitrogen atom, to which R$^2$ and R$^4$ are attached, a ring, which is selected from the group consisting of morpholine, thiomorpholine and piperazyl, and which is optionally substituted with (C$_1$-C$_4$)-alkyl.

A further embodiment of the invention relates to a compound of the following formula XXXI,

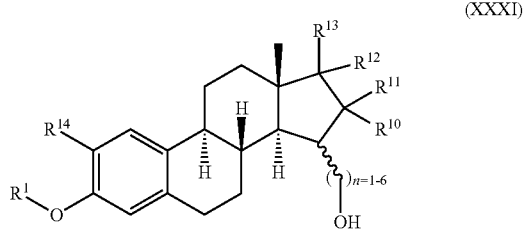

(XXXI)

wherein the preferred meanings of R$^1$, R$^{10}$, R$^{11}$, R$^{12}$, R$^{13}$ and R14 are as indicated above; and n represents 1, 2, 3, 4, 5 or 6, preferably 3 or 4.

Preferred embodiments of the invention relate to the following compounds:
N-Benzyl-4-(2-ethyl-3-hydroxy-17-oxo-estra-1,3,5(10)-trien-15β-yl)-butyramide
N-Benzyl-4-(3-hydroxy-17-oxo-2-propyl-estra-1,3,5(10)-trien-15β-yl)-butyramide
N-Benzyl-4-(3-hydroxy-2-(2-methoxy-ethyl)-17-oxo-estra-1,3,5(10)-trien-15β-yl)-butyramide
N-Benzyl-4-(3-hydroxy-2-methoxy-17-oxo-estra-1,3,5(10)-trien-15β-yl)-butyramide
2-Ethyl-3-hydroxy-15β-(4-morpholin-4-yl-4-oxo-butyl)-estra-1,3,5(10)-trien-17-one
3-Hydroxy-15β-(4-morpholin-4-yl-4-oxo-butyl)-2-propyl-estra-1,3,5(10)-trien-17-one
3-Hydroxy-2-(2-methoxy-ethyl)-15β-(4-morpholin-4-yl-4-oxo-butyl)-estra-1,3,5(10)-trien-17-one
3-Hydroxy-2-methoxy-15β-(4-morpholin-4-yl-4-oxo-butyl)-estra-1,3,5(10)-trien-17-one
4-(2-Ethyl-3-hydroxy-17-oxo-estra-1,3,5(10)-trien-15β-yl)-N-(5-methyl-thiazol-2-yl)-butyramide
4-(3-Hydroxy-2-methoxy-17-oxo-estra-1,3,5(10)-trien-15β-yl)-N-(5-methyl-thiazol-2-yl)-butyramide
N-Benzo[1,3]dioxol-5-ylmethyl-4-(3-hydroxy-17-oxo-2-propyl-estra-1,3,5(10)-trien-15β-yl)-butyramide
4-(3-Hydroxy-17-oxo-2-propyl-estra-1,3,5(10)-trien-15β-yl)-N-pyridin-3-ylmethyl-butyramide
4-(3-Hydroxy-17-oxo-2-propyl-estra-1,3,5(10)-trien-15β-yl)-N-[2-(7-methyl-1H-indol-3-yl)-ethyl]-butyramide
3-Hydroxy-15β-(4-oxo-4-piperidin-1-yl-butyl)-2-propyl-estra-1,3,5(10)-trien-17-one
N-Benzyl-4-(3-hydroxy-17-oxo-2-propyl-estra-1,3,5(10)-trien-15β-yl)-N-methyl-butyramide
N-[2-(3,4-Dimethoxy-phenyl)-ethyl]-4-(3-hydroxy-17-oxo-2-propyl-estra-1,3,5(10)-trien-15β-yl)-N-methyl-butyramide
4-(3-Hydroxy-17-oxo-2-propyl-estra-1,3,5(10)-trien-15β-yl)-N-(1H-indazol-6-yl)-butyramide
4-(3-Hydroxy-17-oxo-2-propyl-estra-1,3,5(10)-trien-15β-yl)-N-(2-methoxy-ethyl)-butyramide
N-(2,4-Difluoro-benzyl)-4-(3-hydroxy-17-oxo-2-propyl-estra-1,3,5(10)-trien-15β-yl)-butyramide
N-Cyclohexyl-4-(2-ethoxy-3-hydroxy-17-oxo-estra-1,3,5 (10)-trien-15α-yl)-butyramide
N-Benzo[1,3]dioxol-5-ylmethyl-4-(2-ethoxy-3-hydroxy-17-oxo-estra-1,3,5(10)-trien-15α-yl)-butyramide
4-(2-Ethoxy-3-hydroxy-17-oxo-estra-1,3,5(10)-trien-15α-yl)-N-[2-(7-methyl-1H-indol-3-yl)-ethyl]-butyramide 2-Ethoxy-3-hydroxy-15α-(4-oxo-4-piperidin-1-yl-butyl)-estra-1,3,5(10)-trien-17-one
4-(2-Ethoxy-3-hydroxy-17-oxo-estra-1,3,5(10)-trien-15α-yl)-N-(1H-indazol-6-yl)-butyramide
N-Cyclohexyl-4-(3-hydroxy-2-methoxy-17-oxo-estra-1,3,5(10)-trien-15α-yl)-butyramide
N-Benzyl-4-(3-hydroxy-2-methoxy-17-oxo-estra-1,3,5(10)-trien-15α-yl)-butyramide
3-Hydroxy-2-methoxy-15α-(4-oxo-4-piperidin-1-yl-butyl)-estra-1,3,5(10)-trien-17-one
4-(3-Hydroxy-2-methoxy-17-oxo-estra-1,3,5(10)-trien-15α-yl)-N-(1H-indazol-6-yl)-butyramide
4-(17,17-Difluoro-3-hydroxy-estra-1,3,5(10)-trien-15α-yl)-1-morpholin-4-yl-butan-1-one
4-(17,17-Difluoro-3-hydroxy-estra-1,3,5(10)-trien-15β-yl)-1-morpholin-4-yl-butan-1-one
4-(17-Fluoro-3-hydroxy-estra-1,3,5(10),16-tetraen-15β-yl)-1-morpholin-4-yl-butan-1-one
3-(17,17-Difluoro-3-hydroxy-estra-1,3,5(10)-trien-15β-yl)-N-(5-methyl-thiazol-2-yl)-propionamide
4-(17-Difluoromethylene-3-hydroxy-estra-1,3,5(10)-trien-15β-yl)-1-morpholin-4-yl-butan-1-one
N-Cyclohexyl-4-(17,17-difluoro-3-hydroxy-estra-1,3,5(10)-trien-15α-yl)-butyramide
N-Benzyl-4-(17,17-difluoro-3-hydroxy-estra-1,3,5(10)-trien-15α-yl)-butyramide
4-(17,17-Difluoro-3-hydroxy-estra-1,3,5(10)-trien-15α-yl)-N-(3,4-dihydroxy-benzyl)-butyramide
4-(17,17-Difluoro-3-hydroxy-estra-1,3,5(10)-trien-15α-yl)-N-[2-(7-methyl-1H-indol-3-yl)-ethyl]-butyramide
4-(17,17-Difluoro-3-hydroxy-estra-1,3,5(10)-trien-15α-yl)-1-piperidin-1-yl-butan-1-one
4-(17,17-Difluoro-3-hydroxy-estra-1,3,5(10)-trien-15α-yl)-N-[2-(3,4-dimethoxy-phenyl)-ethyl]-N-methyl-butyramide
N-Cyclopropyl-3-(17,17-difluoro-3-hydroxy-estra-1,3,5(10)-trien-15β-yl)-propionamide
N-Cyclohexyl-3-(17,17-difluoro-3-hydroxy-estra-1,3,5(10)-trien-15β-yl)-propionamide
N-Benzo[1,3]dioxol-5-ylmethyl-3-(17,17-difluoro-3-hydroxy-estra-1,3,5(10)-trien-15β-yl)-propionamide
N-Benzyl-3-(17,17-difluoro-3-hydroxy-estra-1,3,5(10)-trien-15β-yl)-propionamide
3-(17,17-Difluoro-3-hydroxy-estra-1,3,5(10)-trien-15β-yl)-N-(3,4-dihydroxy-benzyl)-propionamide
3-(17,17-Difluoro-3-hydroxy-estra-1,3,5(10)-trien-15β-yl)-N-(3,5-dimethoxy-benzyl)-propionamide
3-(17,17-Difluoro-3-hydroxy-estra-1,3,5(10)-trien-15β-yl)-N-[2-(7-methyl-1H-indol-3-yl)-ethyl]-propionamide
3-(17,17-Difluoro-3-hydroxy-estra-1,3,5(10)-trien-15β-yl)-1-piperidin-1-yl-propan-1-one
3-(17,17-Difluoro-3-hydroxy-estra-1,3,5(10)-trien-15β-yl)-N,N-diethyl-propionamide
3-(17,17-Difluoro-3-hydroxy-estra-1,3,5(10)-trien-15β-yl)-N-[2-(3,4-dimethoxy-phenyl)-ethyl]-N-methyl-propionamide
3-Hydroxy-15β-(4-morpholin-4-yl-4-oxo-butyl)-estra-1,3,5(10)-trien-[16,17-c]-pyrazole
3-Sulphamate-15β-(4-morpholin-4-yl-4-oxo-butyl)-estra-1,3,5(10)-trien-17-one,
3-Sulphate-15β-(4-morpholin-4-yl-4-oxo-butyl)-estra-1,3,5(10)-trien-17-one, or a physiologically acceptable salt thereof.

Pharmaceutically acceptable salts of the compounds of the invention as well as commonly used pro-drugs and active metabolites of these compounds are also within the scope of the invention.

Additionally, the invention relates to a compound of the invention for use as a pharmaceutical formulation.

Furthermore, the invention relates to the use of an effective amount of a compound of the invention for the treatment or prevention of a steroid hormone dependent disease or disorder in a mammal, in particular a human. Preferably the steroid hormone dependent disease or disorder is an estradiol dependent disease or disorder. Alternatively, the steroid dependent disease or disorder is an androgen-dependent disease or disorder.

In addition, the invention relates to the use of a compound of the invention for the manufacture of a pharmaceutical formulation for the treatment or prevention of a steroid hormone dependent disease or disorder in a mammal, in particular a human. Preferably the steroid hormone dependent disease or disorder is an estradiol dependent disease or disorder. Alternatively, the steroid dependent disease or disorder is an androgen-dependent disease or disorder.

In a further embodiment of the invention, the steroid hormone dependent disease or disorder requires the inhibition of a 17β-HSD enzyme, preferably the human 17β-HSD1 enzyme and/or the inhibition of a STS enzyme, preferably the human STS enzyme. Preferably, the steroid hormone dependent disease or disorder is mediated by the dual action of the 17β-HSD1 and the STS enzyme.

Furthermore, the invention also relates to a method of treating a mammal such as a human having a condition related to 17β-HSD1 activity and/or STS activity or which condition can be treated by inhibition of one or both of said enzymes, comprising administering to the mammal an amount of a compound of this invention, or a salt or a prodrug thereof, which amount is effective to treat the condition. Administration of compounds of this invention in combination with other pharmaceuticals used in treatment of the listed conditions is contemplated.

The conditions to be treated include but are not limited to malignant estradiol dependent disease or disorder such as breast cancer, ovarian cancer, uterine cancer, endometrial cancer, and endometrial hyperplasia. Preferably, the malignant disease or disorder is characterized by a detectable level of 17β-HSD1 and/or STS expression within a cancer tissue sample. A detectable level of 17β-HSD1 and/or STS expression means that a certain level of 17β-HSD1 and/or STS mRNA or of 17β-HSD1 and/or STS protein can be detected by conventional molecular biology methods such as hybridization, PCR reactions, Northern or Western Blotting etc. An alternative detection method for 17β-HSD1 and/or STS expression is the measurement of the corresponding enzyme activity.

According to a further aspect of the invention, the estradiol dependent disease is breast cancer and the mammal is a human post-menopausal female.

Furthermore, the conditions to be treated include but are not limited to benign estradiol dependent diseases or disorders such as endometriosis, uterine fibroids, uterine leiomyoma, adenomyosis, dysmenorrhea, menorrhagia, metrorrhagia, and urinary dysfunction.

In a further embodiment, the invention relates to use of an effective amount of a compound of the invention for the treatment or prevention of one of the aforementioned benign gynaecological diseases or disorders in a mammal whereby the mammal is a human, preferably a female and most preferably a pre- or peri-menopausal female.

According to a further aspect of the present invention, the steroid hormone dependent disease or disorder is an androgen-dependent disease or disorder. Preferably, said androgen-dependent disease or disorder is selected from the group consisting of acne, seborrhea, androgenetic alopecia, hirsutism, and prostate cancer.

According to a further aspect of the invention, the steroid hormone dependent disease or disorder to be treated is an estrogen- or androgen dependent disease or disorder requiring the lowering of the endogeneous estrogen or androgen concentration in a generalized or tissue-specific manner.

Therefore, further steroid-dependent diseases which may be treated with an effective amount of a compound of the invention are selected from the group consisting of prostadynia, benign prostatic hyperplasia, urinary dysfunction, lower urinary tract syndrome, squamous cell carcinoma, rheumatoid arthritis, type I and II diabetes, systemic lupus erythematosus, multiple sclerosis, myastenia gravis, thyroiditis, vasculitis, ulcerative colitis, Crohn's disease, psoriasis, contact dermatitis, graft versus host disease, eczema, asthma, organ rejection following transplantation, colon cancer, tissue wounds, skin wrinkles and cataracts.

According to a further embodiment, a compound of the present invention may be used for the enhancement of cognitive function, i.e. in the treatment or prevention of cognitive dysfunctions, such as senile dementia, including Alzheimer's disease, by increasing the DHEAS levels in the central nervous system.

The disclosed compounds are also useful as diagnostic agents (e.g. in diagnostic kits or for use in clinical laboratories) for screening for the presence or absence of 17β-HSD1 and/or STS enzyme activity.

Some Advantages

One key advantage of the present invention is that the compounds of the present invention can act as selective 17β-HSD1 inhibitors and optionally additionally as STS inhibitors. Another advantage of the compounds of the present invention is that they may be potent in vivo and suited for the therapeutic use in mammals, especially humans. Some of the compounds of the present invention may be non-estrogenic compounds. Here, the term "non-estrogenic" means exhibiting no or substantially no estrogenic activity on the estrogen receptor. Another advantage is that some of the compounds may not be capable of being metabolised to compounds which display or induce hormonal activity. Some of the compounds of the present invention are also advantageous in that they may be orally active.

DETAILED DESCRIPTION OF THE INVENTION

Definitions

The following terms are used to describe the present invention and in particular, to describe various constituents of the chemical composition useful in this invention. The terms are defined as follows:

As used herein, the terms "comprising" and "including" are used herein in their open, non-limiting sense.

The word "compound" shall here be understood to cover any and all isomers (e.g., enantiomers, stereoisomers, diastereomers, rotomers, tautomers) or any mixture of isomers, prodrugs, and any pharmaceutically acceptable salt of said compound, unless the formula depicting the compound explicitly shows a particular stereochemistry.

Where the plural form is used for compounds, salts, and the like, this is taken to mean also a single compound, salt, or the like.

The term "17β-hydroxysteroid dehydrogenase type I" or "17β-HSD1" for short is used for the enzyme EC 1.1.1.62 and reduces estrone (E1) to the biologically active estrogen, estradiol (E2).

The term "Steroid Sulphatase" or "STS" for short is used for the enzyme EC 3.1.6.2 and hydrolyses several sulphate steroids, such as estrone sulphate, dehydroepiandrosterone sulphate and cholesterol sulphate.

The terms "inhibit" and "inhibition" include the meaning of to reduce and/or eliminate and/or mask and/or prevent a certain enzyme action.

The term "17β-HSD1 inhibitor" as used herein with respect to the compound of the present invention means a compound that can inhibit 17β-HSD1 activity, such as to reduce and/or eliminate and/or mask and/or prevent the action of 17β-HSD1. The 17β-HSD1 inhibitor may act as an reversible or irreversible inhibitor of 17β-HSD1. The ability of compounds to inhibit 17β-HSD1 activity can be assessed using cell lines recombinantly expressing the human 17β-HSD1 enzyme. Details on a suitable Assay Protocol are presented in the Examples section. It is to be noted that the compound of the present invention may have other beneficial properties in addition to or in the alternative to its ability to inhibit 17β-HSD1 activity; in particular a 17β-HSD1 inhibitor may have antagonistic activity towards the nuclear estrogen receptor.

The term "STS inhibitor" as used herein with respect to the compound of the present invention means a compound that can inhibit STS activity, such as to reduce and/or eliminate and/or mask and/or prevent the action of STS. The STS inhibitor may act as an antagonist. The ability of compounds to inhibit estrone sulphate activity can be assessed using either intact MCF-7 breast cancer cells or placenta microsomes. In addition, an animal model may be used. Details on suitable Assay Protocols are presented in following sections. It is to be noted that other assays could be used to determine STS activity and thus STS inhibition. For example, reference may also be made to the teachings of international patent application WO 99/50453. Preferably, for some applications, a "STS inhibitor" is further characterized by the feature that if the sulphamate group were to be substituted by a sulphate group to form a sulphate derivative, then the sulphate derivative would be hydrolysable by an enzyme having steroid sulphatase (EC 3.1.6.2) activity, i.e. when incubated with steroid sulphatase EC 3.1.6.2 at pH 7.4 and 37° C. In one preferred embodiment, if the sulphamate group of the compound were to be replaced with a sulphate group to form a sulphate compound then that sulphate compound would be hydrolysable by an enzyme having steroid sutphatase (EC 3.1.6.2) activity and would yield a Km value of less than 200 mM, preferably less than 150 mM, preferably less than 100 mM, preferably less than 75 mM, preferably less than 50 mM, when incubated with steroid sulphatase EC 3.1.6.2 at pH 7.4 and 37° C. In one preferred embodiment, if the sulphamate group of the compound were to be replaced with a sulphate group to form a sulphate compound then that sulphate compound would be hydrolysable by an enzyme having steroid sutphatase (EC 3.1.6.2) activity and would yield a Km value of less than 200 μM, preferably less than 150 μM, preferably less than 100 μM, preferably less than 75 μM, preferably less than 50 μM, when incubated with steroid sulphatase EC 3.1.6.2 at pH 7.4 and 37° C. In a preferred embodiment, the compound of the present invention is not hydrolysable by an enzyme having steroid sulphatase (EC 3.1.6.2) activity. It is to be noted that the compound of the present invention may have other beneficial properties in addition to or in the alternative to its ability to inhibit STS activity.

The terms "selective" and "selectivity" as used herein with respect to the compounds of the present invention means a compound that can inhibit 17β-HSD1 and/or STS activity, and shows a higher inhibition value for these particular targets than with regard to other enzyme targets, in particular with regard to the 17β-HSD1 enzyme, and that has weak or no affinity for nuclear receptors, in particular that has weak or no affinity for the ER. Preferably a compound of the present invention has at least about a 100 fold selectivity to a desired target (e.g. 17β-HSD1 or STS), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

The term "substituted" means that the specified group or moiety bears one or more substituents. Where any group may carry multiple substituents and a variety of possible substituents is provided, the substituents are independently selected and need not be the same. The term "unsubstituted" means that the specified group bears no substituents. The term "optionally substituted" means that the specified group is unsubstituted or substituted by one or more substituents.

Any asymmetric carbon atoms may be present in the (R)-, (S)- or (R,S)-configuration preferably in the (R)- or (S)-configuration, whichever is most active, unless the stereochemistry is explicitly depicted in the corresponding compound formula. Substituents at a double bond or a ring may be present in cis- (.=Z-) or trans (=E-) form, unless the stereochemistry is explicitly depicted in the corresponding compound formula.

The compounds of formula (I) have a defined stereochemistry within the steroidal core structure according to the natural configuration for estrogenic steroids such as estradiol:

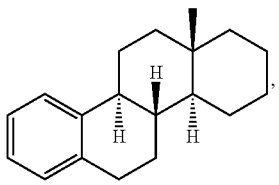

The stereochemistry within the steroidal core structure is always shown in the corresponding compound formula and should not vary within the scope of the present invention, whereas the stereochemistry at the carbon atoms in the steroidal core carrying additional side chains and the stereochemistry of any asymmetric carbon atom within the side chains themselves is not fixed. Therefore, the term "compounds of formula (I)" or "compounds of formula (II)" etc also comprises the stereoisomers of the depicted compounds, unless a particular stereochemistry is explicitly shown within the formula. The stereochemistry shown in the respective formula prevails over the general term "stereoisomers".

The compounds of the formula I contain at least one additional chiral carbon atom, namely the carbon atom carrying the side chain in the 15-position of the steroid structure. The compounds can thus be present at least in two optically active stereoisomeric forms or as a racemate. The present invention includes both the racemic mixtures and the isomerically pure compounds of the formula I. The position of the substituents within the C15 position is characterized by α or β. A C15α derivative according to the present invention is represented by a compound of the following formula (II)

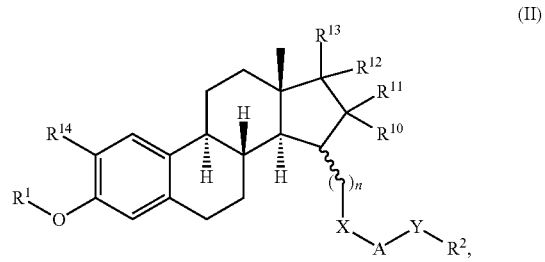

whereas a C15β derivative according to the present invention is represented by a compound of the following formula (III)

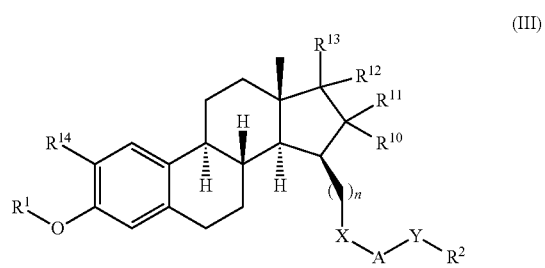

The compounds of the present invention may contain further asymmetric centers on the molecule, depending upon the nature of the various substituents. In certain instances, asymmetry may also be present due to restricted rotation about the central bond adjoining the two aromatic rings of the specified compounds. It is intended that all isomers (including enantiomers and diastereomers), either by nature of asymmetric centers or by restricted rotation as described above, as separated, pure or partially purified isomers or racemic mixtures thereof, be included within the ambit of the instant invention, unless a particular stereochemistry is explicitly depicted in the formula representing a respective compound.

The term "halogen" refers to fluorine (F, Fluoro-), bromine (Br, Bromo-), chlorine (Cl, Chloro), and iodine (J, Iodo-) atoms.

The terms "dihalogen", "trihalogen" and "perhalogen" refer to two, three and four substituents, respectively, each individually selected from the group consisting of fluorine, bromine, chlorine, and iodine atoms.

The term "hydroxyl" refers to the group —OH
The term "oxo" refers to the group =O
The term "carbamoyl" refers to the group —CO—NH$_2$
The term "thio" refers to the group =S
The term "thiol" refers to the group —SH
The term "sulfanyl" refers to the group —S—
The term "sulfoxy" or "sulfonyl" refers to the group —SO$_2$—
The term "sulfamoyl" refers to the group —SO$_2$—NH$_2$
The term "nitro" refers to the group —NO$_2$
The term "nitrile" or "cyano" refers to the group —CN
The term "oxime" refers to the group =N—O-Alkyl or =N—OH.

For the purpose of the present invention, the carbon content of various hydrocarbon containing moieties is indicated by a prefix designating the minimum and maximum number of carbon atoms in the moiety, i.e., the prefix $C_i$-$C_j$ defines the number of carbon atoms present from the integer "i" to the integer "j" inclusive. Thus $C_1$-$C_4$-alkyl refers to alkyl of 1-4 carbon atoms, inclusive, or methyl, ethyl, propyl, butyl and isomeric forms thereof.

The term "alkyl" stands for a hydrocarbon radical which may be linear, cyclic or branched, with single or multiple branching, whereby the alkyl group comprises 1 to 12 carbon atoms. In one embodiment, the term "alkyl" stands for a linear or branched (with single or multiple branching) alkyl chain of 1 to 8 carbon atoms, exemplified by the term ($C_1$-$C_8$)alkyl, more preferably of 1 to 6 carbon atoms exemplified by the term ($C_1$-$C_6$)alkyl. The term ($C_1$-$C_8$)alkyl is further exemplified by such groups as methyl; ethyl; n-propyl; isopropyl; n-butyl; sec-butyl; isobutyl; tert-butyl; n-pentyl; isopentyl; neopentyl; tert-pentyl; 2- or 3-methylpentyl; n-hexyl; isohexyl, heptyl, octyl and the like. The alkyl or ($C_1$-$C_8$)alkyl group may be partially unsaturated, forming such groups as, for example, vinyl, propenyl (allyl), butenyl, pentenyl, pentinyl, hexenyl, octadienyl, and the like. The term "alkyl" further comprises cycloalkyl groups, preferably cyclo($C_3$-$C_8$)alkyl which refers to cyclopropyl, cyclobutyl, cyclopentyl, cyclohexyl, cycloheptyl, cyclooctyl and isomeric forms thereof such as methylcyclopropyl; 2- or 3-methylcyclobutyl; 2-, or 3-methylcyclopentyl, and the like. The cycloalkyl group may also be partly unsaturated, forming such groups as, for example, cyclohexenyl, cyclopentenyl, cyclooctadienyl, and the like. Furthermore, the term "alkyl" comprises a cycloalkyl-alkyl group comprising 4 to 12 carbon atoms, preferably "—($C_1$-$C_4$)alkyl-cyclo($C_3$-$C_8$)alkyl" which refers to a alkyl group of 1 to 4 carbon atoms as described above substituted with a cyclo($C_3$-$C_8$)alkyl group as described above, forming such groups as for example cyclopropylmethyl, cyclohexylmethyl, cyclopentylethyl or cyclohexenylethyl. The term "alkyl" further comprises bicyclic ring systems of 6 to 10 carbon atoms, preferably Bicyclo[2.1.1]hexyl, Bicyclo[2.2.1]heptyl, Bicyclo[3.2.1]octyl, Bicyclo[2.2.2]octyl, Bicyclo[3.2.2]nonanyl, Bicyclo[3.3.1]nonanyl, Bicyclo [3.3.2]decanyl; and the like, preferably Bicyclo[2.2.1]heptyl, and fused ring systems of up to 10 carbon atoms such as adamantyl and the like.

The alkyl group may optionally be substituted by up to five, more preferably by up to three substituents independently selected from the group consisting of halogen, hydroxyl, optionally substituted aryl, optionally substituted heteroaryl, optionally substituted cycloheteroalkyl, thiol, nitro, nitrile, alkoxy, aryloxy, arylalkyloxy, amino, amido, alkylthio, arylthio, arylalkylthio, sulfamoyl, sulfonamide, acyl, carboxyl, and acylamino, as defined herein. These groups may be attached to any carbon atom of the alkyl moiety.

The alkyl group substituted with up to three independently selected aryl preferably refers to "aryl-($C_1$-$C_4$)-alkyl" or "diaryl-($C_1$-$C_4$)-alkyl", wherein the aryl is phenyl, naphthyl, indanyl, indenyl, or 1,2,3,4-tetrahydro-naphthalen-1-yl, preferably aryl is phenyl or naphthyl, forming such groups as for example benzyl, diphenylmethyl, phenethyl, phenylpropyl, diphenylpropyl, phenylbutyl, naphthylmethyl or naphthylethyl. The alkyl chain may be further substituted as defined above; for example the alkyl chain may carry an additional hydroxyl group. Furthermore, the alkyl chain may be partially unsaturated, such as a vinyl group. The aryl moiety may optionally be substituted as defined herein.

The alkyl group substituted with up to three independently selected heteroaryl group preferably refers to "heteroaryl-($C_1$-$C_4$)-alkyl", wherein the heteroaryl is pyrrolyl, thienyl, furyl, imidazolyl, thiazolyl, isothiazolyl, oxazolyl, isoxazolyl, pyrazolyl, pyridinyl, pyrimidinyl, pyrazinyl, indolyl, quinolinyl, isoquinolinyl, benzoimidazolyl, benzofuran, benzo[b]thiophene, preferably heteroaryl is furyl, indolyl, benzoimidazolyl, pyridinyl, thienyl or imidazolyl, forming such groups as for example benzoimidazolylmethyl, pyridinylmethyl, thienylmethyl, furylmethyl, indolylethyl, thienylethyl, pyridinylethyl, or imidazolylpropyl. The heteroaryl moiety may optionally be substituted as defined herein.

The alkyl group substituted with up to three independently selected cycloheteroalkyl groups preferably refers to "cycloheteroalkyl-($C_1$-$C_4$)-alkyl", wherein the cycloheteroalkyl is pyrrolidinyl, tetrahydrofuryl, tetrahydrothiophenyl, piperidinyl, morpholinyl, thiomorpholinyl, piperazinyl, azepanyl, diazepanyl, oxazepanyl or thiazepanyl, preferably cycloheteroalkyl is piperidinyl, pyrrolidinyl, or morpholinyl, forming such groups as for example morpholinylethyl, morpholinylpropyl, piperidinylethyl or pyrrolidinylethyl. The cycloheteroalkyl moiety may optionally be substituted as defined herein.

The term "alkoxy" refers to a group —OR, where R may be alkyl (wherein the alkyl chain may be optionally further substituted as defined herein). Preferably, the term "alkoxy" refers to —O—($C_1$-$C_6$)alkyl (or ($C_1$-$C_6$)alkoxy), with the ($C_1$-$C_6$)alkyl group as defined above and optionally substituted with up to three hydroxyl groups.

The term "aryloxy" refers to a group —OAr, where Ar represents aryl as defined herein, which is optionally substituted in the aryl group with up to five independently selected substituents as defined herein, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy; the number of said substituents being up to five for halogen, and up to three for any combination of said other substituents. Preferably, aryloxy refers to phenoxy, optionally substituted as defined above.

The term "arylalkyloxy" refers to a group —O—($C_1$-$C_4$) alkyl-Ar, where Ar represents aryl, which is optionally substituted in the aryl group with up to five independently selected substituents as defined herein, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy; the number of said substituents being up to five for halogen, and up to three for any combination of said other substituents. Preferably, arylalkyloxy refers to benzyloxy, optionally substituted as defined above.

The term "acyl" refers to a group —(C=O)—R, where R may be hydrogen, optionally substituted alkyl, optionally substituted aryl or aryl-($C_1$-$C_4$)-alkyl, optionally substituted heteroaryl or heteroaryl-($C_1$-$C_4$)-alkyl, as defined herein. Preferably, the term "acyl" refers to a group —(C=O)—R', where R' represents hydrogen, ($C_1$-$C_4$)alkyl, phenyl, or phenyl-($C_1$-$C_4$)alkyl, preferably benzyl, or heteroaryl-($C_1$-$C_4$) alkyl, preferably indolyl-methyl; whereby the phenyl moiety may be optionally substituted with independently selected substituents, especially hydroxyl, halogen, ($C_1$-$C_4$)alkoxy, ($C_1$-$C_4$)-alkyl or halogenated ($C_1$-$C_4$)alkyl, the number of said substituents being up to five for halogen, and up to three for any combination of said other substituents.

The term "carbonyl" represents a preferred selection of the term "acyl" and refers to the group —CHO.

The term "alkylacyl" represents a preferred selection of the term "acyl" and refers to a group —(C=O)-alkyl, preferably —(C=O)—($C_1$-$C_4$)alkyl.

The term "carboxyl" refers to a group —(C=O)—OR, wherein R may be hydrogen, optionally substituted alkyl (preferably substituted with hydroxyl, halogen or ($C_1$-$C_4$)-alkoxy), optionally substituted aryl or aryl-($C_1$-$C_4$)-alkyl, or optionally substituted heteroaryl or heteroaryl-($C_1$-$C_4$)-alkyl, each as defined herein. Preferably, the term "carboxyl" refers to a group —(C=O)—OR', where R' represents hydrogen, ($C_1$-$C_4$)alkyl, phenyl, or phenyl-($C_1$-$C_4$)alkyl, preferably benzyl; whereby the phenyl moiety may be optionally substituted with substituents independently selected from the group consisting of hydroxyl, halogen, ($C_1$-$C_4$)alkoxy, ($C_1$-$C_4$)-alkyl, halogenated ($C_1$-$C_4$)alkyl and halogenated ($C_1$-$C_4$)alkoxy, the number of said substituents being up to five for halogen, and up to three for any combination of said other substituents.

The terms "carboxyl-($C_1$-$C_6$)alkyl" and "carboxyl-($C_1$-$C_4$)alkyl" refer to groups —($C_1$-$C_6$)alkyl-(C=O)—OR and —($C_1$-$C_4$)alkyl-(C=O)—OR, respectively, which refer to an alkyl group of 1 to 6 and 1 to 4 carbon atoms, respectively, as described above, substituted with a —(C=O)—OR group as described above. Preferably the carboxyl group refers to —(C=O)—OR', wherein R' represents hydrogen, ($C_1$-$C_4$) alkyl, phenyl, or ($C_1$-$C_4$)alkyl-phenyl, preferably benzyl. Preferred examples of such carboxyl-($C_1$-$C_6$)alkyl groups include acetic acid methyl ester, acetic acid ethyl ester, propionic acid benzyl ester, propionic acid ethyl ester, butyric acid methyl ester, and 3-methyl-butyric acid methyl ester.

The term "amino" refers to the group —NRR', where R and R' may independently be hydrogen, optionally substituted alkyl (preferred substituents comprise hydroxyl, halogen or ($C_1$-$C_4$)-alkoxy), optionally substituted aryl or aryl-($C_1$-$C_4$)-alkyl, or optionally substituted heteroaryl or heteroaryl-($C_1$-$C_4$)-alkyl, each as defined herein.

The term "alkylamino" represents a preferred selection of the term "amino" and refers to the group —NRR', where R and R' may independently be hydrogen or ($C_1$-$C_4$)alkyl.

The term "alkylthio" or "alkylsulfanyl" refers to a group —SR, where R represents optionally substituted alkyl (preferred substituents comprise hydroxyl, ($C_1$-$C_4$)-alkoxy or halogen), as defined herein; preferably R represents ($C_1$-$C_6$) alkyl, in particular ($C_1$-$C_4$)alkyl.

The term "arylthio" or "arylsulfanyl" refers to a group —S—Ar, where Ar represents optionally substituted aryl (preferred substituents comprise hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy), as defined herein. Preferably, arylthio refers to optionally substituted phenylsulfanyl.

The term "arylalkylthio" or "arylalkylsulfanyl" refers to a group —S—($C_1$-$C_4$)alkyl-Ar, where Ar represents optionally substituted aryl (preferred substituents comprise hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy), as defined herein. Preferably, arylalkylthio refers to optionally substituted benzylsulfanyl.

The term "alkylsulfonyl" refers to a group —$SO_2$—R, where R represents optionally substituted alkyl (preferred substituents comprise hydroxyl, ($C_1$-$C_4$)-alkoxy or halogen), as defined herein; preferably R represents ($C_1$-$C_6$)alkyl, in particular ($C_1$-$C_4$)alkyl.

The term "arylsulfonyl" refers to a group —$SO_2$—Ar, where Ar represents optionally substituted aryl (preferred substituents comprise hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy), as defined herein. Preferably, arylsulfonyl refers to optionally substituted benzenesulfonyl.

The term "arylalkylsulfonyl" refers to a group —$SO_2$—($C_1$-$C_4$)alkyl-Ar, where Ar represents optionally substituted aryl (preferred substituents comprise hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy), as defined herein. Preferably, arylalkyl-sulfonyl refers to optionally substituted benzylsulfonyl.

The term "amido" refers to the group —(C=O)—NRR', where R and R' may independently be hydrogen, optionally substituted alkyl (preferred substituents comprise hydroxyl, halogen or ($C_1$-$C_4$)-alkoxy), optionally substituted aryl or aryl-($C_1$-$C_4$)-alkyl ((preferred substituents comprise hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy), or optionally substituted heteroaryl or heteroaryl-($C_1$-$C_4$)-alkyl, as defined herein.

The term "alkylamido" represents a preferred selection of the term "amido" and refers to the group —(C=O)—NRR', where R and R' may be independently selected from hydrogen or ($C_1$-$C_4$)alkyl.

The term "acylamino" refers to the group —NR—CO—R', where R and R' may independently be hydrogen, optionally substituted alkyl (preferred substituents comprise hydroxyl, halogen or ($C_1$-$C_4$)-alkoxy), optionally substituted aryl or aryl-($C_1$-$C_4$)-alkyl (preferred substituents comprise hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy), optionally substituted heteroaryl or heteroaryl-($C_1$-$C_4$)-alkyl, as defined herein. Preferably, acylamino refers to —NH—CO—($C_1$-$C_4$)-alkyl.

The term "carbonylamino" represents a preferred selection of the term "acylamino" and refers to the group —NR—CO—$CH_2$—R', where R and R' may be independently selected from hydrogen or ($C_1$-$C_4$)alkyl.

The term "sulfonamide" refers to the group —$SO_2$—NRR', wherein R and R' may independently be selected from hydrogen or ($C_1$-$C_4$)alkyl.

Halogenated alkyl, halogenated alkoxy and halogenated alkylthio are substituents in which the alkyl moieties (preferably ($C_1$-$C_6$)alkyl, more preferred ($C_1$-$C_4$)alkyl, and most preferred methyl) are substituted either partially or in full with halogens, generally with chlorine and/or fluorine. Preferred examples of such substituents are trifluoromethyl, trifluoromethoxy, trifluoromethylthio, dichloromethyl, pentafluoroethyl, dichloropropyl, fluoromethyl and difluoromethyl.

The term "cycloheteroalkyl" refers to a four- to eight-membered heterocyclic ring containing at least one heteroatom, such as N, O or S, the number of N atoms being 0-3 and the number of O and S atoms each being 0-1, which system may be saturated, partly unsaturated or hydroaromatic, and which ring can be part of a multiple condensed ring-system in which some rings may be aromatic. Examples of such cycloheteroalkyls include pyrrolidinyl, tetrahydrofuryl, tetrahydrothiophenyl, tetrahydropyridinyl, azetidinyl, thiazolidinyl, oxazolidinyl, piperidinyl, morpholinyl, thiomorpholinyl, piperazinyl, azepanyl, diazepanyl, oxazepanyl, thiazepanyl, dihydro-1H-pyrrolyl, 3,6-dihydro-2H-pyridinyl, 1,3-dihydro-benzoimidazolyl and the like. Preferred examples of such cycloheteroalkyl groups are pyrrolidinyl, morpholinyl, tetrahydrofuryl, piperidinyl or azepanyl.

The cycloheteroalkyl group may optionally be substituted by up to three substituents, independently selected from the group consisting of oxo, alkyl, optionally substituted aryl or aryl-($C_1$-$C_4$)-alkyl, hydroxyl, ($C_1$-$C_6$)alkoxy, halogenated ($C_1$-$C_6$)alkyl, halogenated ($C_1$-$C_6$)alkoxy, carboxyl-($C_1$-$C_6$) alkyl, thiol, nitrile, sulfamoyl, sulfonamide, carboxyl, aryloxy or arylalkyloxy, ($C_1$-$C_6$)alkylthio, arylthio or arylalkylthio, amino, amido, acyl, and acylamino, as defined herein. The substituents of the cycloheteroalkyl groups may be attached to any carbon atom of the cycloheteroalkyl moiety. Substituted cycloheteroalkyl is preferably substituted with oxo, ($C_1$-$C_4$)alkyl, preferably methyl, phenyl and/or phenyl-($C_1$-$C_4$)alkyl, in particular benzyl.

The terms "aryl" or "Ar" refer to an aromatic carbocyclic group comprising 6 to 14, more preferably 6 to 10, carbon atoms and having at least one aromatic ring or multiple condensed rings in which at least one ring is aromatic. Preferably, aryl is phenyl, naphthyl, indanyl, indenyl, or 1,2,3,4-tetrahydro-naphthalen-1-yl.

The term "heteroaryl" refers to an aromatic carbocyclic group of having a single 4 to 8 membered ring or multiple condensed rings comprising 6 to 14, more preferably 6 to 10, ring atoms and containing at least one heteroatom, such as N, O or S, within at least one ring, the number of N atoms being 0-3 and the number of O and S atoms each being 0-1; in which group at least one heterocyclic ring is aromatic. Examples of such groups include pyrrolyl, thienyl, furyl, imidazolyl, thiazolyl, isothiazolyl, oxazolyl, isoxazolyl, pyrazolyl, pyridinyl, pyrimidinyl, pyrazinyl, pyridazinyl, indolyl, quinolinyl, isoquinolinyl, benzothiazolyl, benzoimidazolyl, 1,3-dihydro-benzoimidazolyl, benzofuran, benzo[b]thiophene and the like. Preferably, heteroaryl is quinolinyl, furyl, benzoimidazolyl, pyridinyl, thienyl, indolyl, benzo[b]thiophene, pyridinyl, imidazolyl, pyrazolyl or thiazolyl.

The aryl and the heteroaryl group may optionally be substituted by substituents independently selected from the group consisting of halogen, hydroxyl, ($C_1$-$C_6$)alkoxy, ($C_1$-$C_6$)alkyl, halogenated ($C_1$-$C_6$)alkyl, halogenated ($C_1$-$C_6$) alkoxy, carboxyl-($C_1$-$C_6$)alkyl, oxo, thiol, nitro, nitrile, sulfamoyl, sulfonamide, carboxyl, aryloxy or arylalkyloxy, ($C_1$-$C_6$)alkylthio, arylthio or arylalkylthio, alkylsulfonyl, arylsulfonyl, amino, amido, acyl, and acylamino, as defined herein, the number of said substituents being up to five for halogen, and up to three for any combination of said other substituents; whereby the aryloxy, arylalkyloxy, arylthio or arylalkylthio group may be further optionally substituted in the aryl moiety with independently selected substituents as defined herein. The heteroaryl group may further be optionally substituted with an aryl group, which may be optionally substituted in the aryl moiety with independently selected substituents as defined herein. The aryl group may further be optionally substituted with a heteroaryl group or a second aryl group.

The aryl may be further substituted by two groups which are attached to adjacent carbon atoms and are combined into a saturated or partly unsaturated cyclic 5, 6, 7, or 8 membered ring system, optionally containing up to three heteroatoms, such as N, O or S, the number of N atoms being 0-3 and the number of O and S atoms each being 0-2. Preferably, the two groups which are attached to adjacent carbon atoms, are combined into a saturated cyclic 5 or 6 membered ring system, optionally containing up to three heteroatoms, such as N or O, the number of N atoms being 0-3 and the number of O atoms each being 0-2. This cyclic ring system may optionally be further substituted by an oxo group. Preferred examples of such a substituted aryl groups are benzo[1,3]dioxol and 1,3-dihydro-benzoimidazol-2-one.

The statement is made that when two side chains are found on a single N, they can be combined, including the N to which they are attached, into a heterocyclic ring of 4-, 5-, 6-, 7- or 8 atoms, which can be saturated, partly unsaturated or aromatic, which can optionally contain up to three additional heteroatoms selected from N, O or S, the number of N atoms being 0-3 and the number of O and S atoms each being 0-2; and which ring can be part of a multiple condensed ring-system, in which some rings may be aromatic. Preferred examples of such heterocyclic ring systems, including the N, to which the respective side chains are attached, are:

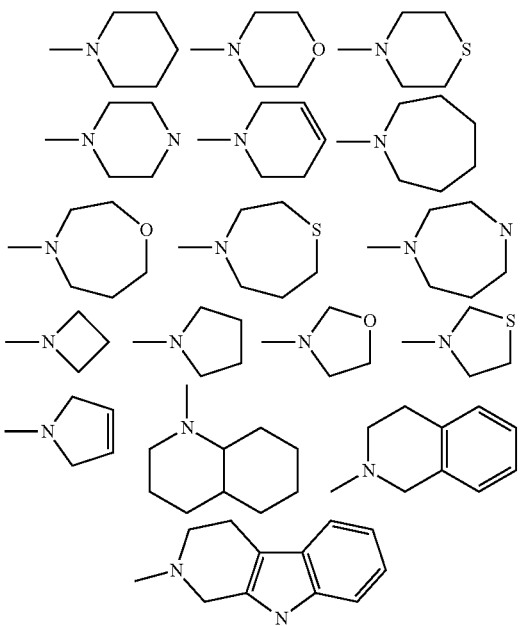

The aforementioned heterocyclic ring system can be optionally substituted by up to three substituents, which can be attached to any carbon or nitrogen atom of the heterocyclic ring system. Preferred examples of substituted heterocyclic ring systems are:

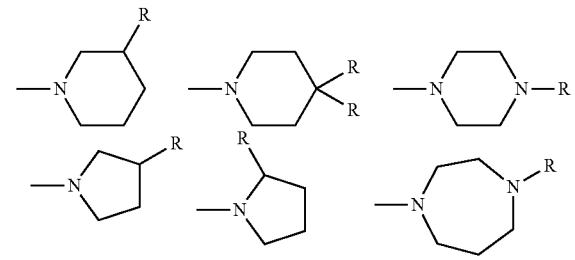

The optional up to three independently selected substituents for the heterocyclic ring system may be chosen among optionally substituted alkyl, halogen, hydroxyl, oxo, thiol, nitro, nitrile, ($C_1$-$C_6$)-alkoxy, aryl, heteroaryl, optionally substituted cycloheteroalkyl, aryloxy, arylalkyloxy, amino, amido, alkylthio, arylthio, arylalkylthio, sulfamoyl, sulfonamide, acyl, carboxyl, and acylamino, as defined herein, whereby all aryl or heteroaryl moieties may be optionally substituted with up to five, preferably up to three independently selected substituents as defined herein.

Furthermore, the aforementioned heterocyclic ring system may be substituted by two groups which are attached to the same carbon atom and are combined into a saturated or partly unsaturated cyclic 4, 5, 6, 7, or 8 membered ring system, optionally containing up to three heteroatoms, such as N, O or S, the number of N atoms being 0-3 and the number of O and S atoms each being 0-2. This cyclic ring system may optionally be further substituted by up to three substitutents independently selected from oxo, ($C_1$-$C_6$)-alkyl, aryl, preferably phenyl, and aryl-($C_1$-$C_4$)-alkyl, preferably benzyl. Preferred examples of such substituted heterocyclic ring systems are 1,4-dioxa-8-aza-spiro[4.5]decane, 1,3,8-triaza-spiro[4.5]decane, 1,3,8-triaza-spiro[4.5]decan-4-one, 1-Phenyl-1,3,8-triaza-spiro[4.5]decane, and 1-Phenyl-1,3,8-triaza-spiro[4.5]decan-4-one.

The term "sulphamate group" as used herein, refers to a group —O—SO$_2$—NR$^3$R$^{3'}$, and includes a steroidal ester of sulphamic acid or a steroidal ester of an N-substituted derivative of sulphamic acid, or a salt thereof. If —O—R$^1$ is a sulphamate group then the compound of the present invention is referred to as a sulphamate compound.

The term "carbamate group" as used herein, refers to a group —O—CO—NR$^3$R$^{3'}$, and includes a steroidal ester of carbamic acid or a steroidal ester of an N-substituted derivative of carbamic acid, or a salt thereof. If —O—R$^1$ is a carbamate group then the compound of the present invention is referred to as a carbamate compound.

The term "phosphonate group" as used herein, refers to a group —O—PO(OR$^{16}$)—R$^3$, and includes a steroidal ester of phosphonic acid or a steroidal ester of an O-substituted derivative of phosphonic acid, or a salt thereof. If —O—R$^1$ is a phosphonate group then the compound of the present invention is referred to as a phosphonate compound.

The term "thiophosphonate group" as used herein, refers to a group —O—PS(OR$^{16}$)—R$^3$, and includes a steroidal ester of thiophosphonic acid or a steroidal ester of an O-substituted derivative of thiophosphonic acid, or a salt thereof. If —O—R$^1$ is a thiophosphonate group then the compound of the present invention is referred to as a thiophosphonate compound.

The term "phosphate group" as used herein, refers to a group —O—PO(OR$^{16}$)—OR$^3$, and includes a steroidal ester of phosphoric acid or a steroidal ester of an O-substituted derivative of phosphoric acid, or a salt thereof. If —O—R$^1$ is a phosphate group then the compound of the present invention is referred to as a phosphate compound.

The term "sulphonate group" as used herein, refers to a group —O—SO$_2$—R$^3$, and includes a steroidal ester of sulphonic acid, or a salt thereof. If —O—R$^1$ is a sulphonate group then the compound of the present invention is referred to as a sulphonate compound.

The term "sulphate group" as used herein, refers to a group —O—SO$_2$—OR$^3$, and includes a steroidal ester of sulphuric acid, or a salt thereof. If —O—R$^1$ is a sulphate group then the compound of the present invention is referred to as a sulphate compound.

For all above-mentioned sulphamate-, carbamate-, phosphonate-, thiophosphonate-, phosphate-, sulphonate-, and sulphate-groups, the substituents R$^3$ and R$^{3'}$, if present, are independently selected from H, alkyl, aryl and arylalkyl, as defined herein, or form together with the nitrogen atom, to which R$^3$ and R$^{3'}$ are attached, a heterocyclic 4-, 5-, 6-, 7- or 8-membered ring, which is optionally saturated, partly unsaturated, or aromatic; which optionally contains up to three additional heteroatoms selected from N, O or S, the number of additional N atoms being 0, 1, 2 or 3 and the number of O and S atoms each being 0, 1 or 2. Preferably, at least one of R$^9$ and R$^{10}$ is H, and even more preferred, each of R$^9$ and R$^{10}$ is H. If the substituent R$^{16}$ is present in one of the aforementioned groups, then represents —H, alkyl, or arylalky, as defined herein above. Preferably, R$^{16}$ represents —H.

The term "prodrug" as used herein, represents derivatives of the compounds of the invention that are drug precursors which, following administration to a patient, release the drug in vivo via a chemical or physiological process. In particular, pro-drugs are derivatives of the compounds of the invention in which functional groups carry additional substituents which may be cleaved under physiological conditions in vivo and thereby releasing the active principle of the compound (e.g., a pro-drug on being brought to a physiological pH or through an enzyme action is converted to the desired drug form).

The term "pharmaceutically acceptable salts" refers to salt forms that are pharmacologically acceptable and substantially non-toxic to the subject being administered the compounds of the invention. Pharmaceutically acceptable salts of compounds of formula I include conventional and stoichiometrical acid-addition salts or base-addition salts formed from suitable non-toxic organic or inorganic acids or inorganic bases. Acid addition salts, for example, from compounds of formula I with a basic nitrogen atom are formed preferably with organic or inorganic acids. Suitable inorganic acids are, for example, halogenic acids such as hydrochloric acid, sulfuric acid, or phosphoric acid. Suitable organic acids are, for example, carboxylic, phosphonic, or sulfonic acids, for example acetic acid, propionic acid, glycolic acid, lactic acid, hydroxybutyric acid, malic acid, malenic acid, malonic acid, salicylic acid, fumaric acid, succinic acid, adipic acid, tartaric acid, citric acid, glutaric acid, 2- or 3-glycerophosphoric acid and other mineral and carboxylic acids well known to those skilled in the art. The salts are prepared by contacting the free base forms with a sufficient amount of the desired acid to produce a salt in the conventional manner. Compounds containing acidic substituents may also form salts with inorganic or organic bases. Examples of suitable bases for salt formation include, but are not limited to, inorganic bases such as alkali or alkaline earth-metal (e.g., sodium, potassium, lithium, calcium, or magnesium) hydroxides, and those derived from ammonium hydroxides (e.g., a quaternary ammonium hydroxide such as tetramethylammonium hydroxide). Also contemplated are salts formed with pharmaceutical acceptable amines such as ammonia, alkyl amines, hydroxyalkylamines, N-methylglucamine, benzylamines, piperidines, and pyrrolidines and the like. Certain compounds will be acidic in nature, e.g. those compounds which possess a carboxyl or phenolic hydroxyl group. Salts of phenols can be made by heating acidic compounds with any of the above mentioned bases according to procedures well known to those skilled in the art.

As used herein, the term "composition" is intended to encompass a product comprising the specified ingredients in the specified amounts, as well as any product which results, directly or indirectly, from combination of the specified ingredients in the specified amounts.

The phrase "effective amount" as used herein, means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically acceptable excipient(s)/carrier(s) utilized, and like factors within the knowledge and expertise of the attending physician.

Administration Forms

The method of the invention is primarily intended for treatment in a mammal, preferably in humans and other primates, of steroid hormone dependent diseases or disorders, in particular estradiol dependent diseases or disorders, wherein the steroid hormone dependent disease or disorder preferably requires the inhibition of a 17β-HSD enzyme, preferably the 17β-HSD1 enzyme.

The compounds may be administered orally, dermally, parenterally, by injection, by pulmonal or nasal delivery, or sublingually, rectally or vaginally in dosage unit formulations. The term "administered by injection" includes intravenous, intraarticular, intramuscular (e.g. by depot injection where the active compounds are released slowly into the blood from the depot and carried from there to the target organs), intraperitoneal, intradermal, subcutaneous, and intrathecal injections, as well as use of infusion techniques. Dermal administration may include topical application or transdermal administration. One or more compounds may be present in association with one or more non-toxic pharmaceutically acceptable auxiliaries such as excipients, adjuvants (e.g. buffers), carriers, inert solid diluents, suspensing agents, preservatives, fillers, stabilizers, anti-oxidants, food additives, bioavailability enhancers, coating materials, granulating and disintegrating agents, binding agents etc., and, if desired, other active ingredients.

The pharmaceutical composition may be formulated for example as immediate release, sustained release, pulsatile release, two or more step release, depot or other kind of release formulations.

The manufacture of the pharmaceutical compositions according to the invention may be performed according to methods known in the art and will be explained in further detail below. Commonly known and used pharmaceutically acceptable auxiliaries as well as further suitable diluents, flavorings, sweetening agents, coloring agents etc. may be used, depending on the intended mode of administration as well as particular characteristics of the active compound to be used, such as solubility, bioavailability etc. Suitable auxiliaries and further ingredients may be such as recommended for pharmacy, cosmetics and related fields and which preferably are listed in the European Pharmacopoeia, FDA approved or cited in the "GRAS" list (FDA List of food additives that are 'generally recognized as safe' (GRAS)).

One mode of application of the compounds of general formula (I) or of pharmaceutical compositions comprising one or more of said compounds is oral application, e.g., by tablets, pills, dragees, hard and soft gel capsules, granules, pellets, aqueous, lipid, oily or other solutions, emulsions such as oil-in-water emulsions, liposomes, aqueous or oily suspensions, syrups, elixiers, solid emulsions, solid dispersions or dispersible powders. For the preparation of pharmaceutical compositions for oral administration, the compounds suitable for the purposes of the present invention as defined above can be admixed with commonly known and used adjuvants and excipients such as for example, gum arabic, talcum, starch, sugars (such as, e.g., mannitose, methyl cellulose, lactose), gelatine, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Geluciretm). In the pharmaceutical composition, the active ingredients may also be dispersed in a microparticle, e.g. a nanoparticulate, composition.

For parenteral administration, the active agents can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration the active agent can be in the form of an aqueous, lipid, oily or other kind of solution or suspension or even administered in the form of liposomes or nano-suspensions.

Transdermal application can be accomplished by suitable patches, as generally known in the art, specifically designed for the transdermal delivery of active agents, optionally in the presence of specific permeability enhancers. Furthermore, also emulsions, ointments, pastes, creams or gels may be used for transdermal delivery.

Another suitable mode of administration is via intravaginal devices (e.g. vaginal rings) or intrauterine systems (IUS) containing reservoirs for controlled release of active agents over extended periods of time. For rectal or vaginal administration of the drug the compounds may also be administered in the form of suppositories. These compositions can be prepared by mixing the drug with a suitable non-irritating excipient which is solid at ordinary temperatures but liquid at the rectal or vaginal temperature and will therefore melt in the rectum or vagina to release the drug.

Another mode of application is by implantation of a depot implant comprising an inert carrier material, such as biologically degradable polymers or synthetic silicones such as e.g. silicone rubber. Such implants are designed to release the active agent in a controlled manner over an extended period of time (e.g., 3 to 5 years).

It will be appreciated by those skilled in the art that the particular method of administration will depend on a variety of factors, all of which are considered routinely when administering therapeutics. It will also be understood, however, that the actual dosages of the agents of this invention for any given patient will depend upon a variety of factors, including, but not limited to the activity of the specific compound employed, the particular composition formulated, the mode of administration, time of administration, route of administration and the particular site, host, and disease being treated, and furthermore the age of the patient, the body weight of the patient, the general health of the patient, the gender of the patient, the diet of the patient, rate of excretion, drug combinations, and the severity of the condition undergoing therapy. It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional treatment tests. Optimal dosages for a given set of conditions may be ascertained by those skilled in the art using conventional dosage-determination tests in view of the experimental data for a given compound. For oral administration, an exemplary daily dose generally employed will be from about 0.01 µg/kg to about 100 mg/kg of total body weight, whereby courses of treatment may be repeated at appropriate time intervals. Administration of pro-drugs may be dosed at weight levels that are chemically equivalent to the weight levels of the fully active compounds. The daily dosage for parenteral administration will generally be from about 0.01 µg/kg to about 100 mg/kg of total body weight. A daily rectal dosage regimen will generally be from about 0.01 µg/kg to about 200 mg/kg of total body weight. A daily vaginal dosage regimen will generally be from about 0.01 µg/kg to about 100 mg/kg of total body weight. The daily topical dosage regimen will generally be from about 0.1 µg to about 100 mg administered between one to four times daily. The transdermal concentration will generally be that required to maintain a daily dose of from 0.01 µg/kg to 100 mg/kg of total body weight.

Abbreviations and Acronyms

As employed herein, the following terms have the indicated meanings.
ACN acetonitrile
Aq aqueous
Bn benzyl BOC tert-butoxycarbonyl
conc. concentrated
d day(s)
DAST N,N-diethylaminosulfur trifluoride
DCM dichloromethane=$CH_2Cl_2$
DHP 3,4-dihydro-[2H]-pyran
DIBAH Diisobutyl aluminiumhydrid
DIPEA N,N-diisopropylethylamine
DME dimethyl ethylene glycol
=1,2-dimethoxyethane
DMF N,N-dimethylformamide
DMSO dimethylsulfoxide
E1 estron
E2 estradiol
EDCI 1-(3-dimethylaminopropyl)-3-ethylcarbodiimide
EDCI.HCl 1-(3-dimethylaminopropyl)-3-ethylcarbodiimide hydrochloride
ER estrogen receptor
EtOAc ethyl acetate
h hour(s)
HMPA hexamethylphosphoramide
HOBT 1-Hydroxybenzotriazole Hydrate
HPLC High Performance Liquid Chromatography
HSD hydroxysteroid dehydrogenase
Hünig base N-Ethyldiisopropylamine=
=N(iPr)$_2$Et=EDIPA):
MeOH methanol
min minute(s)
MOM methoxy methyl
NAD(P)[H] nicotinamide-adenine-dinucleotide (phosphate) [reduced NAD(P)]
NMM N-methylmorpholine
NMO N-methylmorpholine N-oxide
NMR nuclear magnetic resonance
PG protection group
pTosOH para-toluene sulphonic acid
Rt Retention time
RT room temperature
sat saturated
STS steroid sulphatase
T3P propylphosphonic acid anhydride
TBAF Tetrabutylammonium-fluorid-Losung
TBDMS tert-butyl dimethyl siloxy
TBME tert-butyl methyl ether
TEA triethylamine
TEOF Triethylorthoformat (CH(OEt)$_3$)
THF tetrahydrofuran
THP tetrahydropyran
TLC thin-layer chromatography
TMSCl trimethylsilylchloride/Me$_3$SiCl
TPAP tetrapropylammonium perruthenate
Numbering of Compound Formulas and Intermediates The general structure formulas are typically designated with a number in roman format, followed by a or p indicating the stereochemistry at the C15 atom of the estron core if necessary. If the number of methylen groups attached at the C15 position is specified (i.e. the value of "n"), the roman number is followed by a hyphen and a number indicating the amount of methylen groups. Finally, a letter a, b or c is attached after the number "n", indicating the nature of the substituent R$^1$ at the O-atom in C3 position of the estron core (a=hydrogen, b=methyl, and c=benzyl). The prefix C in front of the number indicates that the compound may be substituted in C2 by a residue R$^{14}$. The prefix D in front of the number that the compound may be substituted in C2 by a residue R$^{14}$ and may be additionally modified within the C16-C17 position.

For example, compound IV is the general acid building block:

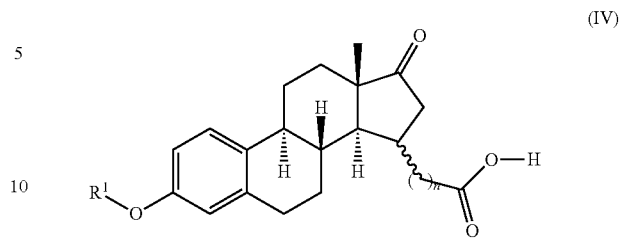

(IV)

Therefore, a compound IVβ-3a would represent a derivative of IV with β stereochemistry at C15, three methylen groups and a hydroxy group in C3 position, i.e.:

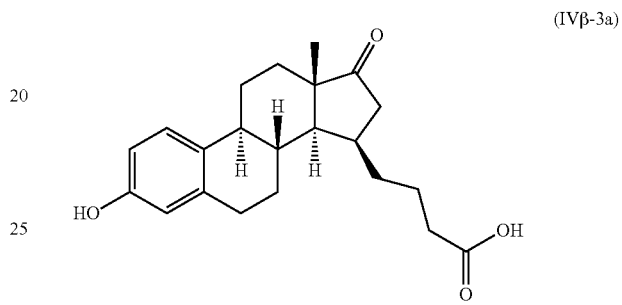

(IVβ-3a)

If particular structures of synthesized examples falling under a general formula are presented, then the designation of the general formula is followed by the particular number of this example, i.e. Example No. 652 of formula (XXXIIIα-1a)-652

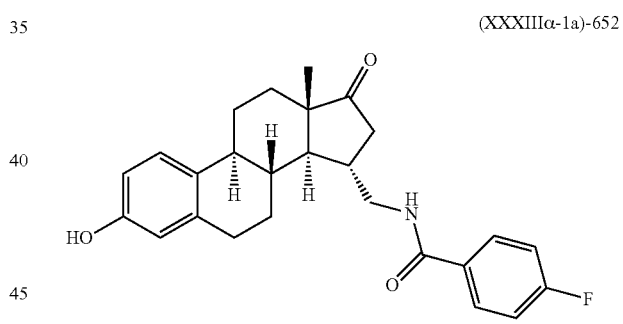

(XXXIIIα-1a)-652

This example 652 is a particular compound of the general formula XXXIIIα-1a, wherein R$^2$ is a 4-fluoro-phenyl residue.

General Preparative Methods

The compounds of the present invention may be prepared by use of known chemical reactions and procedures. Nevertheless, the following general preparative methods are presented to aid the reader in synthesizing the 17β-HSD1 and/or STS inhibitors, with specific details provided below in the experimental section to illustrate working examples.

All variable groups of these methods are as described in the generic description if they are not specifically defined below.

It is recognized that compounds of the invention with each claimed optional functional group may not be prepared by each of the below-listed methods. Within the scope of each method, optional substituents may appear on reagents or intermediates which may act as protecting or otherwise non-participating groups. Utilizing methods well known to those skilled in the art, these groups are introduced and/or removed during the course of the synthetic schemes which provide the compounds of the present invention.

Flow Diagrams

The synthesis of 3, 15 substituted estrone derivatives bearing a side chain of the amide, ester, carbonyl, hydrazone, alcohol, ether, urea, carbamate, "retro"-amide, sulfonyl urea, sulfamide, sulfamate, "retro"-sulfonamide, "retro"-carbamate, "retro"-ester or sulfonylcarbamate type in position C15 is extensively described within the international application WO 2005/047303, which is hereby incorporated by reference in its entity.

The additional modifications of the steroidal core at positions C2, C3, C16 and or C17, which are disclosed in the present invention, may be introduced in the following order of general chemical modifications (General Synthesis Scheme). The introduction of the $R^{14}$ substituent in C2 position—if present in the final compound—has to take place first, starting from the 17β-estradiol using methods well known in the art (Steps A). In parallel, the C17-OH function is oxidized to the corresponding keto function. Depending on the desired nature of $R^1$, a suitable group also functioning as protecting group may be introduced at this point. Then, the estron derivative of formula (V) is converted into the central intermediate, the 15,16-unsaturated estrone of formula X (Steps B), which is further derived in the C15 position by introduction of the basic side chain ("so called building blocks"). These building blocks are reacted with the appropriate compounds carrying the $R^2/R^4$ substitutents to lead to the desired C15 substituted compound (Steps C). The obtained educt may be further modified within the C16 and C17 position by introducing appropriate substituents $R^{10}$, $R^{12}$ and $R^{13}$ or by introducing a heterocyclic ring structure (Steps D). Finally, if necessary, the protection group in C1 position may be separated to deliver the C3-OH derivative or may be further substituted with an alternative $R^1$ side chain or may be derivated to the corresponding sulphamate, phosphonate, carbamate, thiophosphonate, sulphonate, sulphate or phosphate compounds (Steps E).

GENERAL SYNTHESIS SCHEME:

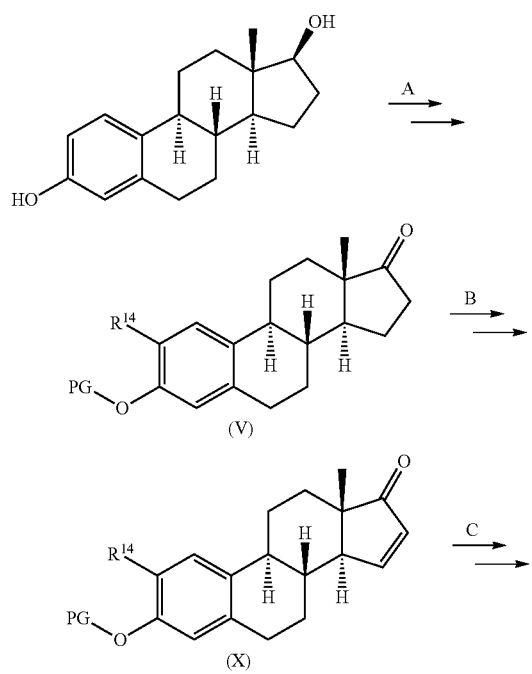

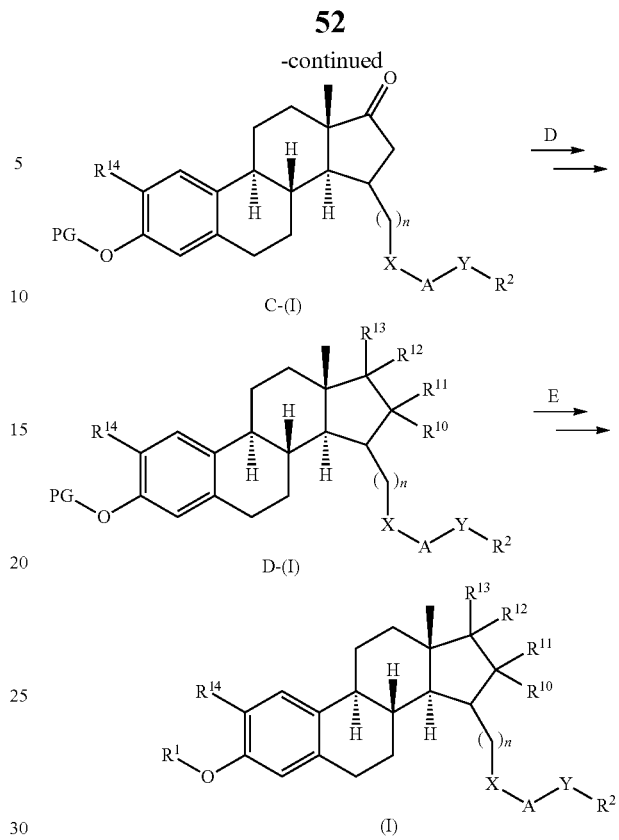

Step A—Introduction of a $R^{14}$ Side Chain in C2 Position of 17β-Estradiol or Estron

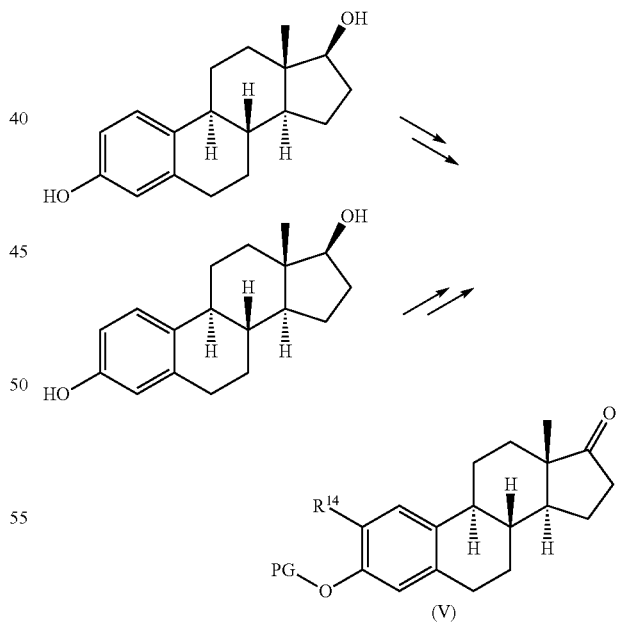

The introduction of various side chains in the estron core is known from the literature, e.g. Rao et al (2002) describe the synthesis of 2-methoxyestradiol, and the synthesis of 2-ethoxy-estradiol was disclosed by Verdier-Pinard et al (2000). 2-Ethyl-estron may be prepared from estrone by Friedel-Crafts acetylation of estrone-3-O-methyl ether and catalytic hydrogenation, followed by demethylation, which produced the desired product. Alternatively, the introduction of substituents on the 2-position may be obtained by using a Fries-rearrangement starting with estradiol and the reagent $(RCO)_2O$ with R=lower alkyl, as described by Rao et al. (2002): After acylation, the compounds should be converted into the R—CO-substituted derivatives in C2 position. Reduction of the acyl function may be achieved by reduction with Pd/C and $H_2$ [Gonzalez et al (1982)]. Alternatively, the acetoxy-group in C2-position could be oxidized with PhI $(CF_3CO_2)_2$ according to [Yoshikawa et al. (2002)]. The newly introduced hydroxy group may be further alkylated, followed by reduction of the ketone, resulting in an alkoxy-alkyl substituted estradiol derivative. An alternative strategy to introduce an alkoxy-alkyl group is exemplified for the methoxyethyl group: After MOM-protection of the 17β-estradiol, the MOM-protected estradiol is iodinated [Mohanakrishnan & Cushman (1999)]. Then, the MOM-group is replaced with a TBDMS group. Negishi coupling with allylbromide gives the 2-allyl substituted estrone derivative, which can be oxidised and methylated (including some protective group manipulations). Further synthetic ways to 2-alkyl-substituted estron or estradiol derivatives have been displayed previously [see e.g. Mohanakrishnan & Cushman (1999); Day et al. (2003); Cushman et al (1995), and Lunn & Farkas (1968)] The synthesis of further estron derivatives with various substituents in 2-position was disclosed by Cushman et al (2002).

During the introduction of the C2 side chain, the 3-hydroxy function of the steroidal core is typically protected with a methyl or benzyl group (exemplified by PG). For example, the methyl derivative can be prepared using MeJ and acetone, whereas the corresponding Benzyl-derivative may be prepared using Benzylbromid, DIPEA and acetone. Enone intermediates with other substituents in $R^1$ (=PG), in particular optionally substituted $C_1$-$C_4$-alkyl, can be prepared accordingly by using the appropriate optionally substituted $C_1$-$C_4$-alkyl-bromide or $C_1$-$C_4$-alkyl-iodide.

Step B—Synthesis of the 15, 16-Unsaturated Estrone of Formula X (Intermediate I)

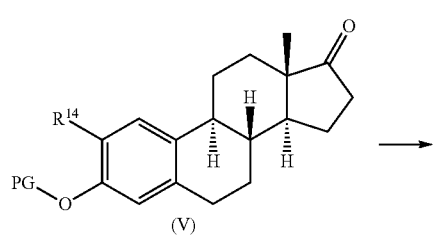

The ketal of the formula (IX) can be prepared according to Nambara from the corresponding 2-substituted estron of formula V [Nambara et al. (1976)] as depicted within the following scheme 1. If not yet protected, the introduction of PG groups in C3 position can be achieved according to a procedure described by Labaree (2003).

SCHEME 1

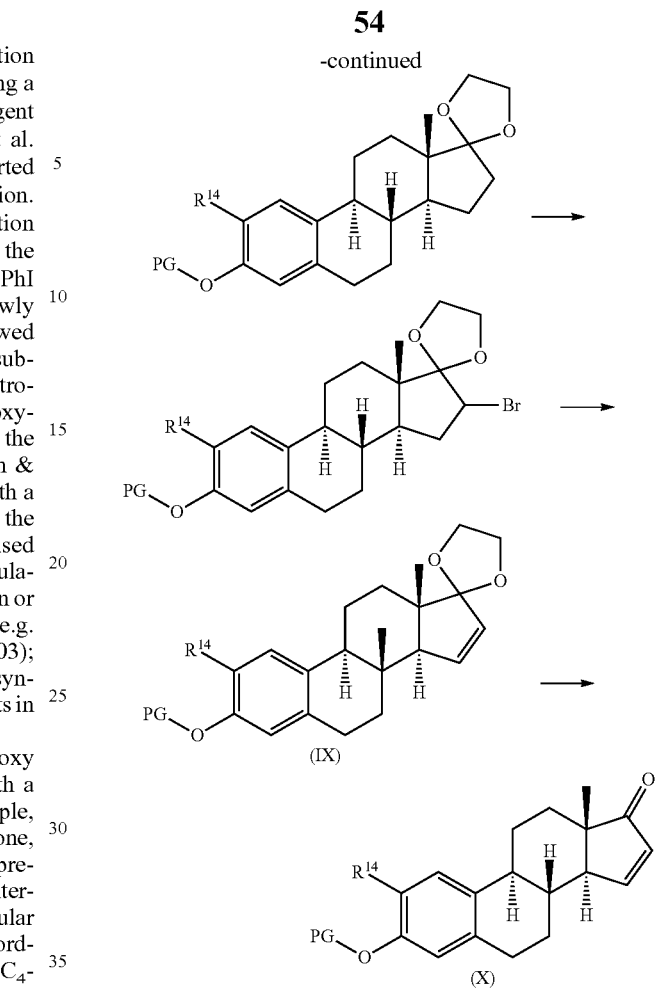

The C17 keto function of the C2 substituted and protected estron derivative of formula (V) is protected as acetal, followed by bromination. The elimination of the bromide yielded the desired 15,16-unsaturated estron. Finally, the ketal derivative is hydrolysed to give the appropriate enonederivative X.

Alternatively, the enone intermediate of formula X can be prepared from the corresponding estrone derivative according to a procedure described by Poirier et al. (1991).

Step C—Introduction of the Side Chain in C15 Position

The "Step C" modification—the introduction of the side chain in C15 position—is carried out in two major steps: In a first step the 15,16-unsaturated Estrone of formula X is converted into a so-called building block carrying an alkyl side chain in C15 position with a terminal amino, carboxy, or alcohol function. The synthesis of some exemplary building blocks is depicted in the Experimental Section "Intermediates", and was fully disclosed in international patent application WO 2005/047303.

The second step of the "Step C" modification—the conversion of the building blocks into the desired derivatives carrying the complete side chain in C15 position—is exemplified below by using one of the following synthetic schemes as shown in Flow Diagrams I to XV.

Certain formula I compounds, in which X represents a bond, A represents CO, Y represents NH or $NR^4$ and n represents an integer from 0 to 5, may be prepared by a reaction as shown in Flow Diagram Ia.

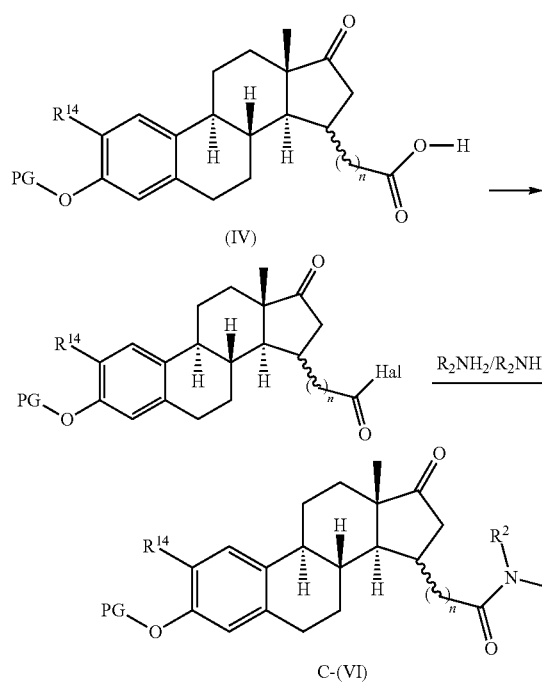

(IV)

(IV) arrow (C-VI)

The free acid (IV) may be converted to the reactive acyl halide, in particular the acid chloride, by reaction with SOCl, COCl$_2$, PCl5 or PBr$_3$ or the like. The amide derivatives C-(VI) may be prepared by a base catalyzed addition-elimination reaction, where the halogen residue is substituted with the appropriate amine $R^2NH_2$ or $R^2NHR^4$ in the presence of a base, for example DIPEA. Alternatively, especially suited for derivatives with n>2, the amide derivatives may be prepared directly from the free acids by nucleophilic substitution with the appropriate amine. Alternatively, the amide derivatives may be prepared directly from the free acids by nucleophilic substitution with the appropriate amine as shown in Flow Diagram Ib:

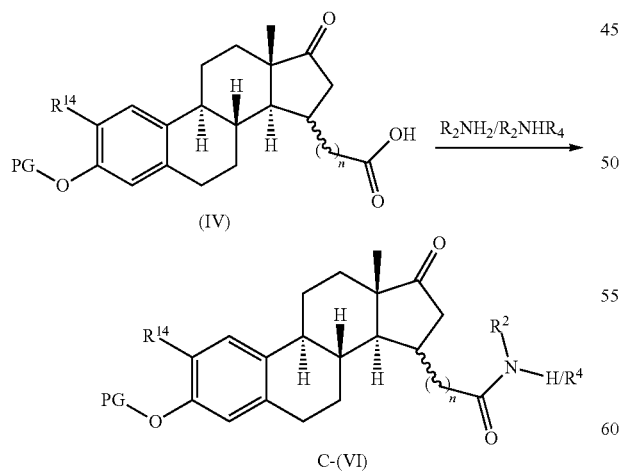

(IV)

(C-VI)

Certain formula I compounds, in which X represents a bond, A represents CO, Y represents O, and n represents an integer from 0 to 5, may be prepared by a reaction as shown in Flow Diagram II:

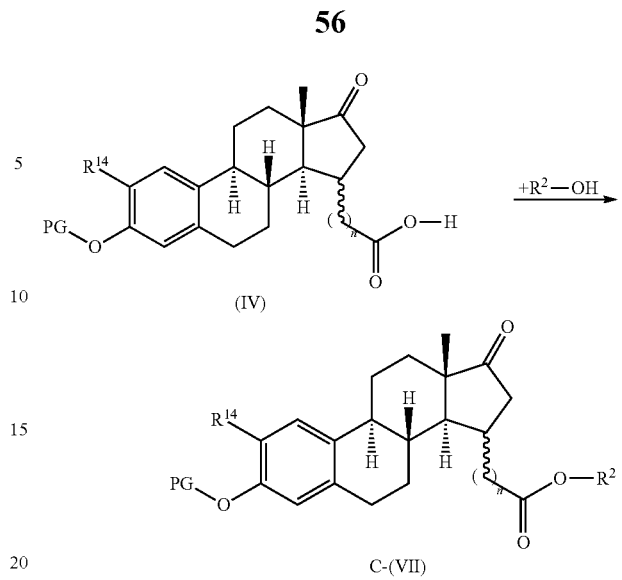

(IV)

(C-VII)

The ester derivatives C-(VII) may be prepared from the free acid (IV) by esterification with the appropriate alcohol $R^2$—OH.

Certain formula I compounds, in which X represents a bond, A represents CO, Y represents a bond, and n represents an integer from 0 to 5, may be prepared by a reaction as shown in Flow Diagram III:

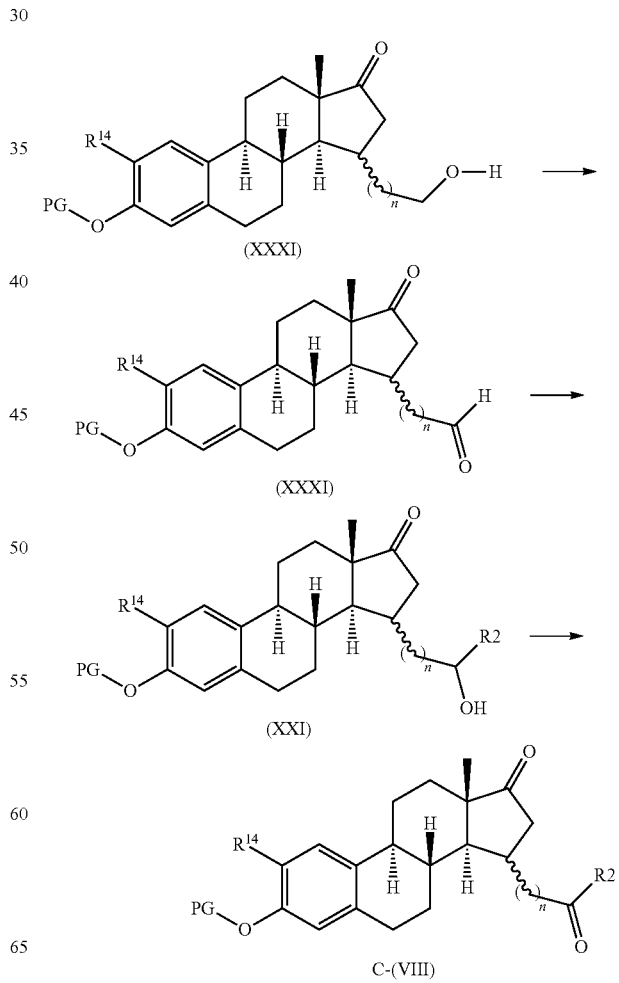

(XXXI)

(XXXI)

(XXI)

(C-VIII)

The alcohol MOM may be converted to the corresponding aldehyde (XXXIII) via Dess-Martin Oxidation. Subsequently the aldehyde may be converted by a nucleophilic addition-elimiation reaction with a Grignard or other organometallic reagent, substituted with the appropriate R² residue to the corresponding secondary alcohol (XXI), which thereafter can be oxidized again to the desired ketone C-(VIII).

Certain formula I compounds, in which X represents a bond, A represents CO, Y represents NH—NR⁴ or NH—NH, and n represents an integer from 0 to 5, may be prepared by a reaction as shown in Flow Diagram IVa.

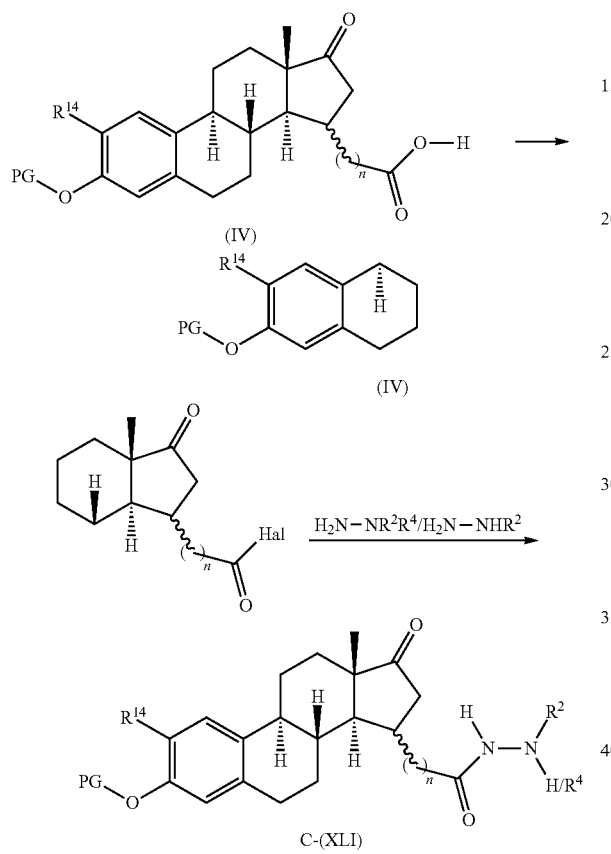

The free acid (IV) may be converted to the reactive acyl halide, in particular the acid chloride, by reaction with SOCl₂, COCl₂, PCl₅ or PBr₃ or the like. The hydrazide derivatives C-(XLI) may be prepared by a base catalysed addition-elimination reaction, where the halogen residue is substituted with the appropriate hydrazine H₂N—NHR² or H₂N—NR²R⁴ in the presence of a base, for example DIPEA. Alternatively, especially suited for derivatives with n>2, the hydrazide derivatives may be prepared directly from the free acids by nucleophilic substitution with the appropriate hydrazine using e.g. polymer bound carbodiimid, HOBT and DCM, as shown in Flow Diagram IVb:

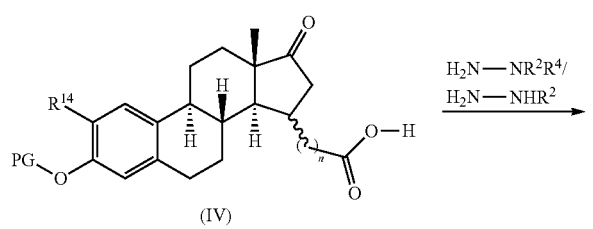

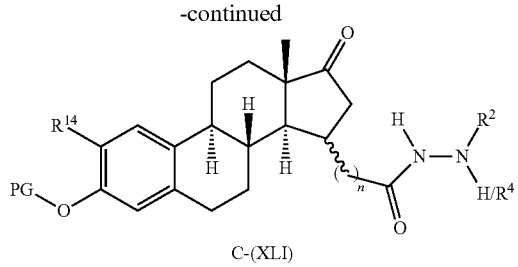

Certain formula I compounds, in which X represents a NH, A represents CO, Y represents NH, and n represents an integer from 1 to 6, may be prepared by a reaction as shown in Flow Diagram Va:

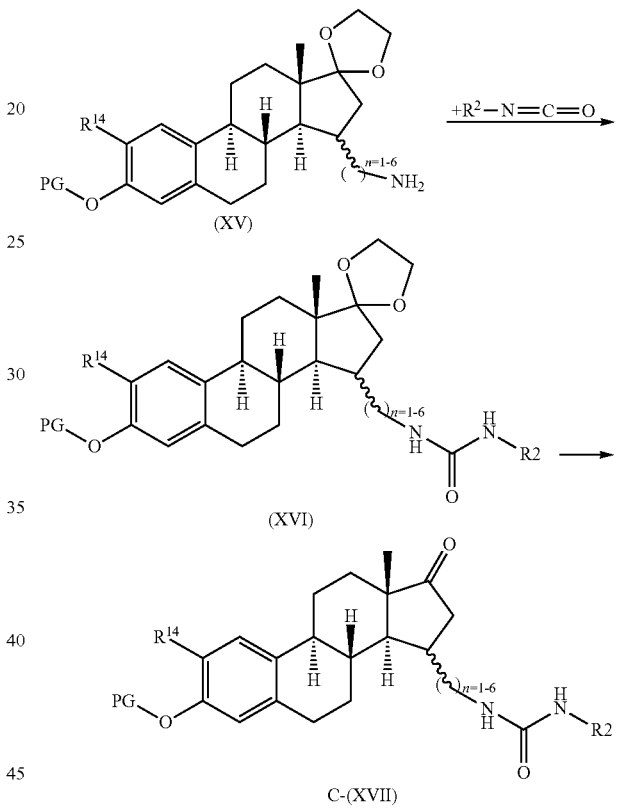

The urea derivatives of the general formula C-(XVII) may be prepared by the reaction of the amine building block (XV) with an appropriately substituted Isocyanate (R²—N=C=O). After the addition, the ketal function is converted into the keto function. Alternatively, the amine may be first reacted with carbodiimidazol or triphosghen to form a reactive carbamoyl compound, which than can react further with a suitable amine R²R⁴—NH. A further synthesis variant may use the unprotected amine (XXIX) as starting material for the reaction with an appropriately substituted Isocyanate (R²—N=C=O) as shown in Flow Diagram Vb

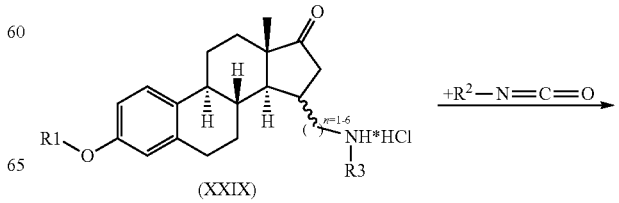

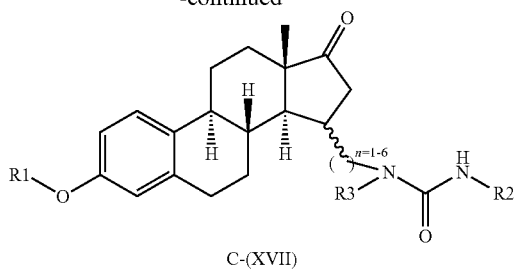

C-(XVII)

Certain formula I compounds, in which X represents a —NH—, A represents SO$_2$, Y represents NH, and n represents an integer from 1 to 6, may be prepared by a reaction as shown in Flow Diagram VI

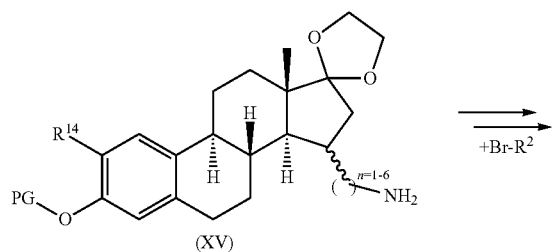

(XVIII)

C-(XIX)

In a first step, the amine building block (XV) may be converted into a protected, for example Boc-protected, sulfamide compound by a reaction with the appropriately protected chlorosulfonyl isocyanate. In a second step, the protected sulfamide compound is allowed to react with the appropriate Bromo-reagent (R$^2$—Br) to provide the still protected, substituted sulfamide derivative of the formula (XVIII). After deprotection, the desired N-substituted sulfamide derivative of formula C-(XIX) is obtained.

Certain formula I compounds, in which X represents a NH, A represents CO, Y represents O, and n represents an integer from 1 to 6, may be prepared by a reaction as shown in Flow Diagram VII:

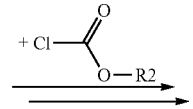

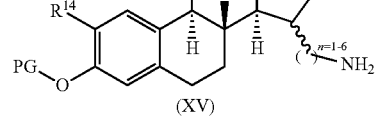

(XV)

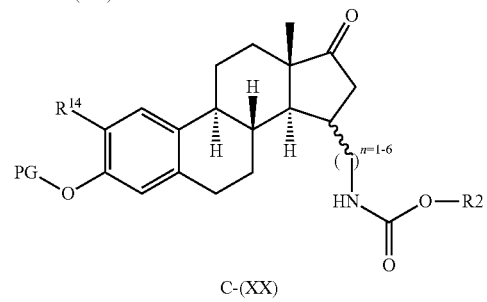

C-(XX)

The carbamate derivatives of the general formula C-(XX) may be prepared by the reaction of the amine building block (XV) with an appropriate chloroformic acid ester (R$^2$—O—CO—Cl). After the addition-elimination reaction, in a second step the ketal function is converted into the keto function.

Certain formula I compounds, in which X represents a NH, A represents SO$_2$, Y represents O, and n represents an integer from 1 to 6, may be prepared by a reaction as shown in Flow Diagram VIII:

(XV)

C-(XXII)

The sulfamate derivatives of the general formula C-(XXII) may be prepared by the reaction of the amine building block (XV) with an appropriate chlorosulfonic acid ester (R$^2$—O—SO$_2$—Cl). After the addition-elimination reaction, in a second step the ketal function is converted into the keto function.

Certain formula I compounds, in which X represents a NH, A represents CO, Y represents a bond, and n represents an integer from 1 to 6, may be prepared by a reaction as shown in Flow Diagram IXa:

(XV)

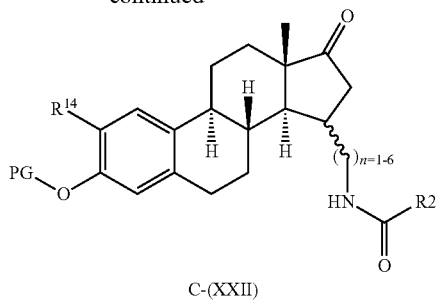

C-(XXII)

The "retro"-amide derivatives of the general formula C-(XXIII) may be prepared by the reaction of the amine building block (XV) with an appropriate acid halide, e.g. an acid chloride ($R^2$—CO—Cl). After the addition-elimination reaction, in a second step the ketal function is converted into the keto function. Alternatively, the reaction with an appropriate acid halide, e.g. an acid chloride ($R^2$—CO—Cl), can be performed using the amino-hydrochloride salt of the estrone (XXIX) as starting material as shown in the following Flow Diagram ab:

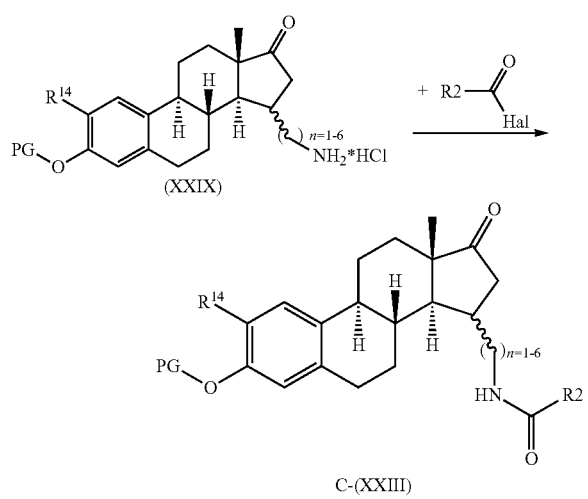

Certain formula I compounds, in which X represents a NH, A represents $SO_2$, Y represents a bond, and n represents an integer from 1 to 6, may be prepared by a reaction as shown in Flow Diagram Xa:

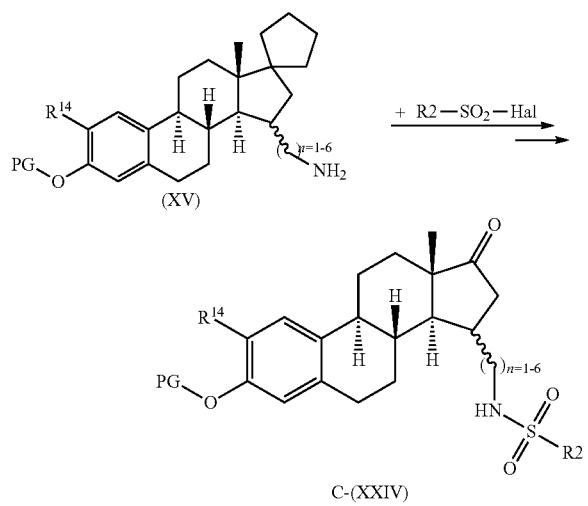

The sulfonamide derivatives of the general formula C-(XXIV) may be prepared by the reaction of the amine building block (XV) with an appropriate sulfonic acid halide, e.g. a sulfonic acid chloride ($R^2$—$SO_2$—Cl). After the addition-elimination reaction, in a second step the ketal function is converted into the keto function. Alternatively, the reaction with an appropriate sulfonic acid halide, e.g. sulfonic acid chloride ($R^2$—$SO_2$—Cl), can be performed using the amino-hydrochloride salt of the estrone (XXIX) as starting material as shown in the following Flow Diagram Xb:

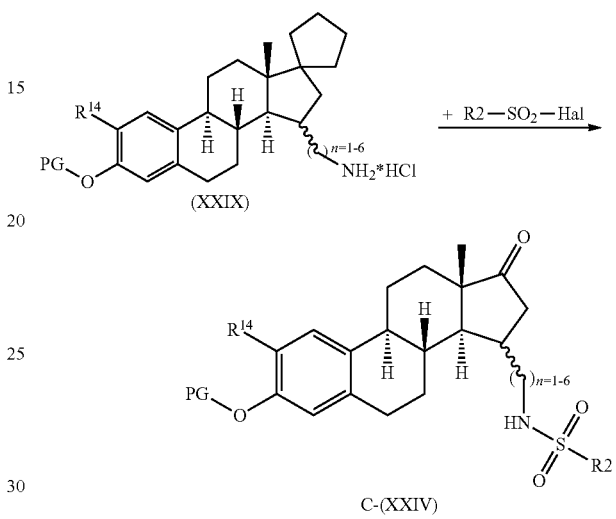

Certain formula I compounds, in which X represents a NH, A represents CO, Y represents NH—$SO_2$, and n represents an integer from 1 to 6, may be prepared by a reaction as shown in Flow Diagram XI:

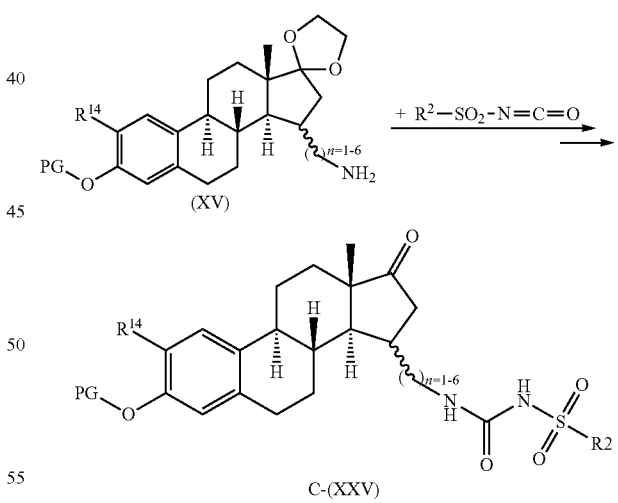

The sulfonyl urea derivatives of the general formula C-(XXV) may be prepared by the reaction of the amine building block (XV) with an appropriately substituted sulfonyl isocyanate ($R^2$—$SO_2$—N=C=O). After the addition, the ketal function is converted into the keto function.

Certain formula I compounds, in which X represents an O, A represents CO, Y represents $NR^4$, and n represents an integer from 1 to 6, may be prepared by a reaction as shown in Flow Diagram XII:

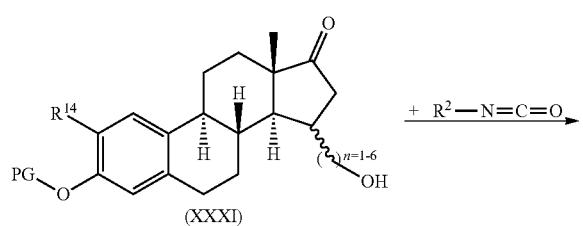

(XXXI)

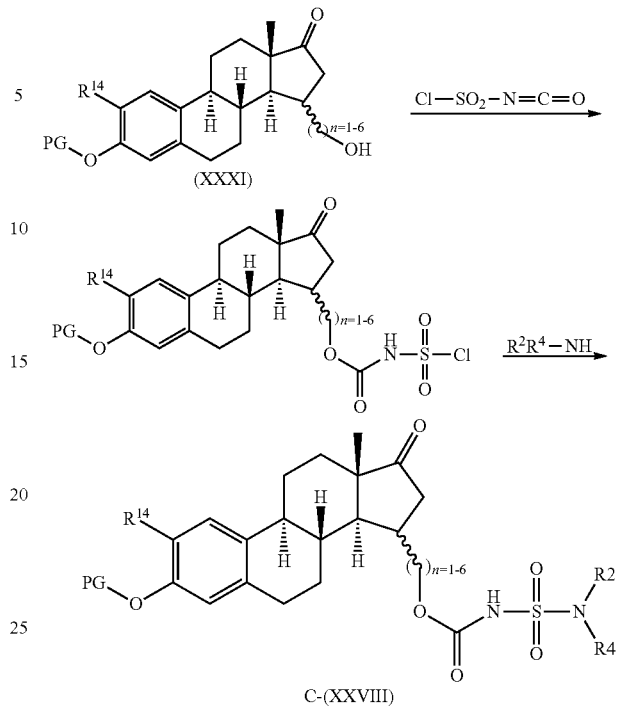

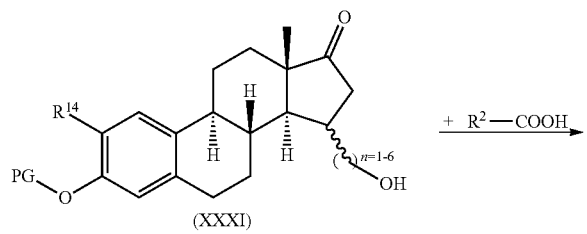

C-(XXVI)

The "retro"-carbamate derivatives of the general formula C-(XXVI) may be prepared by the reaction of the estrone alcohol building block Map with an appropriately substituted isocyanate ($R^2$—N=C=O) and subsequent purification.

Certain formula I compounds, in which X represents a O, A represents CO, Y represents a bond, and n represents an integer from 1 to 6, may be prepared by a reaction as shown in Flow Diagram XIII:

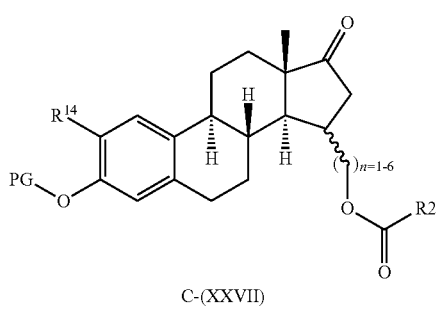

(XXXI)

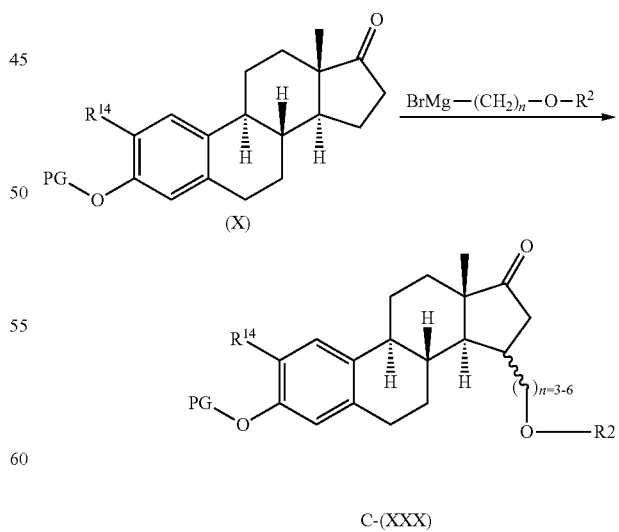

C-(XXVII)

The "retro"-ester derivatives of the general formula C-(XXVII) may be prepared by the esterification of the estrone alcohol building block (XXXI) with the appropriate carboxylic acid $R^2$—COOH and subsequent purification.

Certain formula I compounds, in which X represents a O, A represents CO, Y represents NH—$SO_2$—$NR^4$, and n represents an integer from 1 to 6, may be prepared by a reaction as shown in Flow Diagram XIV:

The sulfonylcarbamate derivatives of the general formula C-(XXVIII) may be prepared by a two-step synthesis: In a first step, the estrone alcohol building block (XXXI) is converted to the chlorosulfonylcarbamate intermediate by reaction with chlorosulfonyl isocyanate. Subsequently, the intermediate is allowed to react with the appropriate primary or secondary amine $HNR^2R^4$ in in order to give the desired sulfonylcarbamate derivative.

Certain formula I compounds, in which X-A-Y represents, and $R^2$ is different from H may be prepared by a reaction as shown in Flow Diagram XV:

The ether derivatives of the general formula C-(XXX) may be prepared the reaction of an appropriate Grignard reagent BrMg—$(CH_2)_n$—O—$R^2$ (for n=3-6) with the 15,16-unsaturated estrone derivative of formula X. Alternatively, ether derivatives may be prepared by derivatisation of the corresponding alcohol of the general formula (XXXI).

The synthesis of certain formula I compounds, in which X-A-Y represents O, $R^2$ represents H, and n represents an integer from 1 to 6, according to general formula C-(XXXI) is described within the section "Intermediates".

C-(XXXI)

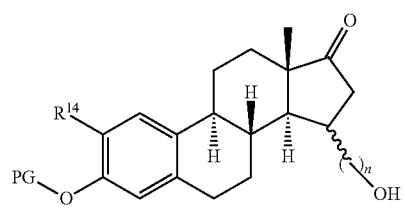

Step D—Modification of the C17-Keto Function or Introduction of a Heterocyclic Ring System in C16-C17

Since the C15-side chain as well as the C2 side chain were already introduced, it is clear for the skilled artisan, that, where necessary, functional groups in the alcohol D(I)-OH may be protected in known manner and the protecting group or groups removed at the end of the reaction.

Step D-1, for compounds when the substituents $R^{10}$, $R^{11}$, $R^{12}$ and $R^{13}$ together with the carbon atoms, to which they are attached, form a structure —$CR^{13}R^{12}$—$CR^{11}R^{10}$—, which is selected from the group of (a)

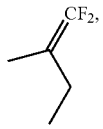

forming a compound of general formula D-(I)-(=CF$_2$)

D-(I)-(=CF$_2$)

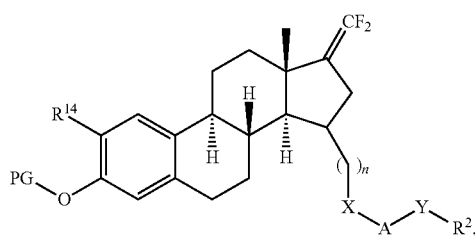

(b)

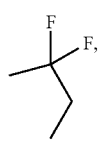

forming a compound of general formula D-(I)-F$_2$

D-(I)-F$_2$

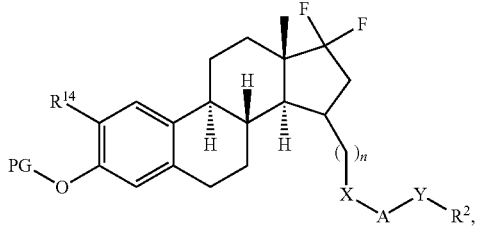

(C)

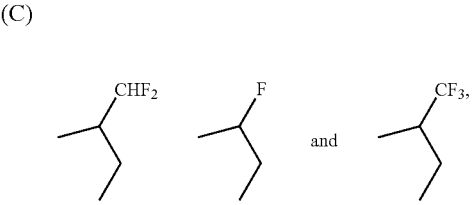

and forming a compound of general formula D-(I)-(c)

D-(I)-(c)

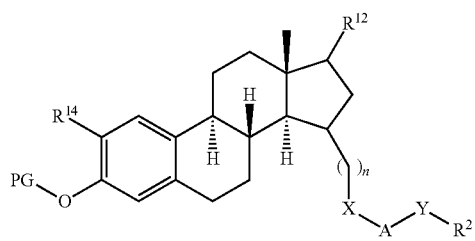

wherein $R^{12}$ represents —F, —CF$_3$, or —CF$_2$H; and (d)

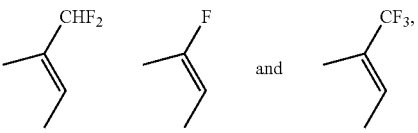

and forming a compound of general formula D-(I)-(d)

D-(I)-(d)

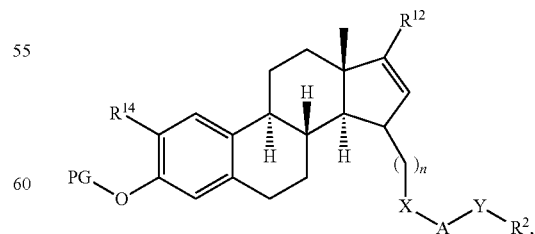

or
wherein $R^{12}$ represents —F, —CF$_3$, or —CF$_2$H.

For synthesis of some D-(I) compounds and in order to enable library synthesis, it might be necessary that some of the reaction steps explained under "STEPS C—the introduction of the C15 side chain" have to be carried out after having introduced the respective fluoro group. A typical scenario might be that after optional introduction of the $R^{14}$ residue in C2 position, the 15,16-unsaturated intermediate (X) is prepared. This is further derivatized to the appropriate acid, alcohol, amid or alkenyl intermediate ("building block"—see section "Intermediates"). Then, the fluoro group is introduced into C17 position of the steroidal core using a synthesis scheme as described in more detail below. The so-obtained intermediate is then used for optional further modification of the C15 side chain and introduction of the $R^2/R^4$ substituents. Finally any protection groups in C3 position might be cleaved off.

D-(I)-(a): Synthesis of Compounds, Wherein $R^{10}$ and $R^{11}$ Both Represent —H and $R^{12}$ and $R^{13}$ Together Represent =$CF_2$

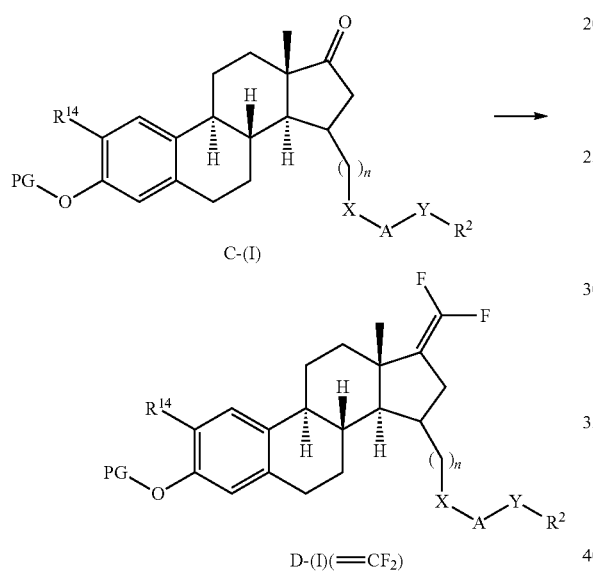

The introduction of a =$CF_2$ group in C17 position of the estron core is a reaction well known in the art, see e.g. Edwards et al (1990) using $F_2CP(O(Ph))_2$ as fluorinating reagent, or by using the Horner reaction with $F_2CP(O)(OEt)_2$ as fluorinating reagent Schwarz et al (2001). In addition, the reaction can be carried out according to procedures described within international patent application WO 96/28462. Subsequent deprotection of the C3-hydroxy function may be obtained using standard techniques.

D-(I)-(b): Synthesis of Compounds, Wherein $R^{10}$ and $R^{11}$ Both Represent —H and $R^{12}$ and $R^{13}$ Both Individually Represent —F

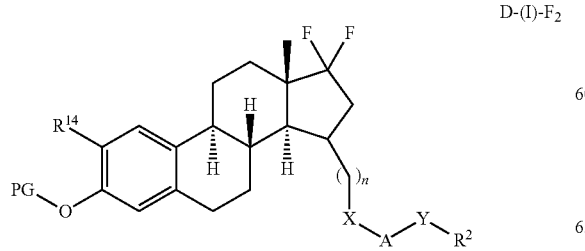

Reaction Scheme:

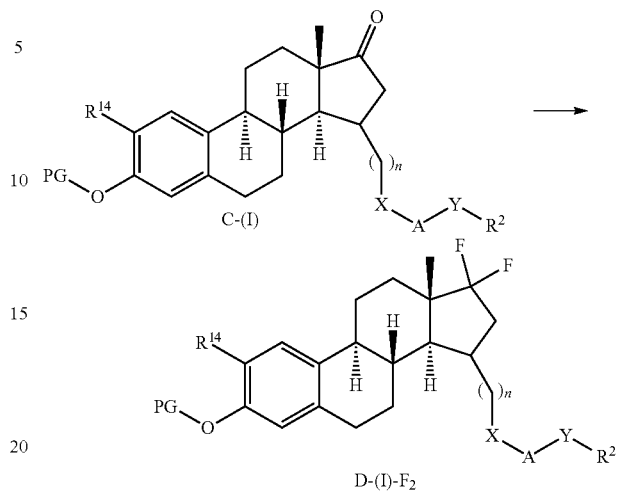

The difluorination of the C17 atom of the estron core is a reaction well known in the art and was already disclosed in U.S. Pat. No. 3,413,321 and U.S. Pat. No. 3,347,878. Furthermore, the difluorination of the C17 atom of the estron core may be achieved using the DAST (N,N-diethylaminosulfur trifluoride) reagent [Liu et al (1992)].

D-(I)-(c): Synthesis of Compounds, Wherein $R^{10}$, $R^{11}$ and $R^{13}$ all Represent —H and $R^{12}$ is Selected from —F, —$CF_3$, and —$CF_2H$

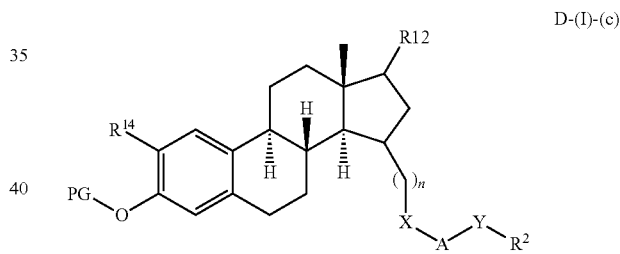

1. $R^{12}$ Represents —F

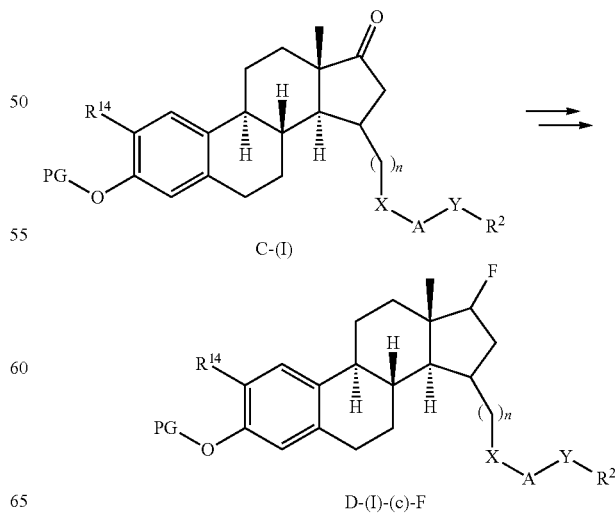

The mono-fluorination of the C17 atom of the estron core is a reaction well known in the art and may be performed according to the disclosure of U.S. Pat. No. 3,275,623.

2. $R^{12}$ Represents —$CF_2H$

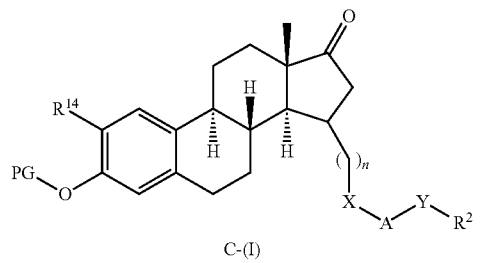

C-(I)

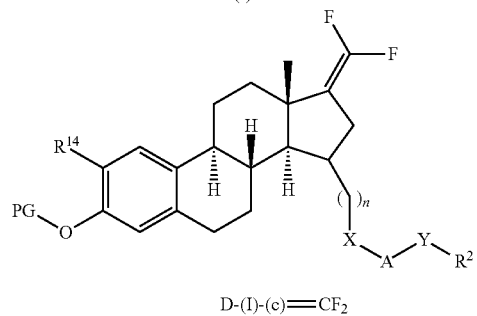

D-(I)-(c)=$CF_2$

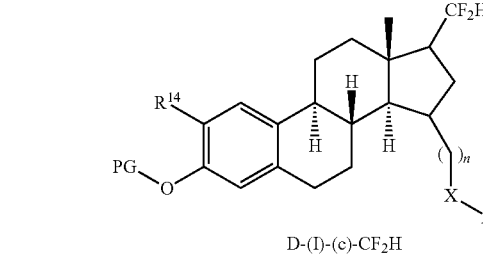

D-(I)-(c)-$CF_2H$

The desired compound of the general formula D-(I)-(c)-$CF_2H$ may be obtained by hydrogenation of the corresponding 17-difluoromethylene substituted derivative, the synthesis of which is described above. If desired, the protection group is subsequently removed.

3. $R^{12}$ Represents —$CF_3$

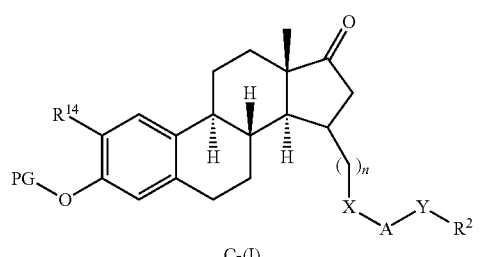

C-(I)

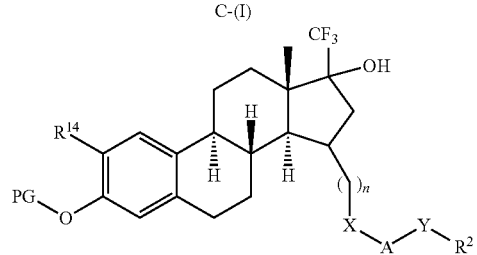

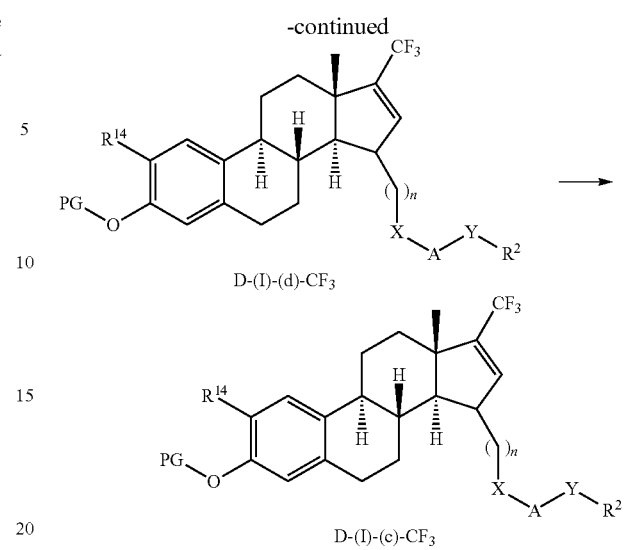

D-(I)-(d)-$CF_3$

D-(I)-(c)-$CF_3$

The introduction of the —$CF_3$ group in C17 position of the estron core may be performed according to Wang & Ruan (1994). Then, the double bond in C16, C17 position is introduced by acidic elimination to deliver a compound of general formula D-(I)-(d)-$CF_3$. The unsaturated derivative may be converted into the corresponding saturated compound by hydrogenation. If desired, the protection group is subsequently removed to deliberate the 3-hydroxy function.

D-(I)-(d): Synthesis of Compounds, Wherein $R^{10}$ Represents —H, $R^{11}$ Together with $R^{13}$ Forms a Bond, and $R^{12}$ is Selected from —F, —$CF_3$, and —$CF_2H$

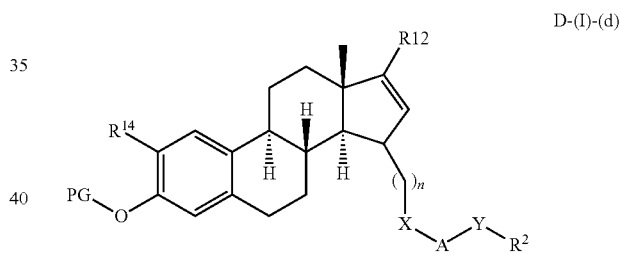

1. $R^{12}$ Represents —F

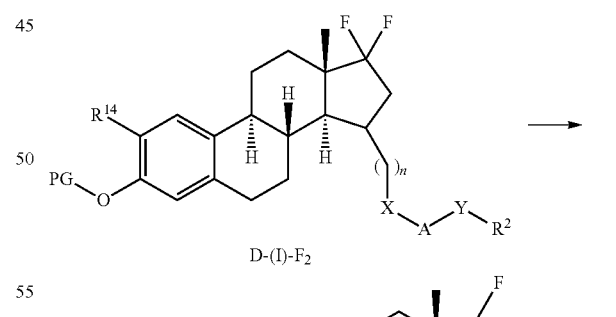

D-(I)-$F_2$

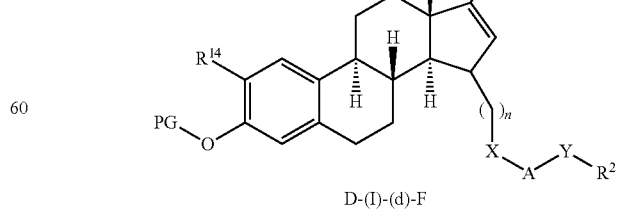

D-(I)-(d)-F

The 17-monofluorinated, 16,17-unsaturated estron derivative may be obtained starting from the corresponding 17-difluorinated compound, the synthesis of which was explained above, according to the procedure described by Liu et al. (1992). If desired, the protection group can be subsequently removed.

2. $R^{12}$ Represents —$CF_2H$

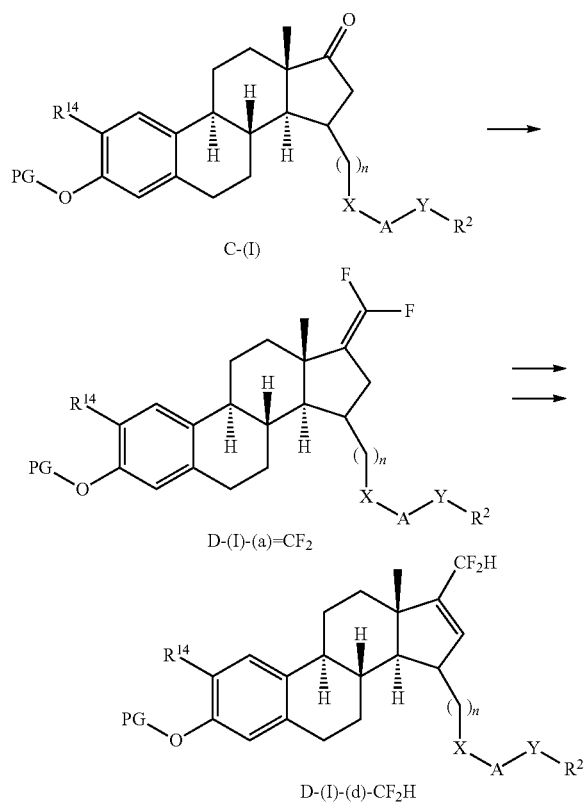

The desired compound of the general formula D-(I)-(d)-$CF_2H$ may be obtained by Pd-catalyzed isomerization of the double bond of the corresponding 17-difluoromethylene substituted derivative, the synthesis of which has been described above. If desired, the protection group can be subsequently removed.

3. $R^{12}$ Represents —$CF_3$

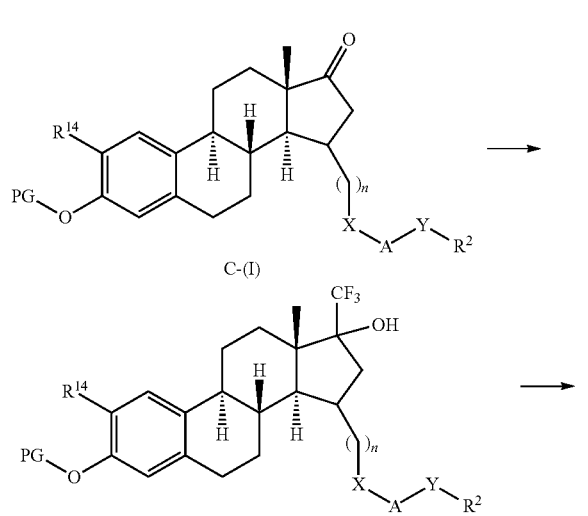

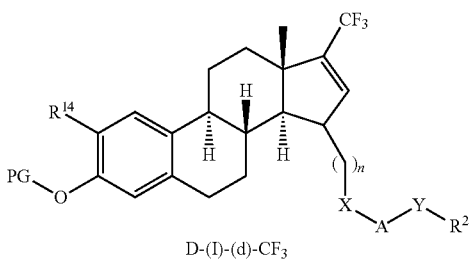

The introduction of the —$CF_3$ group in C17 position of the estron core may be performed according to Wang & Ruan (1994). Then, the double bond in C16, C17 position is introduced by acidic elimination to deliver the 16, 17 unsaturated estron derivative of general formula D-(I)-(d)-CF3. If desired, the protection group is subsequently removed to deliberate the 3-hydroxy function.

Step D-2, for compounds when the substituents $R^{10}$, $R^{11}$, $R^{12}$ and $R^{13}$ together with the carbon atoms, to which $R^{10}$, $R^{11}$, $R^{12}$ and $R^{13}$ are attached, form a heterocyclic 5- or 6-membered ring, which is partly unsaturated or aromatic, which contains one, two or three heteroatoms independently selected from N, O and S, the number of N atoms being 0, 1, 2 or 3 and the number of O and S atoms each being 0, 1 or 2, wherein one heteroatom is directly attached to the C17 C-atom of the steroidal core; and which ring is optionally substituted with an alkyl group.

The synthesis of estron derivatives carrying an additional heterocyclic ring in C16-C17 position of the steroidal core has already been disclosed within international patent application WO 2004/085457; the synthesis schemes depicted there can also be applied to the intermediates of the present invention in order to receive the compounds of the present invention. Some reactions are exemplified in more detail below.

Preferably, the substituents $R^{10}$, $R^{11}$, $R^{12}$ and $R^{13}$ together with the carbon atoms, to which $R^{10}$, $R^{11}$, $R^{12}$ and $R^{13}$ are attached, form a heterocyclic 5- or 6-membered ring to provide a compound of one of the following formulas

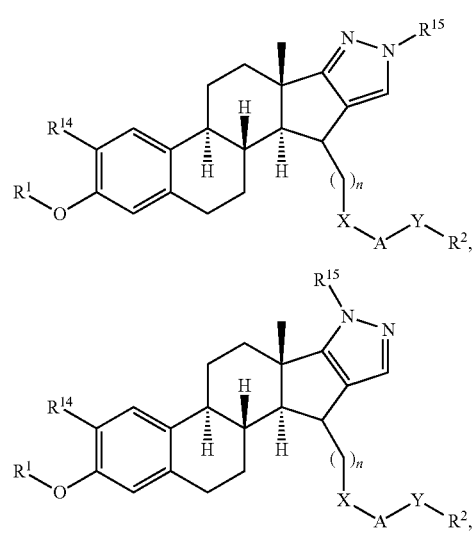

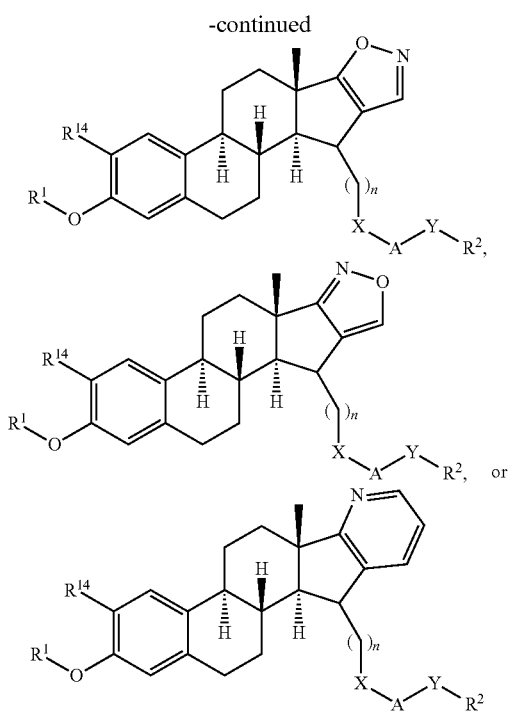

wherein R[15] represents —H or —(C$_1$-C$_4$)alkyl.

For synthesis of the D-(II) compounds it might be necessary that some of the reaction steps explained under "STEPS C—the introduction of the C15 side chain" have to be carried out after having introduced the heterocyclic ring system. A typical scenario might be, that after optional introduction of the R[14] residue in C2 position, the 15,16-unsaturated intermediate (X) is prepared. This is further derivatized to the appropriate acid, alcohol, amid or alkenyl intermediate ("building block"). Then, the heterocyclic ring system is introduced including the C16-C17 carbon atoms attached to the D-ring using a synthesis scheme according to WO 2004/085457 or as described below. The so-obtained intermediate is then used for further modification of the C15 side chain and introduction of the R$^2$/R$^4$ substituents. Finally any protection groups in C3 position might be cleaved off.

D-(II)-(a) and D-(II)-(b): Synthesis of Compounds of Formula D-(II)-(a) and D-(II)-(b)

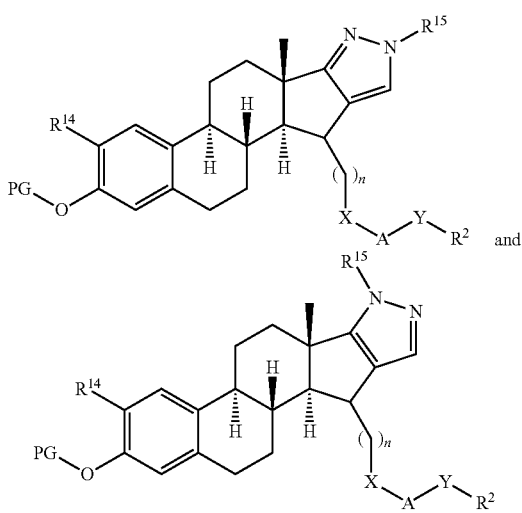

The pyrazole-unit is known in steroid-chemistry and is constructed in 3 steps as depicted in the following scheme for D-(II)-(a):

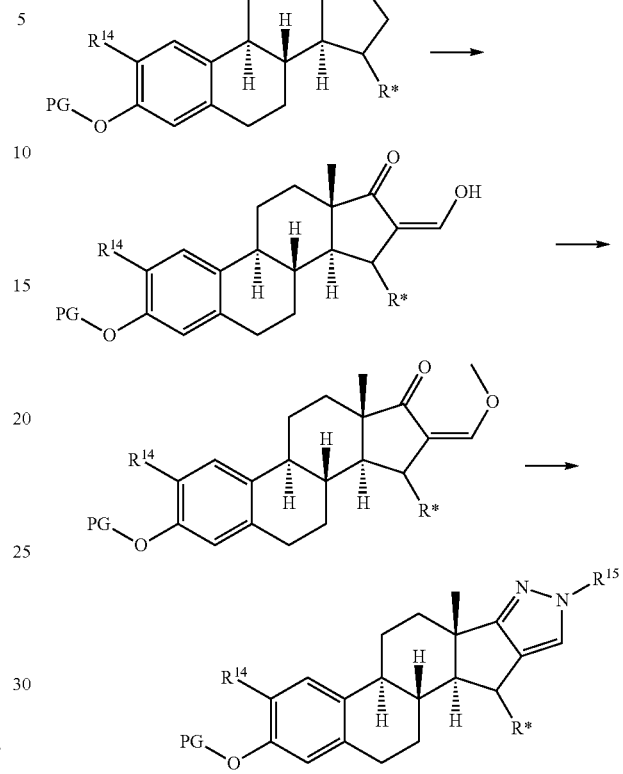

The R* residue may represent the completely introduced C15 side chain —(CH$_2$)$_n$—X-A-Y—R$_2$, or may represent an intermediate side chain such as —CH$_2$—CH=CH$_2$, or —CH$_2$—CH$_2$—CH$_2$—CH=CH$_2$ (see also SCHEMES 7B and 7C for introduction and further modification of this alkenyl side chain).

First a α-hydroxymethylene moiety is introduced with NaOMe (or NaH) and ethylformate [Wölfling et al (2003), Oda et al (1989), Schneider et al (1983)]. After methylation with K$_2$CO$_3$ and MeI (WO 2004/85457) or MeOH and CeCl3 [Akanni & Marples (1993)], the ring is closed with the appropriate hydrazine or alkylhydrazine, e.g. methylhydrazine [Xenos & Catsoulacos (1985)]. Alternatively, the methylpyrazine is constructed from the methoxymethylene compound with hydrazine, followed by alkylation with MeI.

D-(II)-(c) and D-(II)-(d): Synthesis of Compounds of Formula D-(II)-(c) and D-(II)-(c)

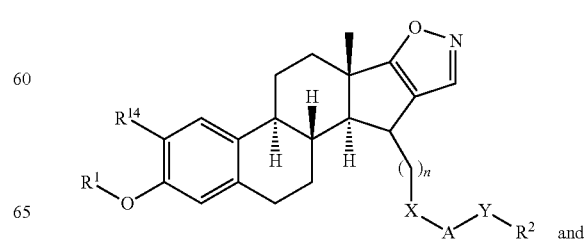

and

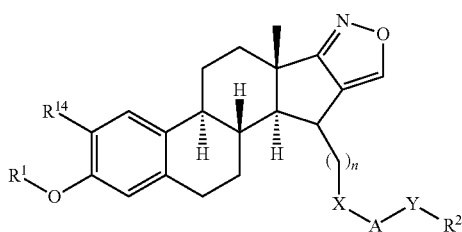

The introduction of the isooxazole group as attached heterocycle to the D-ring of the steroidal core may be achieved according to the synthesis of the corresponding pyrazole derivative and is constructed in 3 steps as depicted in the following scheme for D-(II)-(c/d):

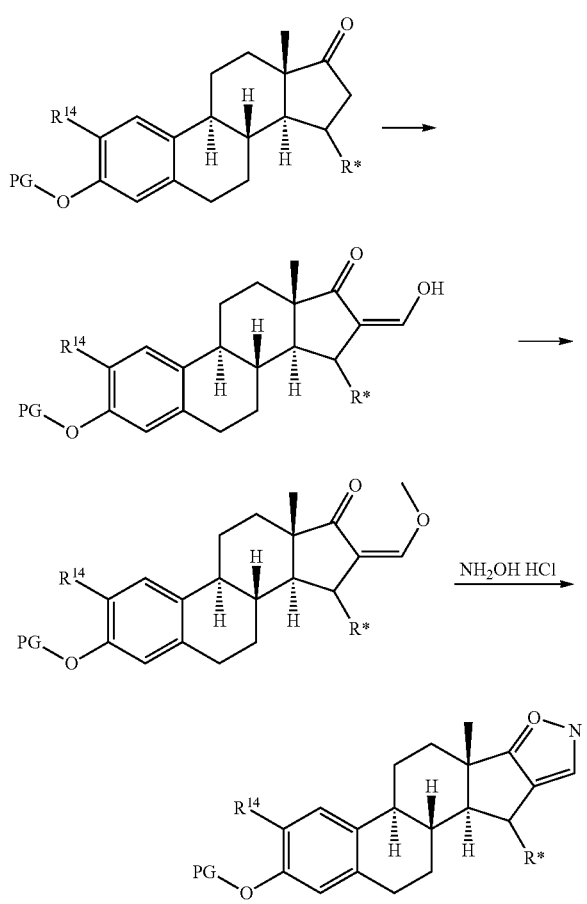

The R* residue may represent the completely introduced C15 side chain —(CH$_2$)$_n$—X-A-Y—R$_2$, or may represent an intermediate side chain such as —CH$_2$—CH=CH$_2$, or —CH$_2$—CH$_2$—CH$_2$—CH=CH$_2$ (see also SCHEMES 7B and 7C for introduction and further modification of this alkenyl side chain).

First a α-hydroxymethylene moiety is introduced with NaOMe (or NaH) and ethylformate [Wölfling et al (2003), Oda et al (1989), Schneider et al (1983)]. After methylation with K$_2$CO$_3$ and MeI (WO 2004/85457 A2) or MeOH and CeCl$_3$ [Akanni & Marples (1993)], the ring is closed with the appropriate hydroxylamine.

D-(II)-(e): Synthesis of Compounds of Formula D-(II)-(e)

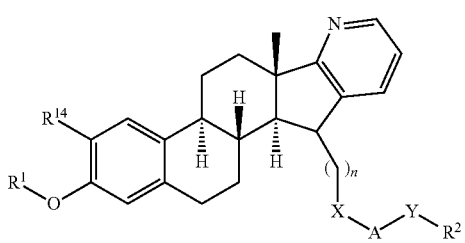

The synthesis of the C15 estrone derivatives with an attached pyridin ring to the D-ring of the steroidal core is fully disclosed in internation patent application WO 2004/085457.

Step E—Modification of the R1 Residue

In case that R1 represents —H, or optionally substituted —(C1-C6)alkyl, phenyl or —(C1-C6)alkylphenyl, then the substituent may already have been introduced during synthesis of the Intermediates as explained for R1=H, R1=methyl and R1=benzyl. In case of further modification of the 3-OH function to a sulphamate, carbamate, phosphonate, thiophosphonate, sulphonate, phosphate or sulphate group, this may be obtained by one of the following reactions:

Sulphamate Compound Preparation

The sulphamate compounds of the present invention may be prepared by reacting the correspondingly substituted estron derivative of the general formula D-(I) with a free 3-OH group with a suitable sulfamoyl chloride of the general formula R$^3$R$^3$'NSO$_2$Cl.

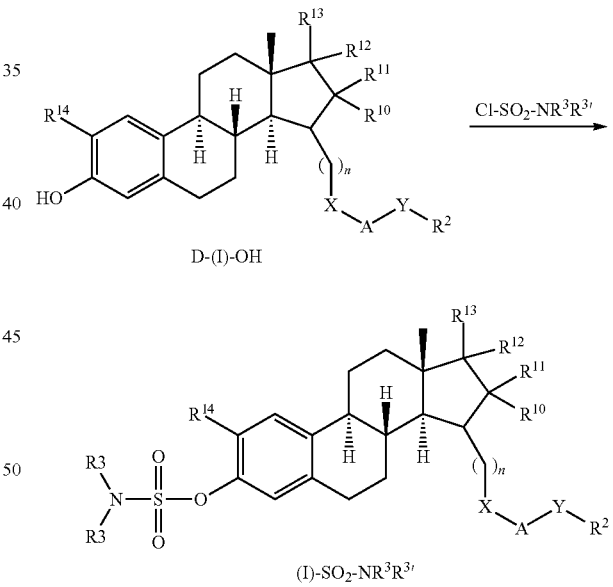

Typical conditions for carrying out the reaction are as follows: Sodium hydride and a sulfamoyl chloride are added to a stirred solution of the alcohol D(I)-OH in anhydrous dimethyl formamide at 0° C. Subsequently, the reaction is allowed to warm to RT whereupon stirring is continued for a further 24 h. The reaction mixture is poured onto a cold saturated solution of sodium bicarbonate and the resulting aqueous phase is extracted with DCMe. The combined organic extracts are dried over anhydrous MgSO$_4$. Filtration followed by solvent evaporation in vacuo and co-evaporated with toluene affords a crude residue which is further purified by flash chromatography.

Alternatively, sulfamoyl chloride (1 mmol) was added to a stirred solution of the alcohol D(I)-OH (0.5 mmol) in anhydrous N,N-dimethylacetamide (0.75 ml) at 0° C. The mixture was stirred at RT for 3 h and then poured into cold brine (10 ml). The resulting mixture was extracted with EtOAc (3×10 ml), the combined organic layers were washed with brine (10 ml), dried (MgSO$_4$), and concentrated under reduced pressure. The product was purified by flash chromatography on silica gel.

Where necessary, functional groups in the alcohol D(I)-OH may be protected in known manner and the protecting group or groups removed at the end of the reaction. Preferably, the sulphate compounds are prepared according to the teachings of Page et al (1990).

Carbamate Compound Preparation

The carbamate compounds of the present invention may be prepared by derivatisation of the correspondingly substituted estron derivative of the general formula D-(I) with a free 3-OH group.

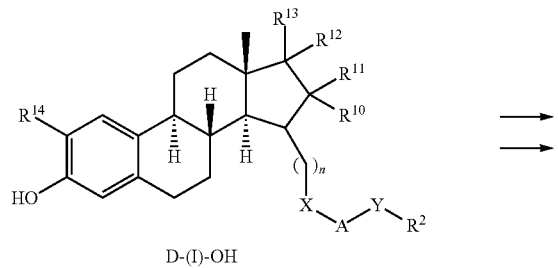

D-(I)-OH

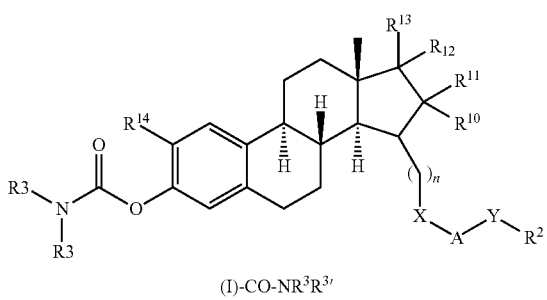

(I)-CO-NR$^3$R$^{3'}$

Typical conditions for carrying out the reaction are as follows: 1 eq Estrone derivative D-(I)-OH, 3 eq N-methylmorpholine and 1/3 eq Triphosgen were dissolved in DCM and stirred for 30 min at 0° C. Then, 1 eq of the desired amine was added and the reaction mixture stirred for 12 h at RT. Thereafter the reaction mixture was quenched by adding 1M NaHCO$_3$. The organic layer was separated and extracted with 1M KHSO$_4$ and 1M NaCl. After drying over Na$_2$SO$_4$ the solution was evaporated to dryness and purified by column chromatography. Where necessary, functional groups in the alcohol D(I)-OH may be protected in known manner and the protecting group or groups removed at the end of the reaction.

Sulphonate Compound Preparation

The sulphonate compounds of the present invention may be prepared starting from the correspondingly substituted estron derivative and by suitably combining the teachings of Page et al (1990) and published international patent application WO 93/05063.

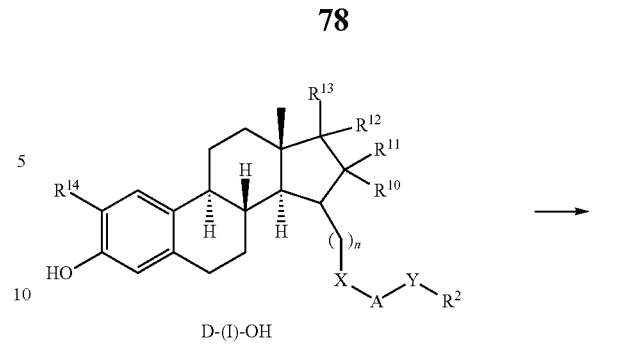

D-(I)-OH

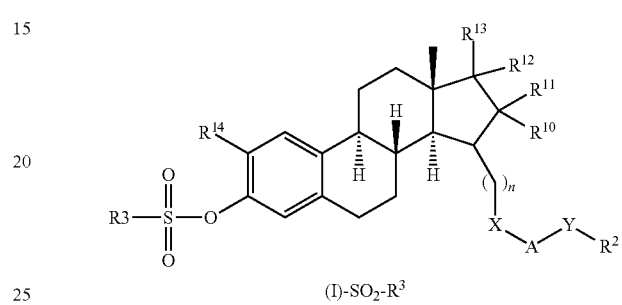

(I)-SO$_2$-R$^3$

Phosphonate Compound Preparation

The phosphonate compounds of the present invention may be prepared starting from the correspondingly substituted estron derivative and by suitably combining the teachings of Page et al (1990) and published international patent application WO 93/05063.

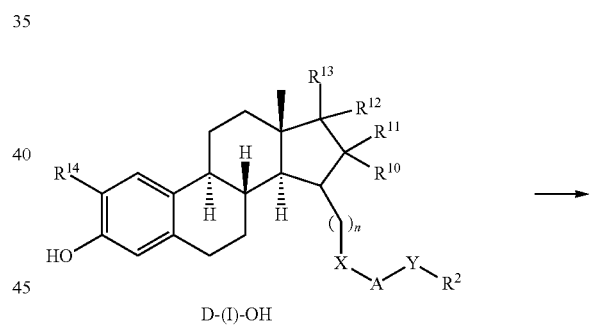

D-(I)-OH

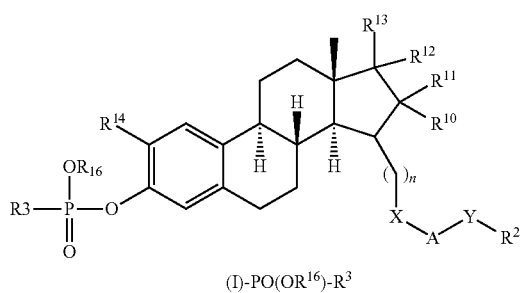

(I)-PO(OR$^{16}$)-R$^3$

Thiophosphonate Compound Preparation

The thiophosphonate compounds of the present invention may be prepared starting from the correspondingly substituted estron derivative and by suitably combining the teachings of Page et al (1990) and published international patent application WO 93/05063.

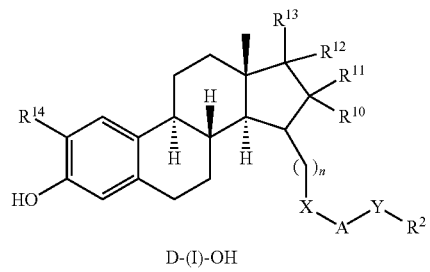

D-(I)-OH

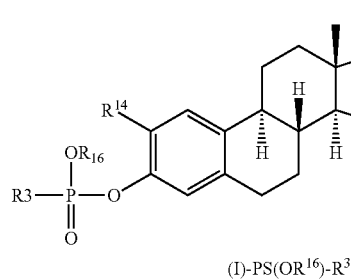

(I)-PS(OR$^{16}$)-R$^3$

Sulphate Compound Preparation

The sulphate compounds of the present invention may be prepared starting from the correspondingly substituted estron derivative using known sulfating reagents, such as complexes of sulfur trioxide with Lewis bases such as trialkylamines (e.g. SO$_3$*Et$_3$N), DMF, or pyridine.

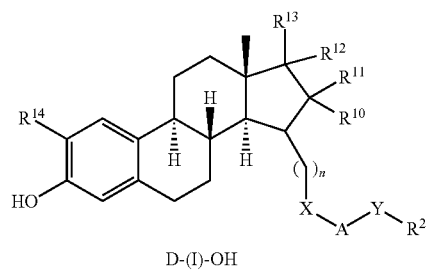

D-(I)-OH

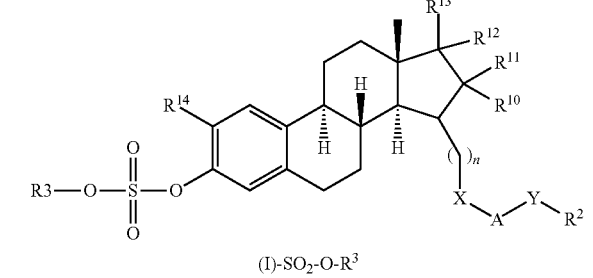

(I)-SO$_2$-O-R$^3$

Phosphate Compound Preparation

The phosphate compounds of the present invention may be prepared starting from the correspondingly substituted estron derivative by phosphorylation using e.g. phosphoramidite chemistry or treatment with pyrophosphoric tetrachloride.

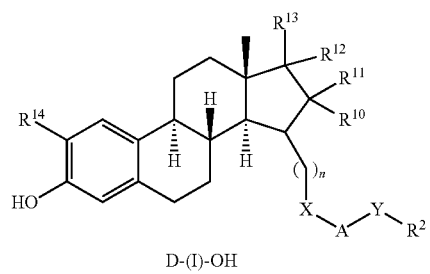

D-(I)-OH

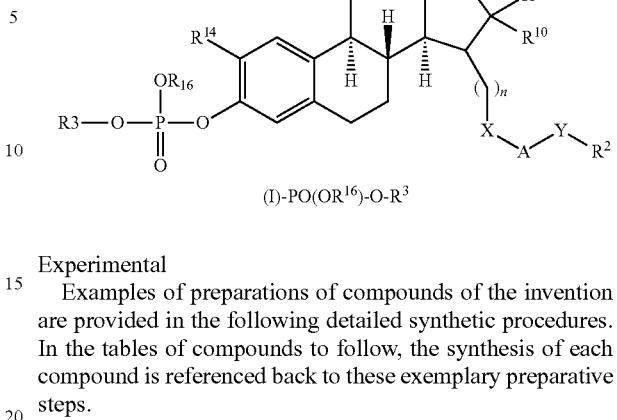

(I)-PO(OR$^{16}$)-O-R$^3$

Experimental

Examples of preparations of compounds of the invention are provided in the following detailed synthetic procedures. In the tables of compounds to follow, the synthesis of each compound is referenced back to these exemplary preparative steps.

In single compound synthesis as well as in combinatorial synthesis all reactions were stirred magnetically or shaked with an orbital shaker unless otherwise indicated. Sensitive liquids and solutions were transferred via syringe or cannula, and introduced into reaction vessels through rubber septa, in these cases the reaction were carried out under a positive pressure of dry argon or dry nitrogen. Commercial grade reagents and solvents were used without further purification.

Unless otherwise stated, the term "concentration under reduced pressure" refers to use of a Buchi or Heidolph rotary evaporator ("Rotavapor") or vacuum centrifuges ("GeneVac" or "Christ alpha RVC") at approximately 15 mm of Hg. All temperatures are reported uncorrected in degrees Celsius (° C.). Unless otherwise indicated, all parts and percentages are by volume.

Thin-layer chromatography (TLC) was performed on Merck® precoated glass-backed silica gel or aluminium sheets 60A F-254 250 μm plates. Visualization of plates was effected by one or more of the following techniques: (a) ultraviolet illumination (254 nm or 266 nm), (b) exposure to iodine vapor, (c) spraying of the plate with Schlittler's reagent solution followed by heating, (d) spraying of the plate with anisaldehyde solution followed by heating, and/or (e) spraying of the plate with Rauxz reagent solution followed by heating. Column chromatography (flash chromatography) was performed using 230-630 mesh ICN, SiliTech 60A silica gel.

Melting points (mp) were determined using a Reichert Thermovar melting point apparatus or a Mettler DSC822 automated melting point apparatus and are uncorrected.

Fourier transform infrared spectra were obtained using a Perkin Elmer spectrophotometer.

Proton ($^1$H) nuclear magnetic resonance (NMR) spectra were measured with a Bruker ARX (400 MHz) or Bruker ADVANCE (500 MHz) spectrometer with either Me$_4$Si (δ 0.00) or residual protonated solvent (CHCl$_3$ δ 7.26; CHD$_2$OD δ 3.30; DMSO-d$_5$ δ 2.50) as standard. Carbon ($^{13}$C) NMR spectra were measured with a Bruker ARX (100 MHz) or Bruker ADVANCE (126 MHz) spectrometer with either Me$_4$Si (δ 0.00) or solvent (CDCl$_3$ δ 77.05; CD$_3$OD δ 49.0; DMSO-ds δ 39.45) as standard.

HPLC electrospray mass spectra (HPLC ES_MS) were obtained using the following method and equipment: Samples were separated by reversed phase high pressure liquid chromatography (RP-HPLC) coupled to a quadrupol MS. HPLC was performed at a flow of 1000 μl/min using XterraMS C18 columns (i.d. 4.6 mm, length 50 mm, particle size 2.5 µm) or Phenomenex Luna C18(2) 30*4.6 mm columns. For most samples, a gradient from 0% eluent B to 95% B was run in 10 min, with eluent A consisting of water, 10 mM ammonium-acetate at pH 5+5% acetonitrile and eluent B consisting of acetonitrile.

Two different setups were used: 1. Waters Alliance 2795 coupled to a Waters ZQ MS, a Waters 2996 diode array detector (DAD) and an evaporative light scattering detector (ELSD, EL-ELS1000, PolymerLabs). Ionization: electrospray positive and negative mode ES+/−; or 2. LC200 pump (PE) coupled to an API100 MS (Applied Biosystems Sciex), a variable wavelength detector Waters 2487 set to 225 nm, and an ELSD (Sedex 75), ES+. In both setup versions spectra were scanned with a scan range of m/z 100 to 800 or 100 to 900.

Gas chromatography—mass spectra (GC-MS) analyses were performed with an Agilent 6890 gas chromatograph equipped with an DB-5MS column (0.25 i.d., length 30 m) and an Agilent 5973 MSD quadrupol detector (ionization with electron impact (E1) at 70 eV; source temperature 230° C.).

Elemental analyses were conducted by a VarioEL elemental analyzer (Elementar Analysensysteme) for determination of C, H, and N. Acetanilide was used for conditioning and calibration.

NMR spectra, LRMS, elemental analyses and HRMS of the compounds were consistent with the assigned structures.
Intermediates Estron Derivatives Substituted in C2 Position of the Steroidal Core of Formula (V) (Step A)

3-Benzyloxy-estra-1,3,5(10)-trien-2,17β-diol (V-C2-A)

3-Benzyloxy-estra-1,3,5(10)-trien-2,17-diol was prepared starting from estradiol by introduction of the hydroxy side chain in C2 position as described by Rao et al. (2002) in which a Fries rearrangement and a Baeyer Villiger reaction is used.

Detailed Synthesis

Estra-1,3,5(10)-triene-3,17o-diol diacetate (C2-2)

Under an $N_2$-atmosphere, $Ac_2O$ (375 ml, 3.993 mol) was added dropwise during 20 min to a solution of estradiol (150 g, 0.551 mol) in pyridine (1500 ml). The clear colourless solution obtained was stirred at RT overnight. The reaction mixture was then cooled to 0° C. and MeOH (375 ml) was added dropwise during 25 min. The reaction mixture was stirred at 0° C. for 2 h, then allowed to warm to RT and concentrated in vacuo. The residue was recrystallized from hot MeOH to yield (C2-2) (176 g, 90%) as white crystals.

2-Acetyl-estra-1,3,5(10)-triene-3,17β-diol 17-acetate (C2-3)

Under an $N_2$-atmosphere, $ZrCl_4$ (530 g, 2.27 mol) was added in one portion to a solution of (C2-2) (176 g, 0.493 mol) in DCM (13 l). The turbid yellow mixture obtained was stirred at RT for 48 h. The reaction mixture was then cooled to 0° C., ice water (3 l) was added and the mixture was allowed to warm to RT for overnight. The mixture was washed with $H_2O$, sat $NaHCO_3$ (aq), brine, dried over $Na_2SO_4$, filtered, and concentrated in vacuo to yield (C2-3) (167 g, 95%) as a yellow powder.

2-Acetyl-3-benzyloxy-estra-1,3,5(10)-triene-17β-ol 17-acetate (C2-4)

Under an $N_2$-atmosphere, $K_2CO_3$ (97 g, 0.702 mol) was added in one portion to a solution of (C2-3) (167 g, 0.468 mol), benzyl bromide (61.6 ml, 0.515 mol) and 18-crown-6 (4.7 g, 0.018 mol) in acetone (1 l). After 108 h at $T_{intern}$=56° C., the reaction mixture was allowed to cool to RT, poured into $H_2O$, stirred for 1 h after which the turbid mixture was filtered over a glass fritted filter. The residue was washed with $H_2O$, and dried in vacuo to yield (C2-4) (209 g, 100%) as a brown solid.

3-Benzyloxy-estra-1,3,5(10)-triene-2,17β-diol diacetate (C2-5)

Under an $N_2$-atmosphere, $NaH_2PO_4$ (354 g, 2.496 mol) was added to a solution of C2-4 (167 g, 0.468 mol) in DCM (7 L). Then m-CPBA (205 g, 75% with $H_2O$, 0.889 mol) was added portionwise during 10 min. The turbid mixture obtained was stirred at RT for overnight. The reaction mixture was poured into $H_2O$ (9 L) and the mixture obtained was stirred for 1 h. The organic layer was isolated and the aqueous layer was extracted with DCM. The combined organic layers were washed with $H_2O$, 10% $Na_2SO_3$ (aq), half-sat. $NaHCO_3$ (aq), brine, dried over $Na_2SO_4$, filtered, and concentrated in vacuo to yield C2-5 (247 g, quant.) as a clear yellow powder.

3-Benzyloxy-estra-1,3,5(10)-triene-2,17β-diol (V-C2-A)

A solution of KOH (250 g, 4.46 mol) in $H_2O$ (5 L) was added in one portion to a solution of (C2-5) (511 g, 1.181 mol) in THF (5 L) and MeOH (5 L). The mixture obtained was stirred at $T_{intern}$=65° C. for over night, after which it was allowed to cool to RT. The reaction mixture was acidified with conc. HOAc to pH 4 and diluted with $H_2O$ and EtOAc (1:3). The organic layer was isolated and the aqueous layer was extracted with EtOAc. The combined organic layers were washed with brine, dried over $Na_2SO_4$, filtered, and concentrated in vacuo to yield 358 g brown solid. The solid was triturated with TBME (2 L) for 2 h, filtered over a glass fritted filter (P2) and the residue was washed with TBME, then with acetone, and dried in vacuo to yield (C2-A) (256 g) as an offwhite solid. The combined filtrates were concentrated in vacuo to yield 125 g brown resin. The resin was dissolved in DCM, applied to $SiO_2$ and eluted with DCM:$NH_3$ 7N in MeOH=97.5:2.5 to yield 76 g yellow solid ($R_f$=0.39). The solid was triturated with TBME (250 ml), filtered over a glass fritted filter (P4). The residue was washed with DCM and dried in vacuo to yield (V-C2-A) (15.4 g) as an off-white solid. Total yield: 61%.

3-Benzyloxy-2-methoxy-estra-1,3,5(10)-triene-17□one (V-C2-B)

3-Benzyloxy-2-methoxy-estra-1,3,5(10)-triene-17□one was prepared starting from (V-C2-A) according to the procedure described by Rao et al. (2002) and within U.S. Pat. No. 6,043,236.

Detailed Synthesis

3-Benzyloxy-2-methoxy-estra-1,3,5(10)-triene-17β-ol (C2-6)

Under an $N_2$-atmosphere, $LiOH·H_2O$ (16.2 g, 0.386 mol) was added to a solution of (V-C2-A) (118 g, 0.312 mol mol) in THF (1.5 l). After adding $Me_2SO_4$ (33.1 ml, 0.350 mol) the mixture obtained was stirred at 55° C. for 3 h. The mixture was allowed to cool to RT overnight, concentrated in vacuo, and the residue was dissolved in DCM (1200 ml). The organic layer was washed with $H_2O$, brine, dried over $Na_2SO_4$, filtered, and concentrated in vacuo to yield (C2-6) (115 g, 94%) as an orange resin.

3-Benzyloxy-2-methoxy-estra-1,3,5(10)-triene-17one (V-C2-B)

To a mixture of (C2-6) (118 g, 0.301 mol) and TPAP (5.0 g, 0.014 mol) in acetone (2 L) was added portion-wise NMO (52.5 g, 0.448 mol) at such rate as to keep $T_{intern}$≦31° C. The mixture obtained was stirred at RT overnight. The reaction mixture was concentrated in vacuo to yield 128 g black solid. The solid was applied and eluted from $SiO_2$ with DCM to yield (V-C2-B) (97 g, 83%) as a pale yellow solid ($R_f$=0.78).

3-Benzyloxy-2-ethyl-estra-1,3,5(10)-triene-17□one (V-C2-C)

3-Benzyloxy-2-ethyl-estra-1,3,5(10)-triene-17□one was prepared starting from (C2-4) by performing a Wolff-Kishner reduction to obtain the ethyl side chain. The oxidation of the C17 hydroxyl function was achieved by TPAP oxidation using the procedures of Ley et al (1994). Alternatively, 3-Benzyloxy-2-ethyl-estra-1,3,5(10)-triene-17-one was prepared starting from (C2-3) by reduction of the acyl function which was achieved by reaction with Pd/C and $H_2$ [Gonzalez et al (1982)], subsequent benzylation of the 3-hydroxy function, deprotection of the C17 hydroxy function and TPAP oxidation.

Detailed Synthesis

3-Benzyloxy-2-ethyl-estra-1,3,5(10)-triene-17β-ol (C2-7)

To benzyl protected acyl ketone (C2-4) (765 g, 1.71 mol) was added diethylene glycol (1900 ml), KOH (288 g, 5.14 mol) and $H_2NNH_2*H_2O$. The mixture was heated to 120-140° C. overnight. A Dean-Stark trap was placed and water and $H_2NNH_2*H_2O$ were removed by distillation by heating the reaction mixture to 190° C. After NMR analysis revealed complete conversion, the mixture was cooled to 50° C. and water (3 L) was added. The mixture became very thick and unstirrable. The dissolved part was poured in a mixture of water (15 L) and EtOAc (5 L) and the sticky oil was first dissolved in EtOAc (5 L) and then added to the mixture. The layers were separated and the organic layer was washed with water and concentrated to give (C2-7) (543 g, 81%) as an orange/yellow oil which solidified upon standing.

3-Benzyloxy-2-ethyl-estra-1,3,5(10)-triene-17□one (V-C2-C)

Alcohol (C2-7) (433 g, 1.39 mol) and powdered 4A molsives (695 g, 500 mg/mmol) in DCM (2.7 L) were cooled with an ice bath and TPAP (19.5 g, 55.6 mmol, 4 mol %) was added. NMO (282 g, 2.09 mol) was added under ice/water cooling. After 3 h the reaction mixture was filtered over $SiO_2$ (10 L, DCM) and all fraction before the black fraction (TPAP) were collected. The DCM was concentrated to give ketone (V-C2-C) (465 g, 86%) as a yellow solid.

3-Benzyloxy-2-ethoxy-estra-1,3,5(10)-triene-17□one (V-C2-D)

3-Benzyloxy-2-(2-methoxy-ethoxy)-estra-1,3,5(10)-triene-17□one (V-C2-E)

In the First Step, the 2-Hydroxy Function of 3-Benzyloxy-Estra-1,3,5(10)-triene-2,17β-diol (C2-A) was alkylated using ethylsulfate and LiOH or methoxyethanol under Mitsunobu conditions. Subsequently, the alcohol was oxidized with TPAP and NMO to the corresponding estron derivative.

Detailed Synthesis

3-Benzyloxy-2-ethoxy-estra-1,3,5(10)-triene-17β-ol (C2-8)

Intermediate (V-C2-A) (15.0 g, 39.68 mmol) was dissolved in THF (250 ml), under nitrogen atmosphere. LiOH (2.0 g, 47.62 mmol) and $Et_2SO_4$ (5.7 ml, 43.65 mmol) were added. The mixture was heated at 55° C. for 5 h, then cooled to RT and stirred for 48 h. The mixture was concentrated in vacuo. DCM (400 ml) was added and the organic layer was washed with water (2×250 ml) and brine (1×250 ml), dried over $Na_2SO_4$ and concentrated in vacuo yielding 21.7 g of a greenish semi-solid. The mixture was dissolved in THF (250 ml) under nitrogen atmosphere. LiOH (0.8 g) and $Et_2SO_4$ (2.0 ml) were added. The mixture was heated to reflux and refluxed over the weekend. The mixture was concentrated in vacuo. DCM (400 ml) was added and the organic layer was washed with water and brine, dried over $Na_2SO_4$ and concentrated in vacuo to afford 16.7 g (41.07 mmol, quant.) of brown oil. Pentane was added and the formed solid was filtered yielding 13.5 g (C2-8) (84%) as a white solid.

3-Benzyloxy-2-(2-methoxyethoxy)-estra-1,3,5(10)-triene-17β-ol (C2-9)

Intermediate (V-C2-A) (15.0 g, 39.68 mmol), $PPh_3$ (20.79 g, 79.37 mmol) and methoxyethanol (6.3 ml, 79.37 mmol) were suspended in DCM (500 ml) and cooled in an ice/water bath, under N2 atmosphere. DIAD (15.6 ml, 79.37 mmol) was added drop wise in 1 h at below 5° C. After addition a clear solution was formed which was warmed to RT overnight. The solution was concentrated in vacuo yielding 58.8 g thick brown oil. Purification via column chromatography ($SiO_2$, eluens DCM to 1% MeOH in DCM) yielded 34 g of thick oil. A second purification via column chromatography was done ($SiO_2$, eluens 10% EtOAc to 50% EtOAc in heptan). Two fractions were collected, 7.61 g (44%) of pure product and 5.3 g which was purified via column chromatography yielding 3.1 g (18%). Both fractions were mixed yielding 10.8 g (C2-9) (62%) as white powder.

3-Benzyloxy-2-ethoxy-estra-1,3,5(10)-triene-17□one (V-C2-D)

Alcohol (C2-8) (13.5 g, 33.25 mmol) was dissolved in aceton (350 ml), under nitrogen atmosphere. TPAP (0.6 g, 1.663 mmol) was added. NMO (5.8 g, 49.88 mmol) was added portion wise. The mixture was stirred at RT overnight. The mixture was concentrated in vacuo yielding 16.3 g of a black tar. The mixture was filtered over silica with DCM. Filtrate was concentrated in vacuo yielding 11.8 g (V-C2-D) (29.6 mmol, 89%) as yellow solid.

3-Benzyloxy-2-(2-methoxy-ethoxy)-estra-1,3,5(10)-triene-17□one (V-C2-E)

Alcohol (C2-9) (10.8 g, 24.54 mmol) was dissolved in aceton (300 ml), under nitrogen atmosphere. TPAP (0.43 g, 1.23 mmol) was added. NMO (4.31 g, 36.81 mmol) was added portion wise. The mixture was stirred at RT overnight. The mixture was concentrated in vacuo yielding 12.5 g of a black tar. The mixture was filtered over silica with 1% MeOH in DCM. Filtrate was concentrated in vacuo yielding 11.6 g (V-C2-E) (26.8 mmol, >100%) as white solid.

3-Benzyloxy-2-(2-methoxy-ethyl)-estra-1,3,5(10)-triene-17□one (V-C2-F)

Building Block V-C2-F was Prepared Starting from Intermediate 2-Acetyl-3-benzyloxy-estra-1,3,5(10)-triene-17β-ol 17-acetate (C2-4).

2-Acetyl-3-benzyloxy-estra-1,3,5(10)-triene-17β-ol (C2-10)

Compound (C2-4) (119 g, 266 mmol) was dissolved in a mixture of THF (500 ml) and MeOH (500 ml) under a N2 atmosphere. A solution of KOH (60.0 g, 1.06 mol) in water (1 L) was added forming a suspension. The reaction mixture was stirred at 75° C. (external) for 16 h. After cooling to RT the pH of the mixture was adjusted to 4 using acetic acid. After dilution with water (1 L) the aqueous layer was separated. The organic layer was washed with brine, dried over $Na_2SO_4$, concentrated in vacuo, stripped with toluene and again dried in vacuo yielding compound (C2-10) (70.0 g, 173.0 mmol, 65%) as a yellow syrup, which was used without further purification.

3-Benzyloxy-2-(2-methoxy-1-oxo-ethyl)-estra-1,3,5(10)-triene-17β-ol (C2-11)

Compound C2-10 (70 g, 173 mmol) was suspended in diethyl ether (2 L) and bromine (18.67 ml, 58.1 g, 363 mmol) slowly dropwise added at 0° C. under N2 atmosphere. The reaction mixture was stirred at ambient temperature for 14 h. The solvent was removed in vacuo and the residue suspended in methanol (2 L). Sodium methoxide (94 g, 173 mmol) was added and the reaction mixture stirred at RT for 72 h. This was poured into water (1 L), acidified with conc. aq. HCl and the water layer extracted with DCM. The organic layer was washed with brine, dried over $Na_2SO_4$ and concentrated in vacuo. Via column chromatography ($SiO_2$, heptane/EtOAc 2/1 to 0/100 stepwise) compound C2-11 (14.3 g, 32.9 mmol, 19%) was isolated.

3-Hydroxy-2-(2-methoxy-ethyl)-estra-1,3,5(10)-triene-17β-ol (C2-12)

Palladium on charcoal (10%, 15 g) was suspended in water (175 ml) under a nitrogen atmosphere and added to a solution of compound C2-11 (14.3 g, 32.9 mmol) in THF (175 ml) and t-butanol (175 ml). $H_2$ at ambient pressure was applied and the reaction mixture was stirred at ambient temperature for 80 h. The reaction mixture was filtered over Celite and the filter cake was washed with ethanol. The filtrate was concentrated in vacuo yielding crude compound C2-12 (8.3 g, 25.1 mmol, 77%). After purification by column chromatography ($SiO_2$, heptane/EtOAc=3/1 to 1/2 stepwise) pure C2-12 (3.6 g, 10.89 mmol, 33%) was isolated.

3-Benzyloxy-2-(2-methoxy-ethyl)-estra-1,3,5(10)-triene-17β-ol (C2-13)

Compound C2-12 (3.6 g, 10.89 mmol) was dissolved in acetone (30 ml) under N2 atmosphere. Subsequently, benzylbromide (2.61 ml, 3.73 g, 21.78 mol), anhydrous $K_2CO_3$ (3.01 g, 21.78 mmol) and 18-crown-6 (290 mg, 1.09 mmol) were added. The reaction mixture was refluxed for 24 h (65° C. external) and allowed to cool to RT. The mixture was poured into water (150 ml) and stirred for 1 h. The water layer was separated and extracted with toluene. The combined organic layers were washed with brine, dried over $Na_2SO_4$ and evaporated in vacuo leaving compound C2-13 (4.92 g, max. 10.89 mmol, quant.) as a yellowish solid.

3-Benzyloxy-2-(2-methoxy-ethyl)-estra-1,3,5(10)-triene-17-one (V-C2-F)

Compound C2-13 (4.92 g, max. 10.89 mmol) was suspended in acetone (75 ml) under N2 atmosphere. Subsequently, tetrapropylammonium perruthenate (TPAP) (191 mg, 0.54 mmol) and N-methylmorpholine N-oxide (NMO) (1.91 g, 16.34 mmol) were added. After the reaction mixture had been stirred for 80 h at ambient temperature, it was filtered over Celite. The filtrate was concentrate in vacuo yielding compound V-C2-F (3.43 g, 8.19 mmol, 70%) as a pale solid after column chromatography ($SiO_2$, DCM/methanol=100/0 to 95/5 stepwise).

3-Benzyloxy-2-propyl-estra-1,3,5(10)-triene-17☐one (V-C2-G)

3-Benzyloxy-2-propyl-estra-1,3,5(10)-triene-17one was prepared starting from estradiol by introduction of the propionate side chain in C2 position as described by Rao et al. (2002) using a Fries rearrangement. Then the keto function is reduced to obtain the propyl side chain by reaction with Pd/C and $H_2$ [Gonzalez et al (1982)]. The subsequent oxidation of the C17 hydroxyl function was achieved by TPAP oxidation using the procedures of Ley et al. (1994).

Detailed Synthesis

Estra-1,3,5(10)-triene-3,17β-diol di propionic acid ester (C2-14)

Estradiol (200 g, 0.734 mol) was dissolved in pyridine (2 l) under N2 atmosphere. Propionic anhydride (344 g, 2.64 mol) was added. The reaction mixture was stirred at ambient temperature until the reaction was completed. The reaction mixture was cooled on an ice-water bath, quenched with MeOH (250 ml) and stirred at ambient temperature for 1½ h. The mixture was concentrated in vacuo and the residue was dissolved in toluene. The organic layer was separated, washed with water, 10% aqueous citric acid, sat. aq. $NaHCO_3$ and dried over $Na_2SO_4$. The organic layer was concentrated in vacuo and the residue was stripped with toluene, yielding compound C2-14 (272 g, 0.708 mol, 96%) as a white solid.

Propionic acid 3-hydroxy-2-propionyl-estra-1,3,5(10)-triene-17-yl ester (C2-15)

Compound C2-14 (272 g, 0.708 mol) was dissolved in DCM (10 L) under N2 atmosphere. Zirconium chloride (758 g, 3.25 mol) was added, which resulted in a yellow suspension. The mixture was stirred at ambient temperature until the conversion was completed. The reaction mixture was cooled to 3° C. before 200 g ice was added in batches. Water (2 L) was added and the mixture was stirred at 4° C. for 1 hr. Then an additional amount of water (5 L) was added. The aqueous layer was separated and extracted with DCM. The combined organic layers were filtered over $Na_2SO_4$ and concentrated in vacuo. The residue was stripped with toluene leaving a green residue. The residue was dissolved in DCM and filtered over $SiO_2$ leaving compound C2-15 (255 g, 0.663 mol, 94%) as an orange solid.

Propionic acid 3-hydroxy-2-propyl-estra-1,3,5(10)-triene-17-yl ester (C2-16)

Pd (10%) on charcoal (120 g) was suspended in water (800 ml) under N2 atmosphere. t-Butanol (800 ml) and a solution of compound C2-15 (115 g, 0.299 mol) in THF (800 ml) were added. The mixture was applied to $H_2$ (ambient pressure) and stirred at ambient temperature until the reaction was completed. The mixture was filtered over Celite (2×) and the filter cake was washed with THF. The filtrate was concentrated in vacuo yielding compound C2-16 (107 g, 0.289 mol, 97%) as gray solid.

Propionic acid 3-benzyloxy-2-propyl-estra-1,3,5(10)-triene-17-yl ester (C2-17)

Compound C2-16 (238 g, 0.642 mol) was dissolved in acetone (1.5 L) under N2 atmosphere. Subsequently, benzylbromide (83 ml, 0.700 mol), anhydrous $K_2CO_3$ (100 g, 0.723 mol) and 18-crown-6 (10 g, 0.038 mol) were added. The reaction mixture was refluxed overnight. Additional amounts of $K_2CO_3$ (25 g, 0.181 mol+50 g, 0.362 mol) and benzylbromide (10 ml, 14 g, 0.084 mol) were added. After refluxing the mixture for additional 64 h, the mixture was allowed to cool to 30° C. and poured into water (4.5 L). The mixture was extracted with toluene, the organic layers were combined and concentrated in vacuo. The residue was stripped with toluene leaving compound C2-17 (335 g, max. 0.642 mol) as a wax like solid.

3-Benzyloxy-2-propyl-estra-1,3,5(10)-triene-17β-ol (C2-18)

Compound C2-17 (69.9 g, max. 134 mmol) was dissolved in a mixture of THF (600 ml) and MeOH (600 ml) under N2 atmosphere. A solution of KOH (34.4 g, 613 mmol) in water (600 ml) was added. The reaction mixture was stirred at 55° C. for 3 h. MeOH was removed in vacuo from the mixture. DCM (400 ml) was added and the pH of the mixture was adjusted to 1 using 3 M HCl. The aqueous layer was separated and extracted with DCM (2×200 ml). The organic layers were combined, washed with sat aq $NaHCO_3$ (200 ml) and dried over $Na_2SO_4$. The organic layer was concentrated in vacuo yielding compound C2-18 (61.6 g, 152 mmol, 88%) as a yellow syrup after column chromatography ($SiO_2$, DCM/heptane=85/15).

3-Benzyloxy-2-propyl-estra-1,3,5(10)-triene-17-one (V-C2-G)

Compound C2-18 (61.6 g, 152 mmol) was dissolved in acetone (1250 ml) under $N_2$ atmosphere. Subsequently, TPAP (5.1 g, 14.5 mmol) and NMO (48.6 g, 415 mmol) were added. After the reaction mixture was stirred for 4½ h at ambient temperature, it was filtered over Celite. The filtrate was concentrated in vacuo yielding compound V-C2-G (57.6 g, 143 mmol, 94%) as a pale solid after column chromatography (SiO$_2$, DCM).

3-Hydroxy-2-propyl-estra-1,3,5(10)-triene-17-one (V-C2-G-a)

Compound V-C2-G (1.10 g, 2.73 mmol) was dissolved in THF (15 ml) under a nitrogen atmosphere. A suspension of palladium on charcoal (10%, 130 mg) in THF (10 ml) was added. H$_2$ was applied at ambient pressure and the reaction mixture was stirred at RT for 3 d. The reaction mixture was filtered over Celite and the filter cake was washed with THF (20 ml). The filtrate was concentrated in vacuo yielding compound (V-C2-G-a) (240 mg, 0.768 mmol, 28%) after column chromatography (SiO$_2$, DCM).

II. 15,16-Unsaturated and C2 Substituted Estrone Derivatives of Formula (X) (Step B)

The estrone of general formula V was converted into the corresponding 15, 16 unsaturated derivative by the 4-step reaction as depicted in SCHEME 1 according to Nambara 1976: After protection of the C17 keto function as acetal (ethylene glycol, TEOF and p-TosOH in toluene, work-up with water and TEA), the acetal was brominated (with pyridinium perbromide and ethylene glycol in DME, work-up with Na$_2$S$_2$O$_3$). Subsequently, HBr was eliminated by reaction with K—O-tert-butyl in DMSO. Finally, the deprotection of the acetal was achieved with p-TosOH in DME and water.

The following intermediates were prepared according to this procedure:
3-Benzyloxy-2-methoxy-estra-1,3,5(10), 15-tetraene-17-one (X-C2-B)
3-Benzyloxy-2-ethyl-estra-1,3,5(10),15-tetraene-17-one (X-C2-C)
3-Benzyloxy-2-ethoxy-estra-1,3,5(10),15-tetraene-17-one (X-C2-D)
3-Benzyloxy-2-methoxy-ethoxy-estra-1,3,5(10), 15-tetraene-17-one (X-C2-E)
3-Benzyloxy-2-methoxy-ethyl-estra-1,3,5(10),15-tetraene-17-one (X-C2-F)
3-Benzyloxy-2-propyl-ethoxy-estra-1,3,5(10),15-tetraene-17-one (X-C2-G)

III. Introduction of the Basic Side Chain in C15 Position

The detailed synthesis of the following intermediates, wherein R$^{14}$ represents H, is fully disclosed within international patent application WO 2005/47303, which is incorporated by reference herein. For intermediates with R$^{14}$ is different from H, detailed synthesis is given for exemplary compounds.

IIIa. The Optionally 2-Substituted Ketal Derivative of the Estron-15α-yl-carbaldehyde of Formula XIII-0

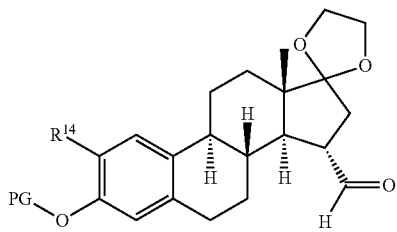
(XIII-0)

The protected aldehyde intermediate of formula XIII-0 with PG=CH$_3$ (XIIIb) or PG=Benzyl (XIIIc) can be prepared according to a procedure depicted within the following scheme 2:

SCHEME 2

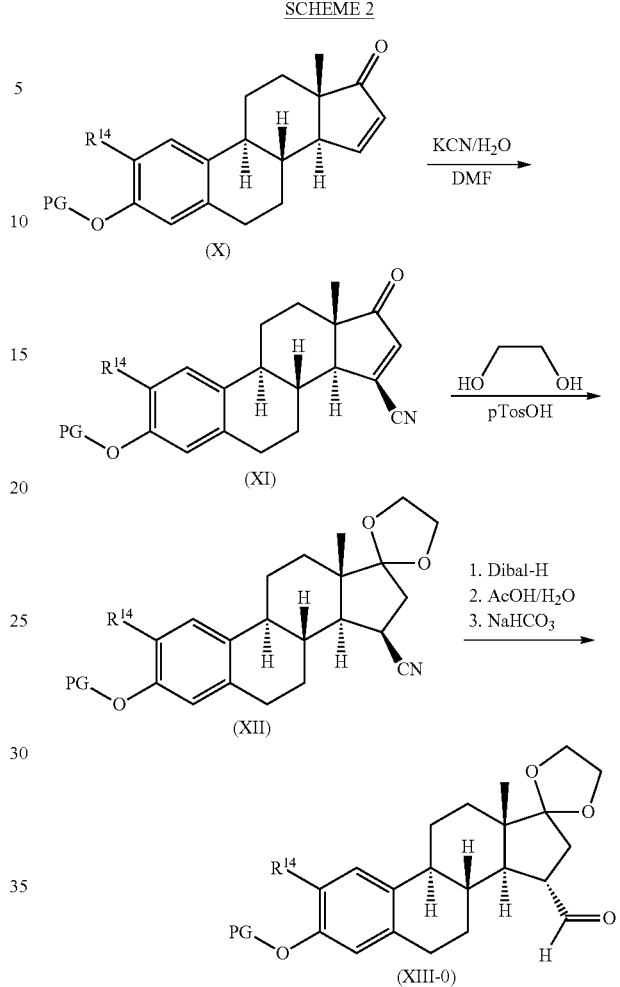

The optionally 2-substituted 15,16-unsaturated estrone of formula (X) was converted into the corresponding cyano-estrone (XI) by a cyanide Michael addition at the D-ring. The nitrile was introduced in the beta configuration as was proven by 2D-NMR. Epimerization of this stereocenter had been accomplished in a following step. First the ketone functionality was protected as the acetal (XII), followed by conversion of the nitrile to the corresponding aldehyde (XIII-0) by the addition of DIBAH to the nitrile and the consecutive hydrolysis of the imine product. At this stage the epimerization took place for about 90% (2D-NMR). Consecutive washing of the mixture with aqueous bicarbonate gave the α-isomer with a d.e≦98%.

IIIb. Optionally 2-substituted compounds of formula IV: Estron-15-yl-C$_0$-C$_5$-alkyl-carboxylic acid Acid Building Block IV-0: (n=0)

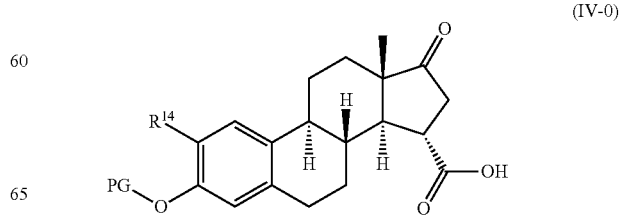
(IV-0)

The individual steps in the synthesis of acid building block of the formula IV-0b are depicted in the following scheme 3.

SCHEME 3

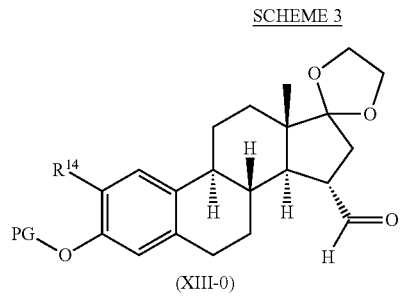

The ketal derivative of the optionally 2-substituted 17-oxo-estra-1,3,5(10)-trien-15α-yl-carbaldehyde of formula XIII-0 is oxidized to the corresponding carboxylic acid and converted into the unprotected 15α-substituted estrone derivative of formula IV-0.

Acid Building Block IV-1: (n=1):

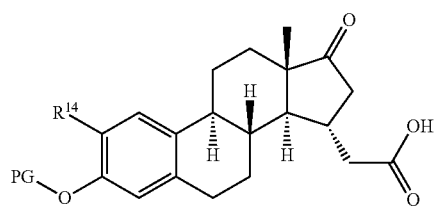

The acid building block IV-1 may be synthesized via two different routes. The individual steps of the first synthesis route of acid building block IV-1 are depicted in the following scheme 4. The same kind of procedure can be applied for n=2 and for other side chains within the PG position.

SCHEME 4

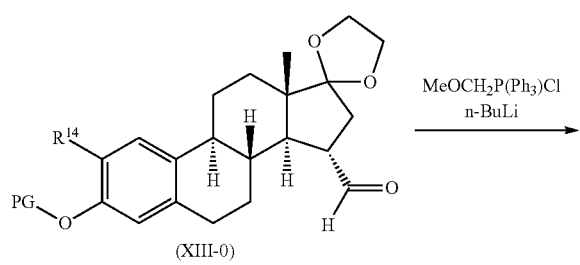

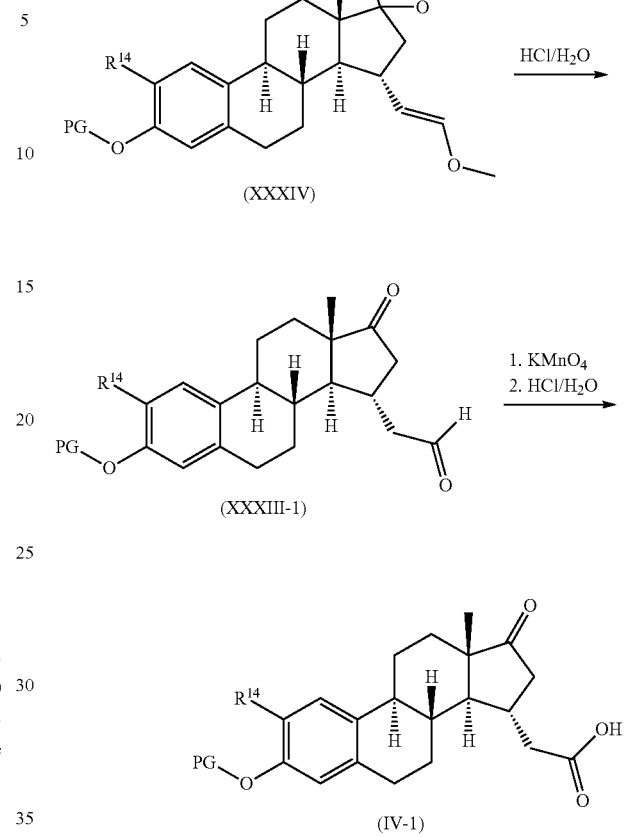

The ketal derivative of the 17-oxo-estra-1,3,5(10)-trien-15α-yl-carbaldehyde of formula XIII-0 is converted into the methyl enol ether of the formula XXXIV via a Wittig reaction with $MeOCH_2LiP(Ph)_3$. Hydrolysis with $HCl_{(aq)}$ delivered the unprotected acetaldehyde derivative XXXIII-1. The acetaldehyde derivative is then further oxidized to the corresponding carboxylic acid IV-1.

Alternative synthesis route for the acid building block IV-1: (n=1): IV-1b: (n=1 and PG=$CH_3$): 3-Methoxy-17-oxo-estra-1,3,5(10)-trien-15α-yl-acetic acid Alternatively, compound IV-1b can be prepared directly from the enone derivative of formula X according to the following synthesis scheme 5:

SCHEME 5

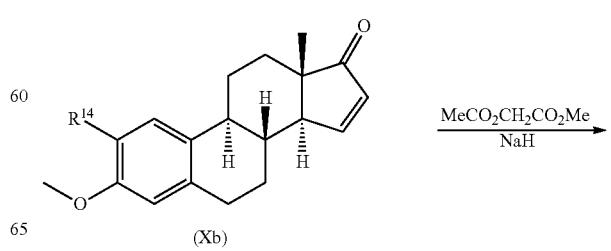

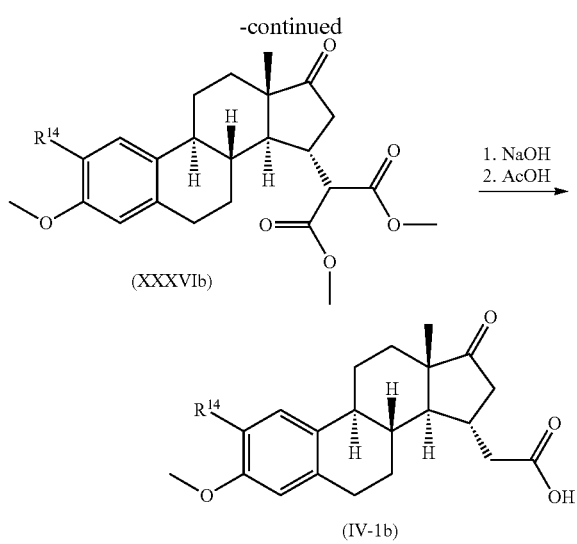

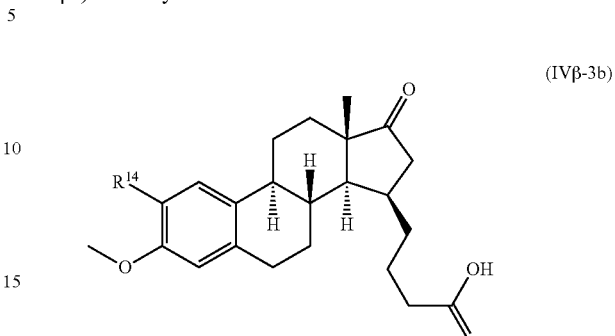

A Michael addition of the dimethylmalonate-anion to the enone derivative delivered the diester XXXVIb, which was converted into the acid building block of formula IV-b by alkaline ester hydrolysis and decarboxylation in refluxing acetic acid.

Optionally 2-substituted acid building blocks IVβ-2, IVβ-3, IVβ-4, 1Vβ-5, IVβ-6 (n=2, 3, 4, 5, 6): IVβ-3b (n=3 and PG=CH$_3$): 4-(3-Methoxy-17-oxo-estra-1,3,5(10)-trien-15β-) 7D-butyric acid The individual steps in the synthesis of acid building block of the formula IVβ-3b are depicted in the following scheme 6. The same kind of procedure can be applied for n=4, 5, or 6 and for other alkyl side chains within the R$^1$ position using the appropriate BrMg—C$_5$-C7-alkoxy-THP as Grignard Reagent. Furthermore, this reaction scheme also delivers the estrone-alcohol building block in form of the intermediate of formula XXXIβ-4b.

SCHEME 6

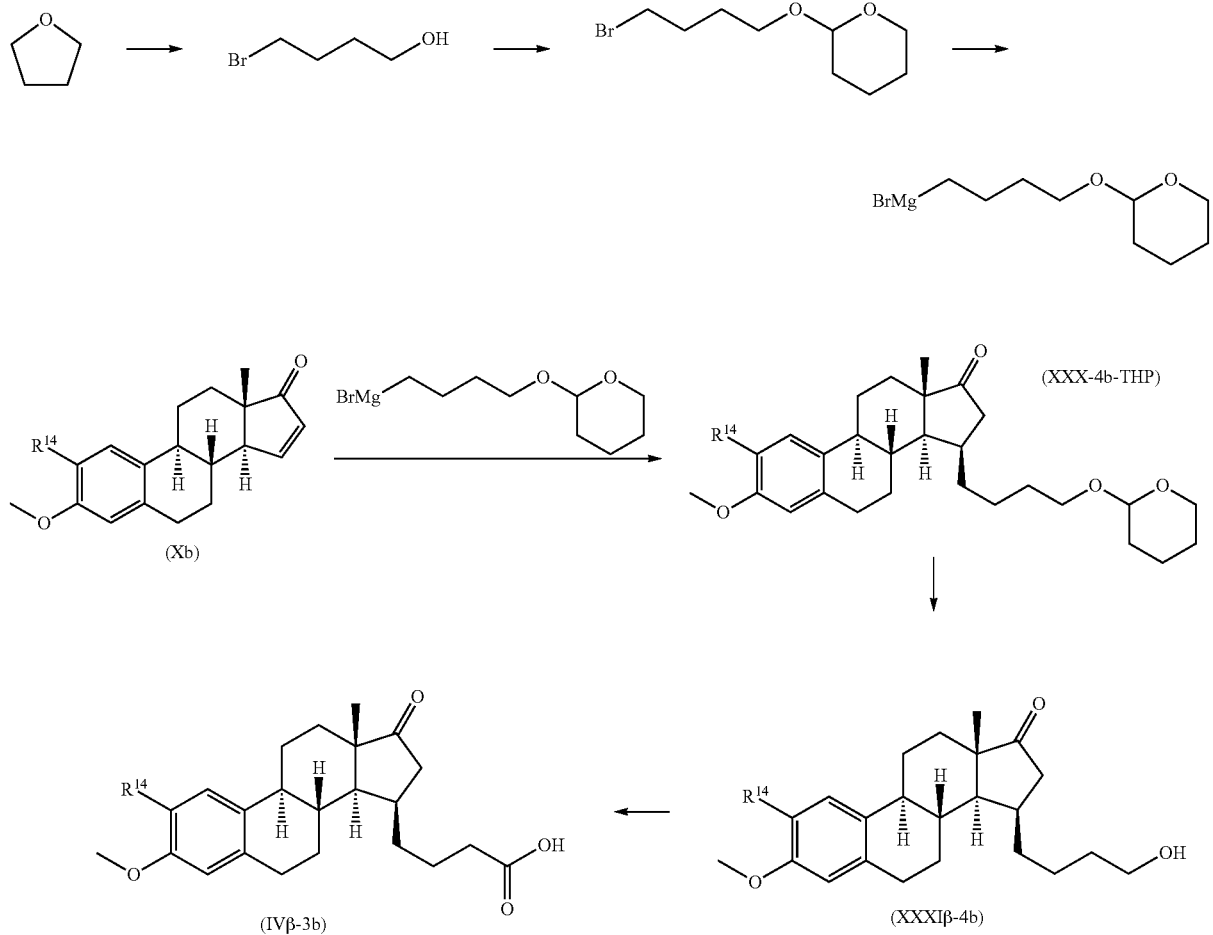

4-Bromo-butanol-THP ether was prepared by adding HBr solution to refluxing THF. The resulting bromide was dissolved in DCM, p-TosOH and DHP were added at 0° C. to give the protected alcohol. This was filtered over $SiO_2$ and further purified by column chromatography, yielding 9.3% over 2 steps. The protected alcohol was dissolved in THF and added to activated magnesium, and the resulting Grignard reagent added to $CuI_2$ in HMPA. The 15,16-unsaturated Estrone derivative of formula Xb, dissolved in dry THF and TMSCl, was added at −40±5° C. Subsequently, after hydrolysis of the silyl ether, the resulting compound XXX-4b-THP was deprotected with p-TosOH/MeOH to give the alcohol derivative XXXI-4b, which was converted, without purification, into the free acid IV-3b by a Jones oxidation. The oil was purified by column chromatography, yielding the free acid of formula IV-3b in 30% yield over three steps.

Acid building blocks IVβ-2 (n=2 and PG=H, $CH_3$ or benzyl): optionally 2-substituted 3-(3-Benzyloxy/Methoxy/Hydroxy-17-oxo-estra-1,3,5(10)-trien-15β-yl)-propanoic acid The optionally 2-substituted carboxylic acid IVβ-2 can be prepared by oxidation of the alcohol derivative of formula XXXIβ-3b or XXXIβ-3c according to the preparation of the carboxylic acid IVβ-3b (see section for the preparation of the alcohol derivatives below for synthesis of XXXIβ-3b and XXXIβ-3c) and optionally subsequent debenzylation of the C3 hydroxy function.

Acid building block IVβ-3c: Optionally 2-substituted 4-(3-Benzyloxy-17-oxo-estra-1,3,5(10)-trien-15β-yl)-butyric acid

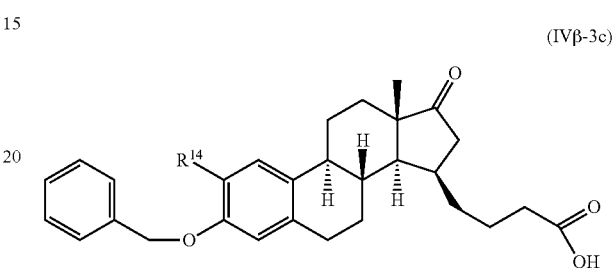

(IVβ-3c)

The individual steps in the synthesis of acid building block of the formula IVβ-3c are performed according to any of the procedures depicted in the following schemes 7A, 7B and 7C. Furthermore, reaction scheme 7A also delivers the estrone-alcohol building block in form of the intermediate of formula XXXIβ-4c. The same kind of procedure can be applied for n=4, 5, or 6 and for other alkylaryl substitutents within the $R^1$ position using the appropriate BrMg—$C_5$-$C_7$-alkoxy-THP as Grignard Reagent.

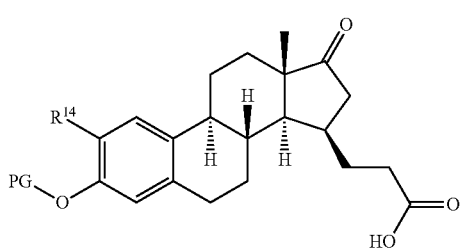

IVβ-2

SCHEME 7A

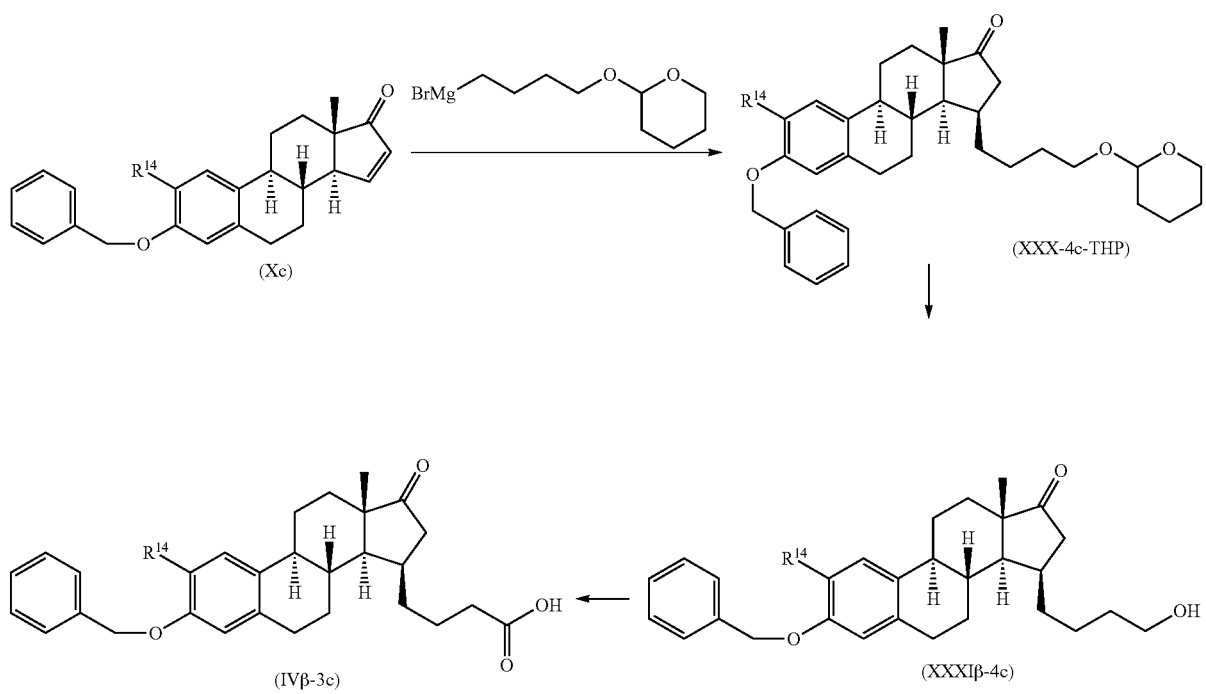

4-Bromo-butanol-THP ether was prepared by adding HBr solution to refluxing THF. The resulting bromide was dissolved in DCM, p-TosOH and DHP were added at 0° C. to give the protected alcohol. This was filtered over SiO$_2$ and further purified by column chromatography, yielding 9.3% over 2 steps. The protected alcohol was dissolved in THF and added to the activated magnesium, and the resulting Grignard reagent added to CuI2 in HMPA. The 15,16-unsaturated Estrone derivative of formula Xc (preferably with R$^{14}$=H), dissolved in dry THF and TMSCl, was added at −40±5° C. Subsequently, the resulting compound XXX-4c-THP was deprotected with p-TosOH/MeOH to give XXXIβ-4c in 47% over 2 steps, which was converted, without purification, into the free acid IVβ-3c by a Jones oxidation in a yield of 96%.

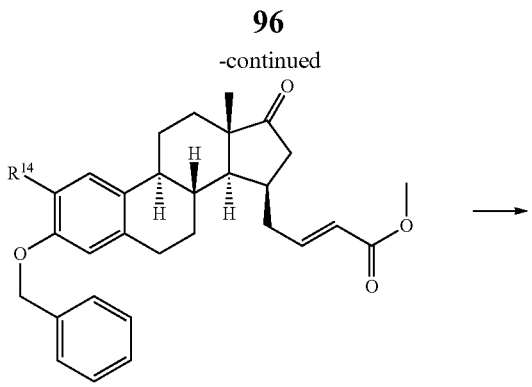

SCHEME 7B

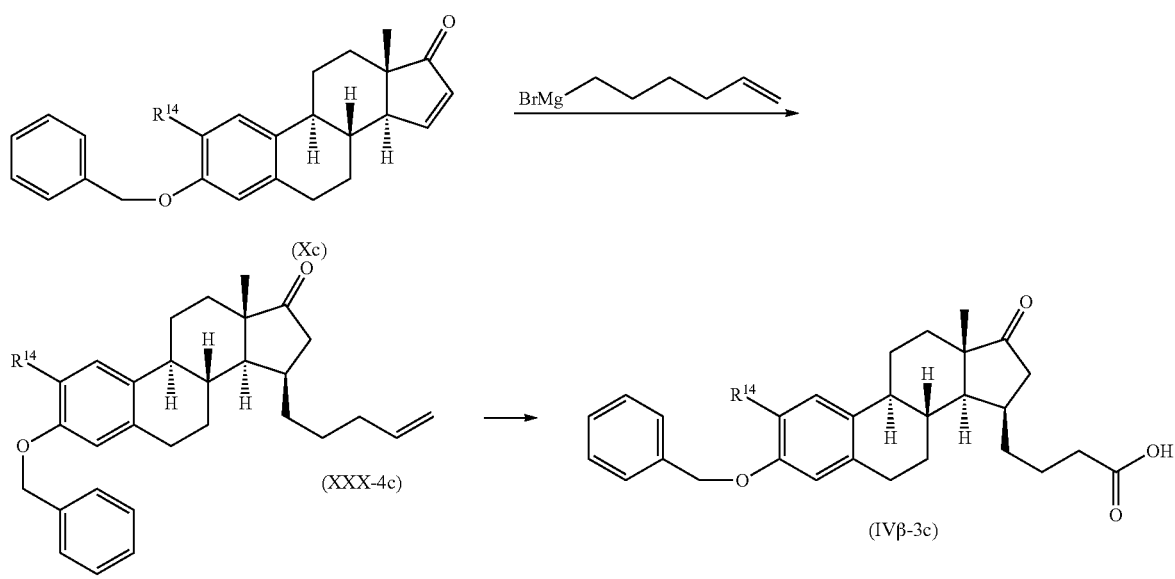

The 15,16-unsaturated Estrone derivative of formula Xc (preferably with R$^{14}$=Ethyl, n-Propyl or Methoxyethyl) was subjected to a 1,4 addition using a freshly prepared Gringard Reagent. Subsequently, the resulting compound XXX-4c was oxidized to the free acid IVβ-3c (see also the reaction SCHEME 12).

SCHEME 7C

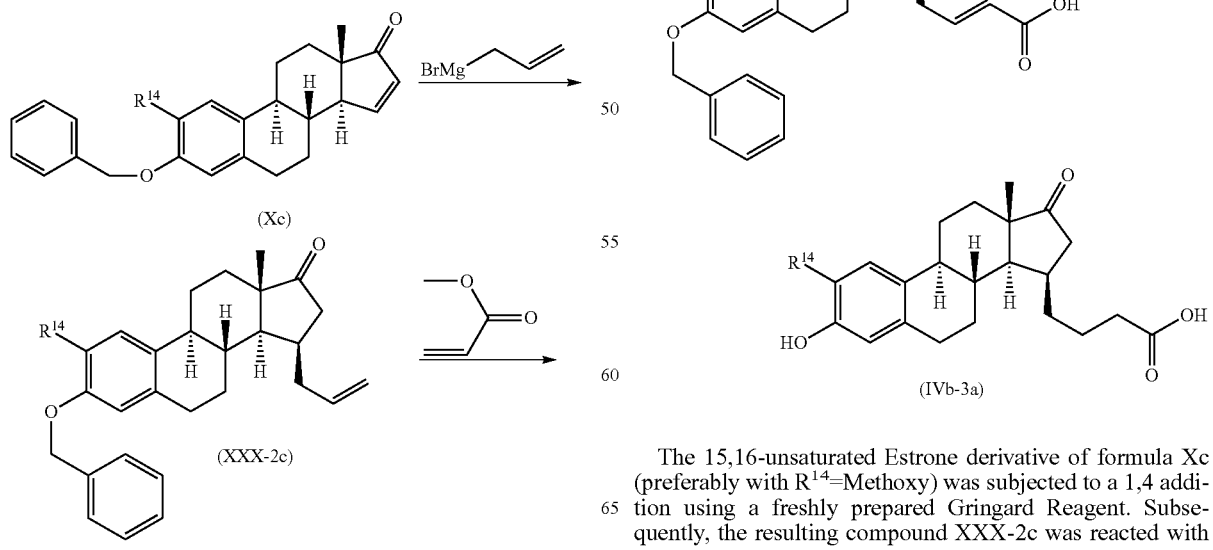

The 15,16-unsaturated Estrone derivative of formula Xc (preferably with R$^{14}$=Methoxy) was subjected to a 1,4 addition using a freshly prepared Gringard Reagent. Subsequently, the resulting compound XXX-2c was reacted with acrylic acid methyl ester using a Grubb II catalyst, known as olefin metathesis. After removal of the methyl group, the free acid (IVb-3a) is obtained by hydrogenation and deprotection. Alternatively, the last two steps may be performed in reversed order.

Detailed Synthesis for Exemplary Compounds
4-(3-Hydroxy-2-methoxy-17-oxo-estra-1,3,5(10)-trien-15β-O-butyric acid (IVβ-(C2-B)-3a)

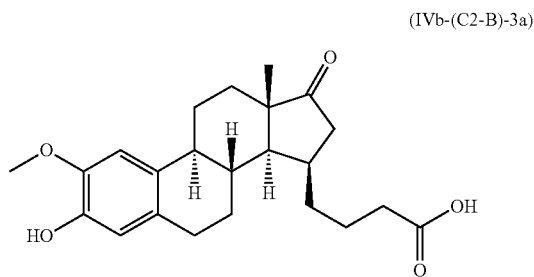

(IVb-(C2-B)-3a)

Compound (IVβ-(C2-B)-3a) was prepared according to general procedure depicted in SCHEME 7C starting from compound (X-C2-B).

15β-Allyl-3-benzyloxy-2-methoxy-estra-1,3,5(10)-trien-17-one (XXXβ-(C2-B)-2c)

Under $N_2$-atmosphere, in flame-dried glassware, LiCl (247 mmol) and CuI (247 mmol) were dissolved in THF (500 ml). The solution obtained was cooled to $T_{intern}$=−78° C., and allyl magnesiumbromide (1 M in $Et_2O$, 246 mmol) was added dropwise during 1.5 h while keeping $T_{intern}$≦−75° C. After stirring for 0.5 h, TMSCl (171 mmol) was added and the reaction mixture was further stirred at $T_{intern}$=−78° C. for 0.5 h. Then, a solution of (X-C2-B) (26.5 g, 68.2 mmol) in THF (250 ml) was added dropwise during 1.5 h, while keeping $T_{intern}$≦−75° C. The reaction mixture was stirred at $T_{intern}$=−78° C. for 1.5 h, after which it was allowed to warm to RT, quenched with sat. $NH_4Cl$ (aq) (600 ml), and stirred at RT overnight. The reaction mixture was filtered over celite and the residue was washed with EtOAc (200 ml). The organic layer was isolated from the combined filtrates, and the aqueous layer was extracted with EtOAc (100 ml). The combined organic layers were washed with 1N HCl (aq) (250 ml), 1N $NH_4OH$ (aq) (3×250 ml), brine (250 ml), dried over $Na_2SO_4$, filtered, and concentrated in vacuo to yield (XXX-(C2-B)-2c) (34.8 g, 98%).

4-(3-Benzyloxy-2-methoxy-17-oxo-estra-1,3,5(10)-trien-15β-yl)-but-2-enoic acid methyl ester Under $N_2$-Atmosphere, in oven-dried glassware, Grubbs II catalyst (2.36 mmol) was added to a solution of (XXX-(C2-B)-2c) (60.4 mmol) and methyl acrylate (150 mmol) in DCM (500 ml). The mixture obtained was stirred at RT overnight, heated at $T_{intern}$=39° C. for 8 h, after which it was allowed to cool to RT. The reaction mixture was evaporated to dryness to furnish 30.8 g resin, which was applied to $SiO_2$ (1500 ml) with DCM and eluted with a DCM:EtOAc gradient (99:1 to 90:10) to yield the desired compound (18.5 g, 63%) ($R_f$=0.1 (DCM)). This was dissolved in THF (250 ml) and heated at reflux with activated charcoal (1 g) for 20 min. The mixture obtained was allowed to cool to RT, filtered and the filtrate was concentrated in vacuo.

4-(3-Hydroxy-2-methoxy-17-oxo-estra-1,3,5(10)-trien-15β-yl)-butyric acid methyl ester (VIIβ-(C2-B)-3a-1)

A solution of 4-(3-Benzyloxy-2-methoxy-17-oxo-estra-1,3,5(10)-trien-15β-yl)-but-2-enoic acid methyl ester (17.3 g, 2.36 mmol) in THF (440 ml) and MeOH (440 ml) was purged with $H_2$ (balloon). Then Pd (10% on carbon, 50% $H_2O$) (1.80 g) was added, and the mixture obtained was stirred under $H_2$ pressure for over night. The reaction mixture was filtered over two filter papers and concentrated in vacuo to yield the desired compound (VIIβ-(C2-B)-3a-1) (13.8 g, 97%), which represents a compound falling under the scope of the present invention.

4-(3-Hydroxy-2-methoxy-17-oxo-estra-1,3,5(10)-trien-15β-yl)-butyric acid (IVβ-(C2-B)-3a)

A solution of $LiOH.H_2O$ (197 mmol) in $H_2O$ (450 ml) was added to a solution of (VIIβ-(C2-B)-3a-1) (34.5 mmol) in THF (450 ml) and the mixture obtained was stirred at RT overnight. The reaction mixture was concentrated in vacuo to remove THF and diluted with $H_2O$ (1300 ml). The mixture was washed with DCM (3×300 ml), acidified with 1N HCl to pH≈1 and extracted with DCM (3×400 ml). The combined extracts were washed with brine (400 ml), dried over $Na_2SO_4$, filtered and concentrated in vacuo to yield (IVβ-(C2-B)-3a) (11.7 g, 88%).

4-(3-Hydroxy-2-(2-methoxy-ethyl)-17-oxo-estra-1,3,5 (10)-trien-15β-A-butyric acid

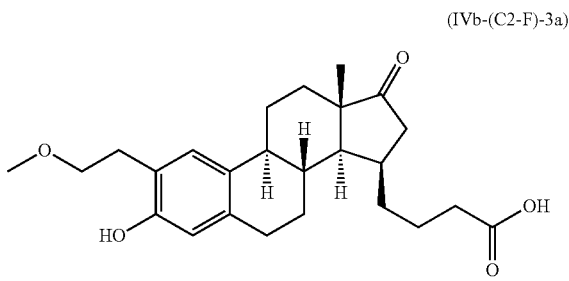

(IVb-(C2-F)-3a)

Compound (IVβ-(C2-F)-3a) was prepared according to general procedure depicted in SCHEME 7C starting from compound (X-C2-F).

15-Allyl-3-(benzyloxy)-2-(2-methoxy-ethyl)-estra-1,3,5 (10)-trien-17-one (XXXβ-(C2-F)-2c)

A flame dried flask was charged with CuI (1.38 mmol) and LiCl (1.38 mmol) under N2 atmosphere. THF (5 ml) was added and stirred at ambient temperature until a clear green solution was obtained. After cooling the solution to −78° C., allylmagnesium bromide in $EtO_2$ (1.38 mmol) was added dropwise and stirred at −78° C. for 1 h. Then TMSCl (1.38 mmol) was added in a single batch. A solution of compound X-C2-F (192 mg, 0.46 mmol) in THF (5 ml) was added dropwise at −78° C. The reaction mixture was stirred at −78° C. for 2 h and the mixture was allowed to reach RT overnight. The mixture was quenched with sat aq $NH_4Cl$ (50 ml). The organic layer was separated and washed with aq. 1M HCl (25 ml), aq. 1M $NH_4OH$ (25 ml) and brine (25 ml). The combined organic layers were dried over $NaSO_4$ and concentrated in vacuo yielding compound (XXXβ-(C2-F)-2c) (220 mg, max. 0.46 mmol). Purification via $SiO_2$ (DMC/methanol=100/0 to 98/2) delivered pure (XXXβ-(C2-F)-2c) (56 mg, 0.122 mmol, 22%).

4-(3-Benzyloxy-2-(2-methoxy-ethyl)-17-oxo-estra-1,3,5 (10)-trien-15β-yl)-but-2-enoic acid ethyl ester Compound (XXXβ-(C2-F)-2c) (46 mg, 0.10 mmol) was dissolved in DCM (5 ml) under N2 atmosphere. Ethyl acrylate (0.135 mmol) and Grubbs II catalyst (0.01 mmol) were added. The reaction mixture was stirred at ambient temperature for 18 h. The reaction mixture was filtered over celite and concentrated in vacuo yielding the title compound (46 mg, 0.086 mmol, 85%) after purification over $SiO_2$ (DCM/MeOH=100/0 to 98/2).

4-(3-Hydroxy-2-(2-methoxy-ethyl)-17-oxo-estra-1,3,5 (10)-trien-15β-yl)-butyric acid ethyl ester (VIIβ-(C2-F)-3a-1)

Palladium on charcoal (10%, 15 mg) was suspended in methanol (5 ml) under N2 atmosphere. A solution of the previous compound (45 g, 0.085 mmol) in THF (5 ml) was added carefully. H$_2$ at ambient pressure was applied and the reaction mixture was stirred at ambient temperature over the weekend. The reaction mixture was filtered over Celite and the filter cake was washed with THF (10 ml). The filtrate was concentrated in vacuo yielding compound (VIIβ-(C2-F)-3a-1) (40 mg, max. 0.085 mmol), which also represents a compound falling under the scope of the present invention.

4-(3-Hydroxy-2-(2-methoxy-ethyl)-17-oxo-estra-1,3,5 (10)-trien-15β-yl)-butyric acid (IVβ-(C2-F)-3a)

The previous compound (40 mg, max. 0.085 mmol) was dissolved in a mixture of THF (2 ml), water (2 ml) and LiOH.H$_2$O (0.45 mmol). The mixture was stirred at ambient temperature for 5 h. THF was removed in vacuo and the residue diluted with water (5 ml). The alkaline layer was washed with DCM (1×10 ml) and the organic layer discarded. The water layer was acidified till pH 3 using aq. 1M HCl and extracted with DCM (4×25 ml). The combined organic layers were washed with brine (25 ml), dried over Na$_2$SO$_4$ and concentrated in vacuo yielding compound (IVβ-(C2-F)-3a) (26 mg, 0.063 mmol, 74%) as pale solid.

The following further building blocks were prepared according to this procedure:
4-(3-Hydroxy-2-ethyl-17-oxo-estra-1,3,5(10)-trien-15β-yl)-butyric acid (IVβ-(C2-C)-3a)
4-(3-Hydroxy-2-propyl-17-oxo-estra-1,3,5(10)-trien-15β-yl)-butyric acid (IVβ-(C2-G)-3a)

Optionally 2-Substituted Acid Building Block with a Stereochemistry at C15: IVα-3a (n=3 and PG=H): 4-(3-Hydroxy-17-oxo-estra-1,3,5(10)-trien-15α-yl)-butyric acid

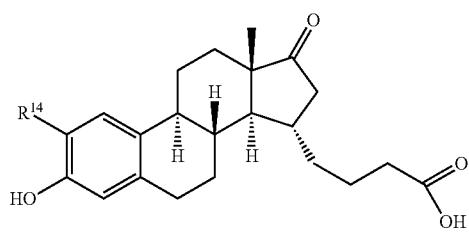

(IVα-3a)

The individual steps in the synthesis of the optionally 2-substituted acid building block of the formula IVα-3a are performed according to any of the procedures depicted in schemes 8A and 8B. Furthermore, reaction scheme 8A also delivers the still ketal-protected estrone-alcohol building block in form of the intermediate of formula XLIVα-1c. Debenzylation and deprotection delivers the estrone-alcohol XXXIα-1a.

SCHEME 8A

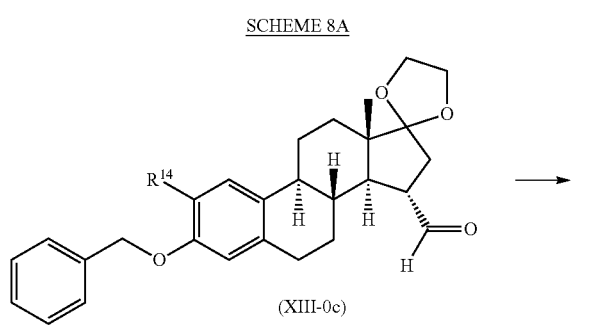

(XIII-0c)

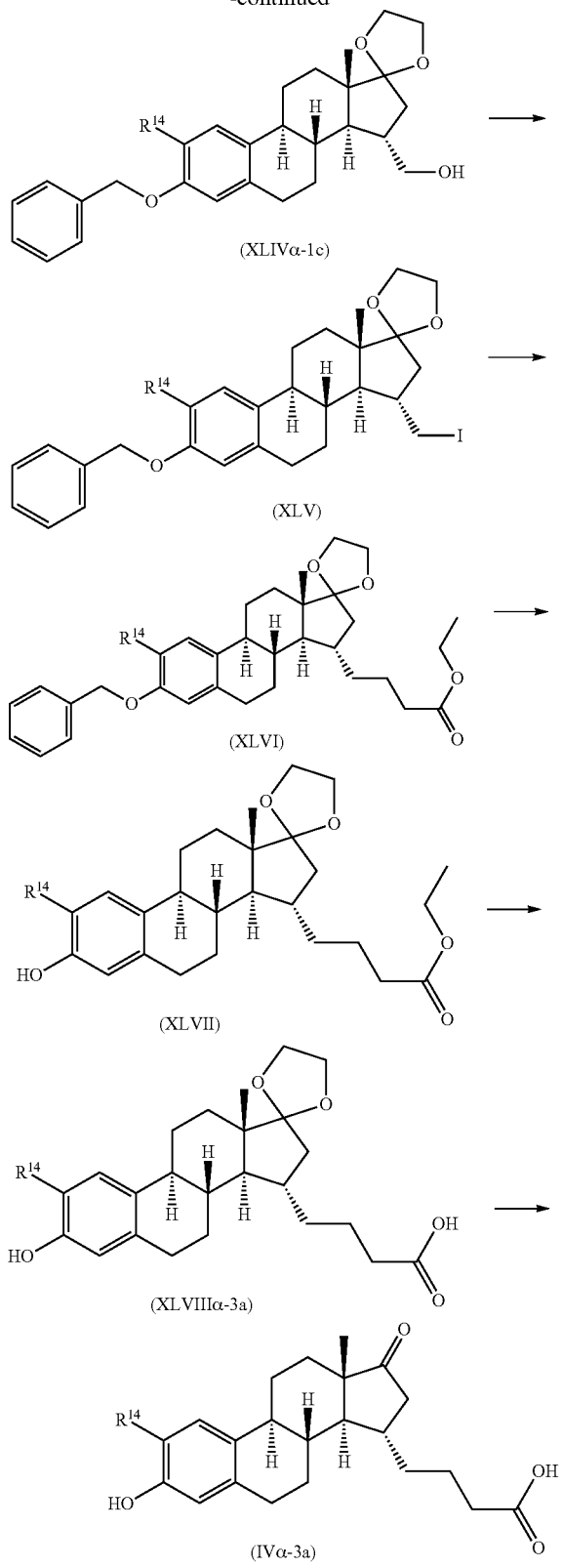

Reduction of the aldehyde XIII-0c with NaBH$_4$ (EtOH, 2 h, RT) gave the alcohol XLIVα-1c, which was further treated with iodine, triphenylphosphine and imidazole to give the iodide XLV. Subsequently, ethylacrylate was coupled to iodine XLV and gave compound XLVI after purification by column chromatography. Reduction of compound XLVI was performed under H₂ atmosphere to give compound XLVII, which was transformed into the protected carboxylic acid building block XLVIIIα-3a by saponification. The carboxylic acid IVα-3a was obtained by deprotection.

SCHEME 8B

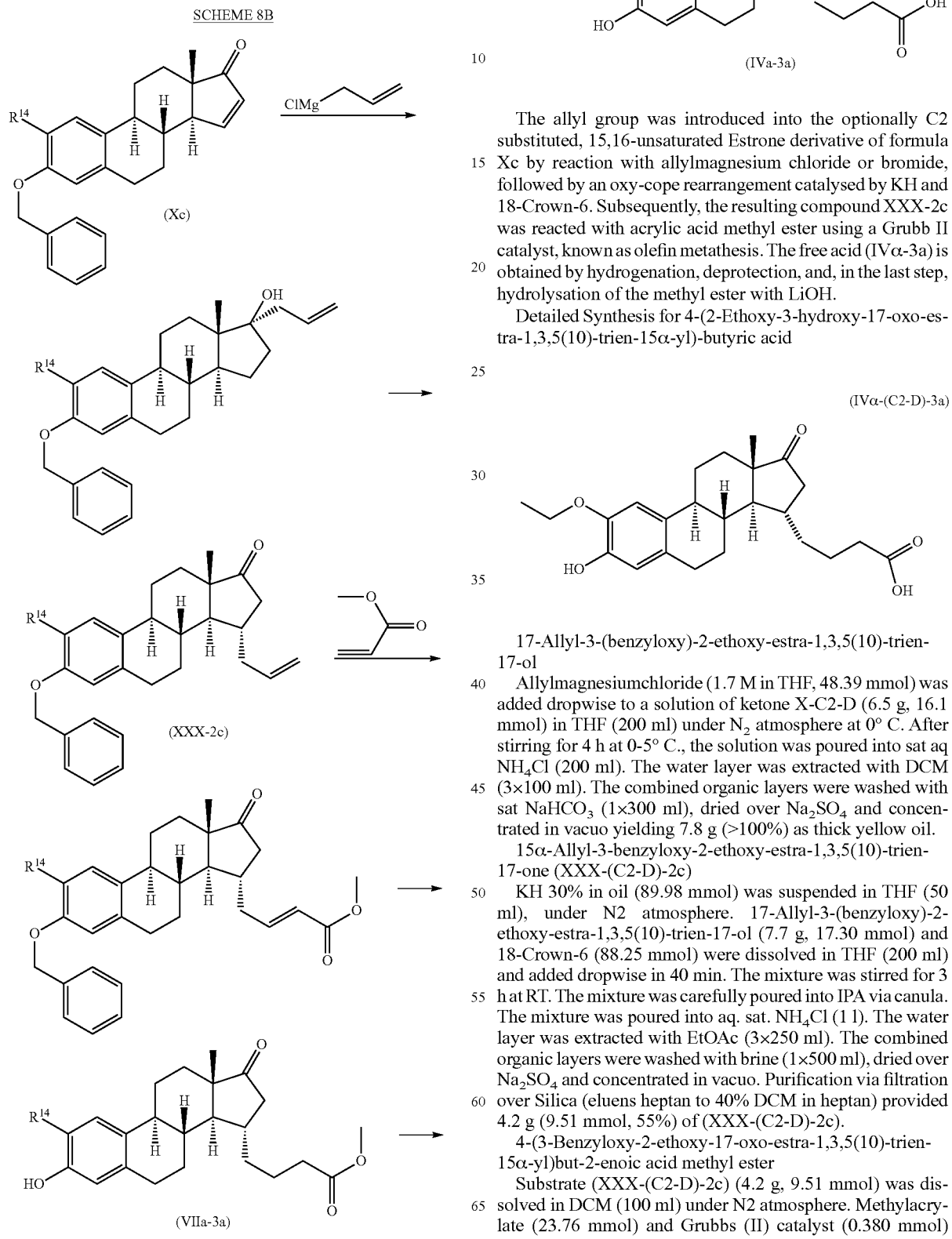

The allyl group was introduced into the optionally C2 substituted, 15,16-unsaturated Estrone derivative of formula Xc by reaction with allylmagnesium chloride or bromide, followed by an oxy-cope rearrangement catalysed by KH and 18-Crown-6. Subsequently, the resulting compound XXX-2c was reacted with acrylic acid methyl ester using a Grubb II catalyst, known as olefin metathesis. The free acid (IVα-3a) is obtained by hydrogenation, deprotection, and, in the last step, hydrolysation of the methyl ester with LiOH.

Detailed Synthesis for 4-(2-Ethoxy-3-hydroxy-17-oxo-estra-1,3,5(10)-trien-15α-yl)-butyric acid 17-Allyl-3-(benzyloxy)-2-ethoxy-estra-1,3,5(10)-trien-17-ol Allylmagnesiumchloride (1.7 M in THF, 48.39 mmol) was added dropwise to a solution of ketone X-C2-D (6.5 g, 16.1 mmol) in THF (200 ml) under N₂ atmosphere at 0° C. After stirring for 4 h at 0-5° C., the solution was poured into sat aq NH₄Cl (200 ml). The water layer was extracted with DCM (3×100 ml). The combined organic layers were washed with sat NaHCO₃ (1×300 ml), dried over Na₂SO₄ and concentrated in vacuo yielding 7.8 g (>100%) as thick yellow oil.

15α-Allyl-3-benzyloxy-2-ethoxy-estra-1,3,5(10)-trien-17-one (XXX-(C2-D)-2c)

KH 30% in oil (89.98 mmol) was suspended in THF (50 ml), under N2 atmosphere. 17-Allyl-3-(benzyloxy)-2-ethoxy-estra-1,3,5(10)-trien-17-ol (7.7 g, 17.30 mmol) and 18-Crown-6 (88.25 mmol) were dissolved in THF (200 ml) and added dropwise in 40 min. The mixture was stirred for 3 h at RT. The mixture was carefully poured into IPA via canula. The mixture was poured into aq. sat. NH₄Cl (1 l). The water layer was extracted with EtOAc (3×250 ml). The combined organic layers were washed with brine (1×500 ml), dried over Na₂SO₄ and concentrated in vacuo. Purification via filtration over Silica (eluens heptan to 40% DCM in heptan) provided 4.2 g (9.51 mmol, 55%) of (XXX-(C2-D)-2c).

4-(3-Benzyloxy-2-ethoxy-17-oxo-estra-1,3,5(10)-trien-15α-yl)but-2-enoic acid methyl ester Substrate (XXX-(C2-D)-2c) (4.2 g, 9.51 mmol) was dissolved in DCM (100 ml) under N2 atmosphere. Methylacrylate (23.76 mmol) and Grubbs (II) catalyst (0.380 mmol) were added. The mixture was heated to reflux and refluxed overnight. The mixture was concentrated in vacuo to afford 4.7 g of a dark brown solid. Purification via column chromatography (ca. 150 ml silica) yielded 3.17 g (66%) of a brown semi-solid.

4-(3-Hydroxy-2-ethoxy-17-oxo-estra-1,3,5(10)-trien-15α-yl)butyric acid methyl ester (VIIa-(C2-D)-3a)

4-(3-Benzyloxy-2-ethoxy-17-oxo-estra-1,3,5(10)-trien-15α-yl)but-2-enoic acid methyl ester (3.17 g, 6.30 mmol) was dissolved in THF (80 ml) and MeOH (80 ml). Pd/C 10% (50% in water, 0.3 g) was added. The mixture was stirred at 1 atm $H_2$ (balloon) at RT for 48 h. The mixture was filtered over Celite. The filter cake was rinsed with MeOH (200 ml) and the filtrate was concentrated in vacuo to provide 2.8 g (6.72 mmol, >100%) of a greenish solid.

4-(2-Ethoxy-3-hydroxy-17-oxo-estra-1,3,5(10)-trien-15α-yl)-butyric acid (IVα-(C2-D)-3a)

Methylester (VIIa-(C2-D)-3a) (2.8 g, 6.72 mmol) was dissolved in THF (80 ml). LiOH (39.86 mmol) was dissolved in water (80 ml) and added in one portion. The solution was stirred at RT overnight. The solution was concentrated in vacuo and water (350 ml) was added. The water layer was washed with DCM (3×200 ml) and acidified to pH=1 with 2N HCl and extracted DCM (3×200 ml). The combined organic layers were washed with brine (1×300 ml), dried over $Na_2SO_4$ and concentrated in vacuo to afford 1.84 g (68%) of a white foam, LC-MS purity of 97-100%.

$^1$H-NMR (CDCl$_3$, 300 MHz): δ 0.95 (s, 3H), 1.25 (m, 2H), 1.4 (t, 3H), 1.5 (m, 3H), 1.60-2.1 (m, 6H), 2.1-2.45 (m, 6H), 2.80 (m, 3H), 4.1 (q, 2H), 6.65 (s, 1H), 6.80 (s, 1H)

4-(3-Hydroxy-2-methoxy-17-oxo-estra-1,3,5(10)-trien-15α-yl)-butyric acid (IVα-(C2-B)-3a) and 4-(3-Hydroxy-2-(2-methoxy-ethoxy)-17-oxo-estra-1,3,5(10)-trien-15α-yl)-butyric acid (IVα-(C2-E)-3a)

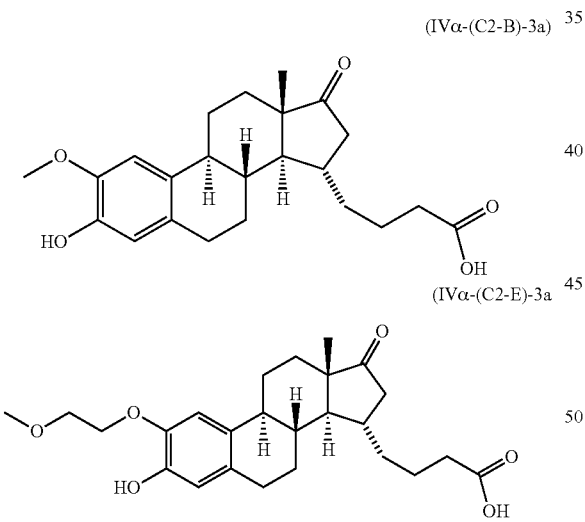

These two intermediates were synthesized accordingly from ketones X-C2-B and X-C2-E, respectively.

4-(3-Hydroxy-2-(2-methoxy-ethoxy)-17-oxo-estra-1,3,5 (10)-trien-15α-yl)-butyric acid (IVα-(C2-E)-3a)

$^1$H-NMR (CDCl$_3$, 300 MHz): δ 0.95 (s, 3H), 1.3 (t, 2H), 1.5 (m, 3H), 1.6-2.1 (m, 6H), 2.1-2.4 (m, 6H), 2.8 (m, 3H), 3.4 (s, 3H), 3.7 (t, 2H), 4.1 (m, 2H), 6.62 (s, 1H), 6.9 (s, 1H)

4-(3-Hydroxy-2-methoxy-17-oxo-estra-1,3,5(10)-trien-15α-yl)-butyric acid (IVα-(C2-B)-3a)

$^1$H-NMR (shifts in ppm): 0.96-1.04 (s, 3H), 1.20-2.48 (m, 16H), 2.70-2.94 (m, 3H), 3.80-3.92 (s, 3H), 6.60-6.68 (s, 1H), 6.76-6.80 (s, 1H).

IIIc. Compounds of formula XXXI (alcohol derivatives): Optionally 2-substituted 15-hydroxy-$C_1$-$C_6$-alkyl-Estron

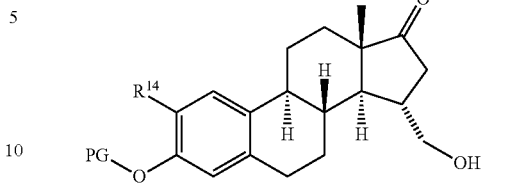

The synthesis of the alcohol derivatives XXXIα-1a (PG=R$^1$=H), XXXIα-1b (PG=R$^1$=CH$_3$), and XXXIα-1c (PG=R$^1$=benzyl) is depicted in the following scheme 9:

SCHEME 9

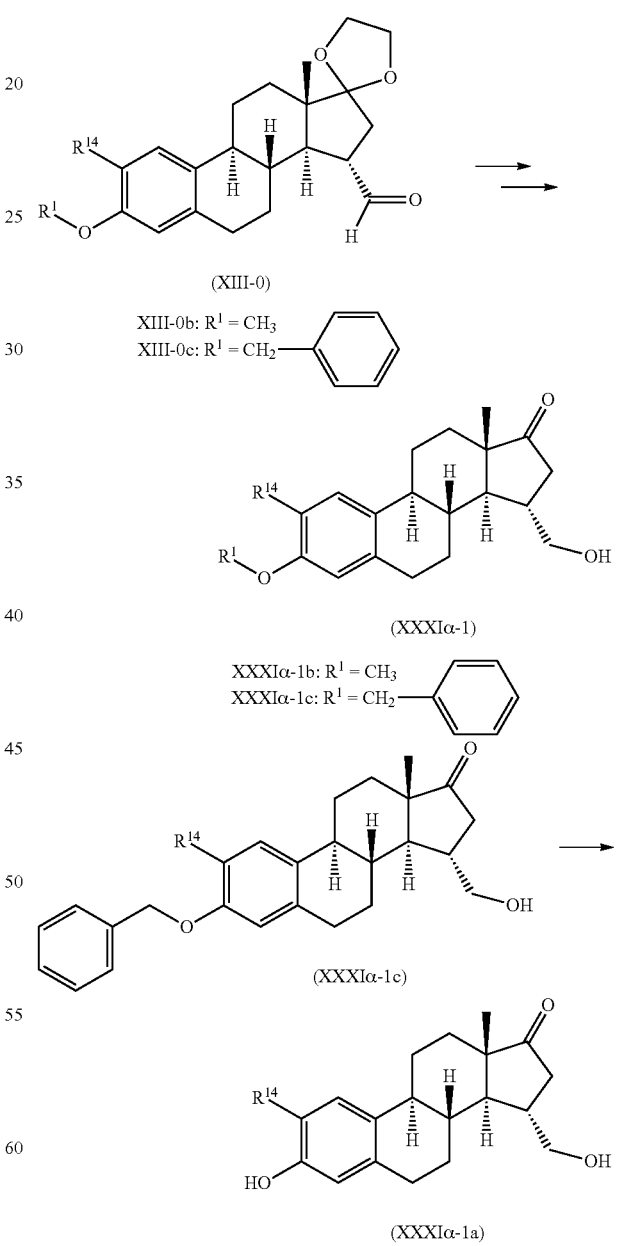

Reduction of the aldehydes XIII-0b or XIII-0c using NaBH$_4$ followed by ketal hydrolysis gave the corresponding alcohols XXXIα-1b and XXXIα-1c. The alcohol XXXIα-1c was debenzylated to give XXXIα-1a using Pd/C and a 5 bar hydrogen atmosphere.

Alcohol Building Blocks XXXI-3c and XXXI-3a (n=3) and XXXI-5c and XXXI-5a (n=5) with PG=$R^1$=Benzyl or PG=$R^1$=H):

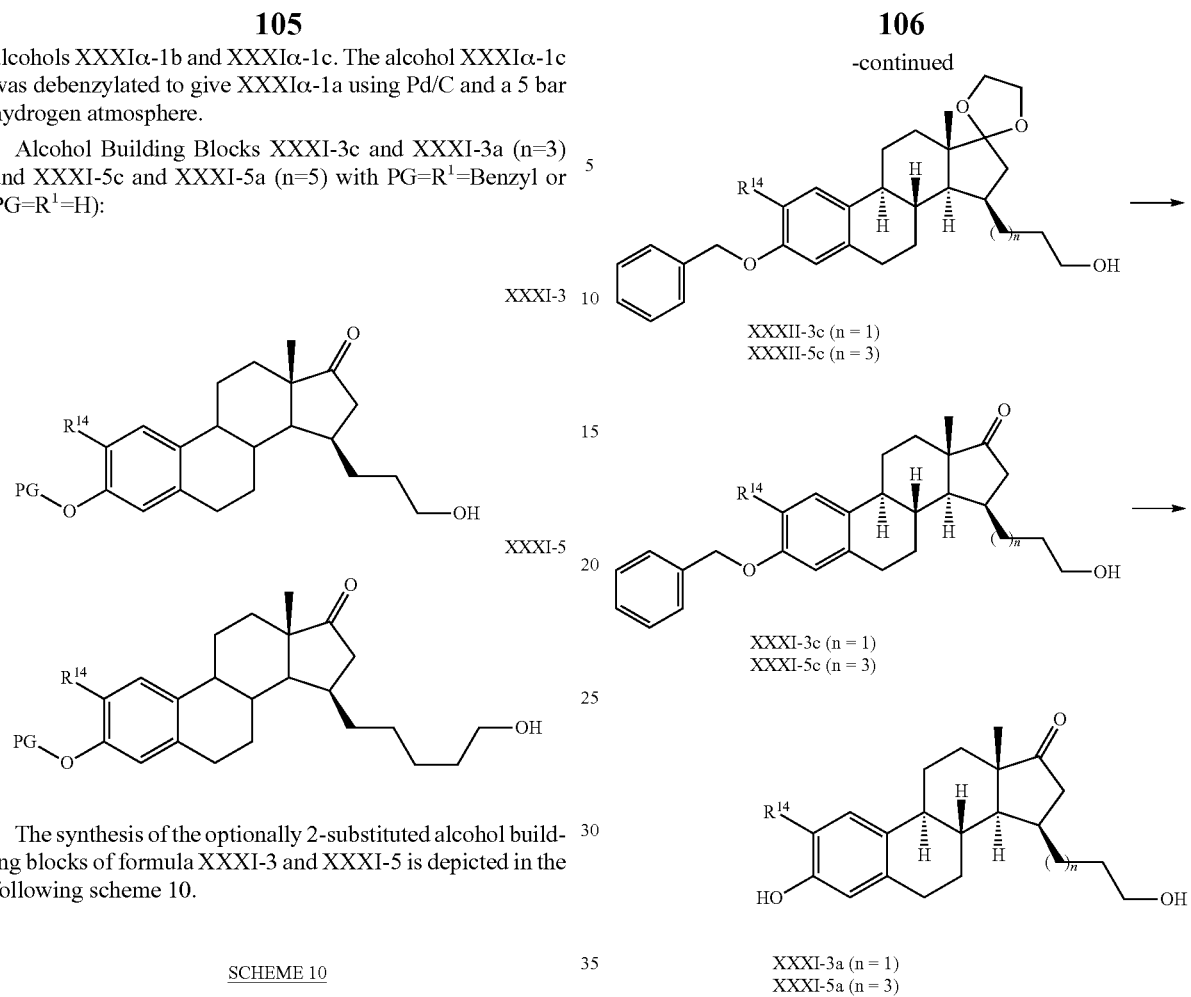

The synthesis of the optionally 2-substituted alcohol building blocks of formula XXXI-3 and XXXI-5 is depicted in the following scheme 10.

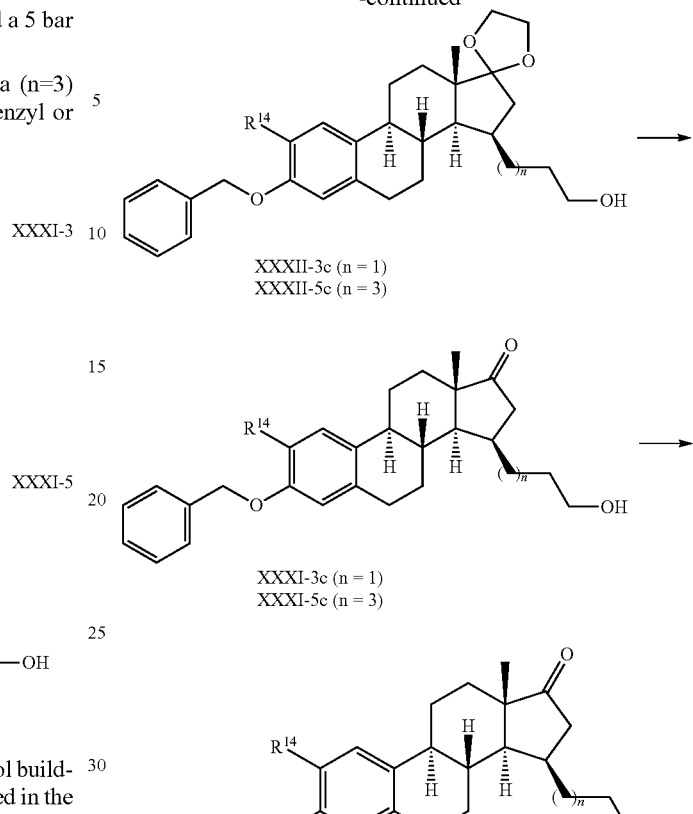

The 15, 16-unsaturated Estrone derivative of formula Xc (preferably with $R^{14}$=H, Ethyl, n-Propyl or Methoxyethyl) was subjected to a 1,4 addition using a freshly prepared Gringard Reagent (allylmagnesiumchloride or pentenylmagnesiumchloride) delivering compound XXXV. After protection of the ketone functionality in C17 as ketal, the alkenyl side chain was hydroborated and subsequently oxidized to provide compound XXXII. After deprotection of the C17 keto function by treatment with pTosOH, the benzyl function is optionally cleaved off to deliver the alcohol building blocks XXXI-3 and XXXI-5, respectively.

Alcohol building blocks XXXI-4b, XXXI-5b, XXXI-6b (n=4, 5, 6): 15β-(4-Hydroxy-$C_4$-$C_6$-alkyl)-3-methoxy-estra-1,3,5(10)-trien-17-one

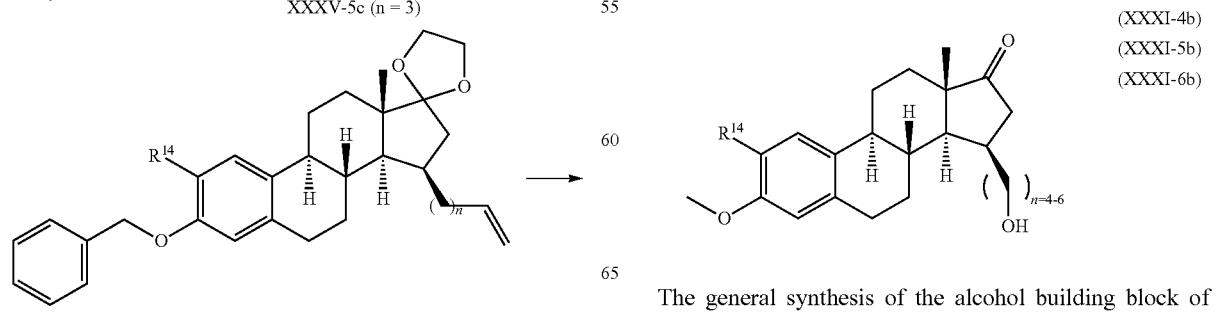

The general synthesis of the alcohol building block of formula XXXI-4/5/6b is depicted in the following scheme 11.

SCHEME 11

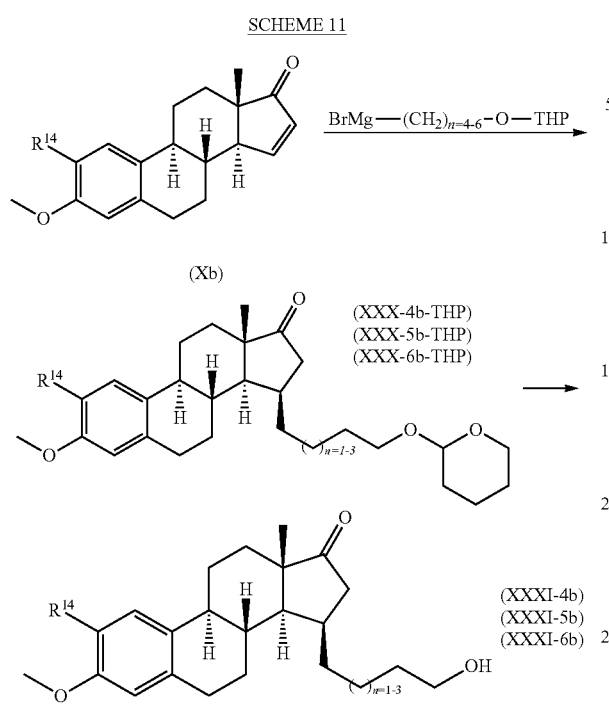

General Procedure

Magnesium (3-10 eq) is added in a dry three-neck flask under N2 atmosphere and activated by iodine. The bromo compound (2-6.5 eq) dissolved in dry THF is added dropwise to the magnesium. The reaction mixture is allowed to react for 1-2 h at RT or reflux. The solution is transferred to dry three-neck flask containing CuI (0.06-0.7 eq) and DMPU or HMPA (2-7 eq) in dry THF cooled to −40° C. The resulting mixture is stirred for 30 min at −40° C. after which a mixture of 15,16-unsaturated estron derivative of formula X (1 eq) and TMSCl (2-2.5 eq) dissolved in THF is added dropwise. After complete addition the mixture is allowed to reach RT. Then NH₄Cl-solution is added, the layers are separated and the aqueous phase is extracted with EtOAc (3×). The combined organic phases are dried over Na₂SO₄ and the solvent is evaporated. The crude product is dissolved in methanol and K₂CO₃ (1 eq) is added to hydrolyse the silyl ether. After complete hydrolysis water is added and most of the methanol is evaporated. The mixture is diluted with EtOAc, the layers are separated and the water layer is extracted with EtOAc. The combined organic layers are dried over Na₂SO₄ and the solvent is evaporated. The resulting product of general formula XXX is then further worked-up to give the alcohol of general formula XXXI.

Alcohol Building Block XXXI-4 (n=4) With PG=Benzyl or H

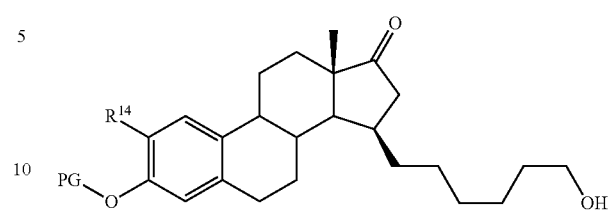

The detailed synthesis of these compounds is already displayed within the section for the synthesis of acid building block of the formula IV-3c above. The 3-hydroxy-derivative can be obtained by debenzylation of the XXXI-4c compound.

Alcohol Building Blocks XXXI-6c and XXXI-6a (n=6):

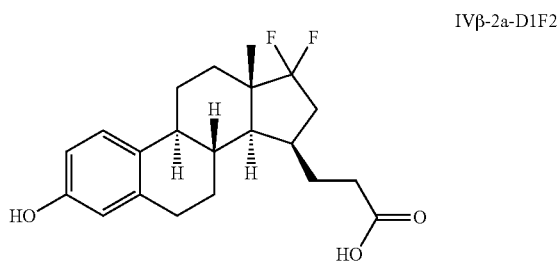

The detailed synthesis of these compounds is performed according to the general procedure displayed in SCHEME 11 starting with the 15,16 unsaturated estron derivative Xc as educt. The 3-hydroxy-derivative can be obtained by hydrolysis of the XXXI-6c compound.

IIId. Optionally 2-Substituted Compounds of Formula IV with a Fluoro Atom Containing Substitution of the C17 Keto Function 3-(17,17-Difluoro-3-hydroxy-estra-1,3,5(10)-trien-15β-yl)-propanoic acid (IVβ-2a-D1F2)

The individual steps in the synthesis of the acid building block of the formula IVβ-2a-D1F2 are depicted in the following scheme 12.

SCHEME 12

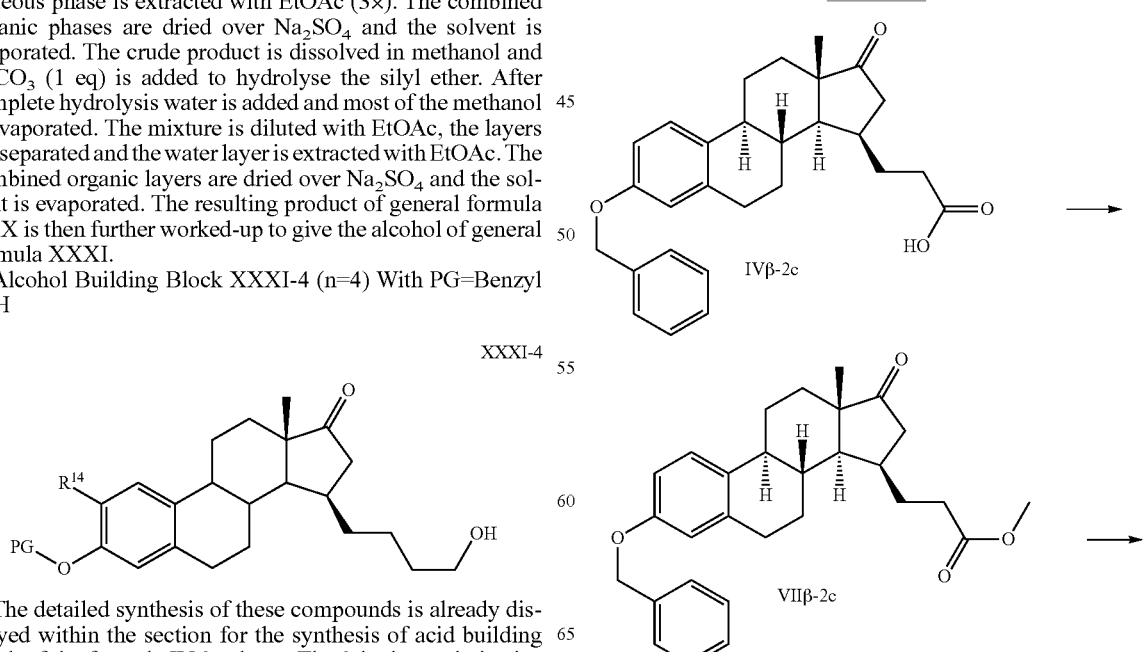

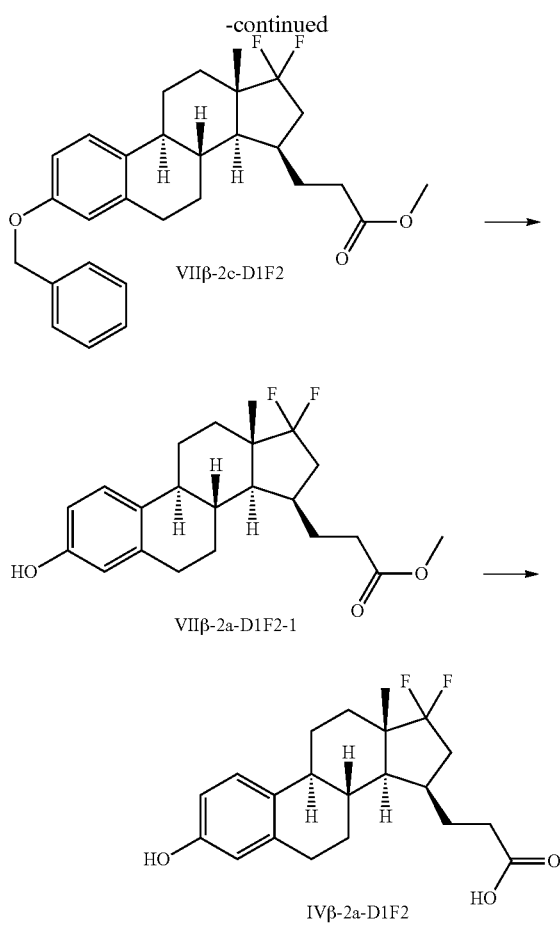

3-(3-Benzyloxy-17-oxo-estra-1,3,5(10)-trien-15β-yl)-propanoic acid of formula IVβ-2c is transformed in the corresponding methyl ester by an esterification reaction as depicted in general flow diagram II using an EDCI coupling. Fluorination of the obtained methyl ester with deoxofluor gave compound VIM-2c-D1F2. Subsequent debenzylation, followed by saponification with LiOH afforded the desired building block IVβ-2a-D1F2.

Detailed Synthesis 3-(3-Benzyloxy-17-oxo-estra-1,3,5(10)-trien-15β-yl)-propionic acid methyl ester (VIIβ-2c)

A mixture of compound IVb-2c (38 mmol), Et₃N (117 mmol), MeOH (44 mmol), HOBt (44 mmol) and EDCI (49 mmol) in DCM (650 ml) was stirred overnight. The reaction mixture was washed with 1N HCl (2×250 ml) and H₂O (250 ml). The organic layer was dried over Na₂SO₄ and concentrated in vacuo to yield VIIβ-2c (38 mmol, 99%) as orange oil.

3-(3-Benzyloxy-17,17-difluoro-estra-1,3,5(10)-trien-15β-yl)-propionic acid methyl ester Deoxofluor (50% in toluene, 247 mL, 670 mmol) was added to a solution of VIIβ-2c (27.2 g, 60.9 mmol) in toluene (130 ml). The mixture was stirred for 5 d, during which two times 10 drops of EtOH were added. DCM (200 ml) was added and the mixture was cooled on ice. Saturated NaHCO₃ (300 mL) was added. The layers were separated and the aqueous layer was extracted with DCM (3×300 ml). The combined organic layers were washed with brine (500 ml), dried over Na₂SO₄ and concentrated in vacuo to give crude VIIβ-2c-D1F2 (26.5 g). Purification by column chromatography (SiO₂, DCM-heptan 2:1 to DCM) gave VIIβ-2c-D1F2 (2.94 g, 6.3 mmol, 10%) as yellow oil.

3-(17,17-Difluoro-3-hydroxy-estra-1,3,5(10)-trien-15β-yl)-propionic acid methyl ester A mixture of VIIβ-2c-D1F2 (2.94 g, 6.3 mmol), Pd/C (10%, 440 mg), MeOH (75 mL) and EtOAc (32 mL) was stirred for 2 d under 1 bar H₂. After 1 day another portion of Pd/C (484 mg) was added. The mixture was filtered over Celite and the filter cake was washed with MeOH and EtOAc. The filtrate was concentrated in vacuo to give 2.1 g of crude VIIβ-2a-D1F2. Purification by column chromatography (SiO₂, DCM) gave VIIβ-2a-D1F2 (1.46 g, 3.9 mmol, 61%) as yellow oil.

3-(17,17-Difluoro-3-hydroxy-estra-1,3,5(10)-trien-15β-yl)-propionic acid (IVβ-2a-D1F2)

A solution of LiOH*H₂O (934 mg, 22 mmol) in water (60 mL) was added to a solution of VIIβ-2a-D1F2 (1.46 g, 3.9 mmol) in THF (60 mL). The mixture was stirred overnight and concentrated in vacuo. Water (250 ml) was added and the mixture was washed with DCM (2×200 mL) and the pH was adjusted to 1. The aq. layer was extracted with DCM (3×200 mL). The combined organic layers were dried over Na₂SO₄ and concentrated in vacuo to yield IVβ-2a-D1F2 (1.2 g, 3.3 mmol, 85%) as yellow foam.

¹H-NMR-listing: 1.027-1.34 (s, 3H), 1.408-2.421 (m, 15H), 2.837-2.960 (m, 2H), 6.573-6.651 (m, 2H), 7.121-7.257 (d, 1H).

¹⁹F-NMR-listing: −104−−106 (d, 1F), −115−−117 (d, 1F).

4-(17,17-Difluoro-3-hydroxy-estra-1,3,5(10)-trien-15α-yl)-butanoic acid (IVα-3a-D1F2)

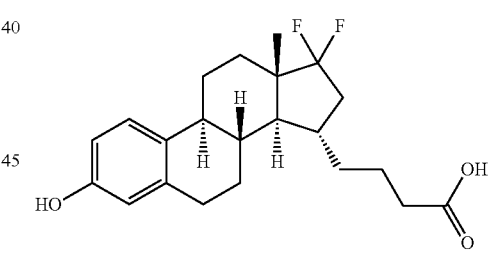

IVα-3a-D1F2

The acid building block of formula IVα-3a-D1F2 was synthesized starting from intermediate compound Xc and using the reaction steps as depicted in SCHEME 8B: The allyl group was introduced into the 15, 16-unsaturated Estrone derivative of formula Xc by reaction with allylmagnesium chloride, followed by an oxy-cope rearrangement catalysed by KH and 18-Crown-6. Subsequently, the resulting compound XXX-2c was reacted with acrylic acid methyl ester using a Grubb II catalyst, known as olefin metathesis. Then, deviating from SCHEME 8B, the 17-keto function of the resulting 4-(3-Benzyloxy-17-oxo-estra-1,3,5(10)-trien-15α-yl) but-2-enoic acid methyl ester was converted to a bisfluoro group using deoxofluor as described for VIIβ-2c-D1F2. Subsequently, the well known hydrogenation step was performed to obtain the butanoic acid ester side chain, and finally the ester was hydrolysed with LiOH to give the target compound.

$^{1}$H-NMR-listing: 0.94 (s, 3H), 1.10-2.06 (m, 4H), 2.18-2.55 (m, 14H), 2.74-2.92 (m, 2H), 6.52 (d, 1H), 6.64 (dd, 1H), 7.15 (d, 1H)

$^{19}$F-NMR-listing: −104.5 (dd, 1F), −117.0 (d, 1F).

4-(3-Benzyloxy-17-difluoromethylene-estra-1,3,5(10)-trien-15-yl)-butan-1-ol 4-(17-Difluoromethylene-3-hydroxy-estra-1,3,5(10)-trien-15-yl)-butyryl bromide

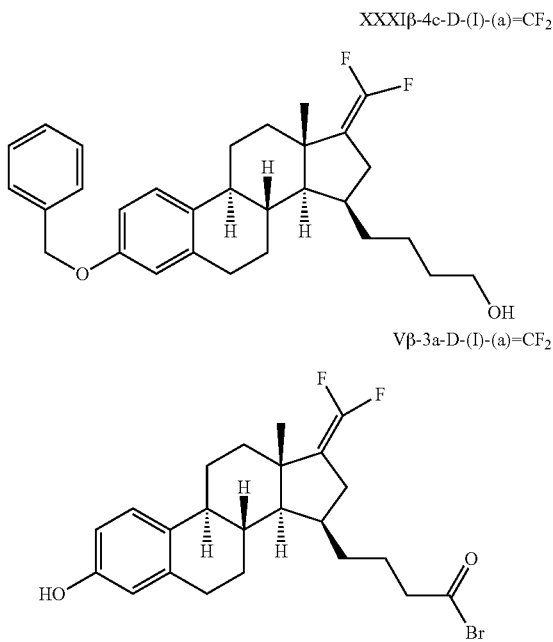

Synthesis of XXXIIβ-4c-D-(I)-(a)=CF$_2$ was achieved in a 3-step reaction starting from intermediate compound XXXIIβ-4c using the Horner reaction as described for general synthesis step D-(I)-(a). Subsequently, the fluorinated alcohol derivative XXXI-4c-D-(I)-(a)=CF$_2$ was converted into the free acid by a Jones oxidation, followed by a debenzylation step using BBr$_3$ to deliver the desired intermediate Vβ-3a-D-(I)-(a)=CF$_2$.

Detailed Synthesis

3-Benzyloxy-15-[4-(tert-butyldimethylsilanyloxy)-butyl]-estra-1,3,5(10)-trien-17-one To a solution of intermediate XXXIβ-4c (108 mg; 0.25 mmol) and imidazole (41.0 mg; 0.60 mmol) in DMF (1 ml) tert-Butyldimethylsilylchloride (0.30 ml; 0.30 mmol; 1M in THF) was added dropwise. After stirring for 16 h at RT, the reaction mixture was poured into H$_2$O and extracted with DCM. The organic phases were dried over MgSO$_4$. After removal of the solvent, the oily residue was purified by column chromatography (SiO$_2$, DCM) to yield 3-Benzyloxy-15-[4-(tert-butyldimethylsilanyloxy)-butyl]-estra-1,3,5(10)-trien-17-one (126 mg, 92%) as colourless oil.

[4-(3-Benzyloxy-17-difluoromethylene-estra-1,3,5(10)-trien-15-yl)-butoxy]-tert-butyldimethylsilane Lithium diisopropylamide (0.60 ml; 1.08 mmol; 1.8 M in THF/Heptane/Ethylbenzene) is added dropwise to a solution of Difluoromethylphosphonic acid diethylester (204 mg; 1.08 mmol) in THF (3 ml) at −78° C. and stirred for 30 min. Subsequently, a solution of the ketone obtained in the previous reaction step (148 mg; 0.27 mmol) in THF (4 ml) is added and the mixture is stirred for 30 min and further until the mixture was warmed to RT. The mixture is heated for 5 h under reflux and allowed to cool to RT. After addition of water, the solution is extracted with DCM. The combined organic phases are dried over MgSO$_4$. After removal of the solvent, the residue is purified by column chromatography (SiO$_2$, DCM/Hexane 1:2) to yield [4-(3-Benzyloxy-17-difluoromethylene-estra-1,3,5(10)-trien-15-yl)-butoxy]-tert-butyldimethylsilane (107 mg, 68%) as colorless oil.

4-(3-Benzyloxy-17-difluoromethylene-estra-1,3,5(10)-trien-15-yl)-butan-1-ol XXXIβ-4c-D-(I)-(a)=CF$_2$ A solution of the obtained TBDMS-Ether (97.0 mg; 167 μmol) in TBAF (1 ml; 1 mmol; 1 M in THF) was stirred for 4 h at RT. The reaction mixture is poured into H$_2$O and extracted with DCM. The combined organic phases are dried over MgSO$_4$. After removal of the solvent, the residue is purified by column chromatography (SiO$_2$, DCM) to yield XXXIβ-4c-D-(I)-(a)=CF$_2$ (76.0 mg, 98%) as yellow solid.

4-(3-Benzyloxy-17-difluoromethylene-estra-1,3,5(10)-trien-15-yl)-butyric acid Vβ-3c-D-(I)-(a)=CF$_2$ After dissolving the alcohol XXXIIβ-4c-D-(I)-(a)=CF$_2$ in 10 ml acetone, Jones reagent (1 g CrO$_3$, 7 ml H$_2$O, 3 ml 100% H$_2$SO$_4$) was added at 0° C. up to the point the solution remained reddish. After stirring for 10 min, any excess of Jones reagent was destroyed by adding isopropanol. After filtration over silicagel, the filtrate was evaporated to dryness. The residue was diluted with DCM and washed several times with water, dried over Na$_2$SO$_4$ and again evaporated to dryness. The crude product was used further without any purification.

4-(17-Difluoromethylene-3-hydroxy-estra-1,3,5(10)-trien-15-yl)-butyryl bromide Vβ-3a-D-(I)-(a)=CF$_2$ The crude benzylated estrone acid derivative IVβ-3c-D-(I)-(a)=CF$_2$ was dissolved in 10 ml dry DCM and few drops BBr$_3$ were added at ambient temperature. The reaction mixture was stirred for 1 h and directly used in further reaction steps without any work-up.

4-(3-Benzyloxy-17-trifluoromethyl-estra-1,3,5(10)16-tetraen-15-yl)-butan-1-ol 4-(3-Hydroxy-17-trifluoromethyl-estra-1,3,5(10),16-tetraen-15-yl)-butyryl bromide

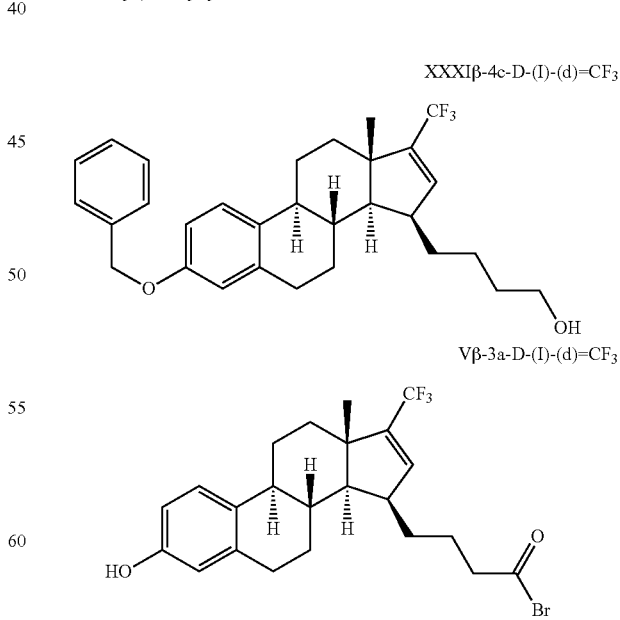

Synthesis of XXXIβ-4c-D-(I)-(d)-CF$_3$ was achieved in a 4-step reaction starting from intermediate compound XXXIIβ-4c as described for general synthesis step D-(I)-(d).

Subsequently, the fluorinated alcohol derivative XXXI-4c-D-(I)-(d)=CF$_3$ was converted into the free acid by a Jones oxidation, followed by a debenzylation step using BBr$_3$ to deliver the desired intermediate Vβ-3a-D-(I)-(d)-CF$_3$.

3-Benzyloxy-15-(4-hydroxybutyl)-17-trifluoromethyl-estra-1,3,5(10)-trien-17-ol (Trifluoromethyl)trimethylsilan (7.60 ml; 15.0 mmol; 2M in THF) was added to a solution of intermediate XXXIβ-4c (1.08 g; 2.50 mmol) in THF pre-cooled to 0° C. After addition of TBAF (60.0 mg; 0.63 mmol), the reaction mixture was stirred for 0.5 h at 0° C. and for 16 h at RT. Water was added and the resulting the solution was extracted with ether. The combined organic phases were dried over MgSO$_4$. After removal of the solvent, the residue was dissolved in TBAF solution (10.0 ml; 10.0 mmol; 1 M in THF) and the resulting mixture was stirred for 4 h at RT. Water was added and the resulting solution was extracted with ether. The combined organic phases were dried over MgSO$_4$. The remaining oil was purified by column chromatography (SiO$_2$; Ether/DCM 1:1) yielding the title compound (942 mg, 75%) as colourless oil.

2,2-Dimethylpropionic acid 4-(3-benzyloxy-17-hydroxy-17-trifluoromethyl-estra-1,3,5(10)-trien-15-yl)-butylester Pivaloylchloride (0.50 ml; 4.10 mmol) was added dropwise to a solution of 3-Benzyloxy-15-(4-hydroxybutyl)-17-trifluoromethyl-estra-1,3,5(10)-trien-17-ol (1.65 g; 3.28 mmol) in pyridine (15 ml) at 0° C. After stirring for 2 h, the reaction mixture was poured into ice water and stirred for another h. After extraction with DCM, the combined organic phases were dried over MgSO$_4$. After evaporation of the solvent, the residue was purified by column chromatography (SiO$_2$, DCM) yielding the title compound (1.85 g, 96%) as colourless oil.

2,2-Dimethylpropionic acid 4-(3-benzyloxy-17-trifluoromethyl-estra-1,3,5(10),16-tetraen-15-yl)-butylester Phosphorylchloride (0.25 ml; 200 μmol) was added to a solution of 2,2-Dimethylpropionic acid 4-(3-benzyloxy-17-hydroxy-17-trifluoromethyl-estra-1,3,5(10)-trien-15-yl)-butylester (80.0 mg; 136 μmol) in pyridine (2.50 ml) and the resulting mixture is heated under reflux for 24 h. Then, the mixture was allowed to cool to RT, diluted with ice water and extracted with ether. The combined organic phases were dried over MgSO$_4$ and the solvent was evaporated. The residue was purified by column chromatography (SiO$_2$, DCM) yielding the title compound (60.0 mg, 78%) as colourless oil.

4-(3-Benzyloxy-17-trifluoromethyl-estra-1,3,5(10),16-tetraen-15-yl)-butan-1-ol XXXIβ-4c-D-(I)-d-CF$_3$ DIBAH (1.00 ml; 1.00 mmol; 1M in THF) was added dorpwise to a solution of the pivaloate (60.0 mg; 106 μmol) in DCM (5 ml) at −78° C. After stirring for 6 h, 1 N HCl (20 ml) was added and the reaction mixture was extracted with DCM. The combined organic phases were dried over MgSO$_4$ and the solvent was evaporated. The residue was purified by column chromatography (SiO$_2$, DCM) yielding XXXIβ-4c-D-(I)-d-CF$_3$ (46.0 mg, 90) as colourless oil.

4-(3-Benzyloxy-17-trifluoromethyl-estra-1,3,5(10),16-tetraen-15-yl)-butyric acid IVβ-3c-D-(I)-(d)-CF$_3$ After dissolving 180 mg of the alcohol XXXIβ-4c-D-(I)-(d)-CF$_3$ in 10 ml acetone, Jones reagent (1 g CrO$_3$, 7 ml H$_2$O, 3 ml 100% H$_2$SO$_4$) was added at 0° C. up to the point the solution remained reddish. After stirring for 10 min, any excess of Jones reagent was destroyed by adding isopropanol. After filtration over silicagel, the filtrate was evaporated to dryness. The residue was diluted with DCM and washed several times with water, dried over Na$_2$SO$_4$ and again evaporated to dryness. The crude product was used further without any purification.

4-(3-Hydroxy-17-trifluoromethyl-estra-1,3,5(10)-trien-15-yl)-butyryl bromide Vβ-3a-D-(I)-(d)-CF$_3$ The crude benzylated estrone acid derivative IVβ-3c-D-(I)-(d)-CF$_3$ was dissolved in 10 ml dry DCM and few drops BBr3 were added at ambient temperature. The reaction mixture was stirred for 1 h and directly used in further reaction steps without any work-up.

IIIe. Optionally 2-Substituted Compounds of Formula XV (Protected Amine Building Block) (n=1–6)

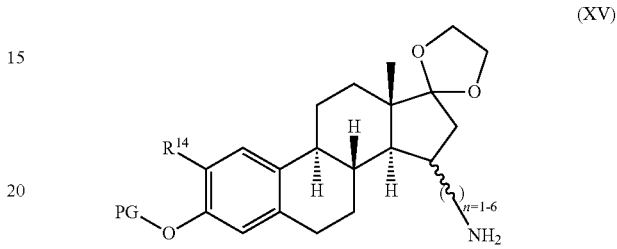

XV-1: (n=1):

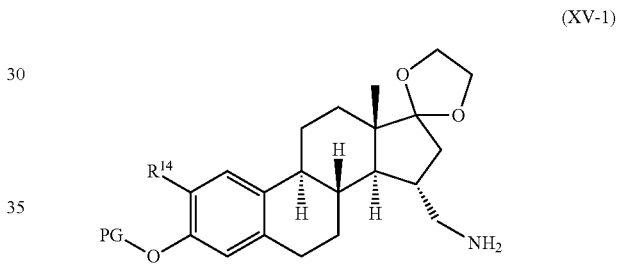

The individual steps in the synthesis of amine building block of the formula XV-1 are depicted in the following scheme 13.

SCHEME 13

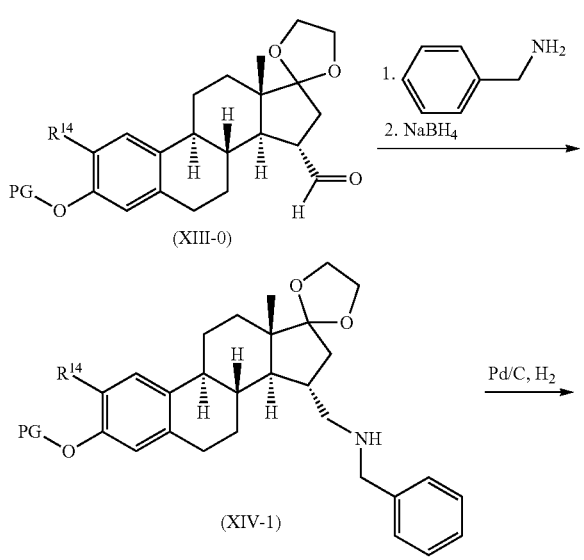

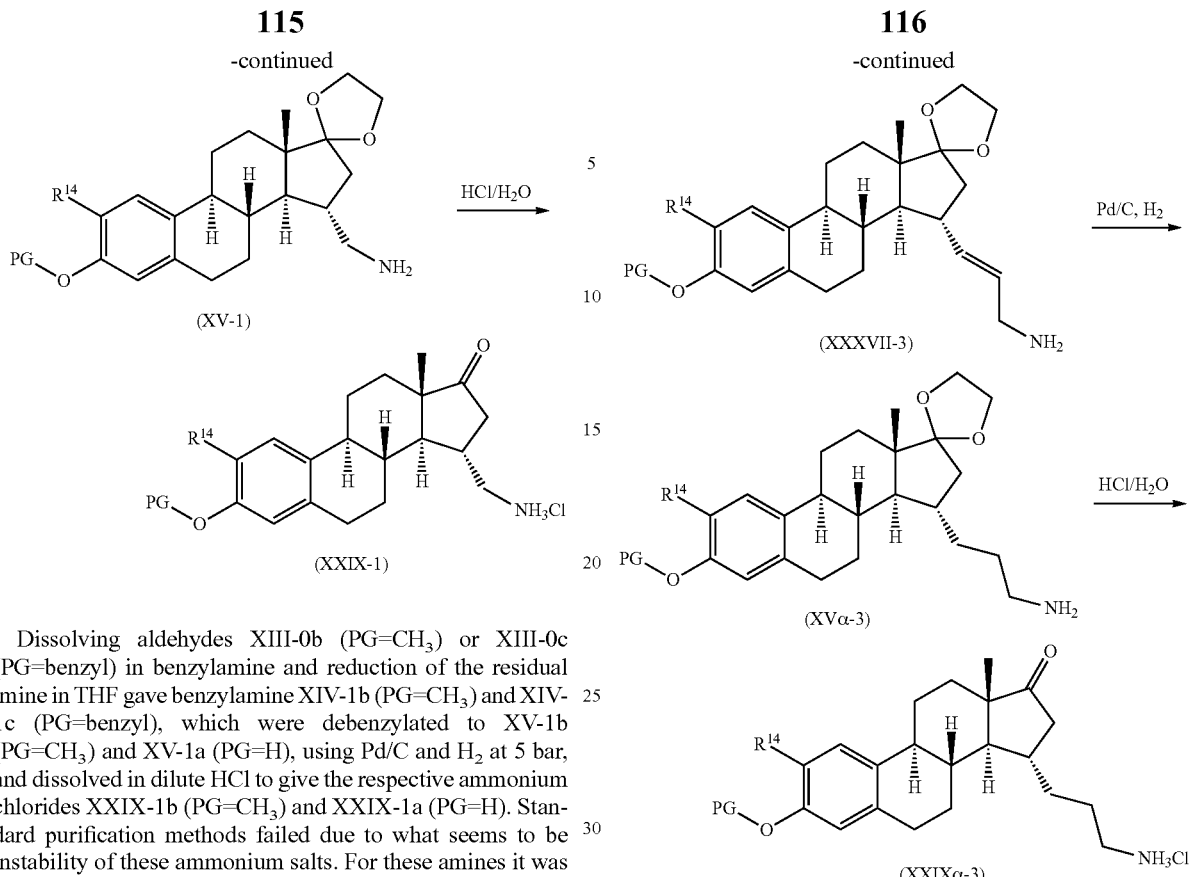

Dissolving aldehydes XIII-0b (PG=CH₃) or XIII-0c (PG=benzyl) in benzylamine and reduction of the residual imine in THF gave benzylamine XIV-1b (PG=CH₃) and XIV-1c (PG=benzyl), which were debenzylated to XV-1b (PG=CH₃) and XV-1a (PG=H), using Pd/C and H₂ at 5 bar, and dissolved in dilute HCl to give the respective ammonium chlorides XXIX-1b (PG=CH₃) and XXIX-1a (PG=H). Standard purification methods failed due to what seems to be instability of these ammonium salts. For these amines it was known that these should be treated as HCl salts since the free amine is not stable (eneamines), but even the salts seem to be at least heat-sensitive. The crude reaction mixture has a purity of ~90% (HPLC-MS).

Amine Building Block XVα-3: (n=3):

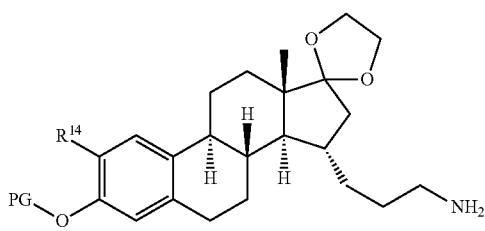

The individual steps in the synthesis of amine building block of the formula XVα-3 are depicted in the following scheme 16.

SCHEME 16:

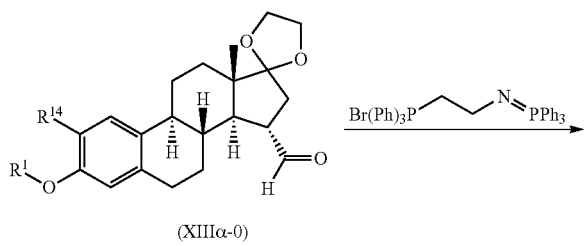

The protected aldehyde derivative of formula (XIIIα-0) is converted into the corresponding aminopropenyl by a Wittig reaction (see also SCHEME 4). The aminopropenyl (XXX-VII-3) is subsequently reduced to the 15-aminopropyl derivative of formula XVα-3. The protecting ketal group is converted into the 17-oxo group via acid hydrolysis.

The same kind of procedure can be applied using different Wittig reagents of the general formula Hal(Ph)₃P—(CH₂)ₙ₌₃₋₅—R* in order to obtain amine building blocks with longer side chains (i.e. n=4, 5, or 6), wherein R* for example represents —N=P(Ph)₃, —N3, or —NH—CO—O—CH₃.

Amine Building Block XVα-4: (n=4):

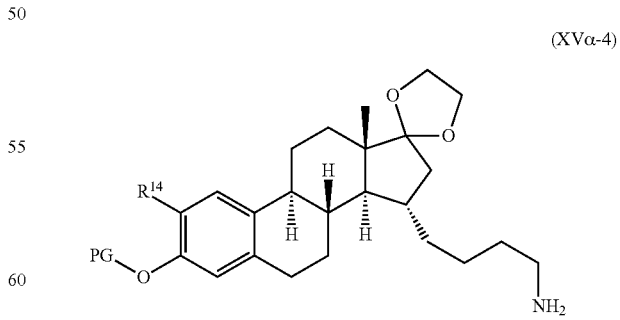

Furthermore, the amine building block XVα-4b was synthesized corresponding to SCHEME 16 using HalPh₃P—CH₂—CH₂—CH₂—N3 as Wittig reagent. (LC-MS (ES+): rt 4.57 min, m/z (rel. Intens) 386 [(M+H)⁺, 100%])

Amine Building Block XVβ-4: (n=4):

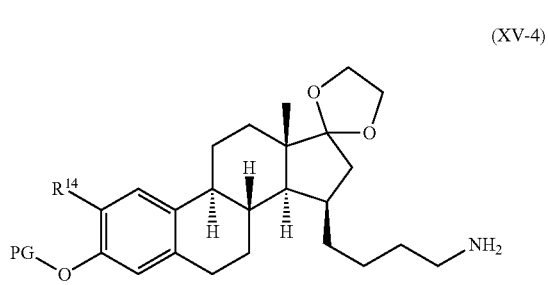

The individual steps in the synthesis of amine building block of the formula XVβ-4 with β configuration at the C15 atom of the steroidal core are depicted in the following scheme 17.

SCHEME 17

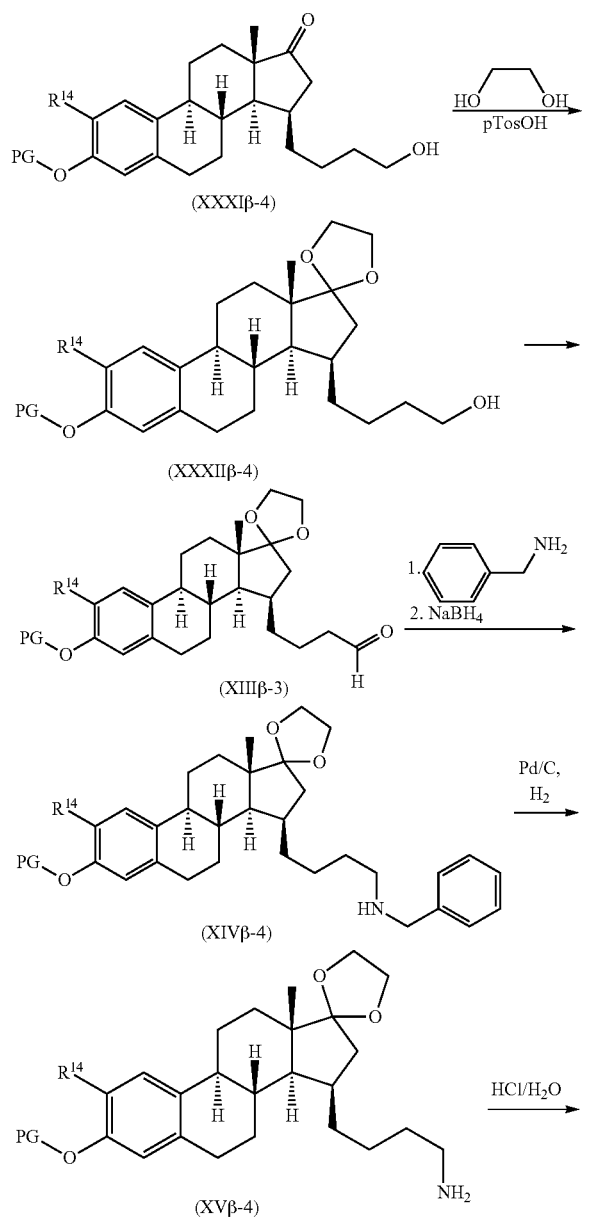

In a first step, the 17 oxo function of the butanol derivative of the formula XXXIβ-4 (for synthesis of XXXIβ-4 see above) is converted into the ketal group (compound of formula XXXIIIβ-4). Then, the alcohol function is selectively reduced to the aldehyde giving compound of the formula XIIIβ-3. The protected aldehyde derivative of the formula XIIIβ-3 is converted into a secondary amine by addition of Benzylamine and subsequent reduction (reductive amination). Further reduction of the secondary amine delivers the desired, still protected amine building block of the formula XVβ-4. The protecting ketal group can be converted into the 17-oxo group via acid hydrolysis.

The same kind of procedure can be applied for n=5 or 6 and for other substituents within the $R^1$ position.

Amine Building Block (n=1-6) of General Formula XXIX

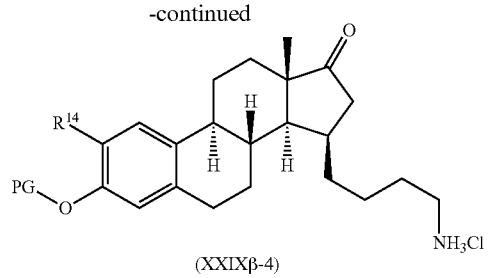

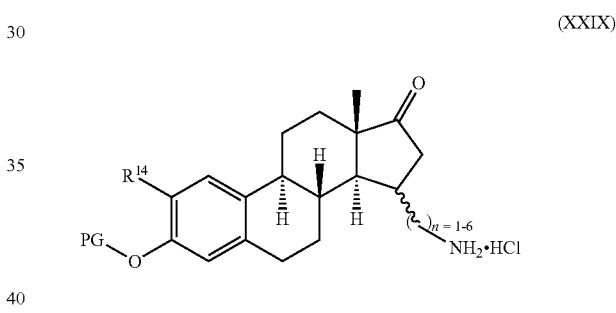

Alternatively, the synthesis of the amine building blocks of general formula XXIX can also be performed starting with an activated alcohol function and a subsequence substitution reaction, and does not need any protection of the Estron-C17 keto function according to the following general scheme 18.

SCHEME 18

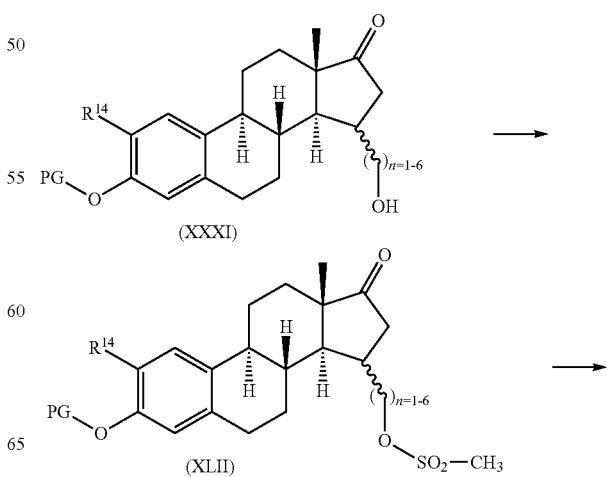

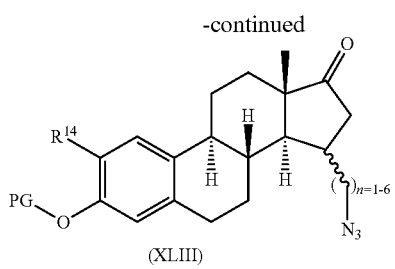

(XLIII)

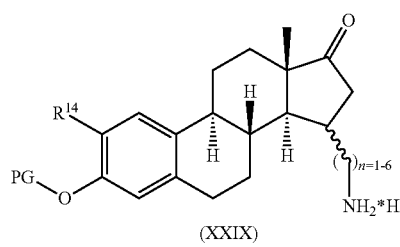

(XXIX)

Step C—Synthesis of Intermediates of General Formula C-(I) with $R^{14}$=H

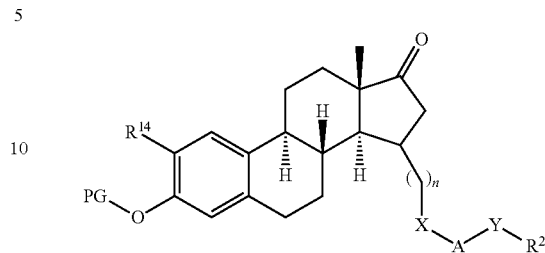

C-(I)

The synthesis of the intermediates falling under the general formula C-(I), wherein $R^{14}$ represents H, is fully disclosed in international patent application WO 2005/047303, and was performed according to the reaction schemes depicted in general flow diagrams I to XV herewithin. The following table gives an overview of exemplary intermediates prepared. The number given in the first column corresponds to the compound number as disclosed in international patent application WO 2005/047303.

TABLE 1

Exemplary intermediates of the general formula VI (amide derivatives)

C-(VI)

| No. | n | C15 stereo | PG or $R^1$ | R2 | R4 | MS m/z | HPLC Rt [min] |
|---|---|---|---|---|---|---|---|
| 1 | 3 | beta | —H | morpholin-4-yl | | | |
| 2 | 3 | beta | —CH₃ | morpholin-4-yl | | | |
| 4B | 3 | beta | —CH₃ | methyl | H | | |
| 4C | 3 | beta | benzyl | methyl | H | | |
| 5 | 3 | beta | —CH₃ | Cyclopropyl | H | 409.3 | 5.89 |
| 7 | 3 | beta | —CH₃ | Furan-2-yl | H | 449.3 | 5.74 |
| 9 | 3 | beta | —CH₃ | 2-Morpholin-4-yl-ethyl | H | 482.2 | 5.05 |
| 12 | 3 | beta | —CH₃ | 1-Benzyl-piperidin-4-yl | H | 542.3 | 5.24 |
| 13 | 3 | beta | —CH₃ | Quinolin-3-yl | H | 496.3 | 5.98 |
| 15 | 3 | beta | —CH₃ | 3,4-Dichloro-benzyl | H | 527.2 | 6.35 |
| 16 | 3 | beta | —CH₃ | 3,4-Dimethoxy-benzyl | H | 519.3 | 5.66 |
| 17 | 3 | beta | —CH₃ | 2-Hydroxy-2-phenyl-ethyl | H | 489.3 | 5.60 |
| 18 | 3 | beta | —CH₃ | 2-Dimethylamino-ethyl | H | 440.3 | 4.71 |
| 19 | 3 | beta | —CH₃ | 2-(2-Hydroxy-ethoxy)-ethyl | H | 457.3 | 5.04 |
| 21 | 3 | beta | —CH₃ | 2-(3,4-Dimethoxy-phenyl)-ethyl | H | 533.3 | 5.79 |
| 23 | 3 | beta | —CH₃ | 3-Imidazol-1-yl-propyl | H | 477.3 | 4.95 |
| 24 | 3 | beta | —CH₃ | 1H-Benzoimidazol-2-yl-methyl | H | 499.3 | 5.39 |
| 25 | 3 | beta | —CH₃ | 4-Hydroxy-3-methoxy-benzyl | H | 505.3 | 5.49 |

TABLE 1-continued

Exemplary intermediates of the general formula VI (amide derivatives)

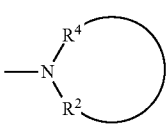

C-(VI)

R2  R4

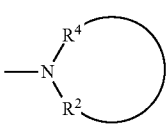

| No. | n | C15 stereo | PG or R¹ | R2 | R4 | MS m/z | HPLC Rt [min] |
|---|---|---|---|---|---|---|---|
| 26 | 3 | beta | —CH₃ | Carbamoyl-methyl | H | 426.2 | 6.30 |
| 28 | 3 | beta | —CH₃ | 2-(4-Sulfamoyl-phenyl)-ethyl | H | 552.3 | 5.37 |
| 30 | 3 | beta | —CH₃ | 4-Trifluoromethoxy-benzyl | H | 543.3 | 6.35 |
| 32 | 3 | beta | —CH₃ | 4-Fluoro-3-trifluoromethyl-benzyl | H | 545.3 | 6.30 |
| 33 | 3 | beta | —CH₃ | 2-Oxo-tetrahydro-furan-3-yl | H | 453.3 | 5.32 |
| 34 | 3 | beta | —CH₃ | 2-Oxo-azepan-3-yl | H | 480.3 | 5.33 |
| 35 | 3 | beta | —CH₃ | 4-Hydroxy-cyclohexyl | H | 467.3 | 5.18 |
| 36 | 3 | beta | H | 2-(7-Methyl-1H-indol-3-yl)-ethyl | H | | |
| 37 | 3 | beta | H | 2,4-Difluoro-benzyl | H | | |
| 38 | 3 | beta | H | Benzyl | methyl | | |
| 39 | 3 | alpha | H | Benzyl | H | | |
| 40 | 3 | alpha | H | Morpholin-4-yl | | | |
| 42 | 0 | alpha | —CH₃ | 2-(1H-Indol-3-yl)-ethyl | H | 470.3 | 1.92 |
| 44 | 0 | alpha | —CH₃ | 1-Benzyl-pyrrolidin-3-yl | H | 486.3 | 1.48 |
| 47 | 0 | alpha | —CH₃ | Phenethyl | H | 431.2 | 1.95 |
| 49 | 0 | alpha | —CH₃ | Cyclopropylmethyl | H | 381.2 | 1.83 |
| 50 | 0 | alpha | —CH₃ | Cyclohexylmethyl | H | 423.3 | 2.06 |
| 51 | 0 | alpha | —CH₃ | 2,2-Diphenyl-ethyl | H | 507.3 | 2.12 |
| 54 | 0 | alpha | —CH₃ | 3,3-Diphenyl-propyl | H | 521.3 | 2.14 |
| 56 | 0 | alpha | —CH₃ | 2-Pyridin-2-yl-ethyl | H | 432.2 | 1.46 |
| 60 | 0 | alpha | —CH₃ | 4-Methoxy-benzyl | H | 447.2 | 1.89 |
| 63 | 0 | alpha | —CH₃ | sec-butyl | H | 383.2 | 1.87 |
| 66 | 0 | alpha | —CH₃ | Bicyclo [2.2.1]hept-2-yl | H | 421.3 | 2.02 |
| 71 | 0 | alpha | —CH₃ | Indan-2-yl | H | 443.2 | 1.97 |
| 73 | 0 | alpha | —CH₃ | 2-Hydroxy-ethyl | H | 371.2 | 1.55 |
| 77 | 0 | alpha | —CH₃ | 3-Morpholpropylin-4-yl-propyl | H | 454.3 | 1.37 |
| 79 | 0 | alpha | —CH3 | 4-Phenyl-butyl | H | 459.3 | 2.08 |
| 80 | 0 | alpha | —CH₃ | —(CH₂)₃-CO-O-CH₃/ (butyric acid methyl ester)-4-yl | H | 427.2 | 1.74 |
| 81 | 0 | alpha | —CH₃ | 1-Oxo-1-benzoxy-propan- 2-yl / (Propionic acid benzyl ester)-2-yl | H | 489.3 | 1.99 |
| 83 | 0 | alpha | —CH₃ | 1,2,3,4-Tetrahydro-naphthalen-l-yl | H | 457.3 | 2.08 |
| 84 | 0 | alpha | —CH₃ | 2-Fluoro-benzyl | H | 435.2 | 1.92 |
| 85 | 0 | alpha | —CH₃ | 3-Hydroxy-propyl | H | 385.2 | 1.58 |
| 89 | 0 | alpha | —CH₃ | 2-Phenyl-propyl | H | 445.3 | 2.02 |
| 97 | 0 | alpha | —CH3 | Thiophen-2-yl-methyl | H | 423.2 | 1.91 |

TABLE 1-continued

Exemplary intermediates of the general formula VI (amide derivatives)

C-(VI)

| No. | n | C15 stereo | PG or R$^1$ | R2 | R4 | MS m/z | HPLC Rt [min] |
|---|---|---|---|---|---|---|---|
| 103 | 0 | alpha | —CH$_3$ | 1-Hydroxymethyl-cyclopentyl | H | 425.3 | 1.81 |
| 105 | 0 | alpha | —CH$_3$ | 5-Methyl-thiazol-2-yl | H | 424.2 | 1.95 |
| 107 | 0 | alpha | —CH$_3$ | 4-Benzyl-piperidin-1-yl | | 485.3 | 2.22 |
| 109 | 0 | alpha | —CH$_3$ | 3,4-Dihydro-1H-isoquinolin-2-yl | | 443.2 | 2.05 |
| 111 | 0 | alpha | —CH$_3$ | 4-Pyridin-2-yl-piperazin-1-yl | | 473.3 | 1.63 |
| 117 | 0 | alpha | —CH$_3$ | 4-(4-Chloro-benzyl)-piperazin-1-yl | | 520.2 | 1.67 |
| 118 | 0 | alpha | —CH$_3$ | 4-(3-Chloro-phenyl)-piperazin-1-yl | | 506.2 | 2.16 |
| 120 | 0 | alpha | —CH$_3$ | 4-[2-(2-Hydroxy-ethoxy)-ethyl]-piperazin-1-yl | | 484.3 | 1.39 |
| 121 | 0 | alpha | —CH$_3$ | 4-(4-Chloro-phenyl)-piperazin-1-yl | | 506.2 | 2.16 |
| 124 | 0 | alpha | —CH$_3$ | 1,3,4,9-Tetrahydro-beta-carbolin-2-yl | | 482.3 | 2.04 |
| 125 | 0 | alpha | —CH$_3$ | 4-Hydroxy-4-phenyl-piperidin-1-yl | | 487.3 | 1.90 |
| 126 | 0 | alpha | —CH$_3$ | 4-(2-Chloro-phenyl)-piperazin-1-yl | | 506.2 | 2.20 |
| 127 | 0 | alpha | —CH$_3$ | 4-(4-Methoxy-phenyl)-piperazin-1-yl | | 502.3 | 2.01 |
| 128 | 0 | alpha | —CH$_3$ | 1-Piperidine-3-carboxylic acid amide / 3-(carboxylic acid amide)-piperidin-1-yl | | 438.3 | 1.63 |
| 130 | 0 | alpha | —CH$_3$ | 4-Methyl-piperazin-1-yl | | 410.3 | 1.40 |
| 132 | 0 | alpha | —CH$_3$ | 2-Methoxymethyl-pyrrolidin-1-yl | | 425.3 | 1.93 |
| 133 | 0 | alpha | —CH$_3$ | 4-(2-Fluoro-phenyl)-piperazin-1-yl | | 490.3 | 2.10 |
| 138 | 0 | alpha | —CH$_3$ | 3,6-Dihydro-2H-pyridin-1-yl | | 393.2 | 1.92 |
| 140 | 0 | alpha | —CH$_3$ | 1-Pyrrolidine-2-carboxylic acid amide/ 2-(carboxylic acid amide)-pyrrolidin-1-yl | | 424.2 | 1.60 |
| 145 | 0 | alpha | —CH$_3$ | 4-Pyrrolidin-1-yl-piperidin-1-yl | | 464.3 | 1.43 |
| 147 | 0 | alpha | —CH$_3$ | Azetidin-1-yl | | 367.2 | 1.74 |
| 150 | 0 | alpha | —CH$_3$ | Propyl | cyclopropylmethyl | 423.3 | 2.13 |
| 151 | 0 | alpha | —CH$_3$ | 2-Cyano-ethyl | pyridin-3-ylmethyl | 471.3 | 1.67 |
| 154 | 0 | alpha | —CH$_3$ | Benzyl | 2-dimethylamino-ethyl | 488.3 | 1.56 |
| 156 | 0 | alpha | —CH$_3$ | 2-Methoxy-ethyl | 2-Methoxy-ethyl | 443.3 | 1.90 |
| 157 | 0 | alpha | —CH$_3$ | Methyl | 1-methyl-piperidin-4-yl | 438.3 | 1.43 |
| 161 | 0 | alpha | —CH$_3$ | Propyl | propyl | 411.3 | 2.11 |
| 162 | 0 | alpha | —CH$_3$ | Methyl | 2-dimethylamino-ethyl | 412.3 | 1.42 |
| 163 | 0 | alpha | —CH$_3$ | Methyl | phenethyl | 445.3 | 2.08 |
| 164 | 0 | alpha | —CH$_3$ | Methyl | allyl | 381.2 | 1.92 |
| 165 | 0 | alpha | —CH$_3$ | Ethyl | pyridin-4-yl-methyl | 446.3 | 1.61 |
| 166 | 0 | alpha | —CH$_3$ | Methyl | methyl | 355.2 | 1.78 |
| 168 | 1 | alpha | —CH$_3$ | Diphenyl-methyl | H | 507.3 | 2.14 |
| 171 | 1 | alpha | —CH$_3$ | Naphthalen-1-ylmethyl | H | 481.3 | 2.10 |
| 183 | 1 | alpha | —CH$_3$ | 2-Piperidin-1-yl-ethyl | H | 452.3 | 1.47 |
| 189 | 1 | alpha | —CH$_3$ | Cyclopentyl | H | 409.3 | 1.95 |
| 191 | 1 | alpha | —CH$_3$ | 3-Phenyl-propyl | H | 459.3 | 2.05 |
| 195 | 1 | alpha | —CH$_3$ | 1-Ethyl-propyl | H | 411.3 | 1.99 |
| 197 | 1 | alpha | —CH$_3$ | 2-Methoxy-ethyl | H | 399.2 | 1.74 |
| 198 | 1 | alpha | —CH$_3$ | 2-Pyrrolidin-1-yl-ethyl | H | 438.3 | 1.46 |
| 199 | 1 | alpha | —CH$_3$ | 2-(5-Methoxy-1H-indol-3-yl)-ethyl | H | 514.3 | 1.91 |
| 203 | 1 | alpha | —CH$_3$ | 1-Phenyl-ethyl | H | 445.3 | 2.02 |
| 204 | 1 | alpha | —CH$_3$ | 1,2-Diphenyl-ethyl | H | 521.3 | 2.17 |

TABLE 1-continued

Exemplary intermediates of the general formula VI (amide derivatives)

C-(VI)

| No. | n | C15 stereo | PG or R[1] | R2 | R4 | MS m/z | HPLC Rt [min] |
|---|---|---|---|---|---|---|---|
| 206 | 1 | alpha | —CH₃ | 2,6-Dimethoxy-benzyl | H | 491.3 | 2.00 |
| 207 | 1 | alpha | —CH₃ | 4-Fluoro-benzyl | H | 449.2 | 1.98 |
| 208 | 1 | alpha | —CH₃ | 3,5-Dimethoxy-benzyl | H | 491.3 | 1.95 |
| 209 | 1 | alpha | —CH₃ | 2-Phenoxy-ethyl | H | 461.3 | 1.99 |
| 211 | 1 | alpha | —CH₃ | 1-Naphthalen-1-yl-ethyl | H | 495.3 | 2.13 |
| 219 | 1 | alpha | —CH₃ | 2,4-Difluoro-benzyl | H | 467.2 | 2.00 |
| 222 | 1 | alpha | —CH₃ | Isobutyl | H | 397.3 | 1.94 |
| 224 | 1 | alpha | —CH₃ | 2-Cyclohex-1-enyl-ethyl | H | 449.3 | 2.18 |
| 225 | 1 | alpha | —CH₃ | 2-Hydroxy-1-methyl-ethyl | H | 399.2 | 1.65 |
| 226 | 1 | alpha | —CH₃ | 2-Methylsulfanyl-ethyl | H | 415.2 | 1.85 |
| 227 | 1 | alpha | —CH₃ | 3,4,5-Trimethoxy-benzyl | H | 521.3 | 1.90 |
| 229 | 1 | alpha | —CH₃ | 2-Hydroxy-cyclohexyl | H | 439.3 | 1.76 |
| 233 | 1 | alpha | —CH₃ | 3-Diethylopyamino-propyl | H | 454.3 | 1.49 |
| 234 | 1 | alpha | —CH₃ | Hexyl | H | 425.3 | 2.11 |
| 235 | 1 | alpha | —CH₃ | 3,4-Difluoro-benzyl | H | 467.2 | 1.99 |
| 236 | 1 | alpha | —CH₃ | 2-Trifluoromethyl-benzyl | H | 499.2 | 2.05 |
| 238 | 1 | alpha | —CH₃ | (3-Methyl-butyric acid methyl ester)-2-yl/ 2-(3-methyl)-butyric acid methyl ester | H | 455.3 | 1.92 |
| 239 | 1 | alpha | —CH₃ | 5-Methyl-thiazol-2-yl | H | 438.2 | 1.95 |
| 240 | 1 | alpha | —CH₃ | Cyclobutyl | H | 395.2 | 1.85 |
| 241 | 1 | alpha | —CH₃ | 4-Benzyl-piperazin-1-yl | | 500.3 | 1.56 |
| 243 | 1 | alpha | —CH₃ | 4-Benzo[1,3]dioxol-5-ylmethyl- piperazin-1-yl | | 544.3 | 1.54 |
| 244 | 1 | alpha | —CH₃ | 4-(2-oxo-1,3-dihydro-benzoimidazol-1-yl)-piperidin-1-yl | | 541.3 | 1.83 |
| 246 | 1 | alpha | —CH₃ | 2,5-Dihydro-pyrrol-1-yl | | 393.2 | 1.89 |
| 247 | 1 | alpha | —CH₃ | 4-Phenyl-piperazin-1-yl | | 486.3 | 2.11 |
| 249 | 1 | alpha | —CH₃ | Pyrrolidin-1-yl | | 395.2 | 1.89 |
| 250 | 1 | alpha | —CH₃ | 4-(4-Fluoro-phenyl)-piperazin-1-yl | | 504.3 | 2.10 |
| 251 | 1 | alpha | —CH₃ | 4-(2-Methoxy-phenyl)-piperazin-1-yl | | 516.3 | 2.08 |
| 252 | 1 | alpha | —CH₃ | 4-(4-Chloro-phenyl)-4-hydroxy- piperidin-1-yl | | 535.2 | 2.04 |
| 253 | 1 | alpha | —CH₃ | 4-(4-trifluoromethyl-phenyl)- piperazin-1-yl | | 554.3 | 2.23 |
| 256 | 1 | alpha | —CH₃ | 4-Methyl-[1,4]diazepan-1-yl | | 438.3 | 1.43 |
| 259 | 1 | alpha | —CH₃ | 1,4-Dioxa-8-aza-spiro[4.5]decan-8-yl | | 467.3 | 1.89 |
| 260 | 1 | alpha | —CH₃ | 1-piperidine-4-carboxylic acid ethyl ester / 4-(carboxylic acid ethyl ester)-piperidin-1-yl | | 481.3 | 1.98 |
| 266 | 1 | alpha | —CH₃ | Azepan-1-yl | | 423.3 | 2.08 |
| 268 | 1 | alpha | —CH₃ | 4-(3-Trifluoromethyl-phenyl)- piperazin-1-yl | | 554.3 | 2.23 |
| 269 | 1 | alpha | —CH₃ | 3-Hydroxy-pyrrolidin-1-yl | | 411.2 | 1.62 |
| 271 | 1 | alpha | —CH₃ | 4-Oxo-1-phenyl-1,3,8-triaza- spiro[4.5]decan-8-yl | | 555.3 | 1.87 |
| 273 | 1 | alpha | —CH₃ | 4-pyridin-4-yl-piperazin-1-yl | | 487.3 | 1.46 |
| 274 | 1 | alpha | —CH₃ | 4-Hydroxy-piperidin-1-yl | | 425.3 | 1.64 |

TABLE 1-continued

Exemplary intermediates of the general formula VI (amide derivatives)

C-(VI)

| No. | n | C15 stereo | PG or R[1] | R2 | R4 | MS m/z | HPLC Rt [min] |
|---|---|---|---|---|---|---|---|
| 275 | 1 | alpha | —CH$_3$ | octahydro-quinolin-1-yl | | 463.3 | 2.29 |
| 276 | 1 | alpha | —CH$_3$ | 3-Hydroxy-piperidin-1-yl | | 425.3 | 1.70 |
| 279 | 1 | alpha | —CH$_3$ | 1-pyrrolidine-2-carboxylic acid methyl ester / 2-(carboxylic acid methyl ester)-pyrrolidin-1-yl | | 453.3 | 1.86 |
| 281 | 1 | alpha | —CH$_3$ | 2-Hydroxymethyl-pyrrolidin-1-yl | | 425.3 | 1.73 |
| 282 | 1 | alpha | —CH$_3$ | 4-o-tolyl-piperazin-1-yl | | 500.3 | 2.23 |
| 283 | 1 | alpha | —CH$_3$ | 4-(2-Ethoxy-phenyl)-piperazin-1-yl | | 530.3 | 2.14 |
| 284 | 1 | alpha | —CH$_3$ | 4-Cyclohexyl-piperazin-1-yl | | 492.3 | 1.48 |
| 286 | 1 | alpha | —CH$_3$ | thiazolidin-3-yl | | 413.2 | 1.89 |
| 288 | 1 | alpha | —CH$_3$ | methyl | 2-pyridin-2-yl-ethyl | 460.3 | 1.66 |
| 289 | 1 | alpha | —CH$_3$ | Methyl | 2,3,4,5,6-pentahydroxy-hexyl | 519.3 | 1.49 |
| 293 | 1 | alpha | —CH$_3$ | methyl | naphthalen-1-ylmethyl | 495.3 | 2.20 |
| 296 | 1 | alpha | —CH$_3$ | benzyl | ethyl | 459.3 | 2.15 |
| 297 | 1 | alpha | —CH$_3$ | benzyl | phenethyl | 535.3 | 2.31 |
| 299 | 1 | alpha | —CH$_3$ | methyl | Butyl | 411.3 | 2.06 |
| 302 | 1 | alpha | —CH$_3$ | Benzyl | 2-cyano-ethyl | 484.3 | 2.01 |
| 303 | 1 | alpha | —CH$_3$ | propyl | methyl | 397.3 | 1.97 |
| 306 | 1 | alpha | —CH$_3$ | phenethyl | methyl | 459.3 | 2.08 |
| 308 | 1 | alpha | —CH$_3$ | ethyl | pyridin-4-ylmethyl | 460.3 | 1.61 |
| 312 | 2 | beta | —CH$_3$ | Furan-2-ylmethyl | H | 435.24 | 5.93 |
| 313 | 2 | beta | —CH$_3$ | Methyl | Cyclohexyl | 451.31 | 6.86 |
| 316 | 2 | beta | —CH$_3$ | morpholin-4-yl | | 425.57 | |
| 318 | 2 | beta | —CH$_3$ | pyridin-3-ylmethyl | H | 446.26 | 5.33 |
| 320 | 2 | beta | —CH$_3$ | benzyl | H | | |
| 323 | 2 | beta | —CH$_3$ | 4-Chloro-benzyl | H | 479.22 | 6.45 |
| 326 | 2 | beta | —CH$_3$ | Butyl | H | 411.28 | 6.1 |
| 329 | 2 | beta | —CH$_3$ | 5-methyl-thiazol-2-yl | H | 452.21 | 6.26 |
| 329A | 2 | beta | —H | 5-methyl-thiazol-2-yl | H | 452.21 | 6.26 |
| 332 | 4 | beta | —CH$_3$ | Cyclooctyl | H | 493.36 | 5.05 |
| 334 | 4 | beta | —CH$_3$ | 2-thiazol-4-yl-acetic acid ethyl ester / 4-(acetic acid ethyl ester)-thiazol-2-yl | H | 552.27 | 4.6 |
| 335 | 4 | beta | —CH$_3$ | Benzo[1,3]dioxol-5-ylmethyl | H | 517.28 | 4.41 |
| 336 | 4 | beta | —CH$_3$ | morpholin-4-yl | | 453.29 | 4.2 |
| 339 | 4 | beta | —CH$_3$ | pyridin-4-ylmethyl | H | 474.29 | 3.93 |
| 341 | 4 | beta | —CH$_3$ | 2-Methoxy-benzyl | H | 503.3 | 4.56 |
| 342 | 4 | beta | —CH$_3$ | 3-Fluoro-benzyl | H | 491.28 | 4.54 |
| 347 | 4 | beta | —CH$_3$ | 2-(7-methyl-1H-indol-3-yl)-ethyl | H | 540.34 | 4.58 |
| 354 | 5 | beta | —CH$_3$ | morpholin-4-yl | | 467.65 | |
| 355 | 5 | beta | —CH$_3$ | thiomorpholin-4-yl | | 483.28 | 6.86 |
| 358 | 5 | beta | —CH$_3$ | Phenyl | H | 473.29 | 7.00 |
| 363A | 5 | beta | —H | 2-(4-Hydroxy-phenyl)-ethyl | H | | |
| 364 | 5 | beta | —CH$_3$ | Methyl | benzyl | 501.32 | 7.25 |
| 366 | 5 | beta | —CH$_3$ | 2-Thiophen-2-yl-ethyl | H | 507.28 | 6.81 |

TABLE 1-continued

Exemplary intermediates of the general formula VI (amide derivatives)

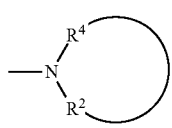

C-(VI)

| No. | n | C15 stereo | PG or R¹ | R2 | R4 (—N‹R⁴/R²) | MS m/z | HPLC Rt [min] |
|---|---|---|---|---|---|---|---|
| 368 | 5 | beta | —CH₃ | 5-methyl-thiazol-2-yl | H | 494.26 | 6.87 |

TABLE 2

Intermediates of the general formula VII (ester derivatives)

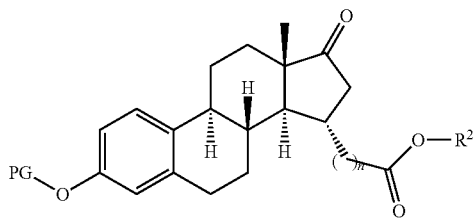

C-(VII)

| No. | n | C15 stereo | PG or R¹ | R² | MS m/z | HPLC Rt [min] |
|---|---|---|---|---|---|---|
| 369 | 5 | beta | —CH₃ | isopropyl | | |

TABLE 3

Intermediates of the general formula VIII (ketone derivatives)

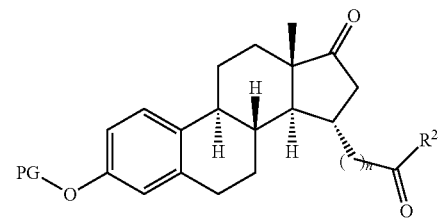

C-(VIII)

| No. | n | C15 stereo | PG or R¹ | R² | MS m/z | HPLC Rt [min] |
|---|---|---|---|---|---|---|
| 370 | 2 | beta | —CH₃ | ethyl | | |

TABLE 4

Intermediates of the general formula XLI (Hydrazide derivatives)

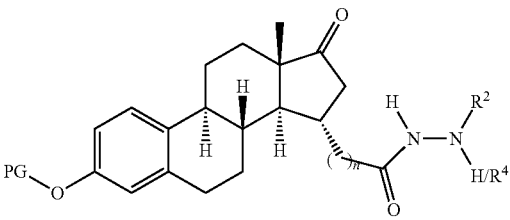

C-(XLI)

| No. | n | C15 stereo | PG or R¹ | R² | R4 (—N‹R⁴/R²) | MS m/z | HPLC Rt [min] |
|---|---|---|---|---|---|---|---|
| 371 | 2 | beta | —CH₃ | morpholin-4-yl | | 440.27 | 3.62 |
| 372 | 2 | beta | —CH₃ | 7-chloro-quinolin-4-yl | H | 531.23 | 3.9 |
| 374 | 2 | beta | —CH₃ | —CO—CH₃ / acetyl | H | 412.24 | 3.43 |
| 376 | 2 | beta | —CH₃ | —CH₂—CO—O—CH₂—CH₃ | H | 456.26 | 3.82 |
| 377 | 2 | beta | —CH₃ | 2-Fluoro-phenyl | H | 464.25 | 4.21 |

TABLE 4-continued

Intermediates of the general formula XLI (Hydrazide derivatives)

C-(XLI)

| No. | n | C15 stereo | PG or R¹ | R² / R⁴ (N-R²R⁴) | R⁴ | MS m/z | HPLC Rt [min] |
|---|---|---|---|---|---|---|---|
| 381 | 3 | beta | —CH₃ | Azepan-1-yl | | 466.32 | 4.45 |
| 382 | 3 | beta | —CH₃ | 2-(1H-indol-3-yl)-acetyl | H | 541.29 | 3.93 |
| 386 | 3 | beta | —CH₃ | —CO-phenyl | H | 488.27 | 3.93 |
| 388 | 3 | beta | —CH₃ | methyl | phenyl | 474.29 | 4.37 |
| 390 | 3 | beta | —CH₃ | 3,5-dichloro-phenyl | H | 528.19 | 4.66 |
| 391 | 3 | beta | —CH₃ | —CO-(3,4,5-trimethoxy)-phenyl | H | 578.3 | 3.92 |
| 393 | 3 | beta | —CH₃ | 3-methoxy-phenyl | H | 490.28 | 4.19 |
| 394 | 3 | beta | —CH₃ | 6-chloro-pyridazin-3-yl | H | 496.22 | 4.47 |
| 395 | 3 | beta | —CH₃ | 2-Methoxymethyl-pyrrolidin-1-yl | | 482.31 | 4.03 |
| 401 | 4 | beta | —CH₃ | methyl | Methyl | 426.29 | 3.94 |
| 405 | 4 | beta | —CH₃ | benzothiazol-2-yl | H | 531.26 | 5.19 |
| 406 | 4 | beta | —CH₃ | 4-methyl-piperazin-1-yl | | 481.33 | 3.46 |
| 408 | 5 | beta | —CH₃ | piperidin-1-yl | | 480.34 | 4.58 |
| 409 | 5 | beta | —CH₃ | 4-methanesulfonyl-phenyl | H | 566.28 | 4.15 |
| 410 | 5 | beta | —CH₃ | —CO-(3-Methoxy-)phenyl | H | 546.31 | 4.26 |
| 411 | 5 | beta | —CH₃ | acetyl | H | 454.28 | 3.8 |
| 413 | 5 | beta | —CH₃ | benzyl | H | 502.32 | 4.78 |
| 416 | 5 | beta | —CH₃ | 3,4-dichloro-phenyl | H | 556.23 | 4.9 |

TABLE 5

Intermediates of the general formula XVII (Urea derivatives)

C-(XVII)

| No. | n | C15 stereo | PG or R¹ | R² / R⁴ (N-R²R⁴) | R⁴ | MS m/z | HPLC Rt [min] |
|---|---|---|---|---|---|---|---|
| 420 | 1 | alpha | —H | 3-nitro-phenyl | —H | 436.22 | 3.74 |
| 421 | 1 | alpha | —H | 3,4-Dichloro-benzyl | —H | 486.21 | 3.98 |
| 423 | 1 | alpha | —H | Benzyl | —H | 490.25 | 3.8 |
| 427 | 1 | alpha | —H | 4-methoxy-phenyl | —H | 463.21 | 3.76 |
| 428 | 1 | alpha | —H | 3-Cyano-phenyl | —H | 432.24 | 3.56 |
| 433 | 1 | alpha | —H | isopropyl | —H | 454.32 | 4.17 |
| 434 | 1 | alpha | —H | octyl | —H | 442.25 | 3.34 |
| 443 | 3 | beta | —CH₃ | 3-Methoxy-phenyl | —H | 490.28 | 4.33 |
| 444 | 3 | beta | —CH₃ | 3-trifluoromethyl-phenyl | —H | 528.26 | 4.69 |
| 445 | 3 | beta | —CH₃ | 4-Fluoro-phenyl | —H | 478.26 | 4.36 |
| 448 | 3 | beta | —CH₃ | 4-trifluoromethyl-phenyl | —H | 528.26 | 4.7 |
| 451 | 3 | beta | —CH₃ | naphthalen-1-yl | —H | 510.29 | 4.5 |

TABLE 5-continued

Intermediates of the general formula XVII (Urea derivatives)

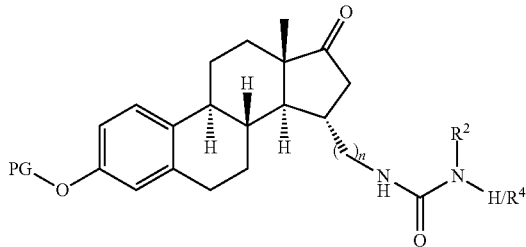

C-(XVII)

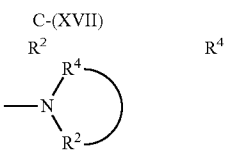

| No. | n | C15 stereo | PG or R¹ | R² | R⁴ | MS m/z | HPLC Rt [min] |
|---|---|---|---|---|---|---|---|
| 453 | 3 | beta | —CH₃ | 2-benzoic acid methyl ester / 2-(carboxylic acid methyl ester)-phenyl | —H | 518.28 | 4.76 |
| 455 | 3 | beta | —CH₃ | 3-Acetyl-phenyl | —H | 502.28 | 4.23 |
| 458 | 3 | beta | —CH₃ | Biphenyl-2-yl | —H | 536.3 | 4.79 |
| 462 | 3 | beta | —CH₃ | 4-(6-methyl-benzothiazol-2-yl)-phenyl | —H | | |
| 466 | 4 | beta | —CH₃ | 2,4-Dichloro-phenyl | —H | 542.21 | 5.19 |
| 467 | 4 | beta | —CH₃ | 3-Fluoro-phenyl | —H | 492.28 | 4.63 |
| 475 | 4 | beta | —CH₃ | Cyclohexyl | —H | 480.34 | 4.56 |
| 481 | 4 | beta | +CH₃ | 4-Acetyl-phenyl | —H | 516.3 | 4.37 |
| 482 | 4 | beta | —CH₃ | 4-trifluoromethoxy-phenyl | —H | 558.27 | 4.89 |
| 485 | 4 | beta | —CH₃ | naphthalen-2-yl | —H | 524.3 | 4.82 |
| 486 | 4 | beta | —CH₃ | 3-propionic acid ethyl ester / 1-ethoxy-1-oxo-propan-3-yl | —H | 498.31 | 4.18 |
| 488 | 4 | beta | —CH₃ | 3,4-Dimethoxy-phenyl | —H | 534.31 | 4.28 |
| 489 | 4 | beta | —CH₃ | Benzo[1,3]dioxol-5-yl | —H | 518.28 | 4.42 |
| 490 | 4 | alpha | —H | 4-benzoic acid ethyl ester / 4-(carboxylic acid ethyl ester)-phenyl | —H | 532 | 5.91 |
| 491 | 4 | alpha | —H | Cyclohexylmethyl | —H | 480 | 6.42 |
| 492 | 4 | alpha | —H | Phenyl | —H | 460 | 5.65 |

TABLE 6

Intermediates of the general formula XIX (sulfamide derivatives)

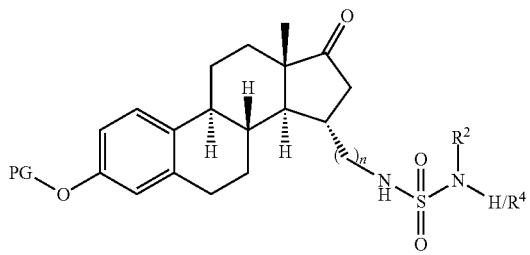

C-(XIX)

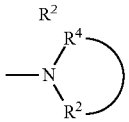

| No. | n | C15 stereo | PG or R1 | R² | R⁴ |
|---|---|---|---|---|---|
| 493 | 2 | alpha | —CH₃ | 2-phenyl-ethyl | —H |
| 494 | 2 | alpha | —CH₃ | 2-naphthalen-1-yl-ethyl | —H |
| 495 | 2 | alpha | —CH₃ | 3,3-Diphenyl-propyl | —H |
| 496 | 2 | alpha | —CH₃ | 3-Methyl-butyl | —H |
| 497 | 2 | alpha | —CH₃ | 2-((Phenylsulfonyl)methyl)-benzyl | —H |
| 498 | 2 | alpha | —CH₃ | Naphthalen-2-yl-methyl | —H |
| 499 | 2 | alpha | —CH₃ | 2-(Difluoromethoxy)benzyl | —H |
| 500 | 2 | alpha | —CH₃ | 2-[N,N-(2-Hydroxy-ethyl)-phenyl-amino]-ethyl | —H |

TABLE 6-continued

Intermediates of the general formula XIX (sulfamide derivatives)

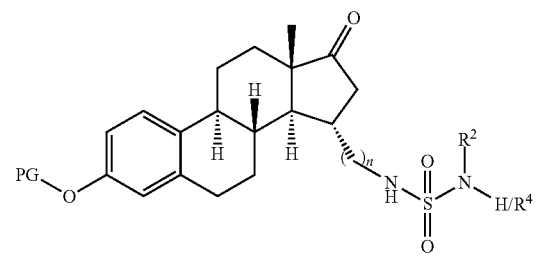

C-(XIX)

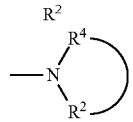

| No. | n | C15 stereo | PG or R1 | R² | R⁴ |
|---|---|---|---|---|---|
| 501 | 2 | alpha | —CH₃ | 2,5-Bis(trifluoromethyl)-benzyl | —H |
| 502 | 2 | alpha | —CH₃ | acetic acid 2-ethyl ester / —CH₂—CH₃—O—CO—CH₃ | —H |
| 503 | 2 | alpha | —CH₃ | Naphthalen-1-yl-carbamic acid 2-ethyl ester | —H |
| 504 | 2 | alpha | —CH₃ | 2,3-Dichlorophenyl-carbamic acid 2-ethyl ester | —H |
| 505 | 2 | alpha | —CH₃ | 2,3-Dihydro-benzo[1,4]dioxin-2-ylmethyl | —H |

TABLE 6-continued

Intermediates of the general formula XIX (sulfamide derivatives)

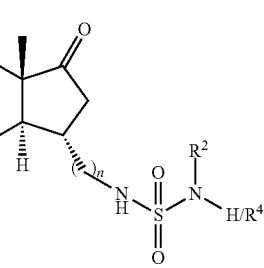

C-(XIX)

| No. | n | C15 stereo | PG or R1 | R² | R⁴ |
|---|---|---|---|---|---|
| 506 | 2 | alpha | —CH₃ | 4-Fluoro-2,3-dihydro-benzofuran-2-yl-methyl | —H |
| 507 | 2 | alpha | —CH₃ | 2-Phenyl-benzyl | —H |
| 508 | 2 | alpha | —CH₃ | 2-Indol-3-yl-ethyl | —H |
| 509 | 2 | alpha | —CH₃ | —CH₂-(3-benzoic acid methyl ester) / (3-carboxylic acid methyl ester)-benzyl | —H |
| 510 | 2 | alpha | —CH₃ | 3,4-Dichlorobenzyl | —H |
| 511 | 2 | alpha | —CH₃ | 3,5-Bis(trifluoromethyl)benzyl | —H |
| 512 | 2 | alpha | —CH₃ | 3-Benzoyl-benzyl | —H |
| 513 | 2 | alpha | —CH₃ | 3,2-Dihydroxy-propyl | —H |
| 514 | 2 | alpha | —CH₃ | 2-(4-Chlorobenzoyl)-benzofuran-3-yl-methyl | —H |
| 515 | 2 | alpha | —CH₃ | 3-propionic acid ethyl ester / 1-ethoxy-1-oxo-propan-3-yl | —H |
| 516 | 2 | alpha | —CH₃ | 3-Phenoxy-propyl | —H |
| 517 | 2 | alpha | —CH₃ | 2-(4-Acetophenone)-ethyl | —H |
| 518 | 2 | alpha | —CH₃ | 1,2,3-Thiadiazol-4-yl-benzyl | —H |
| 519 | 2 | alpha | —CH₃ | —CH₂-(4-benzoic acid methyl ester) / (4-carboxylic acid methyl ester)-benzyl | —H |
| 520 | 2 | alpha | —CH₃ | —CH₂-(4-phenyl-acetic acid phenacyl ester) / —CH₂-(4-phenyl-CH₂—CO—O—CH₂—CO-phenyl) | —H |
| 521 | 2 | alpha | —CH₃ | 4-(Tert-butyl)benzyl | —H |
| 522 | 2 | alpha | —CH₃ | 4-butyric acid ethyl ester / 1-ethoxy-1-oxo-butan-4-yl | —H |
| 523 | 2 | alpha | —CH₃ | 7-Methoxy-coumarin-4-yl-methyl | —H |
| 524 | 2 | alpha | —CH₃ | 4-Methylbenzyl | —H |
| 525 | 2 | alpha | —CH₃ | 4-Methylsulfonylbenzyl | —H |
| 526 | 2 | alpha | —CH₃ | 4-Phenoxy-butyl | —H |
| 527 | 2 | alpha | —CH₃ | Benzofurazan-5-yl-methyl | —H |
| 528 | 2 | alpha | —CH₃ | 2-(6-Amino-9H-purin-9-yl)-ethyl | —H |
| 529 | 2 | alpha | —CH₃ | 3-Cyano-benzyl | —H |
| 530 | 2 | alpha | —CH₃ | 2-Cyano-benzyl | —H |
| 531 | 2 | alpha | —CH₃ | 4-Cyano-benzyl | —H |
| 532 | 2 | alpha | —CH₃ | Benzoic acid 2-ethyl ester / —CH₂—CH₃—O—CO-phenyl | —H |
| 533 | 2 | alpha | —CH₃ | Benzyl | —H |
| 534 | 2 | alpha | —CH₃ | Cyclopropylmethyl | —H |
| 536 | 2 | alpha | —CH₃ | 4-(1,3-Dioxo-1,3-dihydro-isoindol-2-yl)-butyl | —H |

TABLE 7

Intermediates of the general formula XX (carbamate derivatives)

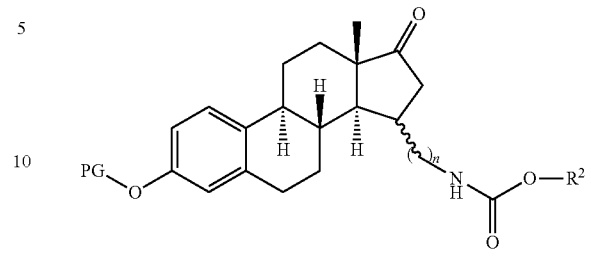

C-(XX)

| No. | n | C15 stereo | PG or R¹ | R² | MS m/z | HPLC Rt [min] |
|---|---|---|---|---|---|---|
| 538 | 1 | alpha | —H | Isobutyl | 400 | 5.58 |
| 539 | 1 | alpha | —H | 4-Nitro-benzyl | 478 | 5.62 |

TABLE 8

Intermediates of the general formula XXII (sulfamate derivatives)

C-(XXII)

| No. | n | C15 stereo | PG or R¹ | R² | MS m/z | HPLC Rt [min] |
|---|---|---|---|---|---|---|
| 540 | 1 | alpha | —CH₃ | Ethyl | | |
| 541 | 1 | alpha | —CH₃ | Butyl | | |
| 542 | 1 | alpha | —CH₃ | Benzyl | | |
| 543 | 1 | alpha | —CH₃ | Phenyl | | |

TABLE 9

Intermediates of the general formula XXIII ("retro"-amide derivatives)

C-(XXIII)

| No. | n | C15 stereo | PG or R¹ | R² | MS m/z | HPLC Rt [min] |
|---|---|---|---|---|---|---|
| 544 | 1 | alpha | —CH₃ | 3,5-Bis-trifluoromethyl-phenyl | 553.21 | 4.73 |
| 548 | 1 | alpha | —CH₃ | 3-Methoxy-phenyl | 447.24 | 4.27 |

TABLE 9-continued

Intermediates of the general formula XXIII ("retro"-amide derivatives)

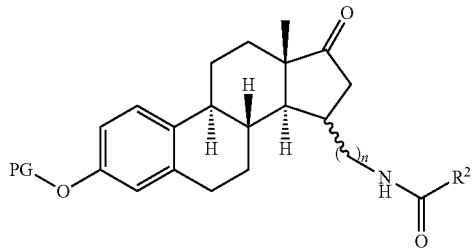

C-(XXIII)

| No. | n | C15 stereo | PG or R¹ | R² | MS m/z | HPLC Rt [min] |
|---|---|---|---|---|---|---|
| 551 | 1 | alpha | —CH₃ | 4-Hexyloxy-phenyl | 517.32 | 5.25 |
| 552 | 1 | alpha | —CH₃ | 4-Trifluoromethyl-phenyl | 485.22 | 4.59 |
| 553 | 1 | alpha | —CH₃ | Tert. Butyl | 397.26 | 4.21 |
| 554 | 1 | alpha | —CH₃ | Phenoxy-methyl | 447.24 | 4.31 |
| 557 | 1 | alpha | —CH₃ | Ethyl | 369.23 | 3.81 |
| 559 | 1 | alpha | —CH₃ | 2-Cyclopentyl-ethyl | 437.29 | 4.56 |
| 561 | 1 | alpha | —CH₃ | Furan-2-yl | 407.21 | 4.03 |
| 562 | 1 | alpha | —CH₃ | Thiophen-2-yl-methyl | 437.2 | 4.15 |
| 564 | 1 | alpha | —CH₃ | Diphenyl-methyl | | |
| 565 | 1 | alpha | —CH₃ | Acetic acid methyl ester/ —CH₂—CO—O—CH₃ | 413.22 | 3.79 |
| 567 | 1 | alpha | —CH₃ | 2,4,5-Trifluorophenyl | 471.2 | 4.51 |
| 568 | 1 | alpha | —CH₃ | 2-(4-Chloro-phenoxy)-pyridin-3-yl | | |
| 569 | 1 | alpha | —CH₃ | 1-Phenyl-5-trifluoromethy 1-1H-pyrazol-4-yl | 551.24 | 4.53 |
| 570 | 1 | alpha | —CH₃ | Adamantan-1-yl | 475.31 | 4.89 |
| 574 | 4 | alpha | —H | 2-methoxy-phenyl | 475.27 | 5.77 |
| 577 | 4 | alpha | —H | 4-Chloro-phenyl | 479.22 | 5.95 |
| 580 | 4 | alpha | —H | methoxymethyl | 413.26 | 5.01 |
| 584 | 4 | alpha | —H | 1-ethoxy-1-oxo-propan-3-yl | 469.28 | 5.25 |
| 588 | 4 | alpha | —H | naphthalen-2-yl | 495.28 | 6.04 |
| 593 | 4 | alpha | —H | Benzo[b]thiophene-2-yl | 501.23 | 6.09 |
| 601 | 3 | alpha | —H | benzyl | 445.26 | 3.69 |
| 602 | 3 | alpha | —H | Phenethyl | 459.28 | 3.78 |
| 606 | 3 | alpha | —H | 3-Cyano-phenyl | 456.24 | 3.72 |
| 609 | 3 | beta | —CH₃ | 2,4-Dichloro-phenyl | 513.18 | 6.74 |
| 615 | 3 | beta | —CH₃ | methyl | 383.25 | 5.5 |
| 622 | 3 | beta | —CH₃ | 4-Cyano-phenyl | 470.26 | 6.24 |
| 625 | 3 | beta | —CH₃ | 3,5-Dichloro-phenyl | 513.18 | 7.16 |
| 627 | 3 | beta | —CH₃ | Benzyloxy-methyl | 489.29 | 6.53 |
| 628 | 3 | beta | —CH₃ | 2-(3-trifluoromethyl-phenyl)-vinyl | | |
| 629 | 4 | beta | —CH₃ | 3,4-Difluoro-phenyl | 495.26 | 6.84 |
| 635 | 4 | beta | —CH₃ | 2-bromo-phenyl | 537.19 | 6.7 |
| 637 | 4 | beta | —CH₃ | 3-Chloro-phenyl | 493.24 | 6.97 |
| 641 | 4 | beta | —CH₃ | 4-methoxy-phenyl | 489.29 | 6.54 |
| 645 | 4 | beta | —CH₃ | 2,2-dimethyl-propyl | 453.32 | 6.72 |
| 648 | 4 | beta | —CH₃ | cyclohexyl | 465.32 | 6.82 |
| 650 | 4 | beta | —CH₃ | naphthalen-1-yl | 509.29 | 6.93 |
| 653 | 3 | alpha | —H | 3,4-Dichlorophenyl | 500 | 4.17 |
| 655 | 4 | alpha | —H | 4-Fluorobenzyl | 478 | 5.72 |
| 657 | 4 | alpha | —H | 2,4-Difluorophenyl | 482 | 5.86 |
| 658 | 5 | beta | —CH₃ | Phenyl | 474 | 6.80 |
| 660 | 5 | beta | —CH₃ | 4-Fluorophenyl | 492 | 6.68 |

TABLE 10

Intermediates of the general formula XXIV ("retro"sulfonamidederivatives)

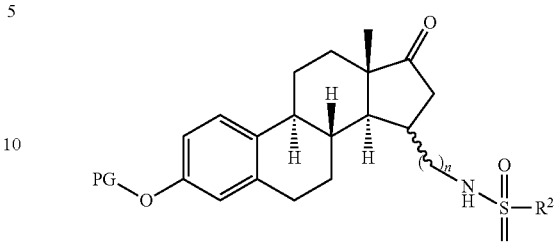

C-(XXIV)

| No. | n | C15 stereo | PG or R¹ | R² | MS m/z | HPLC Rt [min] |
|---|---|---|---|---|---|---|
| 661 | 1 | alpha | —H | Naphthalene-2-yl | 489.2 | 5.75 |
| 663 | 1 | alpha | —H | Quinoline-8-yl | 490.19 | 5.41 |
| 666 | 1 | alpha | —H | 4-(N-acetyl)-amino-phenyl | 496.2 | 4.83 |
| 668 | 1 | alpha | —H | 4-methoxy-phenyl | 469.19 | 5.35 |
| 673 | 1 | alpha | —H | 3,4-Dichloro-phenyl | 507.1 | 5.98 |
| 676 | 1 | alpha | —H | 3- Chloro-p henyl | 473.14 | 5.67 |
| 680 | 1 | alpha | —H | 2,4-Dichloro-phenyl | 507.1 | 5.88 |
| 704 | 3 | beta | —CH₃ | 4-nitro-phenyl | 526.21 | 4.54 |
| 706 | 3 | beta | —CH₃ | benzyl | 495.24 | 4.51 |
| 707 | 3 | beta | —CH₃ | propyl | 447.24 | 4.34 |
| 713 | 3 | beta | —CH₃ | 2,5-Dichloro-thiophene-3-yl | 555.11 | 5.04 |
| 715 | 3 | beta | —CH₃ | 3-methyl-phenyl | 495.24 | 4.67 |
| 716 | 3 | beta | —CH₃ | 3,4-dimethoxy-phenyl | 541.25 | 4.37 |
| 717 | 3 | beta | —CH₃ | 4-Benzenesulfonyl-thiophene-2-yl | 627.18 | 4.59 |
| 720 | 4 | beta | —CH₃ | Thiophene-2-yl | 501.2 | 4.65 |
| 722 | 4 | beta | —CH₃ | phenyl | 495.24 | 4.7 |
| 723 | 4 | beta | —CH₃ | 4-Fluoro-phenyl | 513.23 | 4.74 |
| 727 | 4 | beta | —CH₃ | 3-trifluoromethyl-phenyl | 563.23 | 4.97 |
| 728 | 4 | beta | —CH₃ | 3,5-Bis-trifluoromethyl-ethenyl | 631.22 | 5.23 |
| 729 | 4 | beta | —CH₃ | 2,5-dimethoxy-phenyl | 555.27 | 4.72 |
| 731 | 4 | beta | —CH₃ | 4-trifluoromethoxy-phenyl | 579.23 | 5.03 |
| 739 | 5 | beta | —CH₃ | 4-Methyl-phenyl | 524 | 6.91 |

TABLE 11

Intermediates of the general formula XXV (sulfonylurea derivatives)

C-(XXV)

| No. | n | C15 stereo | PG or R¹ | R² | MS m/z | HPLC Rt [min] |
|---|---|---|---|---|---|---|
| 740 | 2 | alpha | —CH₃ | Phenyl | | |
| 741 | 2 | alpha | —CH₃ | 4- Chloro-phenyl | | |
| 742 | 2 | alpha | —CH₃ | 4-Methyl-phenyl | | |
| 743 | 2 | alpha | —CH₃ | 2-Methyl-phenyl | | |

TABLE 12

Intermediates of the general forula XXVI
("retro"-carbamate derivatives)

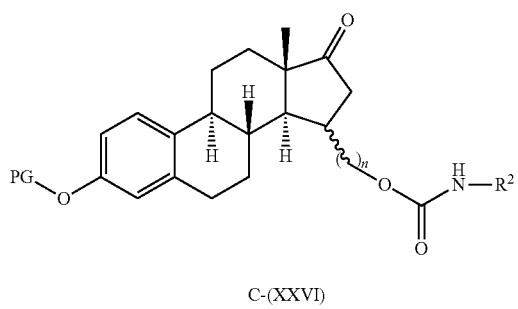

C-(XXVI)

| No. | n | C15 stereo | PG or R¹ | R² | MS m/z | HPLC Rt [min] |
|---|---|---|---|---|---|---|
| 744 | 3 | beta | —CH₃ | 2,4-Dichloro-phenyl | 529 | 5.52 |
| 745 | 3 | beta | —CH₃ | 4-Trifluoromethyl-phenyl | 529 | 5.18 |
| 747 | 3 | beta | —CH₃ | 3-Cyano-phenyl | 486 | 4.74 |
| 748 | 3 | beta | —CH₃ | Benzo[1,3]dioxol-5-yl- | 505 | 4.68 |
| 751 | 4 | beta | —CH₃ | 3-Fluoro-phenyl | 493 | 5.1 |
| 755 | 4 | beta | —CH₃ | 2-benzoic acid methyl ester | 533 | 5.67 |
| 761 | 5 | beta | —CH₃ | 3-Nitro-phenyl | 534 | 5.21 |
| 764 | 5 | beta | —CH₃ | 3,4-Dichloro-benzyl | 571 | 5.48 |
| 767 | 6 | beta | —CH₃ | 4-benzoic acid ethyl ester | 553 | 5.56 |
| 769 | 6 | beta | —CH₃ | Naphthalen-1-yl | 561 | 6.12 |
| 773 | 6 | beta | —CH₃ | 3,4-Dichloro-phenyl | 553 | 5.56 |

TABLE 13

Intermediates of the general formula XXVII ("retro"-ester derivatives)

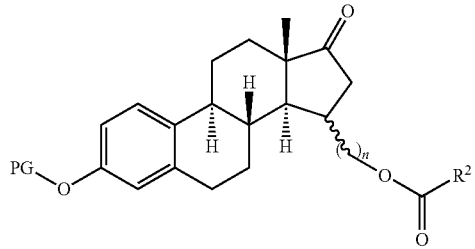

C-(XXVII)

| No. | n | C15 stereo | PG or R¹ | R² | MS m/z | HPLC Rt [min] |
|---|---|---|---|---|---|---|
| 774 | 4 | beta | —CH₃ | Tert-Butyl | 441 | 7.85 |
| 775 | 5 | beta | —CH₃ | Tert-Butyl | 455 | 8.07 |

TABLE 14

Intermediates of the general formula XXVIII
(sulfonylcar-bamate derivatives)

C-(XXVIII)

| No. | n | C15 stereo | PG or R¹ | R² | R⁴ or N-R²,R⁴ ring | MS m/z | HPLC Rt [min] |
|---|---|---|---|---|---|---|---|
| 790 | 3 | beta | —CH₃ | 2-(1H-indol-3-yl)-ethyl | H | 607 | 4.36 |
| 792 | 3 | beta | —CH₃ | cyclohexyl | H | 546 | 4.59 |
| 795 | 3 | beta | —CH₃ | morpholine-4-yl | | 534 | 3.96 |
| 797 | 4 | beta | —CH₃ | 4-methyl-piperazine-1-yl | | 561 | 3.57 |
| 802 | 4 | beta | —CH₃ | methyl | benzyl | 582 | 4.84 |
| 805 | 5 | beta | —CH₃ | benzyl | H | 582 | 4.64 |
| 811 | 5 | beta | —CH₃ | methyl | butyl | 562 | 5.09 |
| 817 | 6 | beta | —CH₃ | butyl | H | 562 | 4.9 |
| 818 | 6 | beta | —CH₃ | phenyl | H | 582 | 4.46 |

Intermediates 820 to 834—alcohols

The synthesis of the following estrone-alcohol derivatives of general formula XXXI is described in the section "Intermediates, Chapter IV—Compounds of formula XXXI".

Intermediate No. 820: 15α-Hydroxymethyl-3-hydroxy-estra-1,3,5(10)-trien-17-one (XXXIα-1a)

Intermediate No. 821: 15α-Hydroxymethyl-3-methoxy-estra-1,3,5(10)-trien-17-one (XXXIα-1b)

Intermediate No. 822: 3-Benzyloxy-15α-hydroxymethyl-estra-1,3,5(10)-trien-17-one (XXXIα-1c)

Intermediate No. 823: 3-Hydroxy-15β-(3-Hydroxypropyl)-estra-1,3,5(10)-trien-17-one (XXXIβ-3a)

Intermediate No. 824: 15β-(3-Hydroxypropyl)-3-methoxyestra-1,3,5(10)-trien-17-one (XXXIβ-3b)

Intermediate No. 825: 3-Benzyloxy-15β-(3-hydroxypropyl)-estra-1,3,5(10)-trien-17-one (XXXIβ-3c)

Intermediate No. 826: 3-Hydroxy-15β-(4-hydroxybutyl)-estra-1,3,5(10)-trien-17-one (XXXIβ-4a)

Intermediate No. 827: 15β-(4-Hydroxybutyl)-3-methoxy-estra-1,3,5(10)-trien-17-one (XXXIβ-4b)

Intermediate No. 828: 3-Benzyloxy-15β-(4-hydroxybutyl)-estra-1,3,5(10)-trien-17-one (XXXIβ-4c)

Intermediate No. 829: 3-Hydroxy-15β-(5-Hydroxypentyl)-estra-1,3,5(10)-trien-17-one (XXXIβ-5a)

Intermediate No. 830: 15β-(5-Hydroxypentyl)-3-methoxy-estra-1,3,5(10)-trien-17-one (XXXIβ-5b)

Intermediate No. 831: 3-Benzyloxy-15β-(5-hydroxypentyl)-estra-1,3,5(10)-trien-17-one (XXXIβ-5c)

Intermediate No. 832: 3-Hydroxy-15β-(6-hydroxyhexyl)-3-estra-1,3,5(10)-trien-17-one (XXXIβ-6a)

Intermediate No. 833: 15β-(6-Hydroxyhexyl)-3-methoxy-estra-1,3,5(10)-trien-17-one (XXXIβ-6b)

Intermediate No. 834: 3-Benzyloxy-15β-(6-hydroxyhexyl)-estra-1,3,5(10)-trien-17-one (XXXIβ-6c)

TABLE 15

Intermediates of the general formula XXX (ether derivatives)

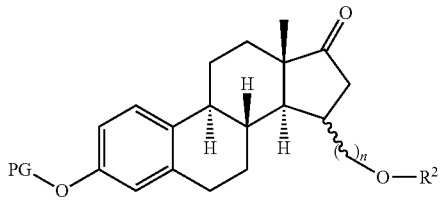

C-(XXX)

| No. | n | C15 stereo | PG or $R^1$ | $R^2$ | MS m/z | HPLC Rt [min] |
|---|---|---|---|---|---|---|
| 835 | 3 | beta | —$CH_3$ | Methyl | 374 | 6.8 |
| 836 | 4 | beta | —$CH_3$ | Phenyl | 450 | 7.77 |

EXAMPLES

In order to more fully illustrate the nature of the invention and the manner of practicing the same, the following examples are presented, but they should not be taken as limiting.

Compounds Carrying an Additional Substituent in C2 Position of the Steroidal Core

Example 1

N-Benzyl-4-(2-ethyl-3-hydroxy-17-oxo-estra-1,3,5 (10)-trien-15β-yl)-butyramide

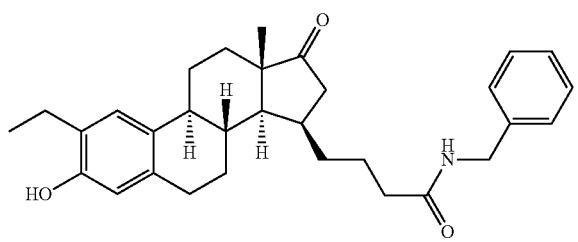

Example 1 was obtained from intermediate compound (IVb-(C2-C)-3a) by amid coupling according to Flow Diagram Ib: Compound (IVb-(C2-C)-3a) (100 mg, 0.26 mmol) was dissolved in a mixture of EtOAc (35 ml), benzyl amine (0.26 mmol), TEA (0.52 mmol) and propylphosphonic acid anhydride in EtOAc (T3P) (50 w/w %, 0.52 mmol) under N2 atmosphere at 0° C. After stirring for 2 h at ambient temperature, the reaction mixture was poured into water (50 ml) and diluted with EtOAc (25 ml). The aqueous layer was neutralized to pH 8 with aq. NaHCO₃, separated and extracted with EtOAc (2×25 ml). The combined organic layers were washed with water (25 ml) and dried over $Na_2SO_4$. The organic layer was concentrated in vacuo yielding Compound No. 1 (56 mg, 0.12 mmol, 46%) after column chromatography ($SiO_2$, DCM/MeOH=100/0 to 95/5).

$^1$H-NMR (300 MHz, CDCl₃): δ 0.99 (s, 3H, Steroid-CH₃), 1.22 (t, J=7.4 Hz, 3H, Ethyl), 1.3-1.8 (m, 11H, Steroid), 2.2-2.42 (m, 8H, Steroid), 2.60 (q, J=7.4 Hz, 2H, Ethyl), 2.8-2.88 (m, 2H, Steroid), 4.44 (d, J=5.8 Hz, 2H, CH₂-Ph), 4.64 (bs, 1H, OH), 5.67 (bs, 1H, NH), 6.53 (s, 1H, Steroid-Ar—H), 7.03 (s, 1H, Steroid-Ar—H), 7.23-7.34 (m, 5H, Bn) ppm.

Example 2

N-Benzyl-4-(3-hydroxy-17-oxo-2-propyl-estra-1,3,5 (10)-trien-15β-yl)-butyramide

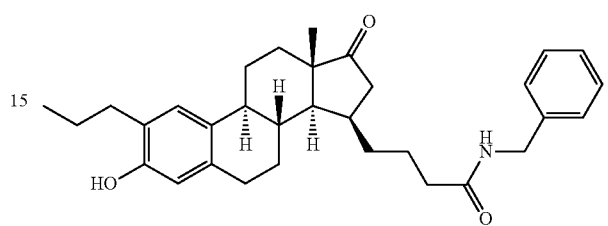

Example 2 was obtained from intermediate compound (IVb-(C2-G)-3a) by amid coupling according to Flow Diagram Ib: Compound (IVb-(C2-G)-3a) (500 mg, 1.25 mmol) was dissolved in a mixture of EtOAc (25 ml), benzyl amine (2.50 mmol), TEA (3.75 mmol) and propylphosphonic acid anhydride in EtOAc (T3P) (50 w/w %, 1.50 mmol) under N2 atmosphere. After the reaction mixture had been stirred at ambient temperature for 1 h, it was stirred at 45° C. for 16 h. The reaction mixture was allowed to reach ambient temperature, poured into water (50 ml) and diluted with EtOAc (25 ml). The aqueous layer was separated and extracted with EtOAc (2×25 ml). The combined organic layers were, washed with aq. 1M HCl (25 ml), washed with brine (25 ml) and dried over $Na_2SO_4$. The organic layer was concentrated in vacuo yielding Compound No. 2 (370 mg, 0.756 mmol, 60%) after column chromatography ($SiO_2$, DCM/MeOH=97.5/2.5).

$^1$H-NMR (300 MHz, CDCl₃): δ 0.96 (t, 3H), 0.98 (s, 3H), 1.3-1.6 (m, 4H), 1.6-1.8 (m, 7H), 1.90 (d, 1H), 2.00 (d, 1H, broad), 2.2-2.5 (m, 7H), 2.58 (t, 2H), 2.7-2.9 (m, 2H), 4.23 (d, 2H), 4.97 (s, 1H, broad), 5.72 (t, 1H, broad), 6.50 (s, 1H), 7.00 (s, 1H), 7.2-7.3 (m, 5H) ppm.

Example 3

N-Benzyl-4-(3-hydroxy-2-(2-methoxy-ethyl)-17-oxo-estra-1,3,5(10)-trien-15β-yl)-butyramide

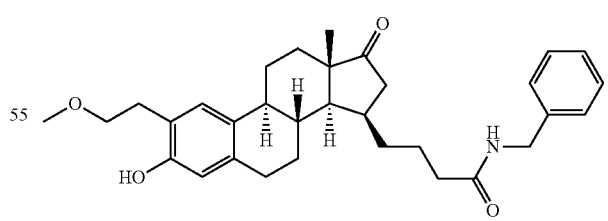

Example 3 was obtained from intermediate compound (IVb-(C2-F)-3a) by amid coupling according to Flow Diagram Ib using the procedure as described for Example 1.

$^1$H-NMR (300 MHz, CDCl₃): δ 0.99 (s, 3H, Steroid-CHs), 1.2-2.0 (m, 11H, Steroid), 2.2-2.42 (m, 7H, Steroid), 2.84 (m, 4H, Steroid), 3.41 (s, 3H, OMe), 3.67 (m, 2H, OCH₂), 4.44 (d, J=5.5 Hz, 2H, CH₂-Ph), 5.71 (bm, 1H, OH or NH), 6.67 (s, 1H, Steroid-Ar—H), 6.94 (s, 1H, Steroid-Ar—H), 7.25-7.34 (m, 5H, Bn), 7.96 (s, 1H, OH or NH) ppm.

Example 4

N-Benzyl-4-(3-hydroxy-2-methoxy-17-oxo-estra-1,3,5(10)-trien-15β-yl)-butyramide

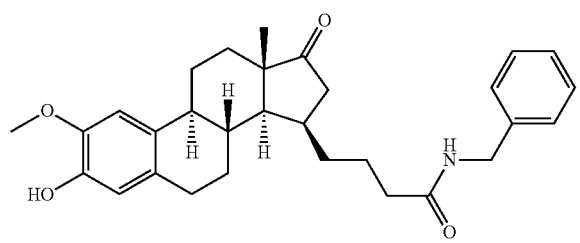

Example 4 was obtained starting from intermediate compound (IVb-(C2-B)-3a) by amide coupling according to Flow Diagram Ib. A solution of the 0.07 mmol (IVb-(C2-B)-3a), 0.077 mmol HOBT, 0.231 mmol NMM and 0.154 mmol EDCI in 5 ml DCM were added to 0.07 mmol of benzyl amine. The reaction mixture was stirred for 24 h at ambient temperature. The solvent was removed in vacuo at 40° C. Than 4 ml EtOAc and 4 ml water were added. After vigorous stirring for 2 min, the organic phase was separated, dried with $Na_2SO_4$ and evaporated in vacuo at 40° C. The crude product was treated with 2 ml THF, 10 mg LiOH and 0.5 ml water. After evaporation and further extraction (EtOAc and 0.1 M $KHSO_4$), 50 mg trisaminoeethlyamine polymer bound were added. After filtration and evaporating to dryness the compound No. 4 was obtained (HPLC Rt=3.79).

Example 5

2-Ethyl-3-hydroxy-15β-(4-morpholin-4-yl-4-oxo-butyl)-estra-1,3,5(10)-trien-17-one

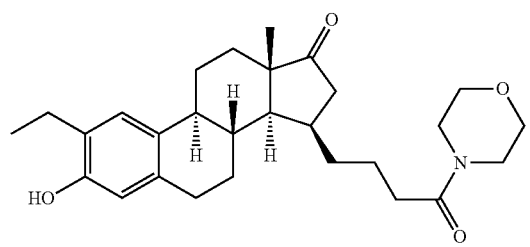

Example 5 was prepared starting from intermediate compound (IVb-(C2-C)-3a), which was converted into the desired amid by amid coupling with morpholine according to Flow Diagram Ib and as described above for Example 2 (Compound (IVb-(C2-C)-3a) (110 mg, 0.28 mmol), EtOAc (30 ml), morpholine (0.28 mmol), TEA (0.57 mmol), T3P (0.34 mmol). Compound No. 5 (68 mg, 0.15 mmol, 54%) obtained after column chromatography ($SiO_2$, DCM/MeOH=100/0 to 95/5).

$^1$H-NMR (300 MHz, $CDCl_3$): δ 1.01 (s, 3H, Steroid-CHs), 1.22 (t, J=7.5 Hz, 3H, Ethyl), 1.3-2.0 (m, 11H, Steroid), 2.2-2.42 (m, 7H, Steroid/Morpholine), 2.60 (q, J=7.7 Hz, 2H, ethyl), 2.82-2.90 (m, 2H, Steroid), 3.44-3.50 (m, 2H), 3.6-3.70 (m, 6H, Morpholine), 4.61 (s, 1H, OH), 6.53 (s, 1H, Steroid-Ar—H), 7.04 (s, 1H, Steroid-Ar—H) ppm.

Example 6

3-Hydroxy-15β-(4-morpholin-4-yl-4-oxo-butyl)-2-propyl-estra-1,3,5(10)-trien-17-one

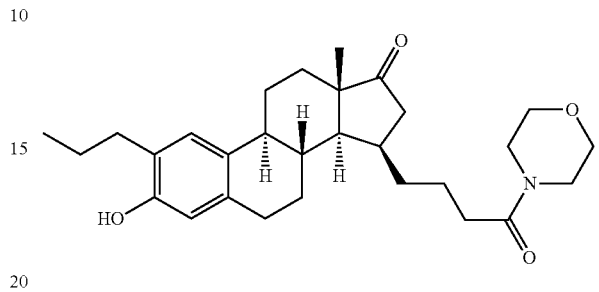

Example 6 was prepared as described above for Example 2 starting from intermediate compound (IVb-(C2-G)-3a), which was converted into the desired amid by amid coupling with morpholine according to Flow Diagram Ib (Compound (IVb-(C2-G)-3a) (500 mg, 1.25 mmol), EtOAc (25 ml), morpholine (2.5 mmol), TEA (3.75 mmol), T3P (1.5 mmol). Compound No. 6 (225 mg, 0.481 mmol, 38%) was obtained after column chromatography ($SiO_2$, DCM/MeOH=97.5/2.5).

$^1$H-NMR (300 MHz, $CDCl_3$): δ 0.98 (t, 3H), 1.01 (s, 3H), 1.3-1.8 (m, 11H), 1.90 (d, 1H), 2.00 (d, 1H, broad), 2.2-2.5 (m, 7H), 2.35 (t, 2H), 2.8-3.0 (m, 2H), 3.45 (t, 2H), 3.6-3.70 (m, 6H), 5.30 (s, 1H), 6.54 (s, 1H), 7.00 (s, 1H) ppm.

Example 7

3-Hydroxy-2-(2-methoxy-ethyl)-15β-(4-morpholin-4-yl-4-oxo-butyl)-estra-1,3,5(10)-trien-17-one

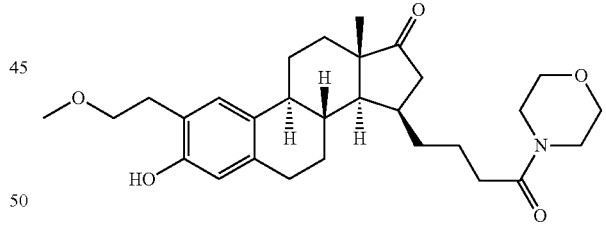

Example 7 was prepared from intermediate compound (IVb-(C2-F)-3a) by amid coupling according to Flow Diagram Ib: Compound (IVb-(C2-F)-3a) (85 mg, 0.221 mmol) was dissolved in a mixture of EtOAc (40 ml), morpholine (0.24 mmol), TEA (0.44 mmol) and T3P in in EtOAc (50 w/w %, 0.26 mmol) under $N_2$ atmosphere at 0° C. After stirring at ambient temperature for 16 h, the reaction mixture was poured into water (100 ml) and diluted with EtOAc (50 ml). The aqueous layer was neutralized to pH 8 with aq. $NaHCO_3$, separated and extracted with EtOAc (3×50 ml). The combined organic layers were washed with water (50 ml) and dried over $Na_2SO_4$. The organic layer was concentrated in vacuo yielding Compound No. 7 (43 mg, 0.088 mmol, 40%) after column chromatography ($SiO_2$, DCM/MeOH=99/1 to 94/6).

$^1$H-NMR (300 MHz, CDCl$_3$): δ 1.00 (s, 3H, Steroid-CH$_3$), 1.2-2.05 (m, 9H, Steroid), 2.2-2.44 (m, 8H, Steroid+morpholine), 2.81 (m, 4H-1, Steroid), 3.40 (s, 3H, OMe), 3.45 (t, J=4.7 Hz, 2H, OCH$_2$), 3.57-3.72 (m, 8H-1, morpholine), 6.67 (s, 1H, Steroid-Ar—H), 6.94 (s, 1H, Steroid-Ar—H), 7.97 (s, 1H, OH or NH) ppm.

Example 8

3-Hydroxy-2-methoxy-15β-(4-morpholin-4-yl-4-oxo-butyl)-estra-1,3,5(10)-trien-17-one

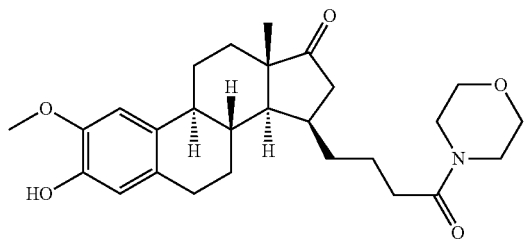

Example 8 was prepared starting from intermediate compound (IVb-(C2-B)-3a), which was converted into the desired amid by amid coupling with morpholine according to Flow Diagram Ib and as described above for Example 4 using 0.07 mmol of (IVb-(C2-B)-3a) and 0.07 mmol morpholine, yielding Compound No. 4.

$^{13}$C NMR (126 MHz, CHLOROFORM-d): 0 ppm 17.7 (q, 1 C) 25.1 (t, 1 C) 25.8 (t, 1 C) 26.8 (t, 1 C) 28.7 (t, 1 C) 30.9 (t, 1 C) 32.8 (t, 1 C) 33.9 (t, 1 C) 34.4 (d, 1 C) 36.0 (d, 1 C) 41.9 (t, 1 C) 42.7 (t, 1 C) 44.8 (d, 1 C) 45.9 (t, 1 C) 47.1 (s, 1 C) 52.8 (d, 1 C) 56.1 (d, 1 C) 66.6 (t, 1 C) 66.9 (t, 1 C) 107.8 (d, 1 C) 114.6 (d, 1 C) 129.2 (s, 1 C) 131.4 (s, 1 C) 143.7 (s, 1 C) 144.7 (s, 1 C) 171.2 (s, 1 C) 220.9 (s, 1 C)

$^1$H NMR (501 MHz, CHLOROFORM-d): □ ppm 1.02 (s, 3H) 1.32-1.85 (m, 7H) 1.87-1.95 (m, 1H) 1.98-2.06 (m, 1H) 2.25-2.51 (m, 5H) 2.75-2.92 (m, 2H) 3.42-3.51 (m, 2H) 3.57-3.72 (m, 6H) 3.86 (s, 3H) 5.52 (s, 1H) 6.67 (s, 1H) 6.78 (s, 1H)

Example 9

4-(2-Ethyl-3-hydroxy-17-oxo-estra-1,3,5(10)-trien-15β-yl)-N-(5-methyl-thiazol-2-yl)-butyramide

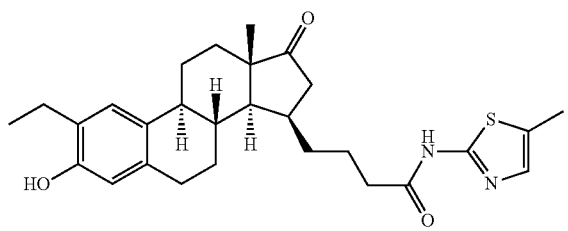

Example 9 was prepared as described above for Example 2 starting from intermediate compound (IVb-(C2-C)-3a), which was converted into the desired amid by amid coupling with 2-amino-5-methylthiazole according to Flow Diagram Ib: (Compound (IVb-(C2-C)-3a) (730 mg, 1.89 mmol), EtOAc (150 ml), 2-amino-5-methylthiazole (216 mg, 1.89 mmol), TEA (3.79 mmol), T3P (2.27 mmol). Compound No. 9 (280 mg, 0.58 mmol, 31%) was obtained after recrystallization from DCM.

$^1$H-NMR (300 MHz, d-DMSO): δ 0.90 (s, 3H, Steroid-CH$_3$), 1.05 (t, J=7.4 Hz, 3H, Ethyl), 1.2-1.4 (m, 4H, Steroid), 1.44-1.74 (m, 6H, Steroid), 1.82-1.93 (m, 1H, Steroid), 2.1-2.7 (m, 14H, Steroid), 6.43 (s, 1H, Steroid-Ar—H), 6.89 (s, 1H, Steroid-Ar—H), 7.08 (d, J=1.0 Hz, 1H, Thiazol-H), 8.82 (bs, 1H, NH or OH), 11.82 (bs, 1H, NH or OH) ppm.

Example 10

4-(3-Hydroxy-2-methoxy-17-oxo-estra-1,3,5(10)-trien-15β-yl)-N-(5-methyl-thiazol-2-yl)-butyramide

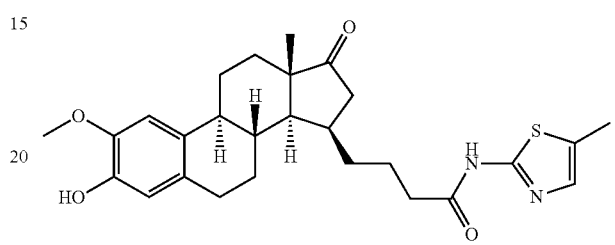

Example 10 was prepared starting from intermediate compound (IVb-(C2-B)-3a), which was converted into the desired amid by amide coupling according to Flow Diagram Ib and as described above for Example 4 using 0.07 mmol of (IVb-(C2-B)-3a) and 0.07 mmol 2-amino-5-methylthiazole, yielding Compound No. 10 (33.7 mg, MS 484, Rt 3.86).

Further Compounds

A variety of compounds numbered 11 to 28 and falling under the scope of general formula (I), in which X-A-Y represents —CO—NR$^4$, R$^1$ represents H, R$^{14}$ represents —O—CH$_3$, C15 is substituted in the β position and n is 3, were prepared by parallel chemistry using a reaction according to general flow diagram Ib and as described in EXAMPLE 4.

TABLE 16

| No. | R$^2$ | R$^4$ | MW | HPLC Rt [min] |
|---|---|---|---|---|
| 11 | Cyclopropyl | H | 425.6 | 3.48 |
| 12 | Cyclohexyl | H | 467.6 | 3.90 |
| 13 | Benzo[1,3]dioxol-5-ylmethyl | H | 519.6 | 3.73 |
| 14 | 2-Pyridin-2-yl-ethyl | H | 490.6 | 3.43 |
| 15 | Pyridin-3-1-methl | H | 476.6 | 3.36 |
| 16 | 2-Methoxy-ethyl | H | 443.6 | 3.41 |
| 17 | 2,4-Difluorobenzyl | H | 511.6 | 3.88 |
| 18 | 3,5-Dimethoxy-benzyl | H | 535.7 | 3.78 |
| 19 | 2-(7-Methyl-1H-indol-3-yl)-ethyl | H | 542.7 | 3.92 |
| 20 | 1-Methyl-1H-imidazol-4-ylmethyl | H | 479.6 | 3.18 |

TABLE 16-continued

| No. | R⁴/R² (N-R⁴/R²) | | MW | HPLC Rt [min] |
|---|---|---|---|---|
| 21 | Piperidin-1-yl | | 453.6 | 3.90 |
| 22 | Methyl | Benzyl | 489.7 | 4.07 |
| 23 | Ethyl | Ethyl | 441.6 | 3.84 |
| 24 | Methyl | 2-(3,4-Dimethoxy-phenyl)-ethyl | 563.7 | 3.87 |
| 25 | 4-Isopropyl-piperazin-1-yl | | 496.7 | 3.19 |
| 26 | 3,4-Difluoro-phenyl | H | 497.6 | 4.15 |
| 27 | 3-Chloro-phenyl | H | 496.0 | 4.24 |
| 28 | 3-Trifluoromethoxy-phenyl | H | 545.6 | 4.40 |

A variety of compounds numbered 29 to 89 and falling under the scope of general formula (I), in which X-A-Y represents —CO—NR⁴, R¹ represents H, and n is 3, were prepared by parallel chemistry using a reaction according to general flow diagram Ib.

Synthesis Protocol: 0.07 mmol of the individual amine was weight out into a reaction flask. A solution of 0.07 mmol of the respective steroidal building block (IVb-(C2-G)-3a), (IVa-(C2-D)-3a), and (IVa-(C2-B)-3a) in 5 ml DCM were added. Then, 0.077 mmol polymer bound HOBT, 0.231 mmol polymer bound NMM and 0.154 mmol polymer bound EDCI were added. The reaction mixture was stirred for 24 h at ambient temperature. Afterwards, the reaction mixture was filtrated, washed twice with 1 ml DCM and evaporated to dryness. The crude product was treated with 2 ml THF, 10 mg LiOH and 0.5 ml water. After evaporation and further extraction (EtOAc and 0.1 M KHSO₄) approx. 50 mg trisaminoeethlyamine polymer bound were added yielding the desired product after filtration and evaporating to dryness.

TABLE 17

| No. | R¹⁴ | C15 stereo | R²/R⁴ | R⁴ | MW | HPLC Rt [min] |
|---|---|---|---|---|---|---|
| 29 | propyl | beta | cyclohexyl | H | 479.7 | 6.09 |
| 30 | propyl | beta | Benzo[1,3]dioxol-5-ylmethyl | H | 531.7 | 5.90 |
| 31 | propyl | beta | 2-pyridin-2-yl-ethyl | H | 502.7 | 5.46 |
| 32 | propyl | beta | pyridin-3-ylmethyl | H | 488.7 | 5.36 |
| 33 | propyl | beta | 3,5-Dimethoxy-benzyl | H | 547.7 | 5.96 |
| 34 | propyl | beta | 2-(7-methyl-1H-indol-3-yl)-ethyl | H | 554.8 | 6.12 |
| 35 | propyl | beta | 1-methyl-1H-imidazol-4-ylmethyl | H | 491.7 | 5.12 |
| 36 | propyl | beta | piperidin-1-yl | | 465.7 | 6.05 |
| 37 | propyl | beta | methyl | benzyl | 501.7 | 6.27 |
| 38 | propyl | beta | 2-(3,4-Dimethoxy-phenyl)-ethyl | H | 575.8 | 6.01 |
| 39 | propyl | beta | 4-isopropyl-piperazin-1-yl | | 508.7 | 5.10 |
| 40 | propyl | beta | 1H-indazol-6-yl | H | 513.7 | 6.26 |
| 41 | propyl | beta | 2-methoxy-ethyl | H | 455.3 | 5.78 |
| 42 | propyl | beta | 2,4-difluorobenzyl | H | 523.3 | 6.50 |
| 43 | ethoxy | alpha | cyclopropyl | H | 439.6 | 5.06 |
| 44 | ethoxy | alpha | cyclohexyl | H | 481.7 | 5.67 |
| 45 | ethoxy | alpha | Benzo[1,3]dioxol-5-ylmethyl | H | 533.7 | 5.49 |
| 46 | ethoxy | alpha | 2-pyridin-2-yl-ethyl | H | 504.7 | 4.98 |
| 47 | ethoxy | alpha | pyridin-3-ylmethyl | H | 490.6 | 4.89 |
| 48 | ethoxy | alpha | benzyl | H | 489.7 | 5.57 |
| 49 | ethoxy | alpha | 2-methoxy-ethyl | H | 457.6 | 4.93 |
| 50 | ethoxy | alpha | 2,4-difluorobenzyl | H | 525.6 | 5.70 |
| 51 | ethoxy | alpha | 3,5-Dimethoxy-benzyl | H | 549.7 | 5.55 |
| 52 | ethoxy | alpha | 7-methyl-1H-indol-3-yl | H | 556.7 | 5.70 |
| 53 | ethoxy | alpha | 1-methyl-1H-imidazol-4-ylmethyl | H | 493.6 | 4.58 |
| 54 | ethoxy | alpha | morpholin-4-yl | | 469.6 | 5.07 |
| 55 | ethoxy | alpha | piperidin-1-yl | | 467.6 | 5.63 |
| 56 | ethoxy | alpha | methyl | benzyl | 503.7 | 5.89 |
| 57 | ethoxy | alpha | 2-(3,4-Dimethoxy-phenyl)-ethyl | H | 577.8 | 5.60 |
| 58 | ethoxy | alpha | 4-isopropyl-piperazin-1-yl | | 510.7 | 4.56 |
| 59 | ethoxy | alpha | 1H-indazol-6-yl | H | 515.7 | 5.88 |
| 60 | ethoxy | alpha | Benzo[1,3]dioxol-5-yl | H | 519.6 | 5.63 |
| 61 | ethoxy | alpha | 3-Cyano-phenyl | H | 500.6 | 5.74 |
| 62 | ethoxy | alpha | 3,4-Difluoro-phenyl | H | 511.6 | 5.98 |
| 63 | ethoxy | alpha | 5-methyl-thiazol-2-yl | H | 496.7 | 5.58 |
| 64 | ethoxy | alpha | ethyl | ethyl | 455.3 | 5.98 |
| 65 | ethoxy | alpha | 3-chloro-phenyl | H | 509.2 | 6.56 |
| 66 | methoxy | alpha | cyclopropyl | H | 425.6 | 4.78 |
| 67 | methoxy | alpha | cyclohexyl | H | 467.6 | 5.42 |
| 68 | methoxy | alpha | Benzo[1,3]dioxol-5-ylmethyl | H | 519.6 | 5.25 |
| 69 | methoxy | alpha | 2-pyridin-2-yl-ethyl | H | 490.6 | 4.72 |
| 70 | methoxy | alpha | pyridin-3-ylmethyl | H | 476.6 | 4.63 |
| 71 | methoxy | alpha | benzyl | H | 475.6 | 5.32 |
| 72 | methoxy | alpha | 2-methoxy-ethyl | H | 443.6 | 4.65 |
| 73 | methoxy | alpha | 2,4-difluorobenzyl | H | 511.6 | 5.46 |
| 74 | methoxy | alpha | 3,5-Dimethoxy-benzyl | H | 535.7 | 5.31 |
| 75 | methoxy | alpha | 7-methyl-1H-indol-3-yl | H | 542.7 | 5.48 |
| 76 | methoxy | alpha | 1-methyl-1H-imidazol-4-ylmethyl | H | 479.6 | 4.30 |
| 77 | methoxy | alpha | morpholin-4-yl | | 455.6 | 4.79 |
| 78 | methoxy | alpha | piperidin-1-yl | | 453.6 | 5.35 |
| 79 | methoxy | alpha | methyl | benzyl | 489.7 | 5.63 |
| 80 | methoxy | alpha | ethyl | ethyl | 441.6 | 5.29 |
| 81 | methoxy | alpha | 2-(3,4-Dimethoxy-phenyl)-ethyl | H | 563.7 | 5.35 |
| 82 | methoxy | alpha | 4-isopropyl-piperazin-1-yl | | 496.7 | 4.30 |
| 83 | methoxy | alpha | 1H-indazol-6-yl | H | 501.6 | 5.63 |
| 84 | methoxy | alpha | 5-methyl-thiazol-2-yl | H | 482.6 | 5.34 |
| 85 | methoxy | alpha | 3,4-dihydroxybenzyl | H | 507.3 | 4.87 |
| 86 | methoxy | alpha | Benzo[1,3]dioxol-5-yl | H | 505.3 | 5.71 |
| 87 | methoxy | alpha | 3-Cyano-phenyl | H | 486.3 | 5.85 |
| 88 | methoxy | alpha | 3,4-Difluoro-phenyl | H | 497.2 | 6.13 |
| 89 | methoxy | alpha | 3-chloro-phenl | H | 495.2 | 6.27 |

II. Compounds Carrying a Substitution of the C17 Oxo Function of the Steroidal Core

Example 90

4-(17,17-Difluoro-3-hydroxy-estra-1,3,5(10)-trien-15β-yl)-1-morpholin-4-yl-butan-1-one

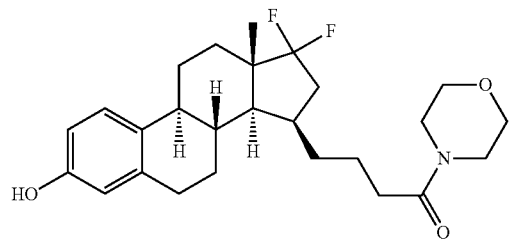

Example 90 was prepared from the Intermediate No. 1 (3-Hydroxy-15β-(4-morpholin-4-yl-4-oxo-butyl)-estra-1,3,5(10)-trien-17-one) according to the reaction depicted in Section D-(I)-(b): To a solution of the estron derivative (106 mg; 250 µmol) in Deoxofluor (0.96 ml; 5.00 mmol) a drop of ethanol was added; the solution was stirred at RT for 5 d. Subsequently, DCM (10 ml) was added and the product was hydrolyzed by addition of saturated NaHCO$_3$ solution under ice cooling. For work up, the organic phase was separated off, and the remaining water phase was extracted with DCM (2×10 ml). The combined DCM fractions were dried over MgSO$_4$. After evaporation and subsequent purification using column chromatography (DCM/Ether 1:1), 81 mg of a colourless solid were obtained (MW 489.64).

$^{13}$C NMR (126 MHz, CHLOROFORM-d): ☐ ppm 17.0 (q, J$_{(C,F)}$, 1 C) 24.5 (t, 1 C) 25.0 (t, 1 C) 27.4 (t, 1 C) 29.3 (t, J$_{(C,F)}$,1 C) 30.7 (t, 1 C) 31.7 (t, 1 C) 32.9 (d, J$_{(C,F)}$,1 C) 34.4 (t, 1 C) 35.9 (d, 1 C) 39.7-40.5 (t, J$_{(C,F)}$,1 C) 42.0 (t, 1 C) 44.1 (d, 1 C) 45.2 (t, 1 C) 46.1 (s, J$_{(C,F)}$, 1 C) 50.3 (d, J$_{(C,F)}$, 1 C) 66.7 (t, 1 C) 67.0 (t, 1 C) 112.7 (d, 1 C) 115.3 (d, 1 C) 126.0 (d, 1 C) 132.3 (s, 1 C) 138.0 (s, 1 C) 153.9 (s, 1 C) 171.5 (s, 1 C)

$^1$H NMR (501 MHz, CHLOROFORM-d): ☐ ppm 0.99 (s, 3H) 1.23-2.5 (m, 18H) 2.82 (m, 2H) 3.43-3.52 (m, 2H) 3.59-3.73 (m, 6H) 5.66 (br. s., 1H) 6.57 (d, J=2.55 Hz, 1H) 6.63 (dd, J=8.5, 2.5 Hz, 1H) 7.10 (d, J=8.5 Hz, 1 H)

Example 91

4-(17,17-Difluoro-3-hydroxy-estra-1,3,5(10)-trien-15α-yl)-1-morpholin-4-yl-butan-1-one

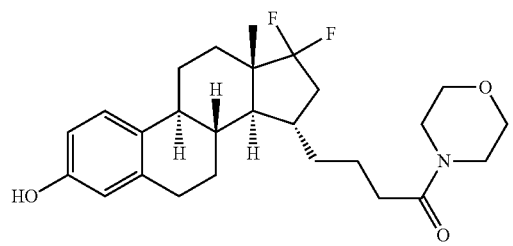

Example 91 was prepared from the Intermediate No. 40 named 3-Hydroxy-15α-(4-morpholin-4-yl-4-oxo-butyl)-estra-1,3,5(10)-trien-17-one as described for Example 90.

$^{13}$C NMR (126 MHz, CHLOROFORM-d): ☐ ppm 14.9 (q, J$_{(C,F)}$=3.89 Hz, 1 C) 23.8 (t, 1 C) 26.2 (t, 1 C) 27.6 (t, 1 C) 28.6 (t, J$_{(C,F)}$=4.67 Hz, 1 C) 29.7 (t, 1 C) 33.2 (t, 1 C) 35.9 (d, J$_{(C,F)}$=6.75 Hz, 1 C) 36.8 (t, 1 C) 39.4 (d, 1 C) 39.5-40.0 (t, J$_{(C,F)}$, 1 C) 42.1 (t, 1 C) 43.8 (d, 1 C) 46.1 (t, 1 C) 46.8 (s, J$_{(C,F)}$=19.98 Hz, 1 C) 53.1 (d, J$_{(C,F)}$=4.15 Hz, 1 C) 66.6 (t, 1 C) 66.9 (t, 1 C) 113.1 (d, 1 C) 115.1 (d, 1 C) 126.8 (d, 1 C) 128.9-133.4 (s, J$_{(C,F)}$, 1 C) 131.5 (s, 1 C) 137.5 (s, 1 C) 154.0 (s, 1 C) 171.8 (s, 1 C)

$^1$H NMR (501 MHz, CHLOROFORM-d): ☐ ppm 0.92 (s, 3H) 1.19-1.36 (m, 3H) 1.38-1.50 (m, 1H) 1.51-1.83 (m, 7H) 1.86-1.99 (m, 2H) 2.13-2.23 (m, 1H) 2.28-2.53 (m, 4H) 2.70-2.83 (m, 2H) 3.43-3.52 (m, 2H) 3.59-3.73 (m, 6H) 6.06 (br. s., 1H) 6.55 (d, J=2.75 Hz, 1H) 6.64 (dd, J=8.54, 2.75 Hz, 1H) 7.12 (d, J=8.24 Hz, 1H)

Example 92

4-(17-Fluoro-3-hydroxy-estra-1,3,5(10),16-tetraen-15β-yl)-1-morpholin-4-yl-butan-1-one

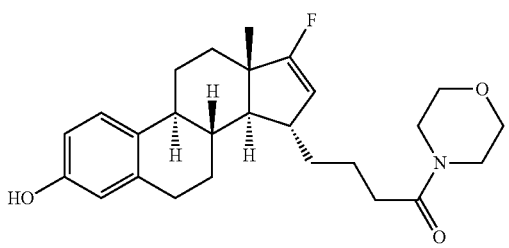

Example 92 was isolated as by-product during the synthesis of Example No. 91.

$^1$H NMR (501 MHz, CHLOROFORM-d): ☐ ppm 0.99 (s, 3H) 1.23-1.85 (m, 9H) 1.93-2.00 (m, 1H) 2.12-2.20 (m, 1H) 2.25-2.48 (m, 5H) 2.68-2.84 (m, 2H) 3.44-3.53 (m, 2H) 3.63-3.70 (m, 6H) 4.83-4.87 (m, 1H) 6.55 (d, J=2.4 Hz, 1H) 6.63 (dd, J=8.5, 2.7 Hz, 1H) 7.08 (d, J=8.5 Hz, 1H)

$^{13}$C NMR (126 MHz, CHLOROFORM-d): ☐ ppm 17.1 (q, J$_{C,F}$=4.2 Hz, 1 C) 23.3 (t, 1 C) 26.4 (t, 1 C) 27.8 (t, 1 C) 29.7 (t, 1 C) 32.9 (t, 1 C) 33.3 (t, 1 C) 34.2 (t, 1 C) 37.8 (d, 1 C) 40.4 (d, J$_{C,F}$=5.7 Hz, 1 C) 42.1 (t, 1 C) 44.3 (s, J$_{C,F}$=20.5 Hz, 1 C) 44.4 (d, 1 C) 46.1 (t, 1 C) 57.9 (d, J$_{C,F}$=5.2 Hz, 1 C) 66.6 (t, 1 C) 66.9 (t, 1 C) 104.2 (d, J$_{C,F}$=8.0 Hz, 1 C) 112.9 (d, 1 C) 115.1 (d, 1 C) 126.3 (d, 1 C) 131.8 (s, 1 C) 137.4 (s, 1 C) 154.1 (s, 1 C) 170.7 (s, J$_{C,F}$=289.9 Hz, 1 C) 172.0 (s, 1 C)

Example 93

3-(17,17-Difluoro-3-hydroxy-estra-1,3,5(10)-trien-15β-yl)-N-(5-methyl-thiazol-2-yl)-propionamide

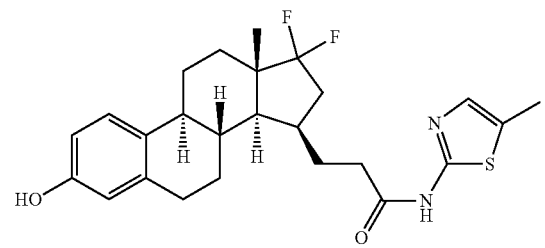

Example 93 was prepared from the Intermediate IVβ-2a-D1F2 using amide coupling with 2-amino-5-methylthiazole according to general flow diagram Ib and as described for synthesis of Example 4.

$^1$H NMR (501 MHz, DMSO-d$_6$): ☐ ppm 1.01 (s, 3H) 1.28-1.37 (m, 2 H) 1.47-1.74 (m, 5H) 1.86-1.96 (m, 1H) 1.97-2.04 (m, 1H) 2.06-2.22 (m, 3 H) 2.24-2.39 (m, 6H) 2.40-2.48 (m, 1H) 2.68-2.84 (m, 2H) 6.47 (d, J=2.4 Hz, 1H)

6.52 (dd, J=8.4, 2.6 Hz, 1H) 7.01-7.05 (m, 1H) 7.09-7.11 (m, 1H) 8.96-9.03 (m, 1H) 11.86 (s, 1H)

$^{13}$C NMR (126 MHz, DMSO-d$_6$): ☐ ppm 11.0 (q, 1 C) 16.6-16.7 (q, J$_{C,F}$, 1 C) 24.5 (t, 1 C) 26.8 (t, 1 C) 26.8 (t, 1 C) 28.8 (t, 1 C) 30.4 (t, J$_{C,F}$=4.9 Hz, 1 C) 33.4 (d, J$_{C,F}$=6.7 Hz, 1 C) 34.2 (t, 1 C) 35.5 (d, 1 C) 38.5-38.8 (t, J$_{C,F}$, 1 C) 43.7 (d, 1 C) 44.5-45.0 (s, J$_{C,F}$, 1 C) 49.7 (d, J$_{C,F}$=4.9 Hz, 1 C) 112.6 (d, 1 C) 114.9 (d, 1 C) 125.6 (d, 1 C) 125.9 (s, 1 C) 130.1 (s, 1 C) 130.6-134.7 (s, J$_{C,F}$, 1 C) 134.6 (d, 1 C) 137.1 (s, 1 C) 155.0 (s, 1 C) 156.1 (s, 1 C) 170.7 (s, 1 C)

Example 94

4-(17-Trifluoromethyl-3-hydroxy-estra-1,3,5(10),16-tetraen-15β-yl)-1-morpholin-4-yl-butan-1-one

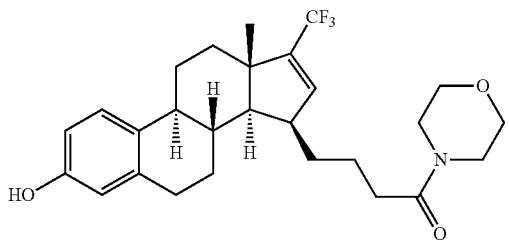

Example 94 was prepared from intermediate Vβ-3a-D-(I)-(d)-CF$_3$ by amide coupling according to general flow diagram Ia: To the solution of Vβ-3a-D-(I)-(d)-CF$_3$ in DCM, a large excess of the Hünig base N(iPr)$_2$Et and morpholine was added. The solution was stirred over night at ambient temperature. After dilution with further DCM and washing twice with 1 M KHSO$_4$, the organic layer was dried over Na$_2$SO$_4$ and evaporated to dryness. The crude material was purified by flash chromatography with DCM/EtOAc and by preparative HPLC yielding 15 mg of compound No. 95 as white solid.

$^{13}$C NMR (126 MHz, CHLOROFORM-d): ☐ ppm 22.2 (q, 1 C) 24.7 (t, 1 C) 25.6 (t, 1 C) 27.3 (t, 1 C) 29.1 (t, 1 C) 29.3 (t, 1 C) 33.1 (t, 1 C) 35.1 (d, 1 C) 36.1 (t, 1 C) 42.1 (t, 1 C) 44.2 (d, 1 C) 44.6 (d, 1 C) 46.1 (t, 1 C) 46.3 (s, 1 C) 57.6 (d, 1 C) 66.7 (t, 1 C) 67.0 (t, 1 C) 112.7 (d, 1 C) 115.3 (d, 1 C) 122.4-124.8 (s, 1 C) 125.8 (d, 1 C) 132.5 (s, 1 C) 137.9 (s, 1 C) 138.5 (d, J=5.7 Hz, 1 C) 143.3-144.3 (s, 1 C) 153.9 (s, 1 C) 171.5 (s, 1 C)

$^1$H NMR (501 MHz, CHLOROFORM-d): ☐ ppm 1.14 (s, 3H) 1.32-1.78 (m, 8H) 1.84 (dd, J=11.9, 7.3 Hz, 1H) 1.95-2.04 (m, 2H) 2.27-2.36 (m, 4 H) 2.57-2.64 (m, 1H) 2.80-2.88 (m, 2H) 3.44-3.51 (m, 2H) 3.62-3.71 (m, 6 H) 5.40-5.73 (m, 1H) 6.45-6.48 (m, 1H) 6.58 (d, J=2.7 Hz, 1H) 6.63 (dd, J=8.2, 2.7 Hz, 1H) 7.09 (d, J=8.2 Hz, 1H)

Example 95

4-(17-Difluoromethylene-3-hydroxy-estra-1,3,5(10)-trien-15β-yl)-1-morpholin-4-yl-butan-1-one

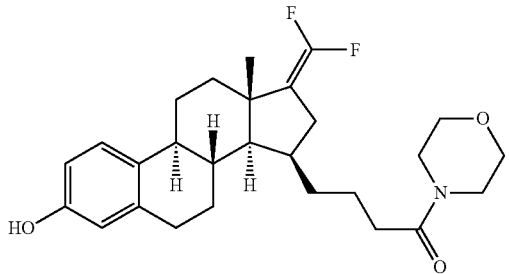

Example 95 was prepared from intermediate Vβ-3α-D-(I)-(a)=CF$_2$ by amide coupling according to general flow diagram Ia: To the solution of Vβ-3a-D-(I)-(a)=CF$_2$ in DCM, a large excess of the Hünig base N(iPr)$_2$Et and morpholine was added. The solution was stirred over night at ambient temperature. After dilution with further DCM and washing twice with 1 M KHSO$_4$, the organic layer was dried over Na$_2$SO$_4$ and evaporated to dryness. The crude material was purified by flash chromatography with DCM/EtOAc and by preparative HPLC yielding 15 mg of compound No. 95 as white solid.

$^1$H NMR (501 MHz, CHLOROFORM-d): ☐ ppm 1.05 (s, 3H) 1.18-1.30 (m, 1H) 1.32-1.81 (m, 7H) 1.87-1.97 (m, 1H) 2.03-2.15 (m, 2H) 2.18-2.36 (m, 4H) 2.53-2.68 (m, 1H) 2.77-2.91 (m, 2H) 3.43-3.53 (m, 2H) 3.59-3.72 (m, 6H) 5.53 (br. s., 1H) 6.57 (d, J=2.44 Hz, 1H) 6.63 (dd, J=8.39, 2.59 Hz, 1H) 7.11 (d, J=8.24 Hz, 1H)

$^{13}$C NMR (126 MHz, CHLOROFORM-d): 0 ppm 20.9 (q, J$_{(C,F)}$=2.60 Hz, 1 C) 25.3 (t, 1 C) 26.2 (t, 1 C) 27.5 (t, 1 C) 29.5 (t, 1 C) 31.0 (t, 1 C) 31.3 (t, 1 C) 33.1 (t, 1 C) 35.8 (d, 1 C) 37.7 (d, 1 C) 38.0 (t, J$_{(C,F)}$=4.15 Hz, 1 C) 42.1 (t, 1 C) 42.3 (s, J$_{(C,F)}$=2.98 Hz, 1 C) 44.3 (d, 1 C) 46.1 (t, 1 C) 57.7 (d, 1 C) 66.7 (t, 1 C) 67.0 (t, 1 C) 99.2 (s, J$_{(C,F)}$=17.26 Hz, 1 C) 112.7 (d, 1 C) 115.3 (d, 1 C) 126.0 (d, 1 C) 132.5 (s, 1 C) 138.0 (s, 1 C) 148.3-153.0 (s, J$_{(C,F)}$, 1 C) 153.8 (s, 1 C) 171.7 (s, 1 C)

Example 96

4-(17-Difluoromethylene-3-hydroxy-estra-1,3,5(10)-trien-15α-yl)-1-morpholin-4-yl-butan-1-one

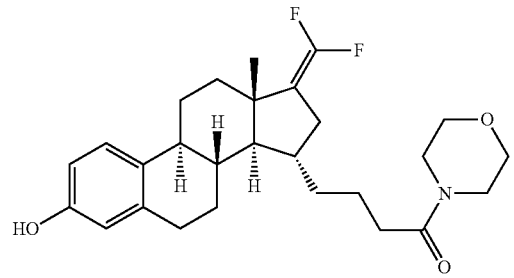

Example 96 can be prepared from the Intermediate No. 40 named 3-Hydroxy-15α-(4-morpholin-4-yl-4-oxo-butyl)-estra-1,3,5(10)-trien-17-one of formula (VIα-3a)-40 according to the reaction depicted in Section D-(I)-(a)/1.

Example 97

4-(17-Trifluoromethyl-3-hydroxy-estra-1,3,5(10),16-tetraen-15α-yl)-1-morpholin-4-yl-butan-1-one

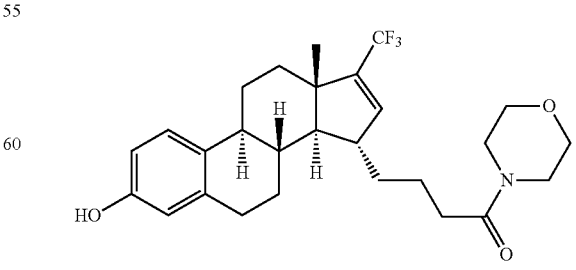

Example 97 can be prepared from the Intermediate No. 40 named 3-Hydroxy-15α-(4-morpholin-4-yl-4-oxo-butyl)-estra-1,3,5(10)-trien-17-one of formula (VIα-3a)-40 according to the reaction depicted in Section D-(I)-(d)/3.

Example 98

4-(17-Trifluoromethyl-3-hydroxy-estra-1,3,5(10)-trien-15α-yl)-1-morpholin-4-yl-butan-1-one

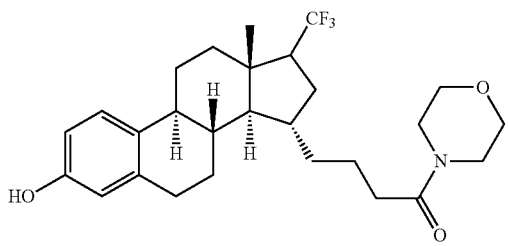

Example 98 can be prepared from Example 16 according to the last reaction step depicted in Section D-(I)-(c)/3.

Example 99

4-(17-Difluoromethyl-2-ethyl-3-hydroxy-estra-1,3,5(10)-trien-15β-yl)-N-(5-methyl-thiazol-2-yl)-butyramide

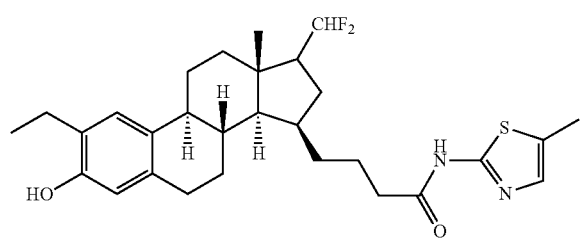

Example 99 can be prepared starting from Example 9 (4-(2-Ethyl-3-hydroxy-17-oxo-estra-1,3,5(10)-trien-15β-yl)-N-(5-methyl-thiazol-2-yl)-butyramide) as educt, according to the reaction depicted in Section D-(I)-(c)/2.

Example 100

4-(17-Difluoromethyl-3-hydroxy-estra-1, 3,5(10),16-tetraen-15β-yl)-1-morpholin-4-yl-butan-1-one

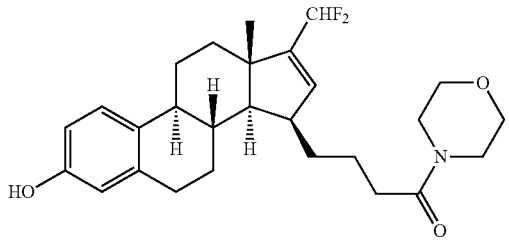

Example 100 can be prepared starting from Example 95 (4417-Difluoromethylene-3-hydroxy-estra-1,3,5(10)-trien-15β-yl)-1-morpholin-4-yl-butan-1-one) according to the reaction scheme depicted in Section D-(I)-(d)/2.

Further Compounds

A variety of compounds numbered 101 to 138 and falling under the scope of general formula (I), in which X-A-Y represents —CO—NR$^4$, R$^1$ represents —H, R$^{14}$ represents —H, and the C17 keto function is replaced by a difluoro group, was prepared by parallel chemistry using a reaction according to general flow diagram Ib starting from the already fluorinated intermediates IVα-3a-D1F2 and IVβ-2a-D1F2, respectively.

Synthesis Protocol: 0.07 mmol of the individual amine was weight out into a reaction flask. A solution of 0.07 mmol of the respective steroidal building block (IVα-3a-D1F2 and IVβ-2a-D1F2), 0.077 mmol HOBT, 0.231 mmol NMM and 0.154 mmol polymer bound EDCI in 5 ml DCM were added. The reaction mixture was stirred for 24 h at ambient temperature. The solvent was removed in a vacuum centrifuge at 40° C. Than 4 ml EtOAc and 4 ml H$_2$O were added. The two phases were stirred vigorously for 2 min, than the organic phase was dried with Na$_2$SO$_4$ and evaporated in a vacuum centrifuge at 40° C. After treatment of the crude product with 2 ml THF, 10 mg LiOH and 0.5 ml water, the solvent was evaporated and the residue further extracted (EtOAc and 0.1 M KHSO$_4$). Then, 50 mg polymer bound trisaminoeethlyamine was added yielding after filtration and evaporating to dryness the desired product. If still necessary, products were further purified by flash chromatography (4 g silica gel, eluent EtOAc/cyclohexane).

TABLE 18

| No. | n | C15 stereo | R$^2$ | R$^4$ | —N(R$^2$)(R$^4$) | MW | HPLC Rt [min] |
|---|---|---|---|---|---|---|---|
| 101 | 3 | alpha | Cyclopropyl | H | | 417 | 5.9 |
| 102 | 3 | alpha | Cyclohexyl | H | | 459 | 6.58 |
| 103 | 3 | alpha | Benzo[1,3]dioxol-5-ylmethyl | H | | 511 | 6.3 |
| 104 | 3 | alpha | 2-Pyridin-2-yl-ethyl | H | | 482 | 5.77 |
| 105 | 3 | alpha | Pyridin-3-yl-methyl | H | | 468 | 5.67 |
| 106 | 3 | alpha | Benzyl | H | | 467 | 6.41 |
| 107 | 3 | alpha | 2-Methoxy-ethyl | H | | 435 | 5.76 |
| 108 | 3 | alpha | 2,4-Difluorobenzyl | H | | 503 | 6.52 |
| 109 | 3 | alpha | 3,4-dihydroxy-benzyl | H | | 499 | 5.65 |
| 110 | 3 | alpha | 3,5-Dimethoxy-benzyl | H | | 527 | 6.37 |
| 111 | 3 | alpha | 2-(7-Methyl-1H-indol-3-yl)-ethyl | H | | 534 | 6.53 |
| 112 | 3 | alpha | 1-Methyl-1H-imidazol-4-ylmethyl | H | | 471 | 5.33 |
| 113 | 3 | alpha | | | Piperidin-1-yl | 445 | 6.65 |
| 114 | 3 | alpha | Methyl | Benzyl | | 481 | 6.84 |
| 115 | 3 | alpha | Ethyl | Ethyl | | 433 | 6.54 |
| 116 | 3 | alpha | Methyl | 2-(3,4-Dimethoxy-phenyl)-ethyl | | 555 | 6.52 |
| 117 | 3 | alpha | | | 4-Isopropyl-piperazin-1-yl | 488 | 5.38 |
| 118 | 3 | alpha | Benzo[1,3]dioxol-5-yl | H | | 497 | 6.51 |
| 119 | 3 | alpha | 5-methyl-thiazol-2-yl | H | | 474 | 6.51 |
| 120 | 2 | beta | Cyclopropyl | H | | 403 | 5.76 |
| 121 | 2 | beta | Cyclohexyl | H | | 445 | 6.48 |
| 122 | 2 | beta | Benzo[1,3]dioxol-5-ylmethyl | H | | 497 | 6.17 |
| 123 | 2 | beta | 2-Pyridin-2-yl-ethyl | H | | 468 | 5.6 |
| 124 | 2 | beta | Pyridin-3-yl-methyl | H | | 454 | 5.51 |
| 125 | 2 | beta | Benzyl | H | | 453 | 6.28 |
| 126 | 2 | beta | 2-Methoxy-ethyl | H | | 421 | 5.6 |
| 127 | 2 | beta | 3,4-dihydroxy-benzyl | H | | 485 | 5.52 |
| 128 | 2 | beta | 3,5-Dimethoxy-benzyl | H | | 513 | 6.25 |

TABLE 18-continued

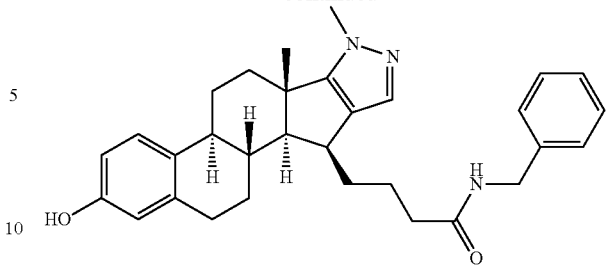

| No. | n | C15 stereo | R² | R⁴ | MW | HPLC Rt [min] |
|---|---|---|---|---|---|---|
| 129 | 2 | beta | 2-(7-Methyl-1H-indol-3-yl)-ethyl | H | 520 | 6.37 |
| 130 | 2 | beta | 1-Methyl-1H-imidazol-4-ylmethyl | H | 457 | 5.17 |
| 131 | 2 | beta | Piperidin-1-yl | | 431 | 6.47 |
| 132 | 2 | beta | Methyl | Benzyl | 467 | 6.72 |
| 133 | 2 | beta | Ethyl | Ethyl | 419 | 6.42 |
| 134 | 2 | beta | Methyl | 2-(3,4-Dimethoxy-phenyl)-ethyl | 541 | 6.4 |
| 135 | 2 | beta | 4-Isopropyl-piperazin-1-yl | | 474 | 5.18 |
| 136 | 2 | beta | Benzo[1,3]dioxol-5-yl | H | 483 | 6.37 |
| 137 | 2 | beta | 5-methyl-thiazol-2-yl | H | 433 | 5.82 |
| 138 | 2 | beta | 2-methoxy-ethyl | 2-methoxy-ethyl | 479.6 | |

III. Compounds with a Heterocyclus Fused to the Steroidal D-Ring

EXAMPLES 151 to 165 were prepared from the corresponding intermediates (e.g. No. 1, 3A, 39, 1, 40 etc.) using the reaction scheme as depicted in SECTION D-(II). Alternatively, depending on the nature of the C15 side chain, some of the reaction steps had to be carried out after having introduced the heterocyclic ring system, i.e. the 15,16-unsaturated intermediate (X) was derivatized to the appropriate acid or alkenyl intermediate (see e.g. SCHEMES 7B, 7C, 8A and 8B). Then, the heterocyclic ring system was introduced including the C16-C17 carbon atoms attached to the D-ring. The so-obtained intermediates were then used for further modification and amidation of the C15 side chain (introduction of the R2/R4 substituents). Finally the protection group in C3 position was cleaved off.

Examples 151 and 152

N-Benzyl-4-(3-hydroxy-(17,16-c)-(1'-methyl)-pyrazolyl-estra-1,3,5(10)-trieno-15β-yl)-butyramide N-Benzyl-4-(3-hydroxy-(17,16-c)-(2'-methyl)-pyrazolyl-estra-1,3,5(10)-trieno-15β-yl)-butyramide

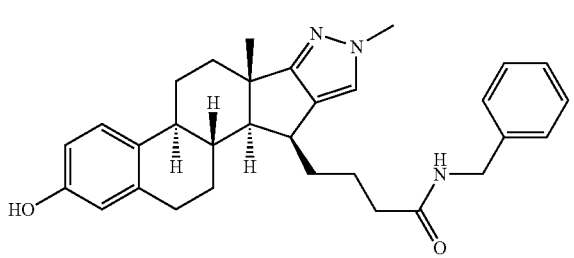

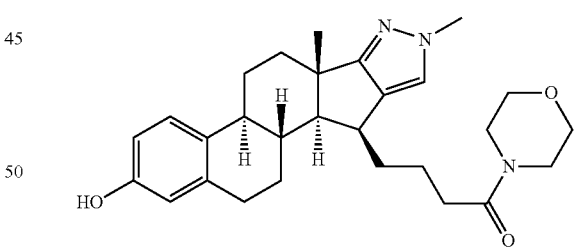

Starting from intermediate compound Xc, an allyl side chain was introduced into C15 position using 1,4-addition of allylbromide according to step 1 of SCHEME 7C, followed by construction of the pyrazol-ring according to D-(II)-(a). Ringclosure with methyl hydrazine gave a mixture of the corresponding isomers. Conversion of the allyl into the N-Benzyl-butyramide side chain was performed according to steps 2-4 of SCHEME 7C and to the reaction as depicted in general flow diagram Ib by reaction with benzylamine. Finally the obtained isomers were separated by preparative HPLC.

EXAMPLE 151: ¹H-NMR (300 MHz, CDCl₃): δ 1.10-1.20 (s, 3H), 1.20-2.32 (m, 17H), 2.68-2.88 (m, 3H), 3.72-3.80 (s, 3H), 4.24-4.40 (dd, 2H), 6.48-6.52 (s, 1H), 6.52-6.60 (d, 1H), 6.96-7.08 (d, 1H), 7.08-7.28 (m, 6H).

EXAMPLE 152: ¹H-NMR (300 MHz, CDCl₃): δ 1.08-1.16 (s, 3H), 1.16-2.40 (m, 17H), 2.68-2.88 (m, 3H), 3.72-3.84 (s, 3H), 4.24-4.44 (dd, 2H), 6.44-6.54 (s, 1H), 6.54-6.60 (d, 1H), 7.00-7.12 (d, 1H), 7.12-7.32 (m, 6H).

Examples 153 and 154

3-Hydroxy-15β-(4-morpholin-4-yl-4-oxo-butyl)-estra-1,3,5(10)-trien-[16,17-c]-(1'-methyl)-pyrazole 3-Hydroxy-15β-(4-morpholin-4-yl-4-oxo-butyl)-estra-1,3,5(10)-trien-[16,17-c]-(2'-methyl)-pyrazole

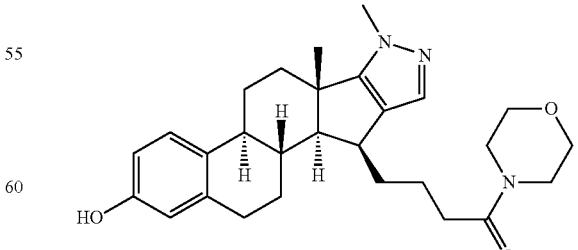

Examples 153 and 154 were prepared according to the procedure described for Examples 151 and 152 using morpholine as amine for the amide coupling step.

EXAMPLE 153: $^1$H-NMR (300 MHz, CDCl$_3$): δ 1.04-1.20 (s, 3H), 1.24-1.84 (m, 9H), 2.00-2.52 (m, 8H), 2.88-2.96 (m, 3H), 3.40-3.70 (m, 8H), 3.70-3.92 (s, 3H), 6.22-6.44 (m, 2H), 6.96-7.12 (d, 1H), 7.20-7.28 (s, 1H).

EXAMPLE 154: $^1$H-NMR (300 MHz, CDCl$_3$): δ 1.16-1.22 (s, 3H), 1.22-1.88 (m, 9H), 2.04-2.56 (m, 8H), 2.76-2.96 (m, 3H), 3.48-3.70 (m, 8H), 3.72-3.84 (s, 3H), 6.48-6.60 (m, 2H), 7.00-7.12 (d, 1H), 7.16-7.24 (s, 1H).

Examples 155 and 156

N-Benzyl-4-(3-hydroxy-(17,16-c)-(1'-methyl)-pyrazolyl-estra-1,3,5(10)-trieno-15α-yl)-butyramide N-Benzyl-4-(3-hydroxy-(17,16-c)-(2'-methyl)-pyrazolyl-estra-1,3,5(10)-trieno-15α-yl)-butyramide

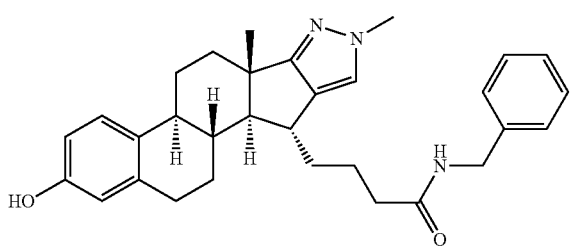

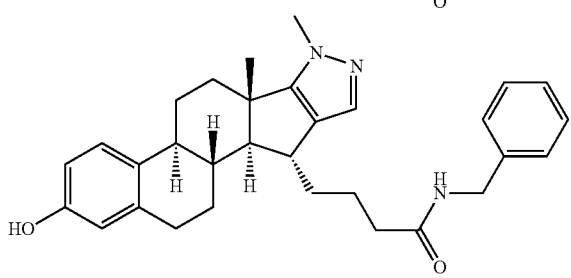

Starting from intermediate compound Xc, an allyl side chain was introduced into C15 position using 1,2-addition of allylbromide and subsequent rearrangement with potassium hydride according to steps 1 and 2 of SCHEME 8B, followed by construction of the pyrazol-ring according to D-(II)-(a). Ringclosure with methyl hydrazine gave a mixture of the corresponding isomers. Conversion of the allyl into the N-Benzyl-butyramide side chain was performed according to steps 3-5 of SCHEME 8B and to the reaction as depicted in general flow diagram Ib by reaction with benzylamine. Finally the obtained isomers were separated by preparative HPLC.

EXAMPLE 155: $^1$H-NMR (300 MHz, CDCl$_3$): δ 0.94-1.04 (s, 3H), 1.20-2.50 (m, 17H), 2.60-2.88 (m, 3H), 3.72-3.84 (s, 3H), 4.28-440 (s, 2H), 6.40-6.50 (s, 1H), 6.52-6.60 (d, 1H), 7.04-7.12 (d, 1H), 7.14-7.36 (m, 5H).

EXAMPLE 156: $^1$H-NMR (300 MHz, CDCl$_3$): δ 0.96-1.08 (s, 3H), 1.24-2.48 (m, 17H), 2.64-2.88 (m, 3H), 3.72-3.84 (s, 3H), 4.28-4.44 (s, 2H), 6.40-6.50 (s, 1H), 6.50-6.60 (d, 1H), 7.00-7.12 (d, 1H), 7.12-7.36 (m, 5H).

Examples 157 and 158

3-Hydroxy-15α-(4-morpholin-4-yl-4-oxo-butyl)-estra-1,3,5(10)-trien-[16,17-c]-(1'-methyl)-pyrazole 3-Hydroxy-15α-(4-morpholin-4-yl-4-oxo-butyl)-estra-1,3,5(10)-trien-[16,17-c]-(2'-methyl)-pyrazole

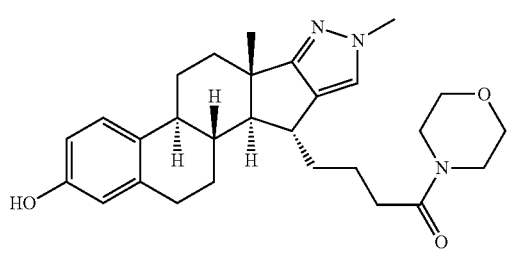

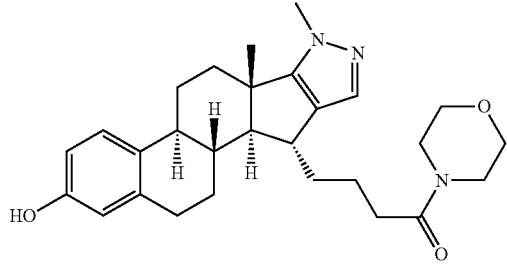

Examples 157 and 158 were prepared according to the procedure described for Examples 155 and 156 using morpholine as amine for the amide coupling step.

EXAMPLE 157: $^1$H-NMR (300 MHz, CDCl$_3$): δ 0.96-1.08 (s, 3H), 1.12-2.36 (m, 17H), 2.72-2.96 (m, 3H), 3.50-3.72 (m, 8H), 3.76-3.86 (s, 3H), 6.44-6.50 (s, 1H), 6.52-6.60 (d, 1H), 7.04-7.12 (d, 1H), 7.24-7.30 (s, 1H).

EXAMPLE 158: $^1$H-NMR (300 MHz, CDCl$_3$): δ 0.92-1.08 (s, 3H), 1.24-2.56 (m, 17H), 2.68-2.92 (m, 3H), 3.22-3.70 (m, 8H), 370-3.88 (s, 3H), 6.40-6.48 (s, 1H), 6.48-6.60 (d, 1H), 7.00-7.10 (d, 1H), 7.12-7.22 (s, 1H).

Examples 159 and 160

4-(3-Hydroxy-(17,16-c)-(1'-methyl)-pyrazolyl-estra-1,3,5(10)-trieno-15α-yl)-N-(5-methylthiazol-2-yl)-butyramide 4-(3-Hydroxy-(17,16-c)-(2'-methyl)-pyrazolyl-estra-1,3,5(10)-trieno-15α-yl)-N-(5-methylthiazol-2-yl)-butyramide

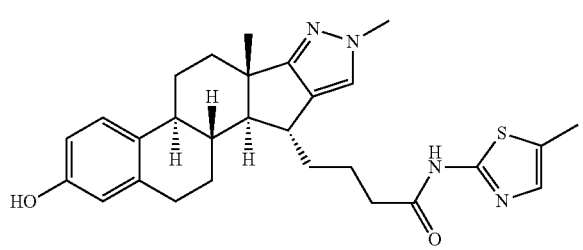

159

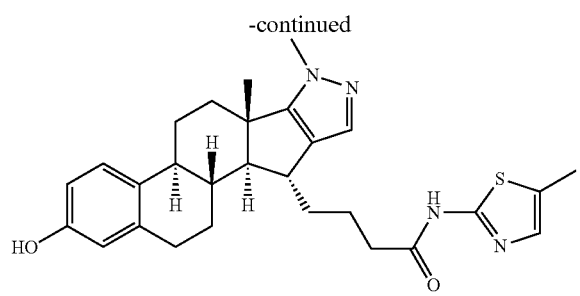

Examples 159 and 160 were prepared according to the procedure described for Examples 155 and 156 using 2-amino-5-methylthiazole for the amide coupling step.

EXAMPLE 159: $^1$H-NMR (300 MHz, CDCl$_3$): δ 0.80-0.90 (s, 3H), 0.90-2.48 (m, 20H), 2.56-2.80 (m, 3H), 3.60-3.68 (s, 3H), 6.36-6.42 (s, 1H), 6.44-6.52 (d, 1H), 6.84-6.92 (s, 1H), 6.96-7.04 (m, 2H).

EXAMPLE 160: $^1$H-NMR (300 MHz, CDCl$_3$): δ 0.84-0.96 (s, 3H), 0.96-2.48 (m, 20H), 2.58-2.80 (m, 3H), 3.60-3.72 (s, 3H), 6.36-6.44 (s, 1H), 6.44-6.56 (d, 1H), 6.84-6.92 (s, 1H), 6.96-7.04 (d, 1H), 7.04-7.08 (s, 1H).

Example 161

3-Hydroxy-15β-(4-morpholin-4-yl-4-oxo-butyl)-estra-1,3,5(10)-trien-[16,17-c]-isoxazole

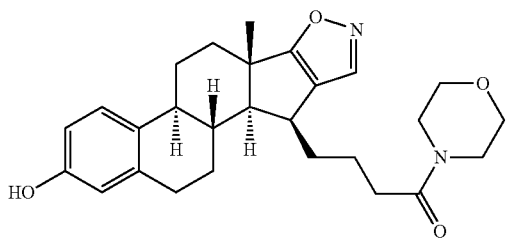

Starting from intermediate compound Xc, an allyl side chain was introduced into C15 position using 1,4-addition of allylbromide according to step 1 of SCHEME 7C, followed by construction of the oxazole-ring according to D-(II)-(c) using hydroxylamine for the ringclosure. Conversion of the allyl into the 4-morpholin-4-yl-4-oxo-butyl side chain can be performed according to steps 2-4 of SCHEME 7C and to the reaction as depicted in general flow diagram Ib by amide coupling with morpholine.

Example 162

3-Hydroxy-15β-(4-morpholin-4-yl-4-oxo-butyl)-estra-1,3,5(10)-trien-[16,17-c]-pyrazole

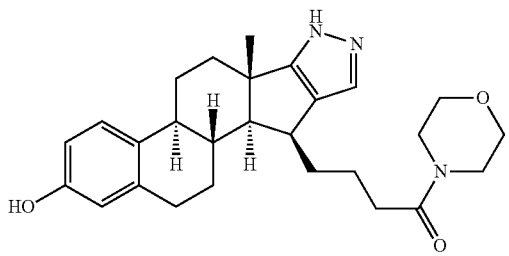

Starting from intermediate compound Xc, an allyl side chain was introduced into C15 position using 1,4-addition of allylbromide according to step 1 of SCHEME 7C, followed by construction of the pyrazol-ring according to D-(II)-(a) using benzylhydrazine for the ringclosure to give a protected pyrazol. Conversion of the allyl into the 4-morpholin-4-yl-4-oxo-butyl side chain was performed according to steps 2 (metathesis) and 3 (saponification) of SCHEME 7C, followed by amide coupling with morpholine according to general flow diagram Ib. Finally, reduction of the double bond and debenzylation gave the desired end product No. 162.

$^1$H-NMR (300 MHz, CDCl$_3$): δ 1.08-1.20 (s, 3H), 1.22-2.48 (m, 17H), 2.72-3.00 (m, 3H), 3.40-3.76 (m, 8H), 6.52-6.56 (s, 1H), 6.56-6.60 (d, 1H), 7.00-7.12 (d, 1H), 7.22-7.28 (s, 1H).

IV. Compounds Carrying a Sulphamate, Carbamate, Phosphonate, Thiophosphonate, Sulphonate, Phosphate or Sulphate Group in R1

Example 163

3-Sulphamate-15β-(4-morpholin-4-yl-4-oxo-butyl)-estra-1,3,5(10)-trien-17-one

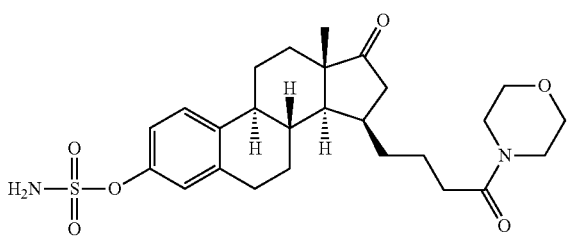

Example 163 was prepared from the Intermediate No. 1 named 3-Hydroxy-15β-(4-morpholin-4-yl-4-oxo-butyl)-estra-1,3,5(10)-trien-17-one of formula (VIβ-3a)-1 using sulfamoyl chloride as sulfamoylating agent.

Example 164

3-Sulphate-15β-(4-morpholin-4-yl-4-oxo-butyl)-estra-1,3,5(10)-trien-17-one

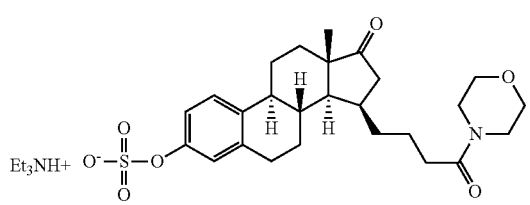

Example 164 was prepared from the Intermediate No. 1 named 3-Hydroxy-15β-(4-morpholin-4-yl-4-oxo-butyl)-estra-1,3,5(10)-trien-17-one of formula (VIβ-3a)-1 using sulfur trioxide-triethylamine complex: The estron derivative (VIβ-3a)-1 (0.25 mmol) and sulfur trioxide-triethylamine complex (54.4 mg, 0.30 mmol, "Fluka") were stirred in anhydrous DMF (1 ml) at RT overnight. Ca. 0.3 g silica gel (for column chromatography) was added, and the solvent was removed in high vacuum at 35° C. The remaining powder was loaded on the column prepacked with ca. 6 g silica gel. Flash chromatography with afforded the desired triethylammonium phenol sulfate.

Biological Testing Materials and Methods

Inhibition of the 17β-Hydroxysteroid Dehydrogenase Type 1 Enzyme

17β-HSD1 purification: Recombinant baculovirus was generated by the "Bac to Bac Expression System" (Invitrogen). Recombinant bacmid was transfected to Sf9 insect cells using "Cellfectin Reagent" (Invitrogen). 60 h later cells were harvested; the microsomal fraction was isolated as described by Puranen et al. (1994). Aliquots were stored frozen until determination of enzymatic activity.

Assay—Inhibition of recombinant human 17β-hydroxysteroid dehydrogenase type 1: Recombinant protein (0.1 µg/ml) was incubated in 20 mM $KH_2PO_4$ pH 7.4 with 30 nM 3H-estrone and 1 mM NADPH for 30 min at RT, in the presence of potential inhibitors at concentrations of 1 µM or 0.1 µM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min of acetonitrile:water 48:52 as running solvent. Radioactivity was monitored in the eluate by a Packard Flow Scintillation Analyzer. Total radioactivity for estrone and estradiol were determined in each sample and percent conversion of estrone to estradiol was calculated according to the following formula:

$$\% \text{ conversion} = 100 \times \frac{\{(cpm \text{ estradiol in sample with inhibitor})/[(cpm \text{ estrone in sample with inhibitor}) + (cpm \text{ estradiol in sample with inhibitor})]\}}{\{(cpm \text{ estradiol in sample without inhibitor})/[(cpm \text{ estrone in sample without inhibitor}) + (cpm \text{ estradiol in sample without inhibitor})]\}}$$

Percent inhibition was calculated as follows: % inhibition=100−% conversion

The values "% inhibition" were determined for exemplified compounds, and the results are summarized in Table 19.

TABLE 19

Inhibition of 17β-HSD enzyme type I

| Compound No. | Compound Structure | Inhibition of rec. 17β-HSD1 | |
|---|---|---|---|
| | | 100 nM | 1 µm |
| 2 | | 54.8 | 74.8 |
| 3 | | 19.6 | 71.2 |
| 6 | | 37.9 | 79.3 |
| 30 | | 39.8 | 73.6 |

TABLE 19-continued

Inhibition of 17β-HSD enzyme type I

| Compound No. | Compound Structure | Inhibition of rec. 17β-HSD1 | |
|---|---|---|---|
| | | 100 nM | 1 μm |
| 32 | | 50.0 | 79.0 |
| 34 | | 68.8 | 71.9 |
| 36 | | 56.9 | 78.1 |
| 37 | | 64.0 | 74.7 |
| 38 | | 51.0 | 76.7 |

TABLE 19-continued
Inhibition of 17β-HSD enzyme type I
| Compound No. | Compound Structure | Inhibition of rec. 17β-HSD1 | |
|---|---|---|---|
| | | 100 nM | 1 μm |
| 40 | 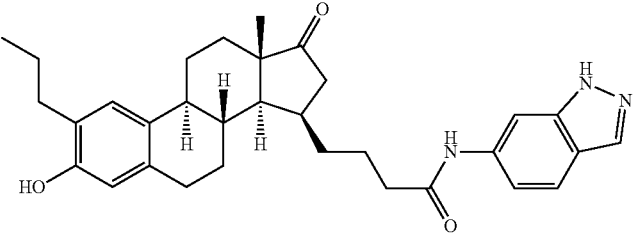 | 72.0 | 75.8 |
| 41 | 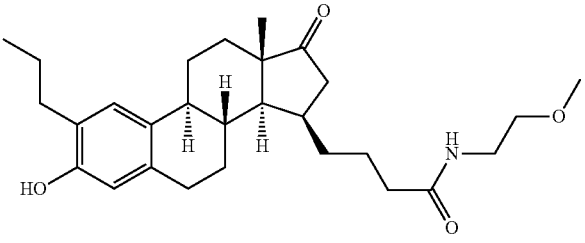 | 25.9 | 70.4 |
| 42 | 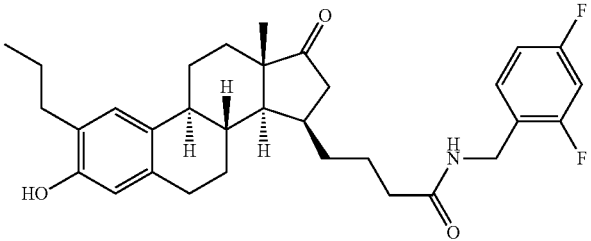 | 53.3 | 71.7 |
| 44 | 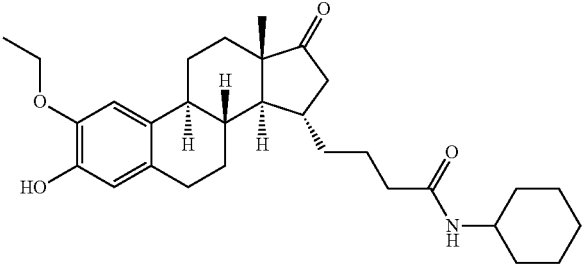 | 55.5 | 75.0 |
| 45 | 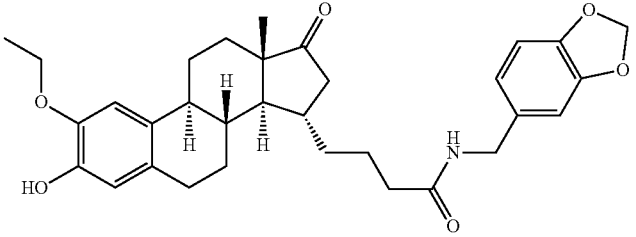 | 54.0 | 75.7 |

TABLE 19-continued

Inhibition of 17β-HSD enzyme type I

| Compound No. | Compound Structure | Inhibition of rec. 17β-HSD1 | |
|---|---|---|---|
| | | 100 nM | 1 μm |
| 52 | | 50.0 | 72.2 |
| 55 | | 42.6 | 71.9 |
| 59 | | 56.1 | 69.7 |
| 67 | | 42.5 | 73.2 |
| 71 | | 45.8 | 70.6 |

TABLE 19-continued

Inhibition of 17β-HSD enzyme type I

| Compound No. | Compound Structure | Inhibition of rec. 17β-HSD1 | |
|---|---|---|---|
| | | 100 nM | 1 μm |
| 78 | | 40.6 | 72.0 |
| 83 | | 53.9 | 71.6 |
| 90 | | 63.5 | 81.6 |
| 91 | | 32.0 | 85.0 |
| 93 | | 59.5 | 86.7 |
| 102 | | 41.6 | 70.6 |

TABLE 19-continued

Inhibition of 17β-HSD enzyme type I

| Compound No. | Compound Structure | Inhibition of rec. 17β-HSD1 | |
|---|---|---|---|
| | | 100 nM | 1 μm |
| 106 | | 36.7 | 68.0 |
| 109 | | 35.1 | 70.7 |
| 111 | | 50.6 | 68.3 |
| 113 | | 47.2 | 76.9 |
| 116 | | 49.3 | 82.4 |
| 120 | | 37.3 | 85.0 |

TABLE 19-continued

Inhibition of 17β-HSD enzyme type I

| Compound No. | Compound Structure | Inhibition of rec. 17β-HSD1 | |
|---|---|---|---|
| | | 100 nM | 1 μm |
| 121 | | 63.6 | 92.5 |
| 122 | | 34.0 | 77.9 |
| 125 | | 29.2 | 76.9 |
| 127 | | 21.1 | 81.3 |
| 128 | | 21.2 | 71.7 |

TABLE 19-continued

Inhibition of 17β-HSD enzyme type I

| Compound No. | Compound Structure | Inhibition of rec. 17β-HSD1 | |
|---|---|---|---|
| | | 100 nM | 1 μm |
| 129 | | 33.1 | 76.9 |
| 131 | | 19.8 | 71.9 |
| 133 | | 71.4 | 90.6 |
| 134 | | 50.5 | 88.6 |
| 161' | | 21.0 | 74.0 |

TABLE 19-continued

Inhibition of 17β-HSD enzyme type I

| Compound No. | Compound Structure | Inhibition of rec. 17β-HSD1 | |
| --- | --- | --- | --- |
| | | 100 nM | 1 μm |
| 162 | (structure) | 63.0 | 93.0 |
| 163 | (structure) | 10.0 | 43.0 |
| 164 | (structure) | 3.0 | 27.0 |

2. Estrogen Receptor Binding Assay

The binding affinity of the compounds of the invention to the estrogen receptor α and to the estrogen receptor β may be determined according to the in vitro ER binding assays described by Koffman et al (1991). Alternatively, an estrogen receptor binding assay may be performed according to international patent application WO 00/07996.

3. Estrogen Receptor Transactivation Assays

Compounds of the invention showing binding affinity towards the estrogen receptor may be further tested with regard to their individual estrogenic or anti-estrogenic potential (agonistic binding or antagonistic binding to the ERα or ERβ). The determination of the estrogen receptor agonist activity may be performed according to an in vitro assay system using the MMTV-ERE-LUC reporter system which is for example described within published US patent application US 2003/0170292:

To assay estrogen receptor agonist activity, Hela cells are grown in 24-well microtiter plates and then transiently co-transfected with two plasmids using lipofectamine. The first plasmid comprises DNA encoding human estrogen receptor (either ER-alpha or ER-beta), and the second plasmid comprises an estrogen-driven reporter system comprising: a luciferase reporter gene (LUC) whose transcription is under the control of upstream regulatory elements comprising 4 copies of the vitellogenin estrogen response element (ERE) cloned into the mouse mammary tumor virus (MMTV) promoter (the full name for the reporter system being "MMTV-ERE-LUC"). Cells are exposed to the compounds of the invention in RPMI 1640 medium, supplemented with 10% charcoal-treated fetal calf serum, 2 mM L-glutamine, 0.1 mM non-essential amino acids and 1 mM sodium pyruvate for 42-48 h at 37° C. in a 5% carbon dioxide incubator. Concurrently, cells exposed to estradiol (1 nM) serve as positive controls. Replicate wells exposed to the solvent in which the compounds of the invention are dissolved (i.e. ethanol or methanol) are used as negative controls. After the 42-48 h incubation period, cells are rinsed with phosphate buffered saline (PBS), lysis buffer (Promega Corp) is added, and cell lysates are collected for measurement of luciferase activity with a luminometer. Estrogenic activity of the compounds of the invention is expressed as fold-increase in luciferase activity as compared to that observed in negative control cells.

Alternatively, the determination of the estrogen receptor transactivation activity (estrogenicity assay or agonist assay) and of the inhibitory potency of transactivation activity (anti-estrogenicity assay or antagonist assay) may be performed according to international patent application WO 00/07996.

4. STS Assay—Inhibition of Steroid Sulphatase Activity in MCF-7 Cells

Steroid sulphate activity is measured in vitro using intact MCF-7 human breast cancer cells. This hormone dependent cell line is widely used to study the control of human breast cancer cell growth. It possesses significant steroid sulphate activity and is available in the U.S.A. form the American Type Culture Collection (ATCC) and in the U.K. (e.g. from The Imperial Cancer Research Fund).

Cells are maintained in Minimal Essential Medium (MEM) (Flow Laboratories, Irvine, Scotland) containing 20 mM HEPES, 5% foetal bovine serum, 2 mM glutamin, non-essential amino acids and 0.075% sodium bicarbonate. Up to 30 replicate 25 cm$^2$ tissue culture flasks are seeded with approximately $1\times10^5$ cells/flask using the above medium. Cells are grown to 80% confluency and the medium is changed every third day.

Intact monolayers' of MCF-7 cells in triplicate 25 cm$^2$ tissue culture flasks are washed with Earle's Balanced Salt Solution (EBSS from ICN Flow, High Wycombe, U.K.) and incubated for 3-4 h at 37° C. with 5 pmol ($7\times10^5$ dpm) [6,7-$^3$H] oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1fM; 0.01 pM; 0.1 pM; 1 pM; 0.01 nM; 0.1 nM; 1 nM; 0.01 mM; 0.1 mM; 1 mM). After incubation each flask is cooled and the medium (1 ml) is pipette into separate tubes containing [$^{14}$C] oestrone ($7\times10^3$ dpm) (specific activity 97 Ci/mmol from Amersham International Radiochemical Centre, Amersham, U.K.). The mixture is shaken thoroughly for 30 seconds with toluene (5 ml). Experiments have shown that >90% [$^{14}$C] oestrone and <0.1% [$^3$H] oestrone-3-sulphate is removed from the aqueous phase by this treatment. A portion (2 ml) of the organic phase is removed, evaporated and the $^3$H and $^{14}$C content of the residue determined by scintillation spectrometry. The mass of oestrone-3-sulphate hydrolyse was calculated from the $^3$H counts obtained (corrected for the volumes of the medium and organic phase used, and for recovery of [$^{14}$C] oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method.

Results for steroid sulphate activity are expressed as the mean±1 S.D. of the total product (oestrone+oestradiol) formed during the incubation period (20 h) calculated for 10$^6$ cells and, for values showing statistical significance, as a percentage reduction (inhibition) over incubations containing no oestrone-3-sulphamate. Unpaired Student's t-test was used to test the statistical significance of results.

5. CHO/STS Assay

CHO cells stably transfected with human steroid sulfatase (CHO/STS) are seeded into microtiter plates. After reaching approximately 90% confluency, they are incubated overnight with graded concentrations of test substances (e.g. compounds of the present invention or compounds for use in the present invention). They are then fixed with 4% paraformaldehyde for 10 min at RT and washed 4 times with PBS, before incubation with 100 µl/well 0.5 mM 4-methylumbelliferyl sulfate (MUS), dissolved in 0.1 M Tris-HCl, pH 7.5. The enzyme reaction is carried out at 37° C. for 30 min. Then 50 µl/well stop solution (1M Tris-HCl, pH 10.4) are added. The enzyme reaction solutions are transferred to white plates (Microfluor, Dynex, Chantilly, Va.) and read in a Fluoroskan II or Tecan fluorescence microtiter plate reader. Reagent blanks are subtracted from all values. Optionally, for drug testing, the fluorescence units (FU) are divided by the optical density readings after staining cellular protein with sulforhodamine B (OD$_{550}$), in order to correct for variations in cell number. IC$_{50}$ values are determined by linear interpolation between two bracketing points. In each assay with inhibitors, estrone 3-O-sulfamate is run as a reference compound, and the IC50 values are normalized to estrone 3-O-sulfamate (relative IC$_{50}$=IC$_{50}$ compound/IC$_{50}$ estrone 3-O-sulfamate).

6. STS Inhibition in Placenta Microsomes

Sulphatase-positive human placenta from normal term pregnancies are thoroughly minced with scissors and washed once with cold phosphate buffer (pH 7.4, 50 mM) then re-suspended in cold phosphate buffer (5 ml/g tissue). Homogenisation is accomplished with an Ultra-Turrax homogeniser, using three 10 second bursts separated by 2 min cooling periods in ice. Nuclei and cell debris are removed by centrifuging (4° C.) at 2000 g for 30 min and portions (2 ml) of the supernatant are stored at 20° C. The protein concentration of the supernatants is determined by the method of Bradford [Anal. Biochem. 72:248-254 (1976)].

Incubations (1 ml) are carried out using a protein concentration of 100 mg/ml, substrate concentration of 20 mM [6,7-$^3$H] oestrone-3-sulphate (specific activity 60 Ci/mmol from New England Nuclear, Boston, Mass., U.S.A.) and an incubation time of 20 min at 37° C. If necessary eight concentrations of compounds are employed: 0 (i.e. control); 0.05 mM; 0.1 mM; 0.2 mM; 0.4 mM; 0.6 mM; 0.8 mM; and 1.0 mM. After incubation each sample is cooled and the medium (1 ml) was pipetted into separate tubes containing [$^{14}$C] oestrone ($7\times10^3$ dpm) (specific activity 97 Ci/mmol from Amersham International Radiochemical Centre, Amersham, U.K.). The mixture is shaken thoroughly for 30 seconds with toluene (5 ml). Experiments have shown that >90% [$^{14}$C] oestrone and <0.1% [3H] oestrone-3-sulphate is removed from the aqueous phase by this treatment.

A portion (2 ml) of the organic phase was removed, evaporated and the $^3$H and $^{14}$C content of the residue determined by scintillation spectrometry. The mass of estrone-3-sulphate hydrolyse is calculated from the $^3$H counts obtained (corrected for the volumes of the medium and organic phase used, and for recovery of [$^{14}$C] oestrone added) and the specific activity of the substrate.

7. Animal Assay Model for Determining STS Activity

The inhibition of STS activity in vivo may be determined by using the compounds of the present invention in an animal model, in particular in ovariectomised rats. In this model compounds which are estrogenic stimulate uterine growth. The compound (10 mg/Kg/day for five days) was administered orally to rats with another group of animals receiving vehicle only (propylene glycol). A further group received the compound EMATE subcutaneously in an amount of 10 µg/day for five days. At the end of the study samples of liver tissue were obtained and oestrone sulphate activity assayed using 3H oestrone sulphate as the substrate as previously described (see international application WO 96/15257).

The foregoing description and examples have been set forth merely to illustrate the invention and are not intended to be limiting. Since modifications of the described embodiments incorporating the spirit and substance of the invention may occur to person skilled in the art, the invention should be construed broadly to include all variations within the scope of the appended claims and equivalents thereof.

CITED LITERATURE

Akanni & Marples (1993) "Preparation of 16-formylestradiol and the 16-(alpha-methylenebutanolide) derivative" Steroids 58(5):234-8.

Cushman et al (1995) "Synthesis, antitubulin and antimitotic activity, and cytotoxicity of analogs of 2-methoxyestradiol, an endogenous mammalian metabolite of estradiol that inhibits tubulin polymerization by binding to the colchicine binding site." J Med. Chem. 38(12):2041-9.

Cushman et al (2002) "The effect of exchanging various substituents at the 2-position of 2-methoxyestradiol on cytotoxicity in human cancer cell cultures and inhibition of tubulin polymerization." J Med. Chem. 45(21):4748-54.

Day et al (2003) "The effects of 2-substituted oestrogen sulphamates on the growth of prostate and ovarian cancer cells." J Steroid Biochem Mol. Biol. 2003 84(2-3):317-25.

Edwards et al. (1990) "Difluoromethyldiphenylphosphine oxide. A new reagent for conversion of carbonyl compounds to 1,1-difluoroolefins." Tetrahedron Lett 31(39): 5571-5574

EP0367576—Estrogen nucleus derivatives for use in the inhibition of sex steroid activity Gonzalez et al (1982) "Synthesis and pharmacological evaluation of 8α-estradiol derivatives" Steroids 40(2):171-188

Koffman et al (1991) "Evidence for involvement of tyrosine in estradiol binding by rat uterus estrogen receptor." J. Steroid. Biochem. Mol. Biol. 38(2):135

Labaree et al (2003) "Synthesis and Evaluation of B-, C- and D-ring substituted estradiol carboxylic acid esters as locally active estrogens" J. Med. Chem. 46:1886-1904

Labrie et al (1997) "The key role of 17 beta-hydroxysteroid dehydrogenases in sex steroid biology." Steroids, 62:148-58

Lawrence et al (2005) "Novel and potent 17beta-hydroxysteroid dehydrogenase type 1 inhibitors." J Med. Chem. 48(8):2759-62.

Ley et al (1994) "Tetrapropylammonium perruthenate, Pr4N+RuO4-, TPAP: a catalytic oxidant for organic synthesis" Synthesis. 07:639-666

Liu et al (1992) "Synthesis of high affinity fluorine-substituted ligands for the androgen receptor. Potential agents for imaging prostatic cancer by positron emission tomography." J Med. Chem. 35(11):2113-29

Lunn & Farkas (1968) "The adamantyl carbonium ion as a dehydrogenating agent, its reactions with estrone" Tetrahedron 24(23):6773-6776.

Mindnich et al (2004) "The role of 17 beta-hydroxysteroid dehydrogenases" Mol Cell Endocrinol. 218(1-2):7-20. Review Mohanakrishnan & Cushman (1999) "Pd(0)-Mediated Cross Coupling of 2-Iodoestradiol with Organozinc Bromides: A General Route to the Synthesis of 2-Alkynyl, 2-Alkenyl and 2-Alkylestradiol Analogs" Synlett 1999(07):1097-1099

Nambara et al. (1976) "Synthesis of Estetrol Monoglucuronides" Steroids 27:111-122

Nussbaumer & Billich (2003) "Steroid sulfatase inhibitors." Expert Opin. Ther. Patents 13(5):605-625

Nussbaumer & Billich (2004) "Steroid sulfatase inhibitors." Med Res Rev. 24(4):529-76

Oda et al (1989) "The hydrogenation of alpha-hydroxymethylene-ketone derivatives to alpha-hydroxymethyl-ketone derivatives with a cell-free system of Streptomyces cinereocrocatus" Chem Pharm Bull (Tokyo) 37(2):502-5.

Page et al (1990) "Efficient regioselective a-ring functionalization of oestrogens" Tetrahedron 46(6):2059-2068

Pelletier & Poirier (1996) "Synthesis and evaluation of estradiol derivatives with 16α-(bromoalkylamide), 16α-(bromoalkyl) or 16α-(bromoalkynyl) side chain as inhibitors of 17β-hydroxysteroid dehydrogenase type 1 without estrogenic activity" Bioorg Med Chem, 4(10):1617-1628.

Poirier (2003) "Inhibitors of 17 beta-hydroxysteroid dehydrogenases" Curr Med. Chem. 10:453-77

Poirier et al. (1991) "Synthesis of 17β-estradiol derivatives with N-Butyl, N-methyl alkylamide side chain at position 15." Tetrahedron, 47(37):7751-7766

Poirier et al. (1996) "D-Ring alkylamine derivatives of estradiol: effect on ER-binding affinity and antiestrogenic activity" Bioorg Med Chem Lett 6(21):2537-2542.

Poirier et al (1998) "A 6α-(Thiaheptanamide) Derivative of Estradiol as inhibitor of 17β-Hydroxysteroid Dehydrogenase Type 1", J. Steroid Biochem. Molec. Biol., 64:83-90

Puranen et al (1994) "Site-directed mutagenesis of the putative active site of human 17 beta-hydroxysteroid dehydrogenase type 1" Biochem. J. 304:289-93.

Rao & Cessac (2002) "A new, practical synthesis of 2-methoxyestradiols." Steroids. 67(13-14):1065-70.

Reed et al (2005) "Steroid sulfatase: molecular biology, regulation, and inhibition." Endocr Rev. 26(2):171-202.

Sam et al. (1998) "C16 and C17 Derivatives of Estradiol as Inhibitors of 17β-Hydroxysteroid Dehydrogenase Type 1: Chemical Synthesis and Structure-Activity Relationships", Drug Design and Discovery, 15:157-180

Schneider et al (1983) "A convenient method for the formation of 16-methylene-17-keto steroids" Synthesis, 8:665-9.

Schwarz et al (2001) "Studies on modified estrogens: Towards the synthesis of novel 14,15-cyclopropa[a]estra-1,3,5(10),8-tetraenes" Pharmazie 56(11):843-849

Tamaya et al. (1985) "Comparison of cellular levels of steroid receptors in uterine leiomyoma and myometrium." Acta Obstet Gynecol Scand., 64:307-9

Tremblay & Poirier (1998) "Overview of a Rational Approach to Design Type I 17β-Hydroxysteroid Dehydrogenase Inhibitors Without Estrogenic Activity: Chemical Synthesis and Biological Evaluation", J. Steroid Biochem. Molec. Biol., 66:179-191

US 2003/0170292
U.S. Pat. No. 3,275,623
U.S. Pat. No. 3,347,878
U.S. Pat. No. 3,413,321
U.S. Pat. No. 6,043,236

Verdier-Pinard et al (2000) "A steroid derivative with paclitaxel-like effects on tubulin polymerization." Mol. Pharmacol. 57(3):568-75.

Wang & Ruan (1994) "Trifluoromethylation of steroidal ketones" J. Fluorine Chem. 69(1):1-3

WO 93/05063
WO 96/15257
WO 96/28462
WO 00/07996
WO 02/32409
WO 03/017973
WO 2004/080271
WO 2004/085345
WO 2004/085457
WO 2004/085459
WO 2005/047303
WO 2006/003012 (also published as US2006052461)
WO 2006/003013 (also published as US2006009434)
WO 2006/027347

Wölfling et al (2003) "Synthesis and receptor-binding examinations of the normal and 13-epi-D-homoestrones and their 3-methyl ethers" Steroids 68:277-288

Xenos & Catsoulacos (1985) "Synthesis of 16,17-pyrazolo-fused derivatives of A-homo-steroidal ring A lactams" Synthesis 3:307-9

Yoshikawa et al. (2002) "Diastereo- and Enantioselective Direct Catalytic Aldol Reaction of 2-Hydroxyacetophenones with Aldehydes Promoted by a Heteropolymetallic Complex Catalytic Asymmetric Synthesis of anti-1,2-Diols" J. Org. Chem. 67(8); 2556-2565.

What is claimed is:

1. A compound corresponding to formula I,

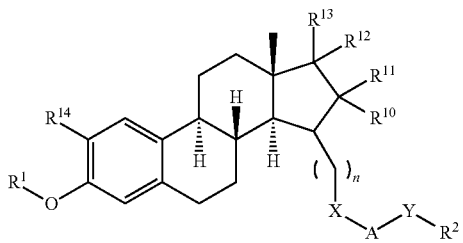

(I)

wherein —X-A-Y— together represent a group selected from
(a) —CO—NR$^4$—,
(b) —CO—O—,
(c) —CO—,
(d) —CO—NH—NR$^4$—,
(e) —NH—CO—NR$^4$—,
(f) —NH—CO—O—,
(g) —NH—CO—,
(h) —NH—CO—NH—SO$_2$—,
(i) —NH—SO$_2$—NR$^4$—,
(j) —NH—SO$_2$—O—,
(k) —NH—SO$_2$—,
(l) —O—CO—NR$^4$—,
(m) —O—CO—,
(n) —O—CO—NH—SO$_2$—NR$^4$—, and
(o) —O—;

n represents 1, 2, 3, 4, 5 or 6, or, if —X-A-Y— represents —CO—NR$^4$—, —CO—O—, —CO—, or —CO—NH—NR$^4$—, then n may also represent 0;

R$^1$ is selected from:
(a) —H,
(b) —(C$_1$-C$_6$)alkyl, which is optionally substituted with at least one of halogen, nitril, —OR$^6$, —SR$^6$, or —COOR$^6$; the number of the substituents being 1, 2 or 3 for halogen, and 1 or 2 for any combination of the halogen, nitril, —OR$^6$, —SR$^6$, or —COOR$^6$ moieties,
(c) -phenyl, which is optionally substituted with at least one of halogen, nitril, —OR$^6$, —SR$^6$, —R$^6$, or —COOR$^6$, the number of the substituents being up to perhalo for halogen, and 1 or 2 for any combination of the halogen, nitril, —OR$^6$, —SR$^6$, —R$^6$ or —COOR$^6$ moieties,
(d) —(C$_1$-C$_4$)alkyl-phenyl, wherein the alkyl portion is optionally substituted with up to three halogens; and the phenyl portion is optionally substituted with at least one of halogen, nitril, —OR$^6$, —SR$^6$, —R$^6$ or —COOR$^6$, the number of substituents on the phenyl portion being up to perhalo for halogen, and 1 or 2 for any combination of the halogen, nitril, —OR$^6$, —SR$^6$, —R$^6$ or —COOR$^6$ moieties,
(e) —SO$_2$—NR$^3$R$^{3'}$,
(f) —CO—NR$^3$R$^{3'}$,
(g) —PO(OR$^{16}$)—R$^3$,
(h) —PS(OR$^{16}$)—R$^3$,
(i) —PO(OR$^{16}$)—O—R$^3$,
(j) —SO$_2$—R$^3$, and
(k) —SO$_2$—O—R$^3$;
wherein
R$^6$ represents H, —(C$_1$-C$_4$)alkyl or halogenated —(C$_1$-C$_4$) alkyl;
R$^3$ and R$^{3'}$ are independently selected from H, alkyl, aryl and arylalkyl, or R$^3$ and R$^{3'}$ form, together with the nitrogen atom to which R$^3$ and R$^{3'}$ are attached, a heterocyclic 4-, 5-, 6-, 7- or 8-membered ring, which is optionally saturated, partly unsaturated, or aromatic; which optionally contains up to three additional heteroatoms selected from N, O and S, the number of additional N atoms being 0, 1, 2 or 3 and the number of O and S atoms each being 0, 1 or 2; and R$^{16}$ represents —H, alkyl, or arylalkyl;

R$^2$ and R$^4$ are independently selected from:
(a) —H,
(b) optionally substituted alkyl,
(c) optionally substituted acyl, provided that —X-A-Y— represent —CO—NH—NR$^4$—,
(d) optionally substituted aryl,
(e) optionally substituted heteroaryl, and
(f) optionally substituted cycloheteroalkyl,
or R$^2$ and R$^4$ form, together with the nitrogen atom to which R$^2$ and R$^4$ are attached, a heterocyclic 4-, 5-, 6-, 7- or 8-membered ring, which is optionally saturated, partly unsaturated, or aromatic; which optionally contains up to three additional heteroatoms selected from N, O and S, the number of additional N atoms being 0, 1, 2 or 3 and the number of O and S atoms each being 0, 1 or 2; and which ring is optionally part of a multiple condensed ringsystem, wherein the ring or the ring-system is optionally substituted;

the substituents R$^{10}$, R$^{11}$, R$^{12}$ and R$^{13}$ together with the carbon atoms to which they are attached, form a structure

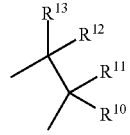

which is selected from the group of

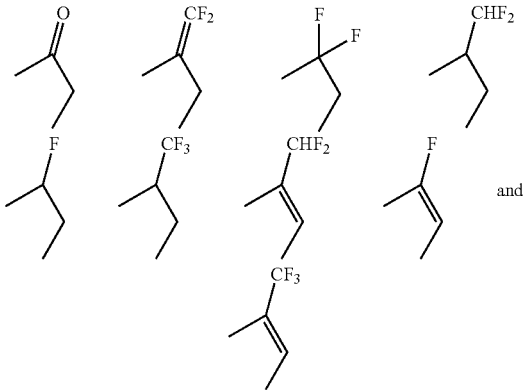

or, the substituents R$^{10}$, R$^{11}$, R$^{12}$ and R$^{13}$ together with the carbon atoms to which they are attached, form a heterocyclic 5- or 6-membered ring, which is partly unsaturated or aromatic, which contains one, two or three heteroatoms independently selected from N, O and S, the number of N atoms being 0, 1, 2 or 3 and the number of O and S atoms each being 0, 1 or 2, wherein one heteroatom is directly attached to the C17 C-atom of the steroidal core; and which ring is optionally substituted with an alkyl group;

R$^{14}$ represents an alkyl, alkoxy, or alkoxy-alkyl group, or

R$^{14}$ may also represent —H, provided that R$^1$ represents —SO$_2$—NR$^3$R$^{3'}$, —CO—NR$^3$R$^{3'}$, —PO(OR$^{16}$)—R$^3$, —PS(OR$^{16}$)—R$^3$, —PO(OR$^{16}$)—OR$^3$, —SO$_2$—R$^3$, or —SO$_2$—OR$^3$;

or a pharmaceutically acceptable salt thereof.

2. A compound according to claim 1,
wherein $R^2$ and $R^4$ are independently selected from:
- (a) —H, wherein, if —X-A-Y— together represents —CO—O— or —CO—, then $R^2$ is different from —H,
- (b) —$(C_1-C_{12})$alkyl, optionally substituted with up to five substituents independently selected from the group consisting of halogen, hydroxyl, thiol, nitrile, alkoxy, aryloxy, arylalkyloxy, amino, amido, alkylthio, arylthio, arylalkylthio, sulfamoyl, sulfonamide, acyl, carboxyl, acylamino, aryl, which aryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, carboxyl-$(C_1-C_6)$alkyl, thiol, nitrile, sulfamoyl, sulfonamide, carboxyl, aryloxy, arylalkyloxy, $(C_1-C_6)$alkylthio, arylthio, arylalkylthio, amino, amido, acyl, acylamino and heteroaryl; or which aryl is optionally substituted by two groups which are attached to adjacent carbon atoms and are combined into a saturated or partly unsaturated cyclic 5, 6, 7, or 8-membered ring system, optionally containing up to three heteroatoms selected from N, O and S, the number of N atoms being 0, 1, 2 or 3 and the number of O and S atoms each being 0, 1 or 2;
  - heteroaryl, which heteroaryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, carboxyl-$(C_1-C_6)$alkyl, thiol, nitrile, sulfamoyl, sulfonamide, carboxyl, aryloxy, arylalkyloxy, $(C_1-C_6)$alkylthio, arylthio, arylalkylthio, amino, amido, acyl, acylamino, aryl-$(C_1-C_4)$-alkyl and aryl;
    - wherein each aryl group is optionally substituted with up to three substituents independently selected from the group consisting of hydroxyl, halogen, $(C_1-C_6)$alkoxy, $(C_1-C_6)$alkyl, halogenated $(C_1-C_6)$alkyl and halogenated $(C_1-C_6)$alkoxy; and
  - cycloheteroalkyl, which cycloheteroalkyl group is optionally substituted with up to three substituents independently selected from the group consisting of oxo, $(C_1-C_8)$-alkyl, aryl, aryl-$(C_1-C_4)$-alkyl, hydroxyl, $(C_1-C_6)$alkoxy, carboxyl-$(C_1-C_6)$alkyl, thiol, nitrile, sulfamoyl, sulfonamide, carboxyl, aryloxy, arylalkyloxy, $(C_1-C_6)$alkylthio, arylthio, arylalkylthio, amino, amido, acyl, and acylamino,
    - wherein each aryl group is optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, and halogenated $(C_1-C_4)$-alkoxy);
- (c) acyl —(C=O)—R', wherein R' represents hydrogen, $(C_1-C_4)$alkyl, aryl, or aryl-$(C_1-C_4)$alkyl, or heteroaryl-$(C_1-C_4)$alkyl;
  - which aryl or aryl-$(C_1-C_4)$alkyl is optionally substituted in the aryl moiety with up to three substituents independently selected from the group consisting of hydroxyl, halogen, $(C_1-C_4)$alkoxy, $(C_1-C_4)$-alkyl or halogenated $(C_1-C_4)$alkyl;
- (d) aryl
  - which aryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, carboxyl-$(C_1-C_6)$alkyl, thiol, nitrile, nitro, sulfamoyl, sulfonamide, carboxyl, aryloxy, arylalkyloxy, $(C_1-C_6)$alkylsulfonyl, arylsulfonyl, $(C_1-C_6)$alkylthio, arylthio, arylalkylthio, amino, amido, acyl, acylamino and heteroaryl; or which aryl is optionally substituted by two groups which are attached to adjacent carbon atoms and are combined into a saturated or partly unsaturated cyclic 5, 6, 7, or 8-membered ring system, optionally containing up to three heteroatoms selected from N, O and S, the number of N atoms being 0, 1, 2 or 3 and the number of O and S atoms each being 0, 1 or 2;
- (e) heteroaryl,
  - which heteroaryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, carboxyl-$(C_1-C_6)$alkyl, thiol, nitrile, sulfamoyl, sulfonamide, arylsulfoxy, carboxyl, aryloxy, arylalkyloxy, $(C_1-C_6)$alkylsulfonyl, arylsulfonyl, $(C_1-C_6)$alkylthio, arylthio, arylalkylthio, amino, amido, acyl, acylamino, aryl-$(C_1-C_4)$-alkyl and aryl,
    - wherein each aryl group is optionally substituted with up to three substituents independently selected from the group consisting of hydroxyl, halogen, $(C_1-C_6)$alkoxy, $(C_1-C_6)$alkyl, halogenated $(C_1-C_6)$alkyl and halogenated $(C_1-C_6)$alkoxy; or
- (f) cycloheteroalkyl,
  - which cycloheteroalkyl is optionally substituted with up to three substituents independently selected from the group consisting of oxo, $(C_1-C_{14})$-alkyl, aryl, aryl-$(C_1-C_4)$-alkyl, hydroxyl, $(C_1-C_6)$alkoxy, carboxyl-$(C_1-C_6)$alkyl, thiol, nitrile, sulfamoyl, sulfonamide, carboxyl, aryloxy, arylalkyloxy, $(C_1-C_6)$alkylthio, arylthio, arylalkylthio, amino, amido, acyl, and acylamino,
    - wherein each aryl group is optionally further substituted with up to three substituents independently selected from the group consisting of hydroxyl, halogen, $(C_1-C_4)$-alkyl, $(C_1-C_4)$-alkoxy, halogenated $(C_1-C_4)$-alkyl, and halogenated $(C_1-C_4)$-alkoxy;
- or wherein $R^2$ and $R^4$ form together with the nitrogen atom, to which $R^2$ and $R^4$ are attached, a heterocyclic 4-, 5-, 6-, 7- or 8-membered ring, which is optionally saturated or partly unsaturated; which optionally contains up to three additional heteroatoms selected from N, O and S, the number of additional N atoms being 0, 1, 2 or 3 and the number of O and S atoms each being 0, 1 or 2; and which ring is optionally part of a multiple condensed ring-system,
  wherein the ring or the ring-system is optionally substituted
- (i) with up to three substituents independently selected from the group consisting of (C1-$C_8$)-alkyl, halogen, hydroxyl, carboxyl, thiol, nitrile, $(C_1-C_6)$-alkoxy, carboxyl-$(C_1-C_6)$alkyl, aryloxy, arylalkyloxy, amino, amido, alkylthio, arylthio, arylalkylthio, sulfamoyl, sulfonamide, aryl, aryl-$(C_1-C_4)$-alkyl, heteroaryl, and cycloheteroalkyl,
  - wherein the $(C_1-C_8)$-alkyl group is optionally substituted with up to three substituents independently selected among hydroxyl, halogen, $(C_1-C_4)$-alkoxy, or halogenated $(C_1-C_4)$-alkoxy,
  - wherein the alkyl-chain of the $(C_1-C_4)$-alkoxy moiety is optionally substituted with hydroxyl;

wherein the aryl group or aryl moiety is optionally substituted with up to three substituents independently selected from the group consisting of hydroxyl, halogen, ($C_1$-$C_4$)-alkyl, ($C_1$-$C_4$)-alkoxy, halogenated ($C_1$-$C_4$)-alkyl, halogenated ($C_1$-$C_4$)-alkoxy and carboxyl-($C_1$-$C_6$)alkyl, or wherein the aryl moiety is optionally substituted by two groups which are attached to adjacent carbon atoms and are combined into a saturated or partly unsaturated cyclic 5, 6, 7, or 8 membered ring system, optionally containing up to three heteroatoms selected from N, O and S, the number of N atoms being 0, 1, 2 or 3 and the number of O and S atoms each being 0, 1 or 2;

wherein the heteroaryl group is optionally substituted with up to three substituents independently selected from the group consisting of hydroxyl, halogen, ($C_1$-$C_4$)-alkyl, ($C_1$-$C_4$)-alkoxy, halogenated ($C_1$-$C_4$)-alkyl, halogenated ($C_1$-$C_4$)-alkoxy) and carboxyl-($C_1$-$C_6$)alkyl;

wherein the cycloheteroalkyl is optionally substituted with up to three substituents independently selected from the group consisting of oxo, ($C_1$-$C_8$)-alkyl, aryl, aryl-($C_1$-$C_4$)-alkyl, hydroxyl, ($C_1$-$C_6$) alkoxy, carboxyl-($C_1$-$C_6$)alkyl, and carboxyl, wherein each aryl group is optionally further substituted with up to three substituents independently selected from the group consisting of hydroxyl, halogen, ($C_1$-$C_4$)-alkyl, ($C_1$-$C_4$)-alkoxy, halogenated ($C_1$-$C_4$)-alkyl, and halogenated ($C_1$-$C_4$)-alkoxy); or (ii) by two groups which are attached to the same carbon atom and are combined into a saturated or partly unsaturated cyclic 4, 5, 6, 7, or 8-membered ring system, optionally containing up to three heteroatoms selected from N, O and S, the number of N atoms being 0, 1, 2 or 3 and the number of O and S atoms each being 0, 1 or 2, wherein the cyclic ring system is optionally substituted by up to two substituents independently selected from oxo, ($C_1$-$C_6$)-alkyl, aryl and aryl-($C_1$-$C_4$)-alkyl;

and wherein n represents (a) 1, 2, 3, 4, 5 or 6, provided —X-A-Y— together represent —NH—CO—NR$^4$—, —NH—CO—O—, —NH—CO—, —NH—CO—NH—SO$_2$—, —NH—SO$_2$—NR$^4$—, —NH—SO$_2$—O—, —NH—SO$_2$—, —O—CO—NR$^4$—, —O—CO—, —O—CO—NH—SO$_2$—NR$^4$—, or —O—, or (b) 0, 1, 2, 3, 4, or 5, provided —X-A-Y— together represent —CO—NR$^4$—, —CO—CO—, or —CO—NH—NR$^4$—.

3. A compound according to claim 1, which is an optically pure enantiomer corresponding to formula (II)

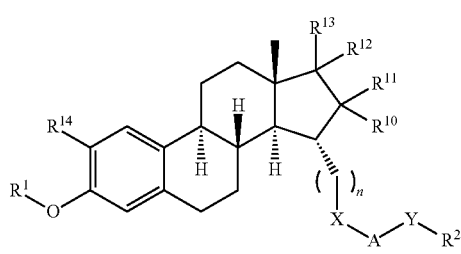

(II)

or a pharmaceutically acceptable salt thereof.

4. A compound according to claim 1, which is an optically pure enantiomer corresponding to formula (III)

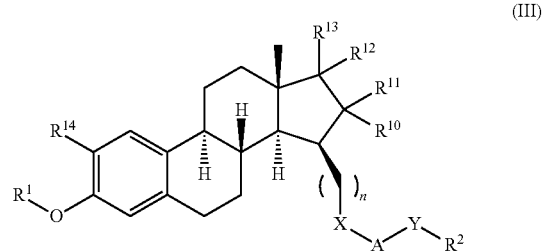

(III)

or a pharmaceutically acceptable salt thereof.

5. A compound according to claim 1, wherein
$R^1$ represents —H, ($C_1$-$C_4$)alkyl, or —($C_1$-$C_4$)alkyl-phenyl;
the substituents $R^{10}$, $R^{11}$, $R^{12}$ and $R^{13}$ together with the carbon atoms, to which they are attached, form a structure

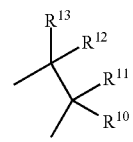

which is selected from the group of

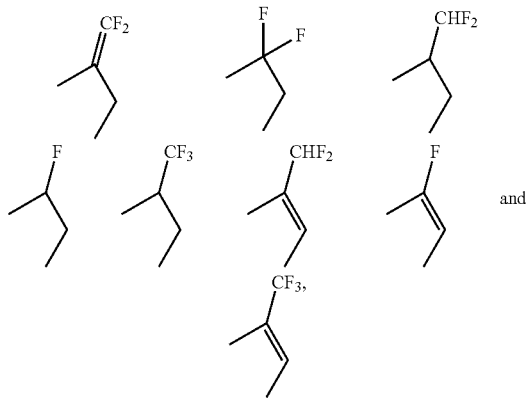

and $R^{14}$ represents —H, —($C_1$-$C_8$)alkyl, —O—($C_1$-$C_8$)alkyl, or —($C_1$-$C_8$)alkyl-O—($C_1$-$C_8$)alkyl.

6. A compound according to claim 5, wherein
the substituents $R^{10}$, $R^{11}$, $R^{12}$ and $R^{13}$ together with the carbon atoms, to which they are attached, form a structure

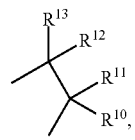

which is selected from the group of

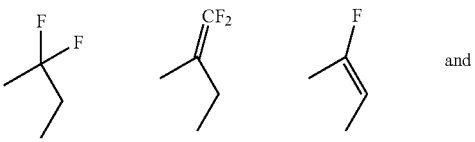

and

-continued

7. A compound according to claim 6, wherein $R^1$ and $R^{14}$ each individually represent —H.

8. A compound according to claim 1, wherein
$R^1$ represents —H, $(C_1-C_4)$alkyl, or —$(C_1-C_4)$alkyl-phenyl;
the substituents $R^{10}$, $R^{11}$, $R^{12}$ and $R^{13}$ together with the carbon atoms, to which $R^{10}$, $R^{11}$, $R^{12}$ and $R^{13}$ are attached, form a heterocyclic 5- or 6-membered ring, which is partly unsaturated or aromatic, which contains one, two or three heteroatoms independently selected from N, O and S, the number of N atoms being 0, 1, 2 or 3 and the number of O and S atoms each being 0, 1 or 2, wherein one heteroatom is directly attached to the C17 C-atom of the steroidal core; and which ring is optionally substituted with an alkyl group; and
$R^{14}$ represents —H, —$(C_1-C_8)$alkyl, —O—$(C_1-C_8)$alkyl, or —$(C_1-C_8)$alkyl-O—$(C_1-C_8)$alkyl.

9. A compound according to claim 8, wherein
the substituents $R^{10}$, $R^{11}$, $R^{12}$ and $R^{13}$ together with the carbon atoms, to which $R^{10}$, $R^{11}$, $R^{12}$ and $R^{13}$ are attached, form a heterocyclic 5- or 6-membered ring to provide a compound corresponding to one of the following formulas

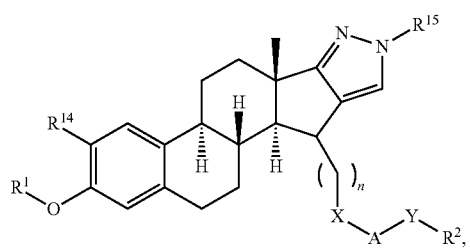

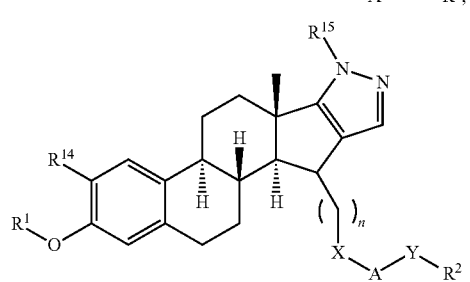

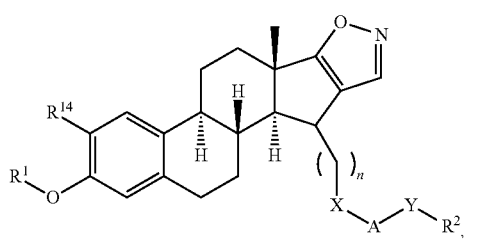

-continued

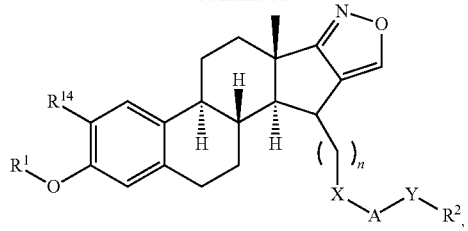

wherein $R^{15}$ represents —H or —$(C_1-C_4)$alkyl.

10. A compound according to claim 9, wherein $R^1$ and $R^{14}$ each individually represent —H.

11. A compound according to claim 1, wherein
$R^1$ represents —H or —$SO_2$—$NH_2$,
the substituents $R^{10}$, $R^{11}$, $R^{12}$ and $R^{13}$ together with the carbon atoms to which they are attached, form a structure

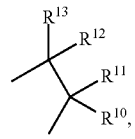

which is selected from the group of

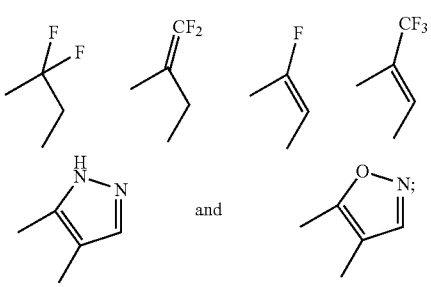

and
$R^{14}$ represents —H, —$(C_1-C_4)$alkyl, —O—$(C_1-C_4)$alkyl, or —$(C_1-C_4)$alkyl-O—$(C_1-C_4)$alkyl.

12. A compound according to claim 1, wherein —X-A-Y— together represent a group selected from —CO—$NR^4$—, —CO—O—, —CO—, and —CO—NH—$NR^4$—; and n represents 0, 1, 2, 3, 4, or 5.

13. A compound according to claim 12, wherein —X-A-Y— together represent —CO—$NR^4$—.

14. A compound according to claim 13, wherein n represents 2, 3 or 4.

15. A compound according to claim 13, wherein
$R^2$ represents
(i) —$(C_1-C_4)$alkyl, which is optionally substituted with one or two substituents independently selected from the group consisting of hydroxyl, halogen, and $(C_1-C_4)$alkoxy;
(ii) —$(C_3-C_8)$cycloalkyl;
(iii) aryl or —$(C_1-C_4)$alkyl-aryl, wherein the aryl is phenyl or naphthyl,
which phenyl is optionally substituted with one or two substituents independently selected from the group consisting of hydroxyl, halogen, cyano, $(C_1-C_4)$ alkoxy and halogenated $(C_1-C_4)$alkoxy; or which phenyl is optionally substituted by two groups which are attached to adjacent carbon atoms and are combined into a saturated cyclic 5 or 6-membered ring system, containing 1 or 2 O atoms; or (iv) heteroaryl or —($C_1$-$C_4$)alkyl-heteroaryl, wherein the heteroaryl is furyl, thienyl, thiazolyl, imidazolyl, pyridinyl, indolyl, indazolyl, or benzoimidazolyl;

which heteroaryl is optionally substituted with one or two substituents independently selected from the group consisting of —($C_1$-$C_4$)alkyl and —($C_1$-$C_4$)alkyl-(C=O)—O—($C_1$-$C_4$)alkyl;

and $R^4$ is independently selected from H or —($C_1$-$C_4$)-alkyl or —($C_1$-$C_4$)-alkyl-phenyl, wherein the phenyl group is optionally substituted with one or two ($C_1$-$C_4$)alkoxy groups; or $R^2$ and $R^4$ form together with the nitrogen atom, to which $R^2$ and $R^4$ are attached, a ring or ring-system, which is selected from the group consisting of morpholine, piperidine, thiomorpholine and piperazine, wherein the ring or the ring-system is optionally substituted with a —($C_1$-$C_4$)alkyl group.

16. A compound according to claim 15, wherein $R^2$ represents (i) —($C_1$-$C_4$)alkyl, which is optionally substituted with one or two ($C_1$-$C_4$)alkoxy groups;

(ii) —($C_3$-$C_8$)cycloalkyl;

(iii) phenyl or —($C_1$-$C_4$)alkyl-phenyl, which phenyl is optionally substituted with one or two substituents independently selected from the group consisting of hydroxyl, halogen, cyano and ($C_1$-$C_4$) alkoxy; or which phenyl is optionally substituted by two groups which are attached to adjacent carbon atoms and are combined into a saturated cyclic 5 or 6-membered ring system, containing 1 or 2 O atoms; or (iv) heteroaryl or —($C_1$-$C_4$)alkyl-heteroaryl, wherein the heteroaryl is thiazolyl, pyridinyl, indolyl, or indazolyl;

which heteroaryl is optionally substituted with one or two —(C1-$C_4$)alkyl groups;

and $R^4$ is independently selected from —H, —(C1-$C_4$)-alkyl or —($C_1$-$C_4$)-alkyl-phenyl, wherein the phenyl group is optionally substituted with one or two ($C_1$-$C_4$)alkoxy groups; or $R^2$ and $R^4$ form together with the nitrogen atom, to which $R^2$ and $R^4$ are attached, a ring, which is selected from the group consisting of morpholine, piperidine, and piperazine, wherein the ring is optionally substituted with a —($C_1$-$C_4$)alkyl group.

17. A compound according to claim 13, wherein $R^2$ represents a —($C_1$-$C_4$)alkyl-phenyl or a thiazolyl group, optionally substituted with —($C_1$-$C_4$)-alkyl, and $R^4$ represents —H; or $R^2$ and $R^4$ form together with the nitrogen atom, to which $R^2$ and $R^4$ are attached, a morpholinyl group, and n represents 2 or 3.

18. A compound according to claim 1, wherein said compound is selected from the group consisting of:

4-(17,17-Difluoro-3-hydroxy-estra-1,3,5(10)-trien-15α-yl)-1-morpholin-4-yl-butan-1-one, 4-(17,17-Difluoro-3-hydroxy-estra-1,3,5(10)-trien-15β-yl)-1-morpholin-4-yl-butan-1-one, 4-(17-Fluoro-3-hydroxy-estra-1,3,5(10),16-tetraen-15β-yl)-1-morpholin-4-yl-butan-1-one, 3-(17,17-Difluoro-3-hydroxy-estra-1,3,5(10)-trien-15β-yl)-N-(5-methyl-thiazol-2-yl)-propionamide, 4-(17-Difluoromethylene-3-hydroxy-estra-1,3,5(10)-trien-15β-yl)-1-morpholin-4-yl-butan-1-one, N-Cyclohexyl-4-(17,17-difluoro-3-hydroxy-estra-1,3,5(10)-trien-15α-yl)-butyramide, N-Benzyl-4-(17,17-difluoro-3-hydroxy-estra-1,3,5(10)-trien-15α-yl)-butyramide, 4-(17,17-Difluoro-3-hydroxy-estra-1,3,5(10)-trien-15α-yl)-N-(3,4-dihydroxy-benzyl)-butyramide, 4-(17,17-Difluoro-3-hydroxy-estra-1,3,5(10)-trien-15α-yl)-N-[2-(7-methyl-1H-indol-3-yl)-ethyl]-butyramide, 4-(17,17-Difluoro-3-hydroxy-estra-1,3,5(10)-trien-15α-yl)-1-piperidin-1-yl-butan-1-one, 4-(17,17-Difluoro-3-hydroxy-estra-1,3,5(10)-trien-15α-yl)-N-[2-(3,4-dimethoxy-phenyl)-ethyl]-N-methyl-butyramide, N-Cyclopropyl-3-(17,17-difluoro-3-hydroxy-estra-1,3,5(10)-trien-15β-yl)-propionamide, N-Cyclohexyl-3-(17,17-difluoro-3-hydroxy-estra-1,3,5(10)-trien-15β-yl)-propionamide, N-Benzo[1,3]dioxol-5-ylmethyl-3-(17,17-difluoro-3-hydroxy-estra-1,3,5(10)-trien-15β-yl)-propionamide, N-Benzyl-3-(17,17-difluoro-3-hydroxy-estra-1,3,5(10)-trien-15β-yl)-propionamide, 3-(17,17-Difluoro-3-hydroxy-estra-1,3,5(10)-trien-15β-yl)-N-(3,4-dihydroxy-benzyl)-propionamide, 3-(17,17-Difluoro-3-hydroxy-estra-1,3,5(10)-trien-15β-yl)-N-(3,5-dimethoxy-benzyl)-propionamide, 3-(17,17-Difluoro-3-hydroxy-estra-1,3,5(10)-trien-15β-yl)-N-[2-(7-methyl-1H-indol-3-yl)-ethyl]-propionamide, 3-(17,17-Difluoro-3-hydroxy-estra-1,3,5(10)-trien-15β-yl)-1-piperidin-1-yl-propan-1-one, 3-(17,17-Difluoro-3-hydroxy-estra-1,3,5(10)-trien-15β-yl)-N,N-diethyl-propionamide, 3-(17,17-Difluoro-3-hydroxy-estra-1,3,5(10)-trien-15β-yl)-N-[2-(3,4-dimethoxy-phenyl)-ethyl]-N-methyl-propionamide, and 3-Hydroxy-15β-(4-morpholin-4-yl-4-oxo-butyl)-estra-1,3,5(10)-trien-[16,17-c]-pyrazole, or a pharmaceutically acceptable salt thereof.

19. A pharmaceutical composition comprising as an active ingredient a compound corresponding to formula I of claim 1 and at least one pharmaceutically acceptable carrier.

20. A method for the treatment of breast cancer in a mammal, the method comprising the step of administering to a subject in need thereof a pharmaceutically effective amount of a compound corresponding to formula I of claim 1.

21. The method of claim 20, wherein the breast cancer is characterized by a detectable level of 17β-HSD1 or STS expression within a cancer tissue sample.

22. The method of claim 20, wherein the mammal is a human postmenopausal female.

23. The method of claim 20, wherein the mammal is a human pre- or peri-menopausal female.

* * * * *

UNITED STATES PATENT AND TRADEMARK OFFICE
CERTIFICATE OF CORRECTION

PATENT NO. : 8,030,298 B2  Page 1 of 1
APPLICATION NO. : 11/441200
DATED : October 4, 2011
INVENTOR(S) : Messinger et al.

It is certified that error appears in the above-identified patent and that said Letters Patent is hereby corrected as shown below:

Column 183, line 55, claim 1: "$NR^3R^{3\dagger}$," to read as --$NR^3R^{3'}$,--

Column 183, line 56, claim 1: "$NR^3R^{3\dagger}$," to read as --$NR^3R^{3'}$,--

Column 184, line 64, claim 1: "$NR^3R^{3\dagger}$," to read as --$NR^3R^{3'}$,--

Column 184, line 64, claim 1: "$NR^3R^{3\dagger}$," to read as --$NR^3R^{3'}$,--

Column 185, line 53, claim 2: "alkoxy);" to read as --alkoxy;--

Column 187, line 19, claim 2: "alkoxy)" to read as --alkoxy--

Column 187, line 31, claim 2: "alkoxy);" to read as --alkoxy;--

Column 187, line 50, claim 2: "-CO-CO-," to read as -- -CO-O-, -CO-,--

Signed and Sealed this
Twenty-eighth Day of August, 2012

David J. Kappos
*Director of the United States Patent and Trademark Office*